(12) United States Patent
Takahashi et al.

(10) Patent No.: US 10,593,889 B1
(45) Date of Patent: Mar. 17, 2020

(54) COMPOUND AND ORGANIC ELECTROLUMINESCENCE DEVICE

(71) Applicant: Idemitsu Kosan Co., Ltd., Chiyoda-ku, Tokyo (JP)

(72) Inventors: Ryota Takahashi, Sodegaura (JP); Hidetsugu Ikeda, Sodegaura (JP); Yuki Nakano, Sodegaura (JP); Keita Seda, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/355,222

(22) Filed: Mar. 15, 2019

(30) Foreign Application Priority Data

Sep. 26, 2018 (JP) ................. 2018-180465

(51) Int. Cl.
*H01L 51/00* (2006.01)
*C07D 491/22* (2006.01)
(Continued)

(52) U.S. Cl.
CPC ........ *H01L 51/0071* (2013.01); *C07D 491/22* (2013.01); *C09K 11/06* (2013.01);
(Continued)

(58) Field of Classification Search
None
See application file for complete search history.

(56) References Cited

U.S. PATENT DOCUMENTS 5,843,607 A 12/1998 Hu et al.
5,942,340 A 8/1999 Hu et al.
(Continued)

FOREIGN PATENT DOCUMENTS

CN 104119347 A 10/2014
CN 107652295 A 2/2018
(Continued)

OTHER PUBLICATIONS

Brigitte Wex et al., "Perspective on carbazole-based organic compounds as emitters and hosts in TADF applications", J. Mater. Chem. C, 2017, 5, 8622-8653.
(Continued)

*Primary Examiner* — Jay Yang
(74) *Attorney, Agent, or Firm* — Foley & Lardner LLP

(57) ABSTRACT

To provide a compound represented by the following formula (1-5).

Two of *1 are fused with a group represented by the formula (1A) to form a nitrogen atom-containing five-membered ring; and two of *2 are fused with a group represented by the
(Continued)

formula (1A), which is different from the group bonded with the two of *1, to form a nitrogen atom-containing five-membered ring.

21 Claims, 1 Drawing Sheet

(51) Int. Cl.
  *C09K 11/06* (2006.01)
  *H01L 51/50* (2006.01)
(52) U.S. Cl.
  CPC .. *C09K 2211/1018* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 6,337,404 | B1 | 1/2002 | Han et al. |
| 6,562,982 | B1 | 5/2003 | Hu et al. |
| 6,649,772 | B2 | 11/2003 | Lin et al. |
| 6,670,054 | B1 | 12/2003 | Hu et al. |
| 7,227,027 | B2 | 6/2007 | Qiu et al. |
| 8,227,801 | B2 | 7/2012 | Xia et al. |
| 8,343,637 | B2 | 1/2013 | Parham et al. |
| 8,405,070 | B2 | 3/2013 | Iwaki et al. |
| 9,233,922 | B2 | 1/2016 | Nakayama et al. |
| 9,530,969 | B2 | 12/2016 | Mizuki et al. |
| 9,825,239 | B2 | 11/2017 | Matsuki et al. |
| 10,249,832 | B1 | 4/2019 | Takahashi et al. |
| 2009/0066235 | A1 | 3/2009 | Yabunouchi et al. |
| 2010/0051928 | A1 | 3/2010 | Fukuzaki |
| 2011/0062429 | A1 | 3/2011 | Kai et al. |
| 2012/0241732 | A1 | 9/2012 | Endo et al. |
| 2013/0026422 | A1 | 1/2013 | Parham et al. |
| 2014/0319507 | A1 | 10/2014 | Yamamoto et al. |
| 2015/0295186 | A1 | 10/2015 | Parham et al. |
| 2015/0357579 | A1 | 12/2015 | Itoi et al. |
| 2016/0126471 | A1 | 5/2016 | Lui et al. |
| 2016/0233435 | A1 | 8/2016 | Zeng et al. |
| 2016/0268516 | A1 | 9/2016 | Tanaka et al. |
| 2017/0179406 | A1 | 6/2017 | Kang et al. |
| 2017/0213984 | A1 | 7/2017 | Kim et al. |
| 2017/0324045 | A1 | 11/2017 | Takahashi et al. |
| 2018/0114924 | A1 | 4/2018 | Lee et al. |
| 2018/0198076 | A1 | 7/2018 | Takahashi et al. |
| 2018/0315930 | A1 | 11/2018 | Han et al. |
| 2019/0055222 | A1 | 2/2019 | Han et al. |
| 2019/0097142 | A1 | 3/2019 | Takahashi et al. |

FOREIGN PATENT DOCUMENTS

| | | |
|---|---|---|
| JP | 2012-191031 A | 10/2012 |
| JP | 2013-523847 A | 6/2013 |
| JP | 2013-147481 A | 8/2013 |
| JP | 2014-073965 A | 4/2014 |
| JP | 2015-153911 A | 8/2015 |
| JP | 2015-530357 A | 10/2015 |
| JP | 2017-141167 A | 8/2017 |
| JP | 2017-521525 A | 8/2017 |
| KR | 10-2013-0106255 A | 9/2013 |
| KR | 2014034710 A | 3/2014 |
| KR | 20150135125 A | 12/2015 |
| KR | 2017103358 A | 9/2017 |
| KR | 2017108895 A | 9/2017 |
| KR | 2017113398 A | 10/2017 |
| KR | 20170116983 A | 3/2018 |
| WO | WO-2013/077344 A1 | 5/2013 |
| WO | WO-2015/099507 A1 | 7/2015 |
| WO | WO-2016/006925 A1 | 1/2016 |
| WO | WO-2017/074052 A1 | 5/2017 |
| WO | WO-2017/138755 A1 | 8/2017 |
| WO | WO-2017/142310 A1 | 8/2017 |
| WO | WO-2017/175690 A1 | 10/2017 |
| WO | WO-2018/026197 A1 | 2/2018 |
| WO | WO-2018/038544 A1 | 3/2018 |
| WO | WO-2018/151065 A1 | 8/2018 |
| WO | WO-2019-111971 A1 | 6/2019 |

OTHER PUBLICATIONS

International Search Report dated Feb. 19, 2019 in corresponding application No. PCT/JP2018/044792.
J.V. Grazulevicius et al. "Carbazole-containing polymers: synthesis, properties and applications", 2003,-Prog. Polym. Sci. 28 1297-1353.
Notice of Allowance on U.S. Appl. No. 16/043,074, dated Oct. 3, 2018.
Non-Final Office Action on U.S. Appl. No. 16/290,702 dated May 8, 2019.
International Search Report issued in the corresponding Japanese Patent Application Ser. No. PCT/JP2019/023611, dated Aug. 6, 2019.
Niebel, Claude et al., "Dibenzo[2,3:5,6]pyrrolizino[1,7-bc]indolo[1,2,3-lm]carbazole: a new electron donor", New Journal of Chemistry, 2010, vol. 34, pp. 1243-1246.
Database Registry [online] Chemical Abstract Service, US; Nov. 16, 1984 (Nov. 16, 1984), Retrieved from STN, Database accession No. RN: 14458-65-2, 1, 7b, 8, 14b-Tetraazabenz[a]indeno[1,2,4-hi]aceanthrylene [Nov. 21, 2019].
International Search Report dated Dec. 10, 2019 for corresponding Application No. PCT/JP2019/037865.
Moehrle, H., et al., Ring opening reactions of carbinolamine equivalents of the tetrahydro-B-carboline series. I, Archivder Pharmazie (Weinheim, Germany), 1986, 319(11), 1043-9.
Szantay, C. et al., Synthesis of substituted octahydroindolo [2,3-a]-quinolizines. The formation of a new type of ring system, Journal of Organic Chemistry, 1967, 32(2), 423-7.
Tsuge, O., et al., Polyazapentalenes. I. Preparation of 6-dehydroindazolo[1,2-a]benzotriazole, Journal of Heterocyclic Chemistry, 1971, 8(5), 707-10.

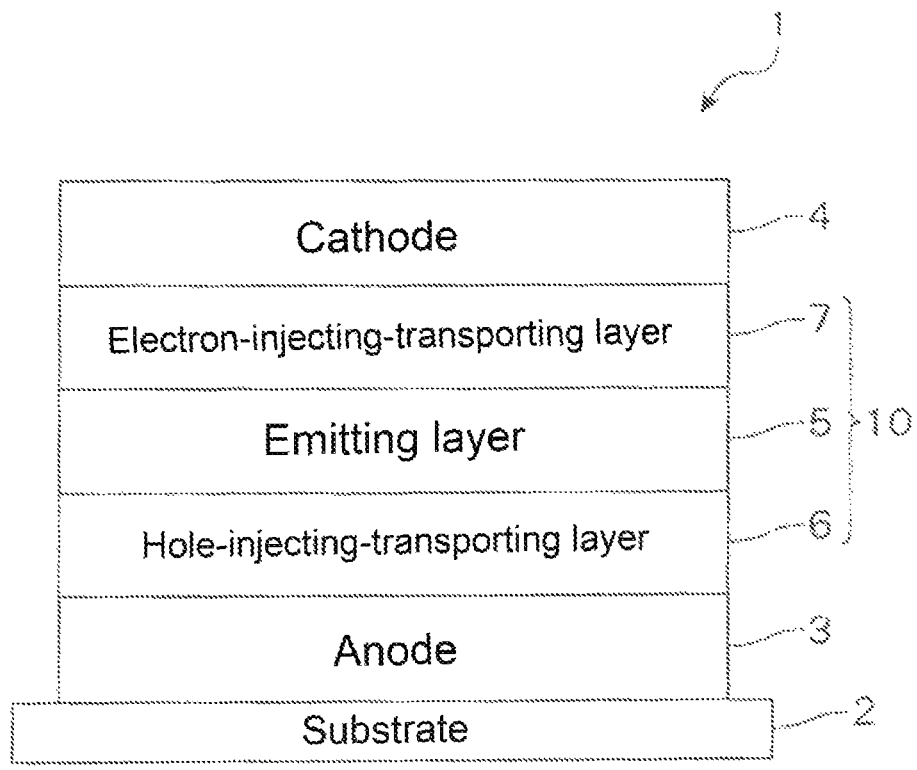

COMPOUND AND ORGANIC ELECTROLUMINESCENCE DEVICE

TECHNICAL FIELD

The invention relates to a new compound and an organic electroluminescence device using the same.

BACKGROUND ART

When voltage is applied to an organic electroluminescence device (hereinafter, referred to as an organic EL device in several cases), holes and electrons are injected into an emitting layer from an anode and a cathode, respectively. Then, thus injected holes and electrons are recombined in the emitting layer, and excitons are formed therein.

The organic EL device includes the emitting layer between the anode and the cathode. Further, the organic EL device has a stacked structure including an organic layer such as a hole-injecting layer, a hole-transporting layer, an electron-injecting layer, and an electron-transporting layer in several cases.

Patent Document 1 discloses a compound used as a material for an organic electroluminescence device.

RELATED ART DOCUMENTS

Patent Documents

Patent Document 1: WO2013/077344

SUMMARY OF THE INVENTION

One of objects of the invention is to provide a compound which can be used as a material for an organic electroluminescence device. Further, another object of the invention is to provide an organic electroluminescence device having high luminous efficiency.

One aspect of the invention provides a compound having structures represented by the following formulas (a) and (b).

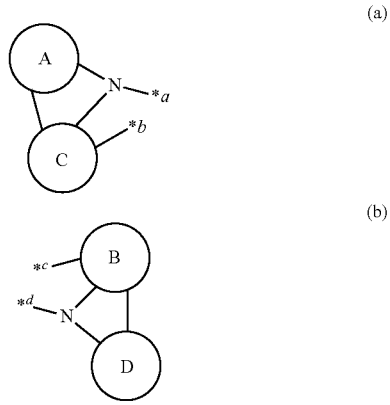

wherein, in the structures represented by the formulas (a) and (b), a ring A, a ring B, a ring C and a ring D are independently a substituted or unsubstituted aromatic hydrocarbon ring having 6 to 50 carbon atoms that form a ring (hereinafter referred to as "ring carbon atoms") or a substituted or unsubstituted heterocyclic ring having 5 to 50 atoms that form a ring (hereinafter referred to as "ring atoms");

two or more of the ring A, the ring B, the ring C and the ring D are the heterocyclic ring;

each of sites *a, *b, *c and *d in the formula (a) and the formula (b) represents a position of an atom; and the atoms located in the sites *a, *b, *c and *d form a substituted or unsubstituted and saturated or unsaturated six-membered ring including the four atoms located in the sites.

Another aspect of the invention provides an organic electroluminescence device having a cathode, an anode, and one or more organic layer arranged between the cathode and the anode, wherein at least one layer in the one or more organic layers contains the compound according to one aspect of the invention, and a compound represented by the following formula (10):

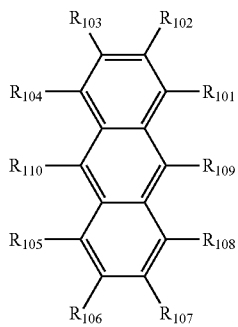

(10)

wherein, in the formulas (10), at least one of $R_{101}$ to $R_{110}$ is a group represented by the following formula (31); when two or more groups represented by the following formula (31) exist, two or more groups represented by the following formula (31) may be the same with or different from each other;

$$-L_{101}-Ar_{101} \quad (31)$$

wherein, in the formula (31), $L_{101}$ is a single bond, a substituted or unsubstituted arylene group having 6 to 30 ring carbon atoms, or a substituted or unsubstituted divalent heterocyclic group having 5 to 30 ring atoms;

$Ar_{101}$ is a substituted or unsubstituted aryl group having 6 to 50 ring carbon atoms, or a substituted or unsubstituted monovalent heterocyclic group having 5 to 50 ring atoms;

one or more sets of two or more adjacent to each other among $R_{101}$ to $R_{110}$ that are not the group represented by the formula (31) form a substituted or unsubstituted and saturated or unsaturated ring, or do not form the ring;

$R_{101}$ to $R_{110}$ that are neither the group represented by the formula (31) nor form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),
—O—($R_{904}$),
—S—($R_{905}$)
—N($R_{906}$)($R_{907}$)
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms; and
when two or more of $R_{901}$ to $R_{907}$ exist, two or more of $R_{901}$ to $R_{907}$ may be the same with or different from each other.

Another aspect of the invention provides an electronic apparatus provided with the organic electroluminescence device.

ADVANTAGEOUS EFFECTS OF THE INVENTION

According to the invention, an organic electroluminescence device having high luminous efficiency can be provided.

BRIEF DESCRIPTION OF THE DRAWINGS

The FIGURE is a diagram showing a schematic configuration of one embodiment of an organic EL device of the invention.

DETAILED DESCRIPTION OF THE INVENTION

Definition

In the present specification, a hydrogen atom means an atom including isotopes different in the number of neutrons, namely, a protium, a deuterium and a tritium.

In the present specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In the present specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In the present specification, a term "XX to YY carbon atoms" in an expression of "substituted or unsubstituted ZZ group having XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In the present specification, a term "XX to YY atoms" in an expression of "substituted or unsubstituted ZZ group having XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described herein will be described.

The number of the ring carbon atoms of the "unsubstituted aryl group" described herein is 6 to 50, preferably 6 to 30, and more preferably 6 to 18, unless otherwise specified.

The number of the ring carbon atoms of the "unsubstituted heterocyclic group" described herein is 5 to 50, preferably 5 to 30, and more preferably 5 to 18, unless otherwise specified.

The number of the carbon atoms of the "unsubstituted alkyl group" described herein is 1 to 50, preferably 1 to 20, and more preferably 1 to 6, unless otherwise specified.

The number of the carbon atoms of the "unsubstituted alkenyl group" described herein is 2 to 50, preferably 2 to 20, and more preferably 2 to 6, unless otherwise specified.

The number of the carbon atoms of the "unsubstituted alkynyl group" described herein is 2 to 50, preferably 2 to 20, and more preferably 2 to 6, unless otherwise specified.

The number of the ring carbon atoms of the "unsubstituted cycloalkyl group" described herein is 3 to 50, preferably 3 to 20, and more preferably 3 to 6, unless otherwise specified.

The number of the ring carbon atoms of the "unsubstituted arylene group" described herein is 6 to 50, preferably 6 to 30, and more preferably 6 to 18, unless otherwise specified.

The number of the ring atoms of the "unsubstituted divalent heterocyclic group" described herein is 5 to 50, preferably 5 to 30, and more preferably 5 to 18, unless otherwise specified.

The number of the carbon atoms of the "unsubstituted alkylene group" described herein is 1 to 50, preferably 1 to 20, and more preferably 1 to 6, unless otherwise specified.

Specific examples (specific example group G1) of the "substituted or unsubstituted aryl group" described herein include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed herein are only one example, and the "substituted aryl group" described herein also includes a group in which a group in which "unsubstituted aryl group" has a substituent or the like further has a substituent, and a group in which "substituted aryl group" further has a substituent.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranethenyl group,
a benzofluoranethenyl group, and
a perylenyl group.

A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described herein is a ring group having at least one hetero atom in the ring atom. Specific examples of the hetero atom include a nitrogen atom, an oxygen atom, a sulfur atom, a silicon atom, a phosphorus atom and a boron atom.

The "heterocyclic group" described herein may be a monocyclic group, or a fused ring group.

The "heterocyclic group" described herein may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocyclic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocyclic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed herein are merely one example, and the "substituted heterocyclic group" described herein also includes a group in which "unsubstituted heterocyclic group" which has a substituent or the like further has a substituent, and a group in which "substituted heterocyclic group" further has a substituent.

An unsubstituted heterocyclic group having a nitrogen atom:
a pyrrolyl group,
an imidazolyl group,
a pyrazolyl group,
a triazolyl group,
a tetrazolyl group,
an oxazolyl group,
an isoxazolyl group,
an oxadiazolyl group, a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group having an oxygen atom:
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzooxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group having a sulfur atom:
a thienyl group,
a thiazolyl group,
an isothiazolyl group,
a thiadiazolyl group,
a benzothiophenyl group,
an isobenzothiophenyl group,
a dibenzothiophenyl group,
a naphthobenzothiophenyl group,
a benzothiazolyl group,
a benzisothiazolyl group,
a phenothiazinyl group,
a dinaphthothiophenyl group,
an azadibenzothiophenyl group,
a diazadibenzothiophenyl group,
an azanaphthobenzothiophenyl group, and
a diazanaphthobenzothiophenyl group.

A substituted heterocyclic group having a nitrogen atom:
a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

A substituted heterocyclic group having an oxygen atom:
a phenyldibenzofuranyl group,
a methyldibenzofuranyl group,
a t-butyldibenzofuranyl group, and
a monovalent residue of spiro[9H-xanthene-9,9'-[9H]fluorene].

A substituted heterocyclic group having a sulfur atom:
a phenyldibenzothiophenyl group,
a methyldibenzothiophenyl group,
a t-butyldibenzothiophenyl group, and
a monovalent residue of spiro[9H-thioxantene-9,9'-[9H]fluorene].

A monovalent group derived from the following unsubstituted heterocyclic ring containing at least one of a nitrogen atom, an oxygen atom and a sulfur atom, and a group in which a monovalent group derived from the following unsubstituted heterocyclic ring has a substituent:

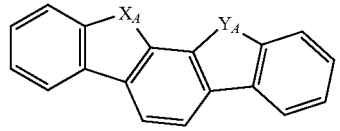

(XY-1)

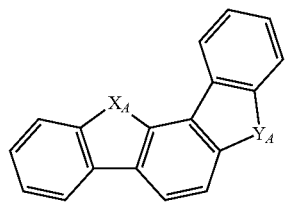

(XY-2)

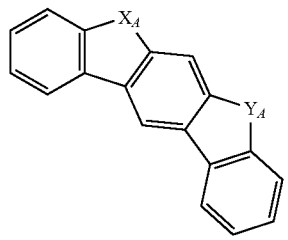

(XY-3)

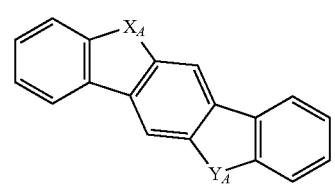

(XY-4)

(XY-5)
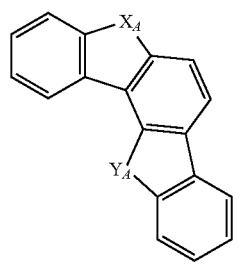

(XY-6)
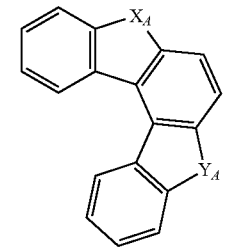

(XY-7)
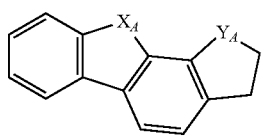

(XY-8)
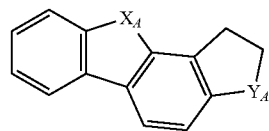

(XY-9)
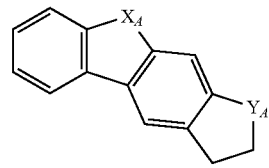

(XY-10)
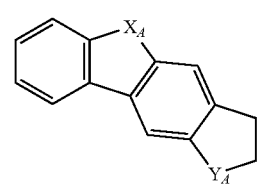

(XY-11)
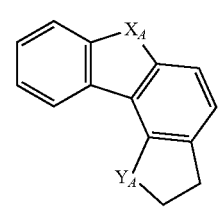

(XY-12)
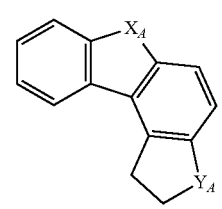

(XY-13)
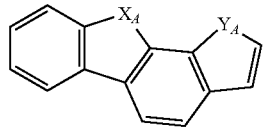

(XY-14)
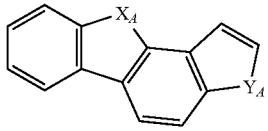

(XY-15)
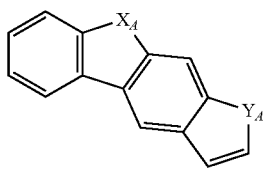

(XY-16)
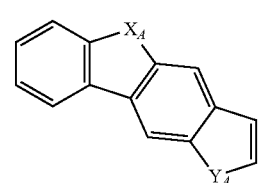

(XY-17)
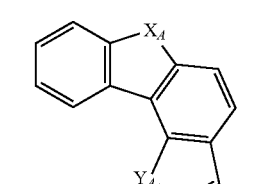

(XY-18)
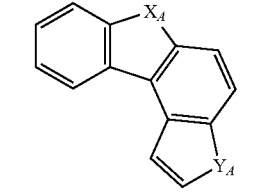

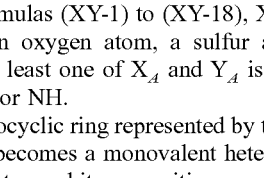

In the formulas (XY-1) to (XY-18), $X_A$ and $Y_A$ are independently an oxygen atom, a sulfur atom, NH or $CH_2$. However, at least one of $X_A$ and $Y_A$ is an oxygen atom, a sulfur atom or NH.

The heterocyclic ring represented by the formulas (XY-1) to (XY-18) becomes a monovalent heterocyclic group having a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed herein are merely one example, and the "substituted alkyl group" described herein also includes a group in which "unsubstituted alkyl group" has a substituent further has a substituent, a group in which "substituted alkyl group" further has a substituent, and the like.

An unsubstituted alkyl group:
a methyl group,
an ethyl group,
a n-propyl group,
an isopropyl group,
a n-butyl group,
an isobutyl group,
a s-butyl group, and
a t-butyl group.

A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed herein are merely one example, and the "substituted alkenyl group" described herein also includes a group in which "unsubstituted alkenyl group" has a substituent further has a substituent, a group in which "substituted alkenyl group" further has a substituent, and the like.

An unsubstituted alkenyl group and a substituted alkenyl group:
a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described herein include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed herein are merely one example, and the "substituted cycloalkyl group" described herein also includes a group in which "unsubstituted cycloalkyl group" has a substituent further has a substituent, a group in which "substituted cycloalkyl group" further has a substituent, and the like.

An unsubstituted aliphatic ring group:
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

A substituted cycloalkyl group:
a 4-methylcyclohexyl group.

Specific examples (specific example group G7) of the group represented by —Si($R_{901}$)($R_{902}$)($R_{903}$) described herein include
—Si(G1)(G1)(G1),
—Si(G1)(G2)(G2),
—Si(G1)(G1)(G2),
—Si(G2)(G2)(G2),
—Si(G3)(G3)(G3),
—Si(G5)(G5)(G5) and
—Si(G6)(G6)(G6).

In which,
G1 is the "aryl group" described in the specific example group G1.
G2 is the "heterocyclic group" described in the specific example group G2.
G3 is the "alkyl group" described in the specific example group G3.
G5 is the "alkynyl group" described in the specific example group G5.

G6 is the "cycloalkyl group" described in the specific example group G6.

Specific examples (specific example group G8) of the group represented by —O—($R_{904}$) described herein include
—O(G1),
—O(G2),
—O(G3) and
—O(G6).

In which,

G1 is the "aryl group" described in the specific example group G1.

G2 is the "heterocyclic group" described in the specific example group G2.

G3 is the "alkyl group" described in the specific example group G3.

G6 is the "cycloalkyl group" described in the specific example group G6.

Specific examples (specific example group G9) of the group represented by —S—($R_{905}$) described herein include
—S(G1),
—S(G2),
—S(G3) and
—S(G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G10) of the group represented by —N($R_{906}$)($R_{907}$) described herein include
—N(G1)(G1),
—N(G2)(G2),
—N(G1)(G2),
—N(G3)(G3) and
—N(G6)(G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G11) of the "halogen atom" described herein include a fluorine atom, a chlorine atom, a bromine atom and an iodine atom.

Specific examples of the "alkoxy group" described herein include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthio group" described herein include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described herein include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described herein include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described herein include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described herein is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described herein is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group, a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group, a (9-biphenylyl)carbazolyl group, a (9-phenyl) phenylcarbazolyl group, a diphenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

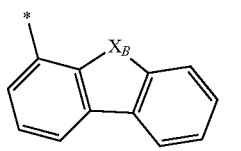
(XY-76)

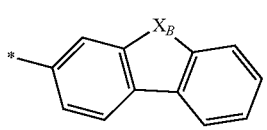
(XY-77)

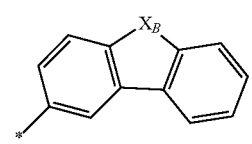
(XY-78)

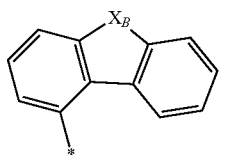
(XY-79)

In the formulas (XY-76) to (XY-79), $X_B$ is an oxygen atom or a sulfur atom.

The substituted or unsubstituted alkyl group described herein is, unless otherwise specified, preferably a methyl group, an ethyl group, a propyl group, an isopropyl group, a n-butyl group, an isobutyl group, a t-butyl group, or the like.

The "substituted or unsubstituted arylene group" descried herein refers to a group in which the above-described "aryl group" is converted into divalence, unless otherwise specified.

Specific examples (specific example group G12) of the "substituted or unsubstituted arylene group" include a group in which the "aryl group" described in the specific example group G1 is converted into divalence.

Specific examples (specific example group G13) of the "substituted or unsubstituted divalent heterocyclic group" include a group in which the "heterocyclic group" described in the specific example group G2 is converted into divalence.

Specific examples (specific example group G14) of the "substituted or unsubstituted alkylene group" include a group in which the "alkyl group" described in the specific example group G3 is converted into divalence.

The substituted or unsubstituted arylene group described herein is any group below, unless otherwise specified.

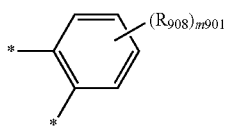
(XY-20)

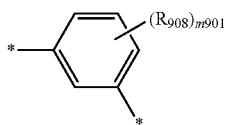
(XY-21)

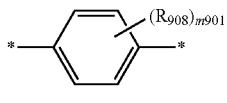
(XY-22)

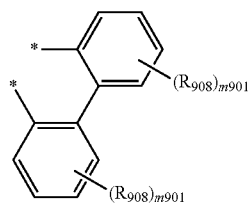
(XY-23)

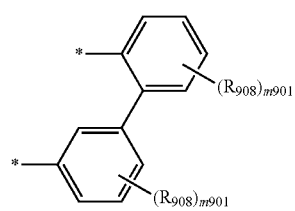
(XY-24)

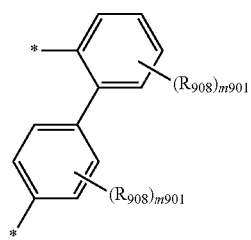
(XY-25)

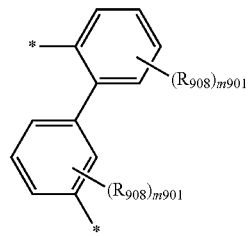
(XY-26)

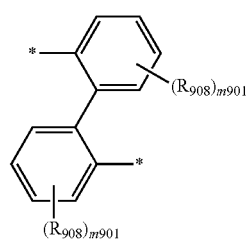
(XY-27)

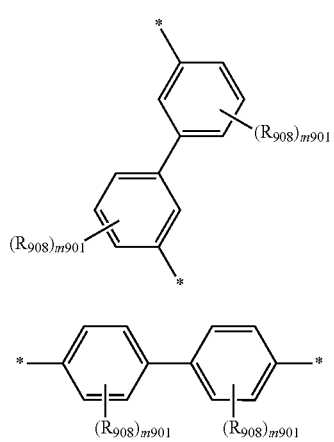
(XY-28)
(XY-29)
In the formulas (XY-20) to (XY-29), $R_{908}$ is a substituent.
Then, m901 is an integer of 0 to 4, and when m901 is 2 or more, a plurality of $R_{908}$ may be the same with or different from each other.
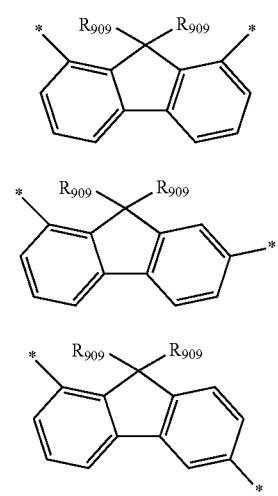
(XY-30)
(XY-31)
(XY-32)
(XY-33)
(XY-34)
(XY-35)
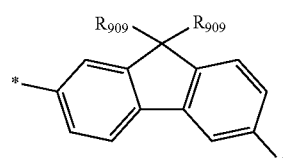
(XY-36)
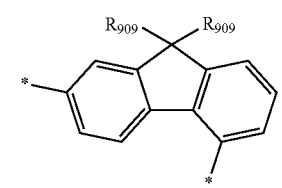
(XY-37)
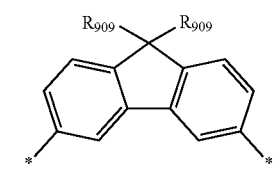
(XY-38)
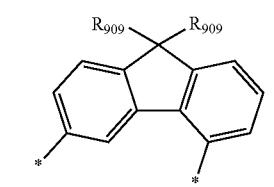
(XY-39)
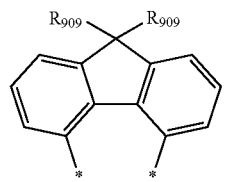
(XY-40)
In the formulas (XY-30) to (XY-40), $R_{909}$ is independently a hydrogen atom or a substituent. Two of $R_{909}$ may be bonded with each other through a single bond to form a ring.
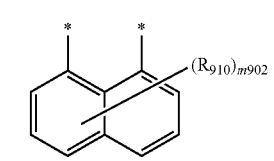
(XY-41)
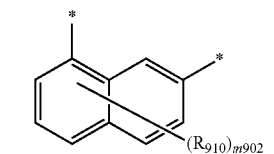
(XY-42)
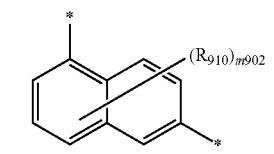
(XY-43)

-continued (XY-44)
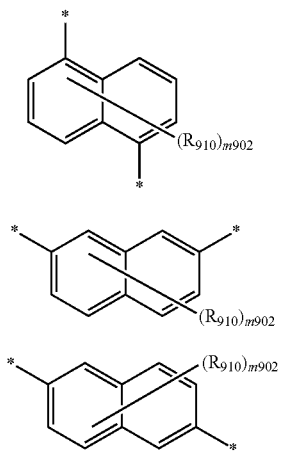

(XY-45)

(XY-46)

In the formulas (XY-41) to (XY-46), $R_{910}$ is a substituent.

Then, m902 is an integer of 0 to 6. When m902 is 2 or more, a plurality of $R_{910}$ may be the same with or different from each other.

The substituted or unsubstituted divalent heterocyclic group described herein is preferably any group described below, unless otherwise specified.

(XY-50)
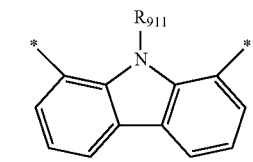

(XY-51)

(XY-52)
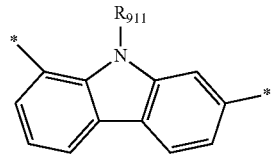

(XY-53)

(XY-54)
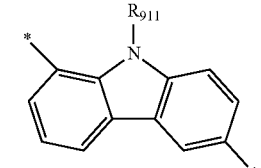

-continued (XY-55)
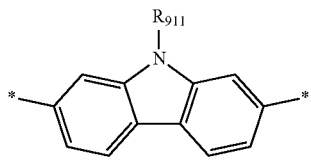

(XY-56)
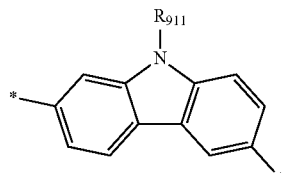

(XY-57)
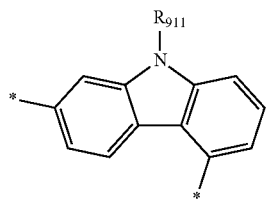

(XY-58)
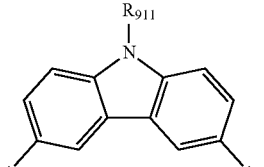

(XY-59)
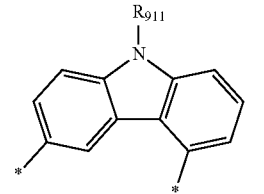

(XY-60)
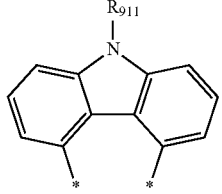

(XY-61)
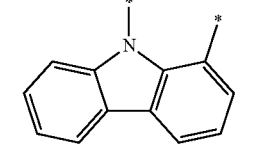

(XY-62)
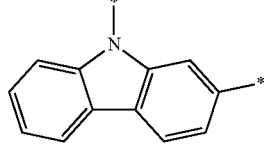

(XY-63)

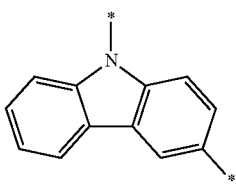

(XY-64)

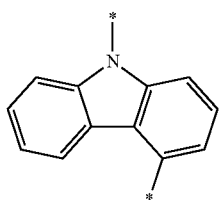

In the formulas (XY-50) to (XY-60), $R_{911}$ is a hydrogen atom or a substituent.

(XY-65)

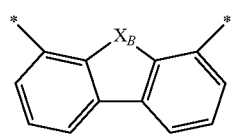

(XY-66)

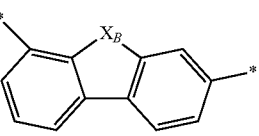

(XY-67)

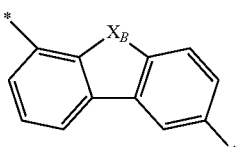

(XY-68)

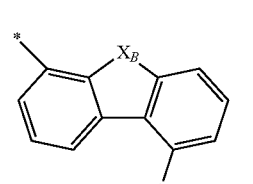

(XY-69)

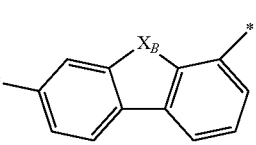

(XY-70)

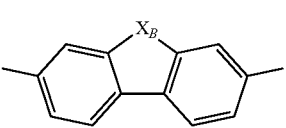

(XY-71)

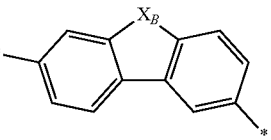

(XY-72)

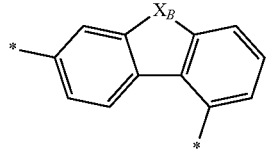

(XY-73)

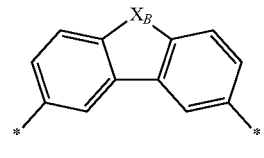

(XY-74)

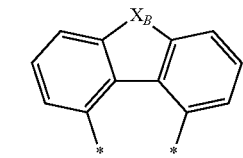

(XY-75)

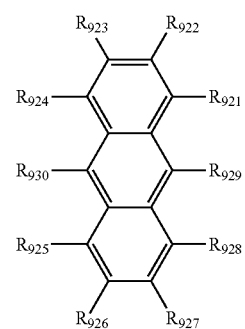

In the formulas (XY-65) to (XY-75), $X_B$ is an oxygen atom or a sulfur atom.

Herein, a case where "one or more sets of two or more groups adjacent to each other are bonded with each other to form a substituted or unsubstituted and saturated or unsaturated ring" will be described by taking, as an example, a case of an anthracene compound represented by the following formula (XY-80) in which a mother skeleton is an anthracene ring.

(XY-80)

For example, two adjacent to each other into one set when "one or more sets of two or more groups adjacent to each other are bonded with each other to form the ring" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ are bonded with each other to form a ring A, and simultaneously $R_{925}$ and $R_{926}$ are bonded with each other to form a ring B is represented by the following formula (XY-81).

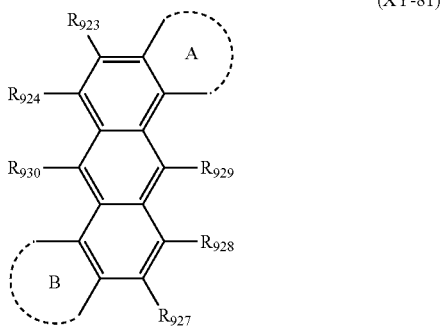

(XY-81)

A case where "two or more groups adjacent to each other" form a ring means that, for example, $R_{921}$ and $R_{922}$ are bonded with each other to form a ring A, and $R_{922}$ and $R_{923}$ are bonded with each other to form a ring C. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

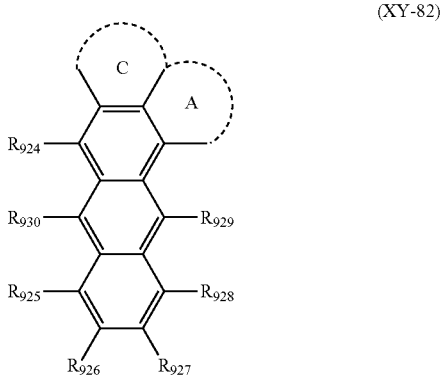

(XY-82)

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the carbon atoms of the anthracene mother skeleton that do not form the ring may be terminated with the hydrogen atom or the like, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

When the above-described "saturated or unsaturated ring" has a substituent, the substituent is as described above.

In one embodiment of the present specification, the substituent (hereinafter, referred to as an "arbitrary substituent" in several cases) in the case of the "substituted or unsubstituted" is a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms,
—Si($R_{901}$)($R_{902}$)($R_{903}$),
—O—($R_{904}$),
—S—($R_{905}$)
—N($R_{906}$)($R_{907}$)
wherein,
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms; and
when two or more of $R_{901}$ to $R_{907}$ exist, two or more of $R_{901}$ to $R_{907}$ may be the same with or different from each other,
a halogen atom, a cyano group, a nitro group,
an unsubstituted aryl group having 6 to 50 ring carbon atoms, and
an unsubstituted monovalent heterocyclic group having 5 to 50 ring atoms.

In one embodiment, the substituent in the case of "substituted or unsubstituted" is a group selected from the group consisting of
an alkyl group having 1 to 50 carbon atoms,
an aryl group having 6 to 50 ring carbon atoms, and
a monovalent heterocyclic group having 5 to 50 ring atoms.

In one embodiment, the substituent in the case of "substituted or unsubstituted" is a group selected from the group consisting of
an alkyl group having 1 to 18 carbon atoms,
an aryl group having 6 to 18 ring carbon atoms, and
a monovalent heterocyclic group having 5 to 18 ring atoms.

Specific examples of each group of the arbitrary substituent described above are as described above.

Herein, unless otherwise specified, the saturated or unsaturated ring (preferably substituted or unsubstituted and saturated or unsaturated five-membered or six-membered ring, more preferably a benzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[Compound]

The compound according to one aspect of the invention has a structure represented by the following formulas (a) and (b).

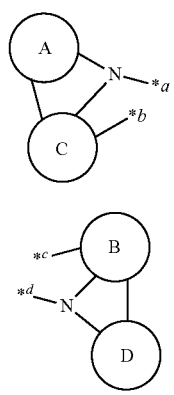

In the formulas (a) and (b), a ring A, a ring B, a ring C and a ring D are independently a substituted or unsubstituted aromatic hydrocarbon ring having 6 to 50 ring carbon atoms, or a substituted or unsubstituted heterocyclic ring having 5 to 50 ring atoms.

Two or more of the ring A, the ring B, the ring C and the ring D are a heterocyclic ring.

Then, each of sites *a, *b, *c and *d in the formula (a) and the formula (b) represents a position of an atom, and the atoms located in the sites *a, *b, *c and *d form one substituted or unsubstituted and saturated or unsaturated six-membered ring including four atoms thereof.

The "aromatic hydrocarbon ring" of the ring A, the ring B, the ring C and the ring D has the same structure as the ring in which the hydrogen atom is introduced into the "aryl group" described above. Specific examples of the "substituted or unsubstituted aromatic hydrocarbon ring having 6 to 50 ring carbon atoms" include the ring in which the hydrogen atom is introduced into the "aryl group" described in the specific example group G1.

The "heterocyclic ring" of the ring A, the ring B, the ring C and the ring D has the same structure as the ring in which the hydrogen atom is introduced into the "heterocyclic group" described above. Specific examples of the "substituted or unsubstituted heterocyclic ring having 5 to 50 ring atoms" include the ring in which the hydrogen atom is introduced into the "heterocyclic group" described in the specific example group G 2.

Specific examples of one substituted or unsubstituted and saturated or unsaturated six-membered ring having the sites *a, *b, *c and *d include a six-membered carbon ring such as benzene, cyclohexane, cyclohexene and cyclohexadiene; and a six-membered heterocyclic ring such as pyridine, 1,4-dihydropyridine, piperidine, pyrazine, 1,4-dihydropyrazine, piperazine, diazine, 1,4-dioxane, dioxin, morpholine and oxazine.

In one embodiment, the compound according to the present aspect has a structure represented by the following formulas (a), (b) and (c).

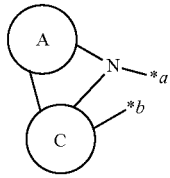

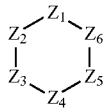

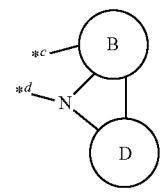

In the formula, a ring A, a ring B, a ring C and a ring D are as defined in the formulas (a) and (b).

In the formula (c), $Z_1$ to $Z_6$ independently is a carbon atom or a hetero atom forming a saturated or unsaturated six-membered ring.

Two adjacent to each other among $Z_1$ to $Z_6$ are bonded with the sites *a and *b in the formula (a) to form a fused ring.

Two adjacent to each other among $Z_1$ to $Z_6$ that are not bonded with the sites *a and *b in the formula (a) are bonded with sites *c and *d in the formula (b) to form a fused ring.

$Z_1$ to $Z_6$ that are not bonded with the sites *a, *b, *c and *d are independently $C(R_a)$, $C(R_b)(R_c)$, a hetero atom or a hetero atom bonded with a hydrogen atom or a substituent.

When two of $R_a$, $R_b$ and $R_c$ exist, respectively, two of $R_a$, $R_b$ and $R_c$ may be the same with or different from each other.

When the number of the substituents of the hetero atom is two or more, two or more substituents may be the same with or different from each other.

$R_a$, $R_b$, $R_c$ and the substituent of the hetero atom are bonded with one or more of the ring A to the ring D to form a substituted or unsubstituted and saturated or unsaturated ring, or do not form the ring.

$R_a$, $R_b$, and $R_c$ that do not form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms.

$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms. When two or more of $R_{901}$ to $R_{907}$ exist, two or more of $R_{901}$ to $R_{907}$ may be the same with or different from each other.

Specific examples of the saturated or unsaturated six-membered ring represented by the formula (c) include a six-membered carbon ring such as benzene, cyclohexane, cyclohexene and cyclohexadiene; and a six-membered heterocyclic ring such as pyridine, 1,4-dihydropyridine, piperidine, pyrazine, 1,4-dihydropyrazine, piperazine, diazine, 1,4-dioxane, dioxin, morpholine and oxazine.

When $Z_1$ to $Z_6$ in the formula (c) are a hetero atom bonded with a substituent, specific examples of the substituent include to the ones same as the substituent in the case of "substituted or unsubstituted" in the section of [Definition] in the present specification.

In one embodiment, the formula (c) is a structure represented by the following formula (c1).

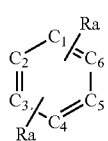
(c1)

In the formula (c1),
$C_1$ to $C_6$ are a carbon atom, and two adjacent to each other among $C_1$ to $C_6$ are bonded with sites *a and *b in the formula (a) to form a fused ring.

Two adjacent to each other among $C_1$ to $C_6$ that are not bonded with the sites *a and *b in the formula (a) are bonded with sites *c and *d in the formula (b) to form a fused ring.

$C_1$ to $C_6$ that are not bonded with the sites *a, *b, *c and *d are independently bonded with $R_a$. Two of $R_a$ may be the same with or different from each other.

$R_a$ is as defined in the formula (c).

The structure represented by the formula (c1) is a structure in which two of $R_a$ are bonded with a benzene ring.

In one embodiment, the compound having a structure represented by the formulas (a), (b) and (c) is a compound represented by the following formula (1-1).

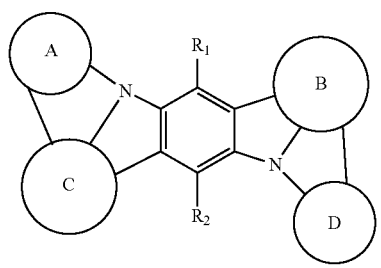
(1-1)

In the formula (1-1), a ring A, a ring B, a ring C and a ring D are as defined in the formulas (a) and (b).

$R_1$ is bonded with either or both of the ring A and the ring B to form a substituted or unsubstituted and saturated or unsaturated ring, or does not form the ring.

$R_2$ is bonded with either or both of the ring C and the ring D to form a substituted or unsubstituted and saturated or unsaturated ring, or does not form the ring.

$R_1$ and $R_2$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or
a substituted or unsubstituted monovalent heterocyclic group having 5 to 50 ring atoms.

$R_{901}$ to $R_{907}$ are as defined in the formula (c).

The ring A, the ring B, the ring C and the ring D are a ring fused with a fused bicyclic structure containing the nitrogen atoms on both sides of the benzene ring in a center of the formula (1-1) (a substituted or unsubstituted aromatic hydrocarbon ring having 6 to 50 ring carbon atoms, or a substituted or unsubstituted heterocyclic ring having 5 to 50 ring atoms).

$R_1$ may be bonded with either or both of the ring A and the ring B to form a substituted or unsubstituted and saturated or unsaturated ring. Similarly, $R_2$ may be bonded with either or both of the ring C and the ring D to form a substituted or unsubstituted and saturated or unsaturated ring.

The heterocyclic ring in this case contains the nitrogen atom on the fused bicyclic structure in the formula (1-1). The heterocyclic ring in this case may contain a hetero atom other than the nitrogen atom. An expression "$R_1$ and $R_2$ are bonded with the ring A, the ring B, the ring C and the ring D" specifically means that the atoms forming the ring A, the ring B, the ring C and the ring D are bonded with the atoms forming $R_1$ and $R_2$. For example, $R_1$ may be bonded with the ring A to form a nitrogen-containing heterocyclic ring in which the ring containing $R_1$ is fused with the ring A. Specific examples of the nitrogen-containing heterocyclic ring include a compound corresponding to two heterocyclic rings containing nitrogen in the specific example group G2.

In one embodiment, the compound represented by the formula (1-1) is a compound represented by the following formula (1-2).

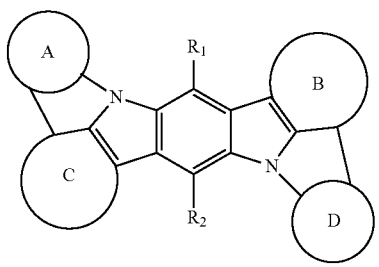
(1-2)

In the formula (1-2), $R_1$, $R_2$, a ring A, a ring B, a ring C and a ring D are as defined in the formula (1-1).

The ring B and the ring C in the compound of the formula (1-2) contain, as the ring atoms, three carbon atoms on the fused bicyclic structure containing the nitrogen atom described above.

In one embodiment, the compound represented by the formula (1-1) is a compound represented by the following formula (1-3).

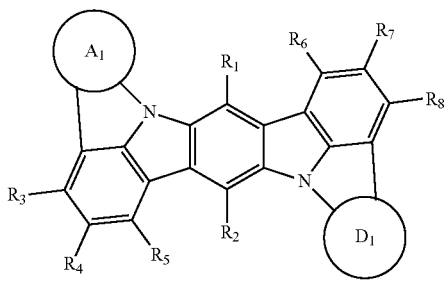

(1-3)

In the formula (1-3), a ring $A_1$ and a ring $D_1$ are a substituted or unsubstituted heterocyclic ring having 5 to 50 ring atoms.

One or more sets of two or more adjacent to each other among $R_1$, $R_2$, $R_3$ to $R_8$, the ring $A_1$ and the ring $D_1$ are bonded with each other to form a substituted or unsubstituted and saturated or unsaturated ring, or do not form the ring.

$R_1$, $R_2$ and $R_3$ to $R_8$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{916}$)($R_{907}$),
a substituted or unsubstituted aryl group having 6 to 50 ring carbon atoms, or
a substituted or unsubstituted monovalent heterocyclic group having 5 to 50 ring atoms.

$R_{901}$ to $R_{907}$ are as defined in the formula (c).

In the formula (1-3), the ring B and the ring C in the formula (1-1) are formed into a benzene ring structure. The ring $A_1$ and the ring $D_1$ in the formula (1-3) correspond to the ring A and the ring D in the formula (1-1), respectively. One or more sets of two or more adjacent to each other among $R_1$, $R_2$, $R_3$ to $R_8$, the ring $A_1$ and the ring $D_1$ may be bonded with each other to form a substituted or unsubstituted and saturated or unsaturated ring. For example, $R_3$ and $R_4$ are bonded to form a structure in which a benzene ring, an indole ring, a pyrrole ring, a benzofuran ring, a benzothiophene ring, or the like is fused with the six-membered ring to which $R_3$ and $R_4$ are bonded.

In one embodiment, the compound represented by the formula (1-1) is a compound represented by the following formula (1-4).

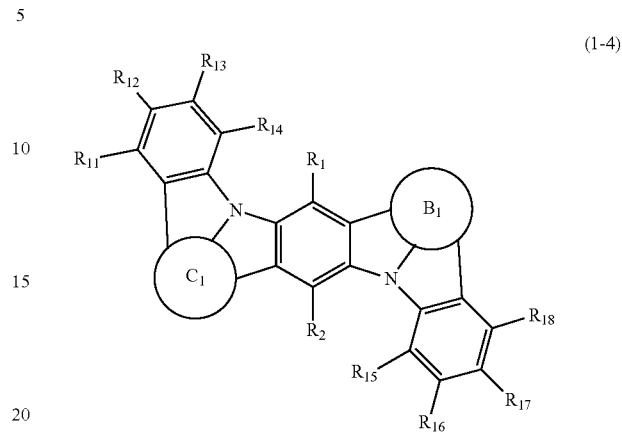

(1-4)

In the formula (1-4), a ring $B_1$ and a ring $C_1$ are a substituted or unsubstituted heterocyclic ring having 5 to 50 ring atoms.

One or more sets of two or more adjacent to each other among $R_1$, $R_2$, $R_{11}$ to $R_{18}$, the ring $B_1$ and the ring $C_1$ are bonded with each other to form a substituted or unsubstituted and saturated or unsaturated ring, or do not form the ring.

$R_1$, $R_2$ and $R_{11}$ to $R_{18}$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or
a substituted or unsubstituted monovalent heterocyclic group having 5 to 50 ring atoms.

$R_{901}$ to $R_{907}$ are as defined in the formula (c).

In the formula (1-4), the ring A and the ring D in the formula (1-1) are formed into a benzene ring structure. The ring $B_1$ and the ring $C_1$ in the formula (1-3) correspond to the ring B and the ring C in the formula (1-1), respectively. One or more sets of two or more adjacent to each other among $R_1$, $R_2$, $R_{11}$ to $R_{18}$, the ring $B_1$ and the ring $C_1$ may be bonded with each other to form a substituted or unsubstituted and saturated or unsaturated ring. For example, $R_{11}$ and $R_{12}$ are bonded to form a structure in which a benzene ring, an indole ring, a pyrrole ring, a benzofuran ring, a benzothiophene ring or the like is fused with the six-membered ring to which $R_{11}$ and $R_{12}$ are bonded.

In one embodiment, in the compounds represented by the formulas (1-1) to (1-4), the hetero atom contained in the substituted or unsubstituted heterocyclic ring having 5 to 50 ring atoms, represented by the ring A to the ring D and the ring $A_1$ to the ring $D_1$, is an atom selected from O, S and N.

In one embodiment, one or more sets of two or more adjacent to each other among $R_1$, $R_2$, $R_3$ to $R_8$, the ring $A_1$ and the ring $D_1$ in the formula (1-3) do not form a substituted or unsubstituted and saturated or unsaturated ring.

In one embodiment, one or more sets of two or more adjacent to each other among $R_1$, $R_2$, $R_{11}$ to $R_{18}$, the ring $B_1$ and the ring $C_1$ in the formula (1-4) do not form a substituted or unsubstituted and saturated or unsaturated ring.

In one embodiment, the substituted or unsubstituted heterocyclic ring having 5 to 50 ring atoms represented by the ring A to the ring D and the ring $A_1$ to the ring $D_1$ in the compounds represented by the formulas (1-1) to (1-4) independently has a structure selected from dibenzofuran, benzimidazole, indolocarbazole, pyridine, pyrazine, pyridazine, pyrimidine, triazine, quinoline, isoquinoline, quinazoline, cinnoline, phthalazine, quinoxaline, pyrrole, indole, pyrrolo[3,2,1-jk]carbazole, furan, benzofuran, thiophene, benzothiophene, pyrazole, imidazole, benzimidazole, triazole, oxazole, benzoxazole, thiazole, benzothiazole, isothiazole, benzisothiazole, thiadiazole, isoxazol, benzisoxazole, pyrrolidine, piperidine, piperazine, imidazolidine, carbazole, indro[3,2,1-jk]carbazole and dibenzothiophene, or a heterocyclic structure containing the structure thereof as a partial structure.

In one embodiment, the compound represented by the formula (1-3) is a compound represented by the following formula (1-5).

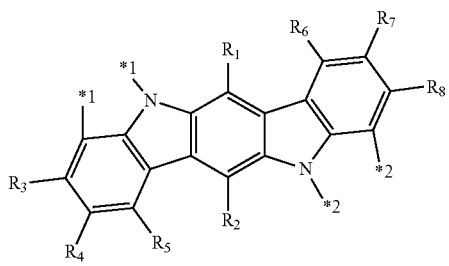

(1-5)

In the formula (1-5), $R_1$, $R_2$ and $R_3$ to $R_8$ are as defined in the formula (1-3).

Tow of *1 are fused with a group represented by the following formula (1A) to form a nitrogen atom-containing five-membered ring.

Two of *2 are fused with a group represented by the following formula (1A), which is different from the group bonded with the two of *1, to form a nitrogen atom-containing five-membered ring.

Two groups represented by the formula (1A) may be the same with or different from each other.

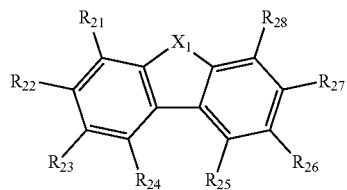

(1A)

In the formula (1A), one set selected from $R_{21}$ and $R_{22}$, $R_{22}$ and $R_{23}$, $R_{23}$ and $R_{24}$, $R_{25}$ and $R_{26}$, $R_{26}$ and $R_{27}$, and $R_{27}$ and $R_{28}$ is bonded with the two of *1 or the two of *2 in the formula (1-5).

One or more sets of two or more adjacent to each other among $R_{21}$ to $R_{28}$ that are not bonded with the two of *1 or the two of *2 in the formula (1-5) are bonded with each other to from a substituted or unsubstituted and saturated or unsaturated ring, or do not form the ring.

$R_{21}$ to $R_{28}$ that are neither bonded with the two of *1 or the two of *2 in the formula (1-5), nor form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms.

$R_{901}$ to $R_{907}$ are as defined in the formula (c).

$X_1$ is selected from O, S and N($R_{35}$), and two of $X_1$ may be the same with or different from each other.

$R_{35}$ is bonded with either or both of $R_{21}$ and $R_{28}$ to form a substituted or unsubstituted and saturated or unsaturated ring, or does not form the ring.

$R_{35}$ that does not form the ring is a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

In the compound represented by the formula (1-5), examples of a fused form of the group represented by the formula (1A) are shown in the following formulas (1-5-1) to (1-5-6).

(1-5-1)
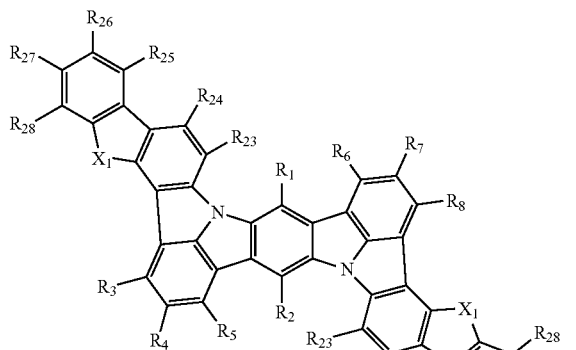
(1-5-2)
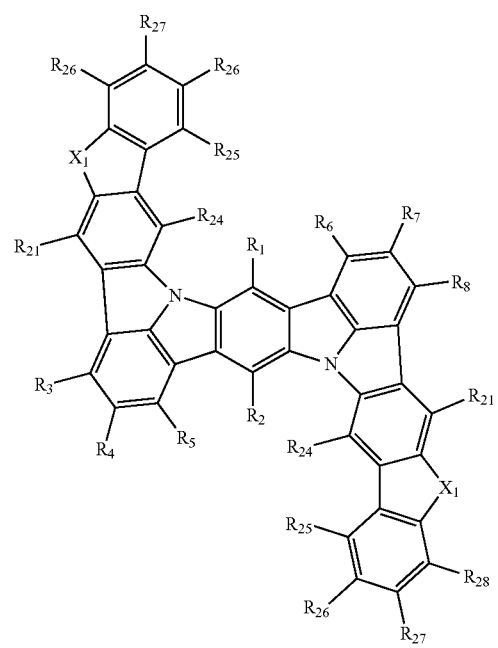
(1-5-3)
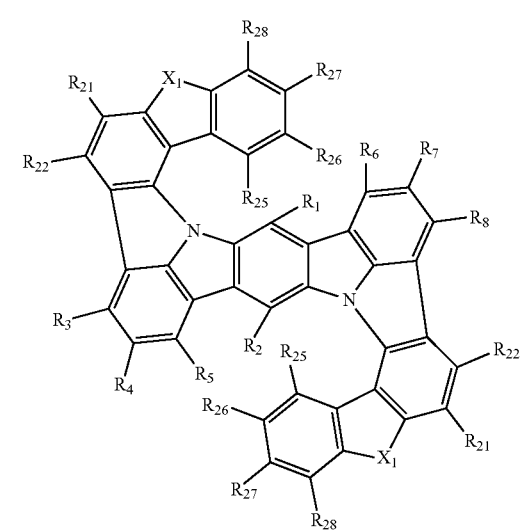
(1-5-4)
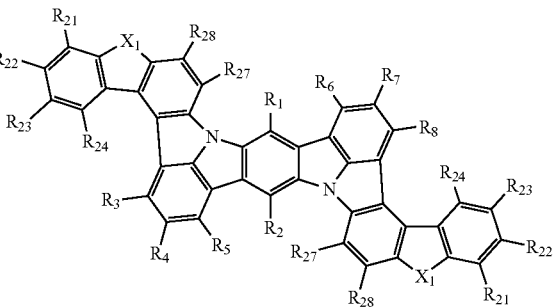
(1-5-5)
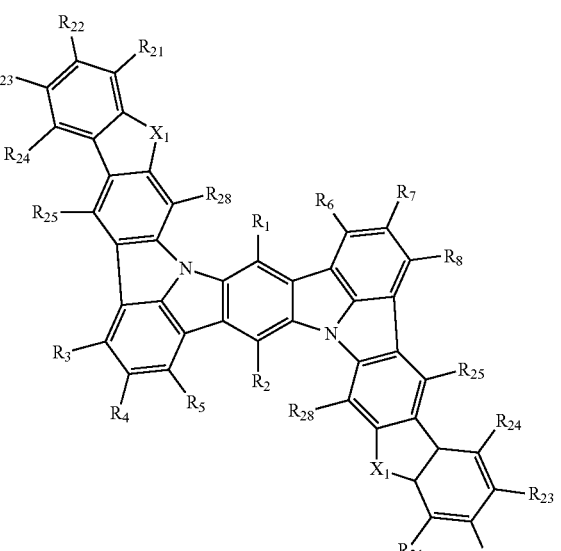
(1-5-6)
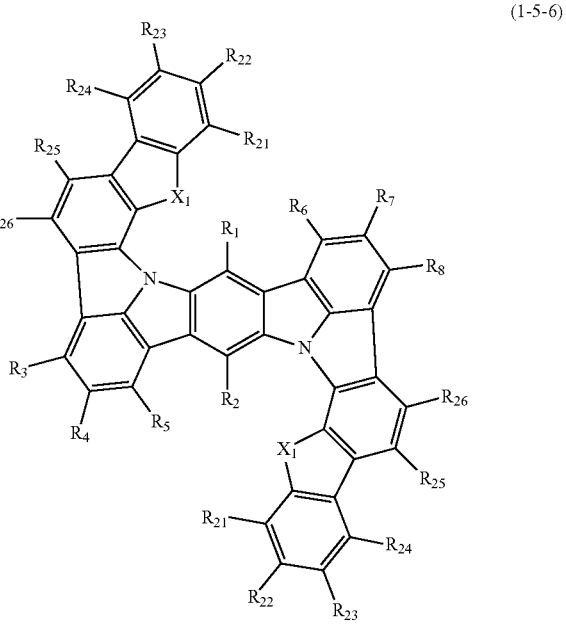
In the formulas (1-5-1) to (1-5-6), $X_1$, $R_1$, $R_2$, $R_3$ to $R_8$ and $R_{21}$ to $R_{28}$ are as defined in the formula (1-5).
Between two groups represented by the formula (1A) in the formula (1-5-1), $R_{21}$ and $R_{22}$ in one left group are bonded with the two of *1 in the formula (1-5), and $R_{21}$ and $R_{22}$ in the other (right) group are bonded with the two of *2 in the formula (1-5).

Between two groups represented by the formula (1A) in the formula (1-5-2), $R_{22}$ and $R_{23}$ in one left group, are bonded with the two of *1 in the formula (1-5), and $R_{22}$ and $R_{23}$ in the other group are bonded with the two of *2 in the formula (1-5).

Between two groups represented by the formula (1A) in the formula (1-5-3), $R_{23}$ and $R_{24}$ in one left group are bonded with the two of *1 in the formula (1-5), and $R_{22}$ and $R_{23}$ in the other group are bonded with the two of *2 in the formula (1-5).

Between two groups represented by the formula (1A) in the formula (1-5-4), $R_{25}$ and $R_{26}$ in one group on left side are bonded with the two of *1 in the formula (1-5), and $R_{25}$ and $R_{26}$ in the other group are bonded with the two of *2 in the formula (1-5).

Between two groups represented by the formula (1A) in the formula (1-5-5), $R_{26}$ and $R_{27}$ in one left group are bonded with the two of *1 in the formula (1-5), and $R_{26}$ and $R_{27}$ in the other group are bonded with the two of *2 in the formula (1-5).

Between two groups represented by the formula (1A) in the formula (1-5-6), $R_{27}$ and $R_{28}$ in one left group are bonded with the two of *1 in the formula (1-5), and $R_{27}$ and $R_{28}$ in the other group are bonded with the two of *2 in the formula (1-5).

It should be noted that, in the above-described formulas, only examples in which two groups represented by the formula (1A) are bonded with the two of in the formula (1-5) in the same bonding positions are shown, but bonding is not limited thereto. Since synthesis is easy, the compounds represented by the formulas (1-5-1) to (1-5-6) are preferable.

In one embodiment, the compound represented by the formula (1-4) is a compound represented by the following formula (1-6).

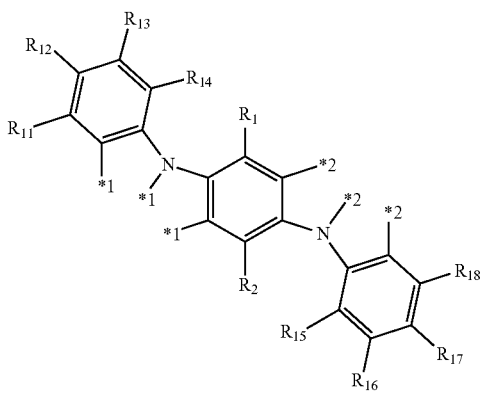

(1-6)

In the formula (1-6), $R_1$, $R_2$ and $R_{11}$ to $R_{18}$ are as defined in the formula (1-4).

Three of *1 are fused with a group represented by the following formula (1A) to form a nitrogen-containing fused ring.

Three of *2 are fused with a group represented by the following formula (1A), which is different from the group bonded with the two of *1, to form a nitrogen-containing fused ring.

Two groups represented by the formula (1A) may be the same with or different from each other.

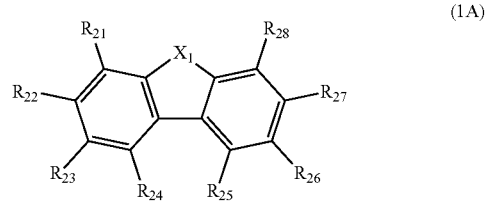

(1A)

In the formula (1A), one set selected from $R_{21}$ to $R_{23}$, $R_{22}$ to $R_{24}$, $R_{25}$ to $R_{27}$ and $R_{26}$ to $R_{28}$ is bonded with the three of *1 or the three of *2 in the formula (1-6).

One or more sets of two or more adjacent to each other among $R_{21}$ to $R_{28}$ that are not bonded with the three of *1 and the three of *2 in the formula (1-6) are bonded with each other to form a substituted or unsubstituted and saturated or unsaturated ring, or do not form the ring.

$R_{21}$ to $R_{28}$ that are neither bonded with the three of *1 and the three of *2 in the formula (1-6) nor form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms.

$R_{901}$ to $R_{907}$ are as defined in the formula (c).

$X_1$ is selected from O, S and N($R_{35}$), and two of $X_1$ may be the same with or different from each other.

$R_{35}$ is bonded with either or both of $R_{21}$ and $R_{28}$ to form a substituted or unsubstituted and saturated or unsaturated ring, or does not form the ring.

$R_{35}$ that does not form the ring is a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

In the compound represented by the formula (1-6), examples of a fused form of the group represented by the formula (1A) are shown in the following formulas (1-6-1) to (1-6-4).

(1-6-1)

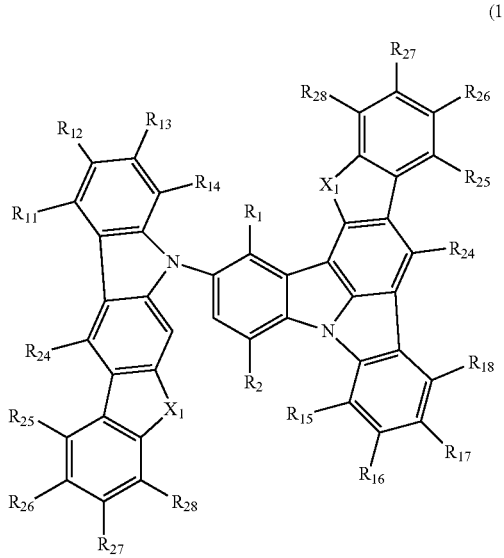

(1-6-2)

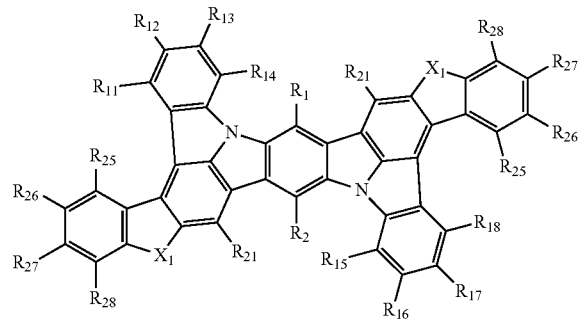

(1-6-3)

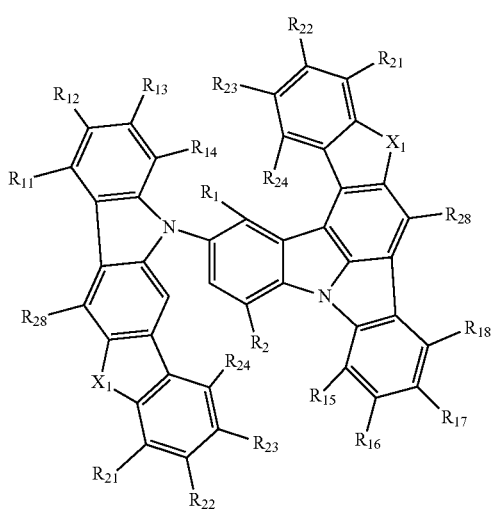

(1-6-4)

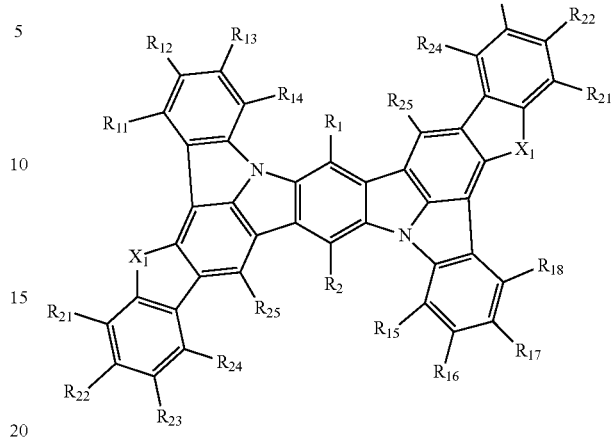

In the formulas (1-6-1) to (1-6-4), $X_1$, $R_1$, $R_2$, $R_{11}$ to $R_{18}$ and $R_{21}$ to $R_{28}$ are as defined in the formula (1-6).

Between two groups represented by the formula (1A) in the formula (1-6-1), $R_{21}$, $R_{22}$ and $R_{23}$ in one left group are bonded with the three of *1 in the formula (1-6), and $R_{21}$, $R_{22}$ and $R_{23}$ in the other (right) group are bonded with the three of *2 in the formula (1-6).

Between two groups represented by the formula (1A) in the formula (1-6-2), $R_{22}$, $R_{23}$ and $R_{24}$ in one left group are bonded with the three of *1 in the formula (1-6), and $R_{22}$, $R_{23}$ and $R_{24}$ in the other group are bonded with the three of *2 in the formula (1-6).

Between two groups represented by the formula (1A) in the formula (1-6-3), $R_{25}$, $R_{26}$ and $R_{27}$ in one left group are bonded with the three of *1 in the formula (1-6), and $R_{25}$, $R_{26}$ and $R_{27}$ are bonded with the three of *2 in the formula (1-6) in the other group.

Between two groups represented by the formula (1A) in the formula (1-6-4), $R_{26}$, $R_{27}$ and $R_{28}$ in one left group are bonded with the three of *1 in the formula (1-6), and $R_{26}$, $R_{27}$ and $R_{28}$ in the other group are bonded with the three of *2 in the formula (1-6).

It should be noted that, in the above-described formulas, only examples in which two groups represented by the formula (1A) are bonded with the three of in the formula (1-6) in the same bonding positions are shown, but bonding positions are not limited thereto. Since the synthesis is easy, the compounds represented by the formulas (1-6-1) to (1-6-4) are preferable.

Each substituent in the formulas (1-1) to (1-6), (1-5-1) to (1-5-6), (1-6-1) to (1-6-4) and (1-A), and a detail of the substituent in the case of "substituted or unsubstituted" are as described in the section of [Definition] in the present specification.

Known alternative reaction or raw materials according to an intended product are used in copying the synthesis in Examples described later, whereby the compound represented by the formula (1-1) can be synthesized.

Hereinafter, specific examples of the compound represented by the formula (1-1) will be described, but are illustrative only, and the compound represented by the formula (1-1) is not limited to the following specific examples.

39 40
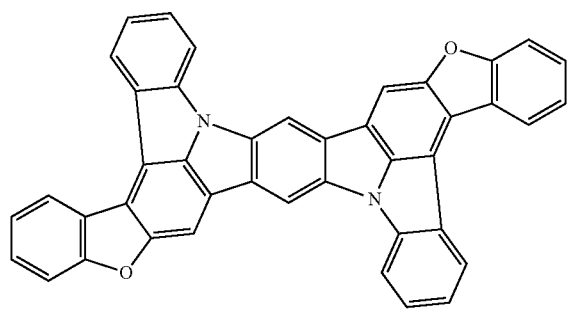
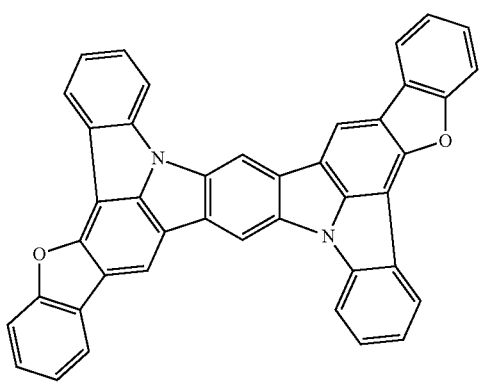
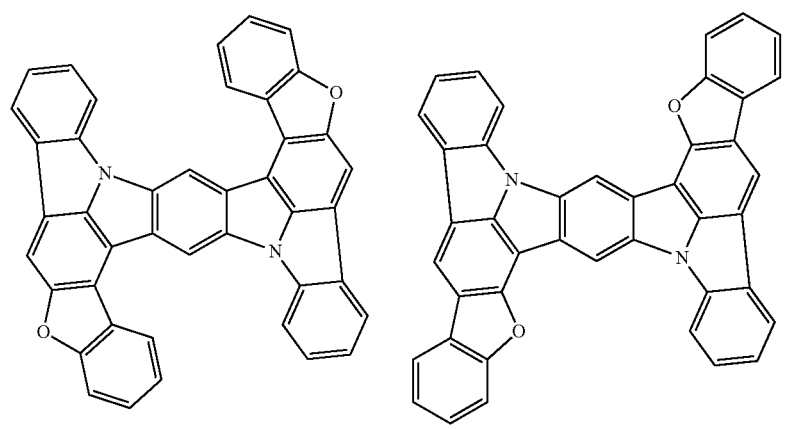
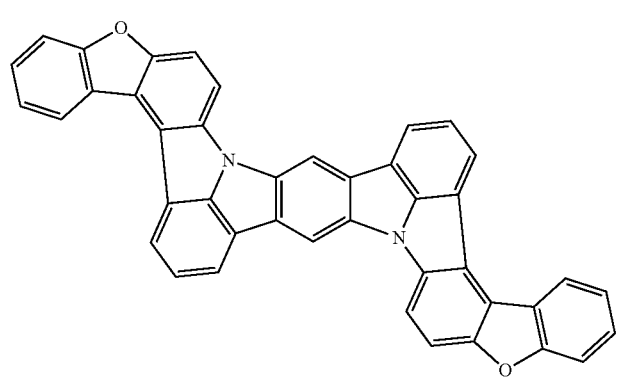
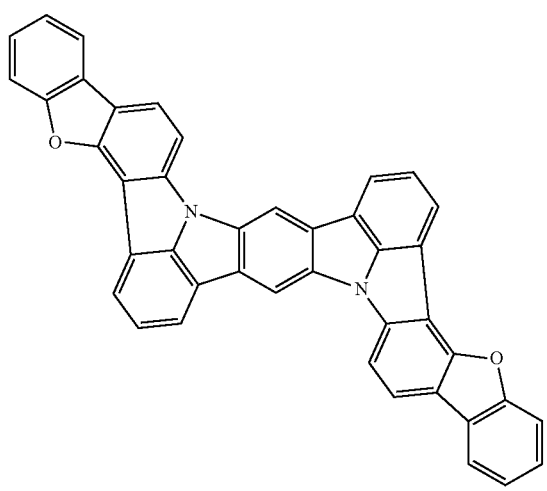

-continued
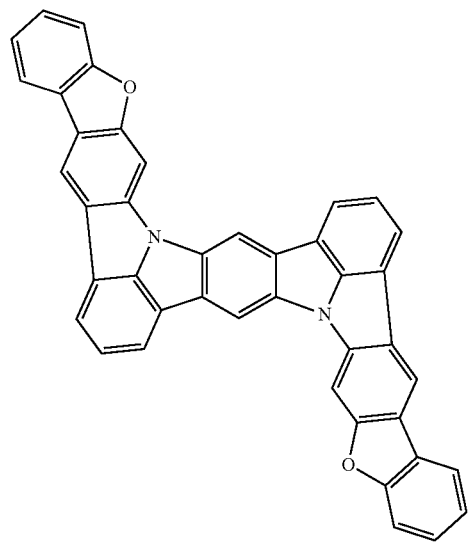
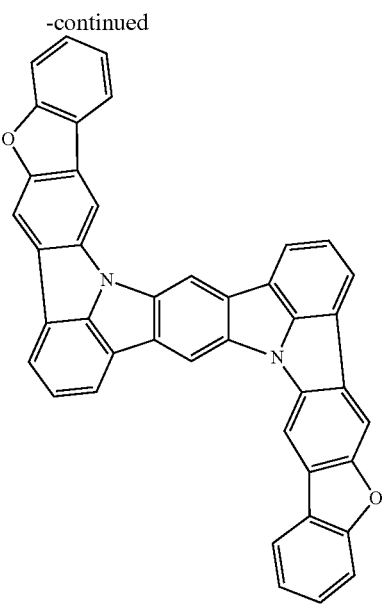
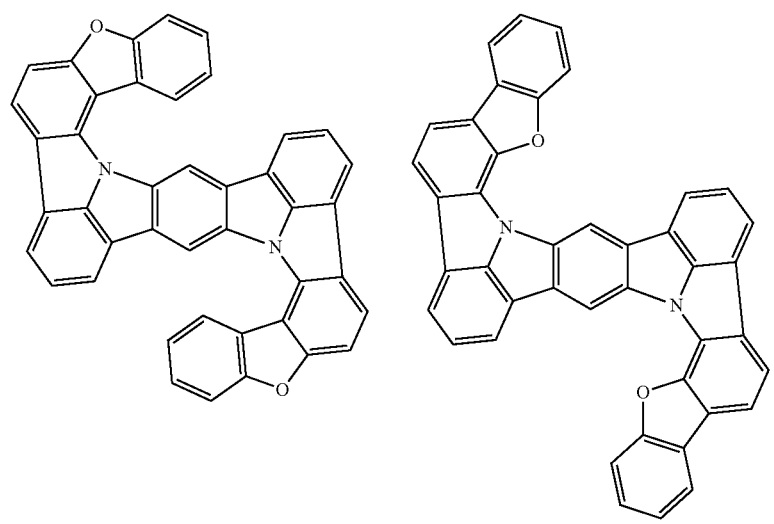
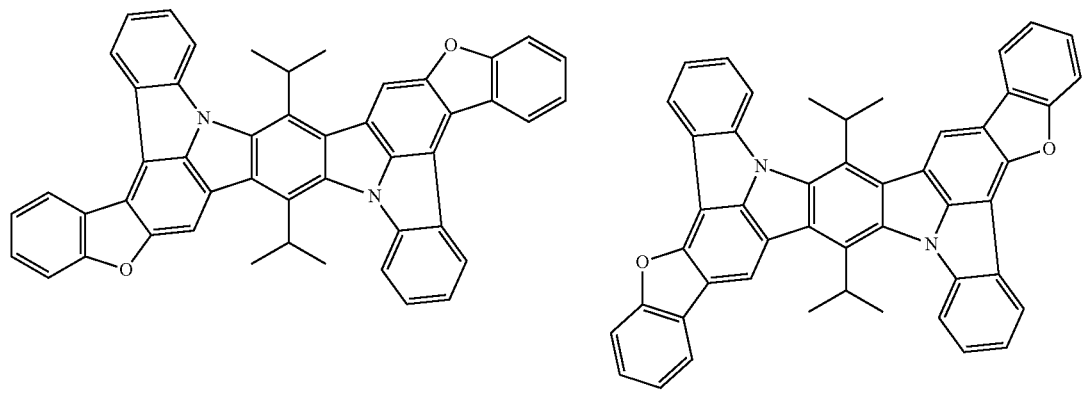

-continued
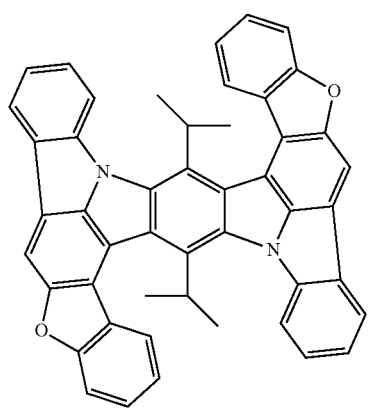
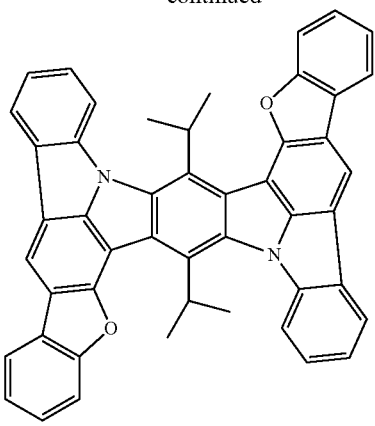
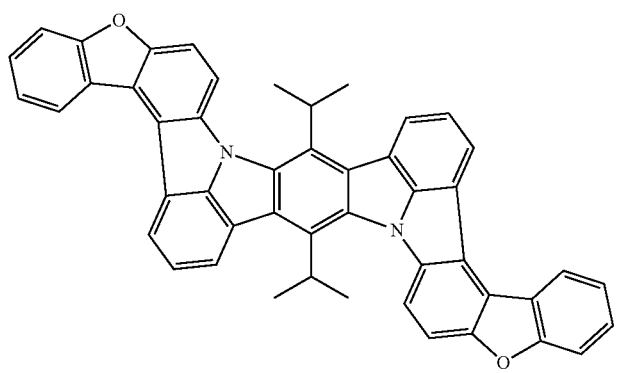
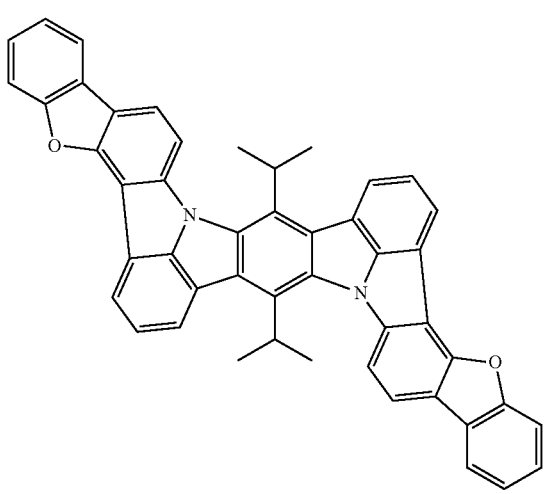
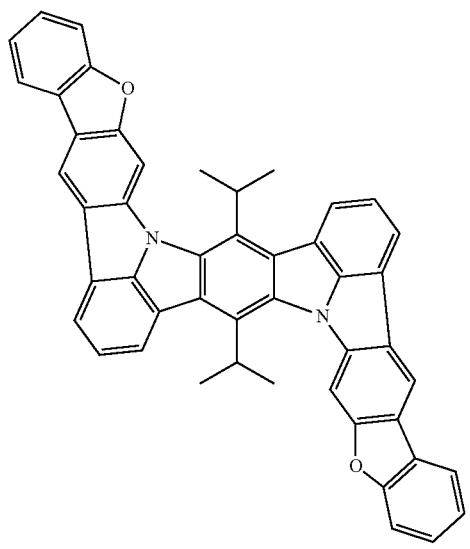
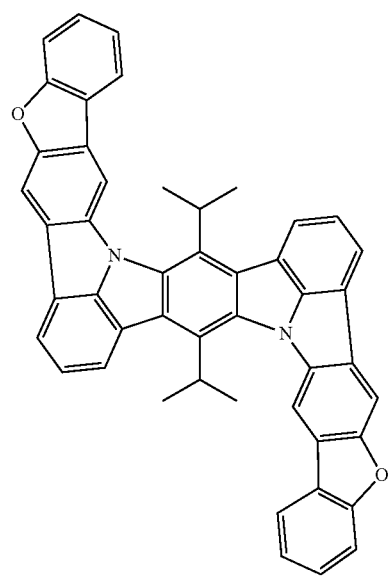

-continued
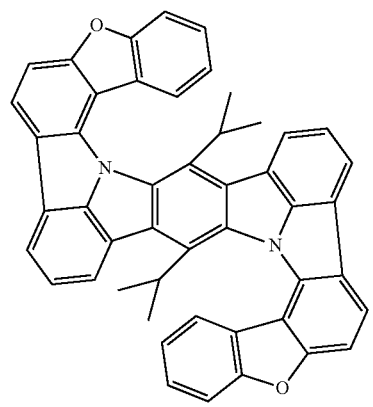 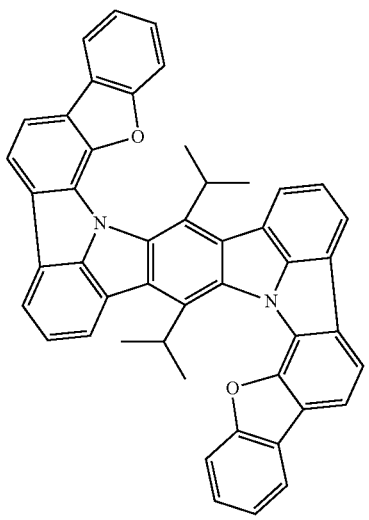
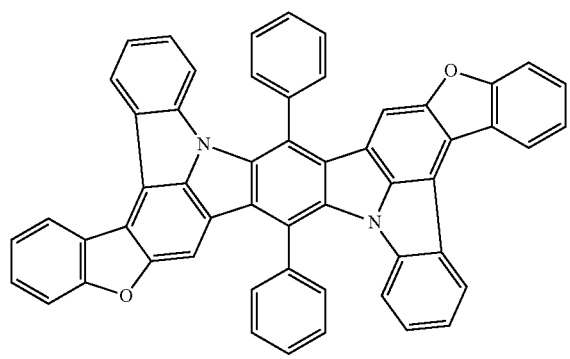 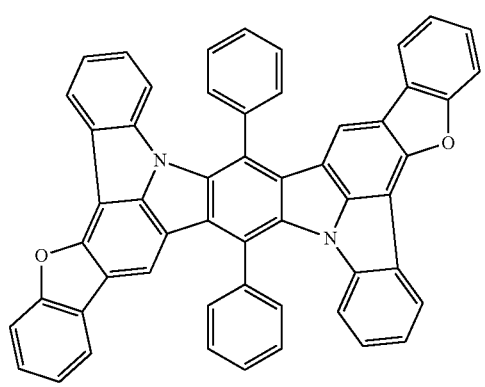
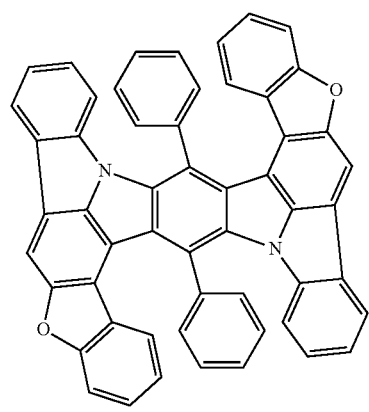 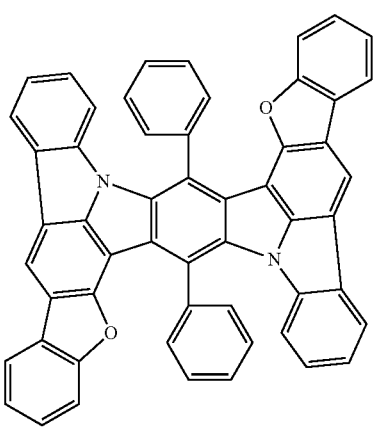

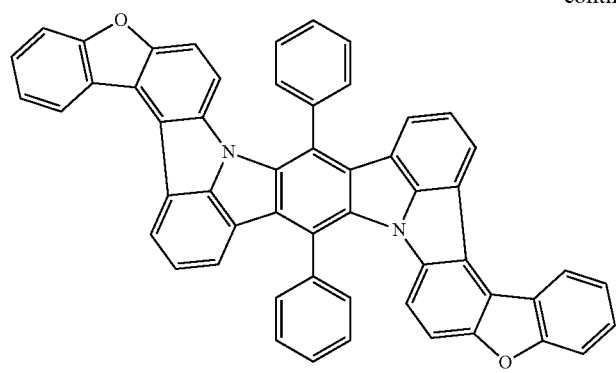
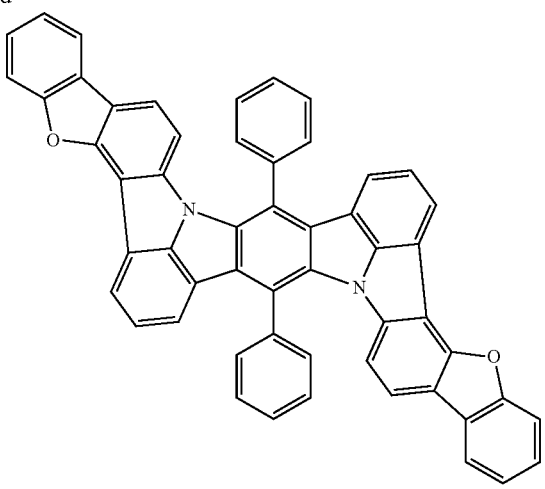
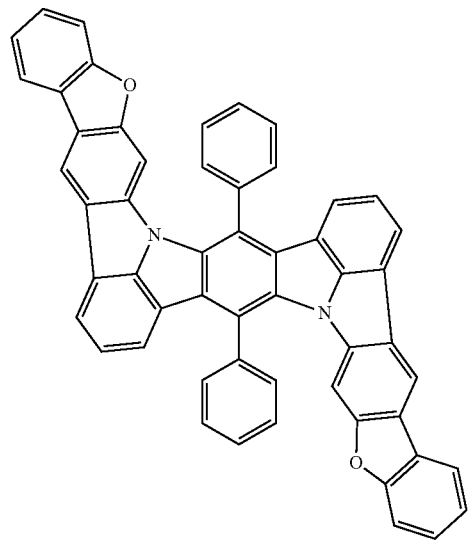
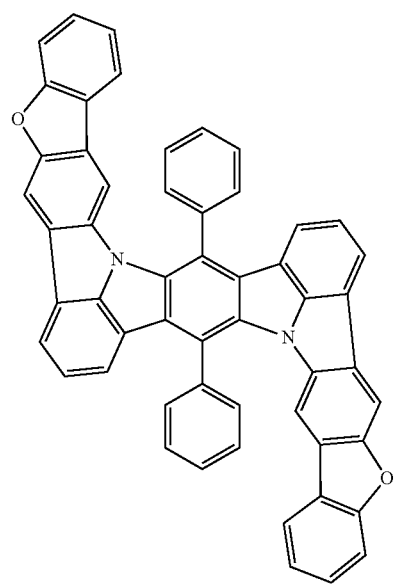
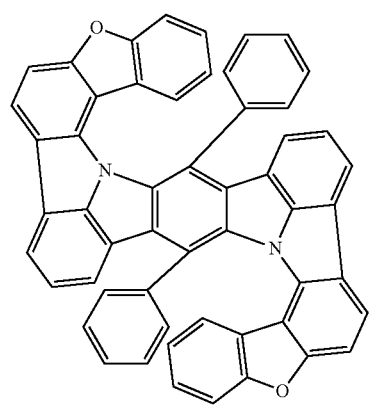
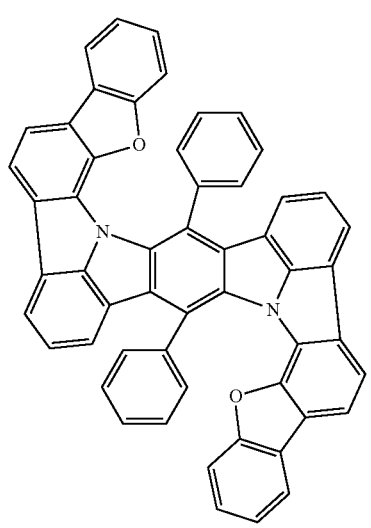

-continued
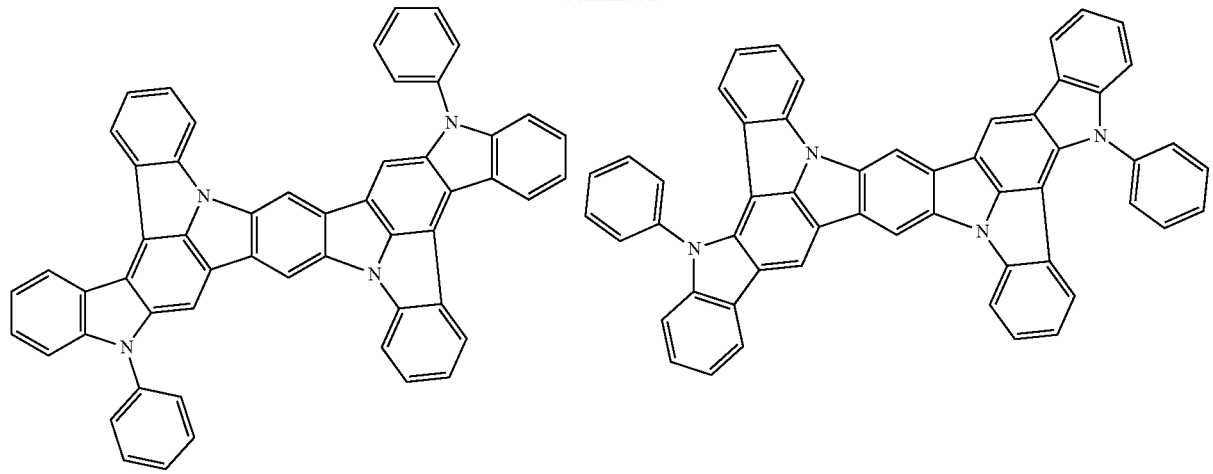
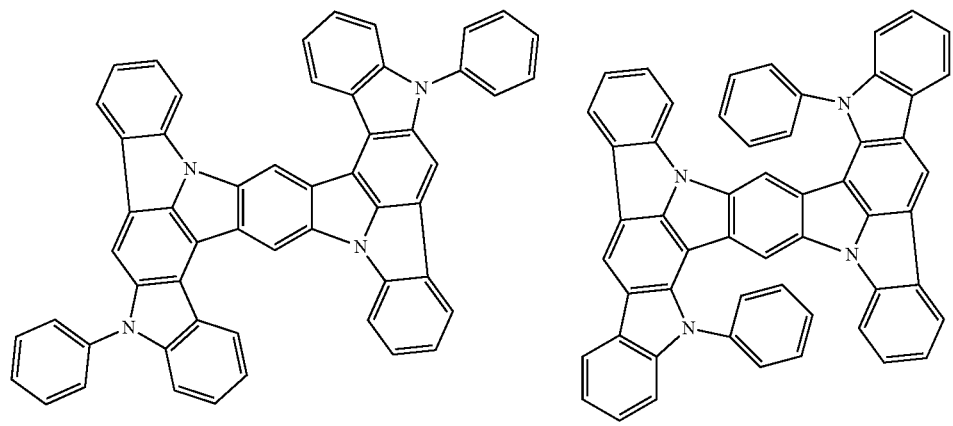
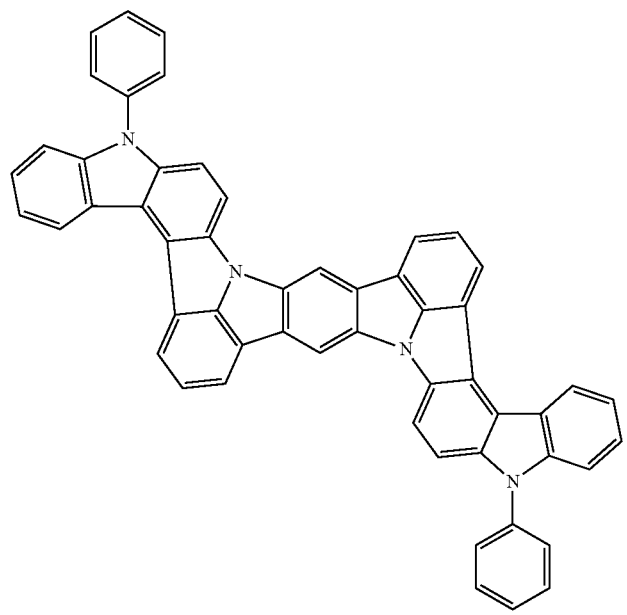

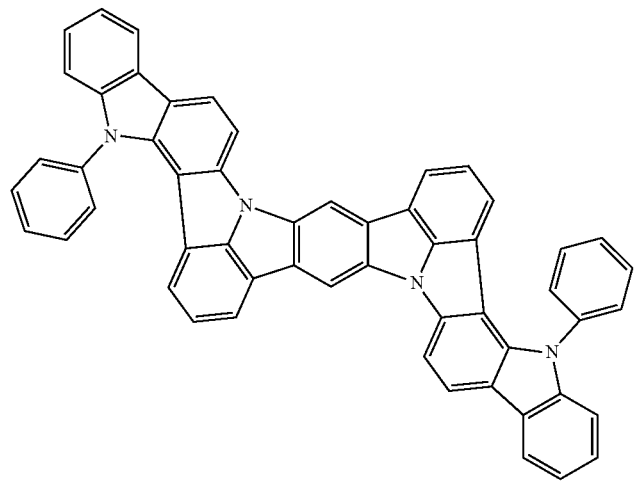
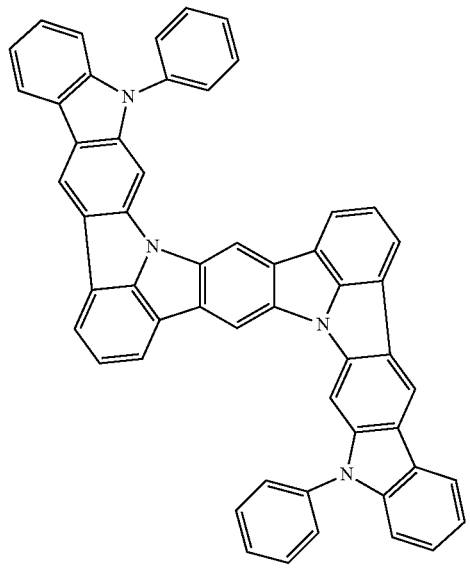
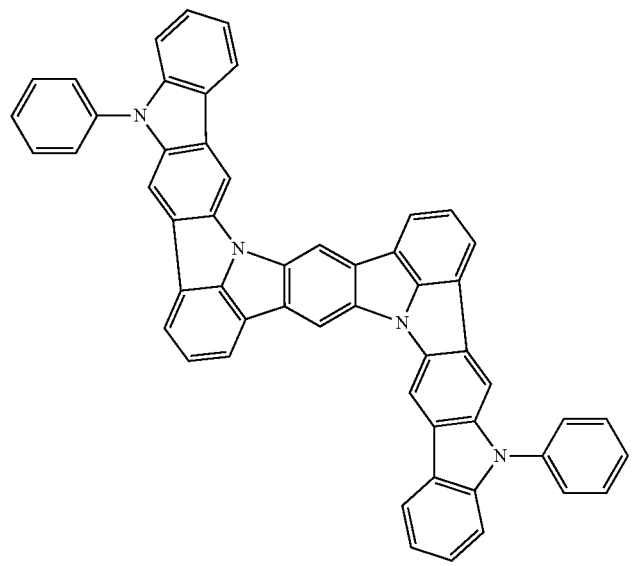
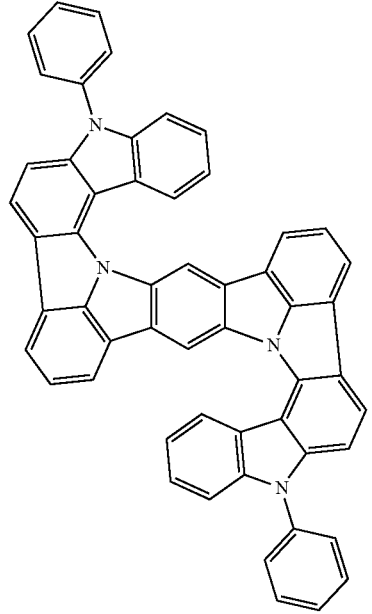
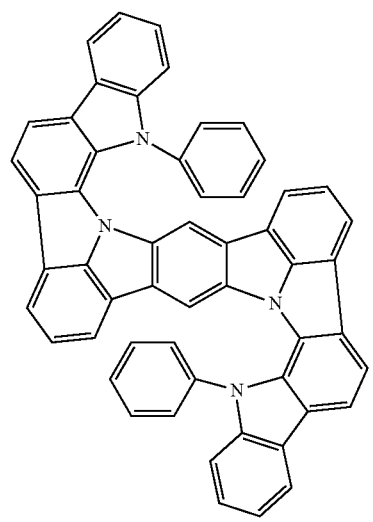
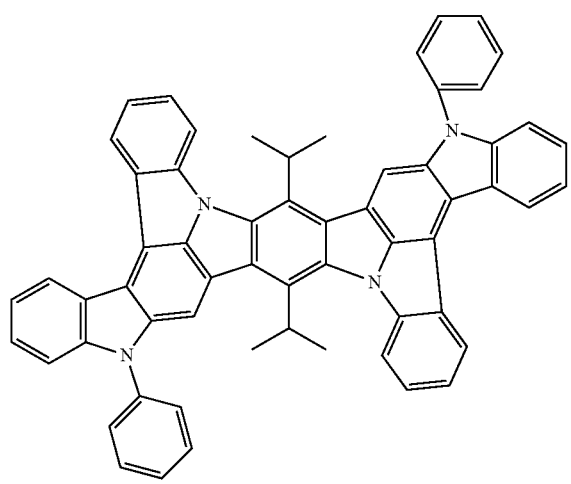

53
-continued
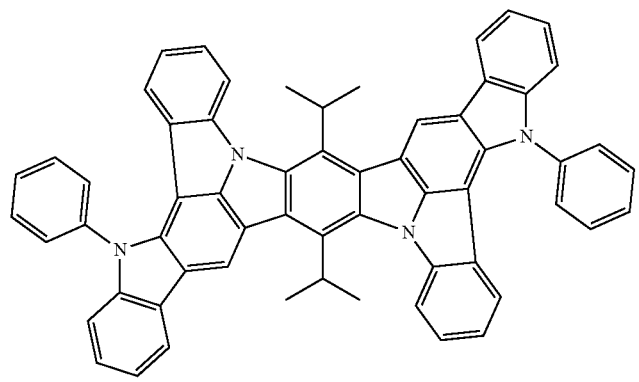
54
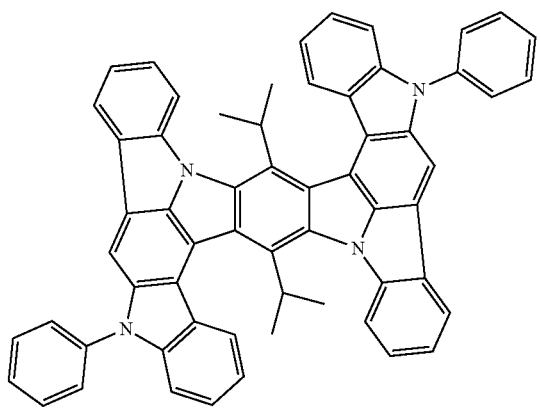
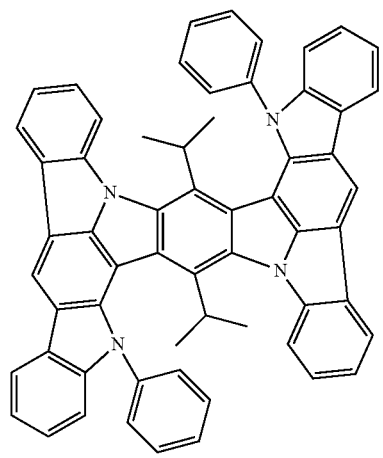
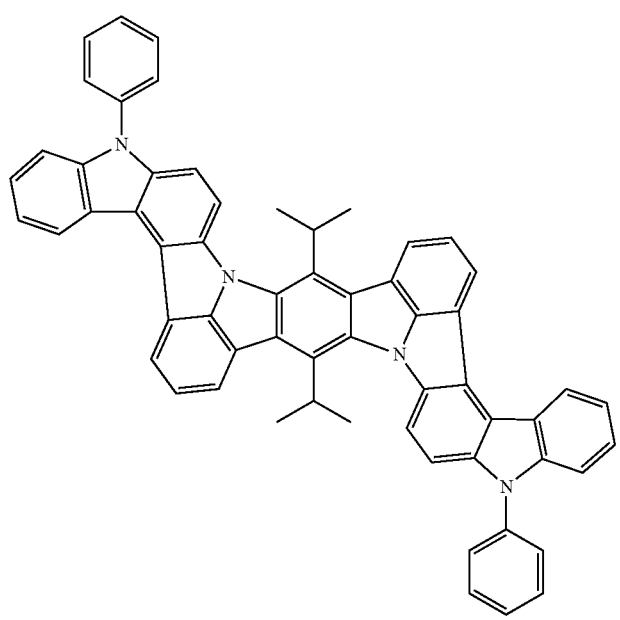
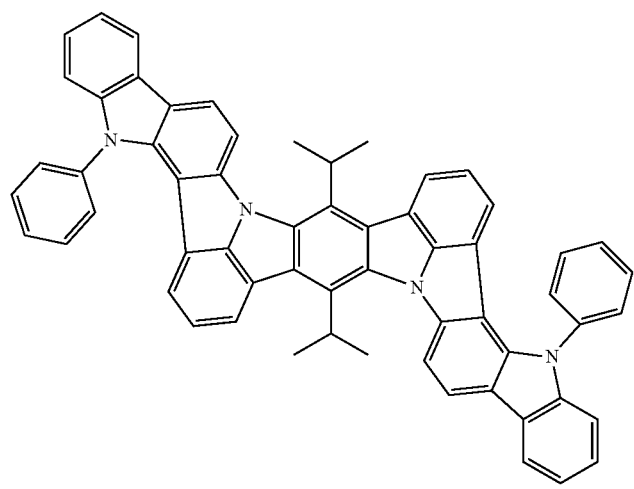

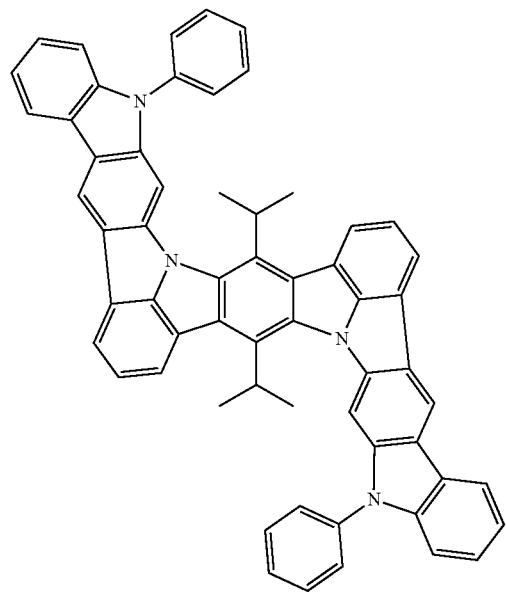
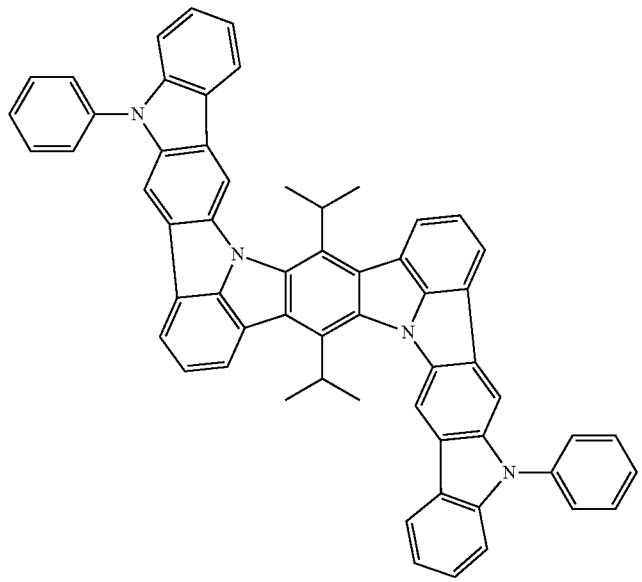
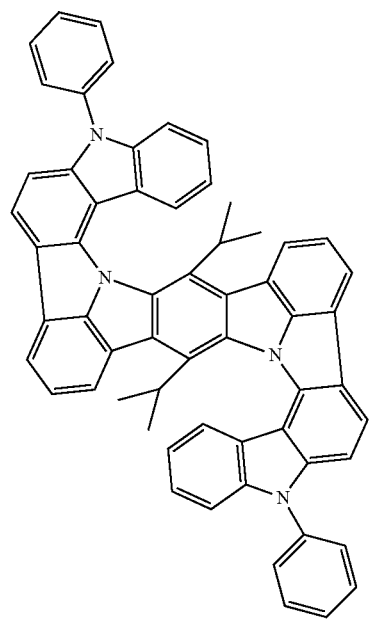
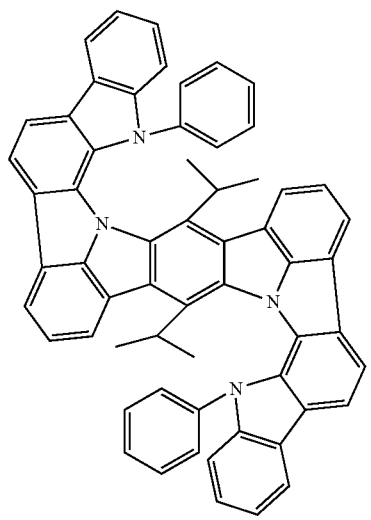
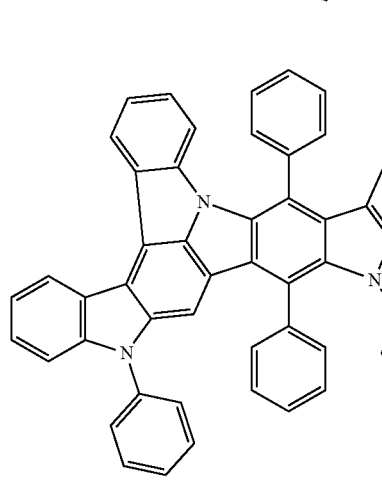
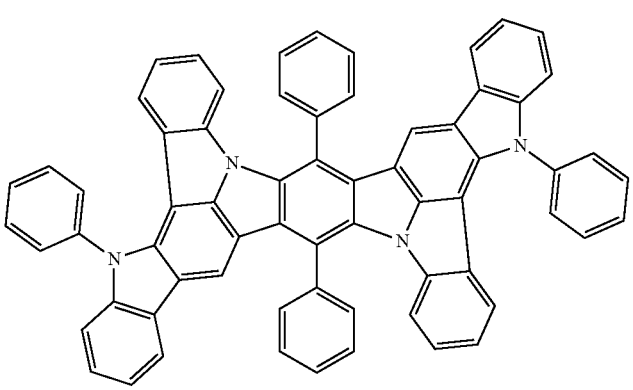

-continued
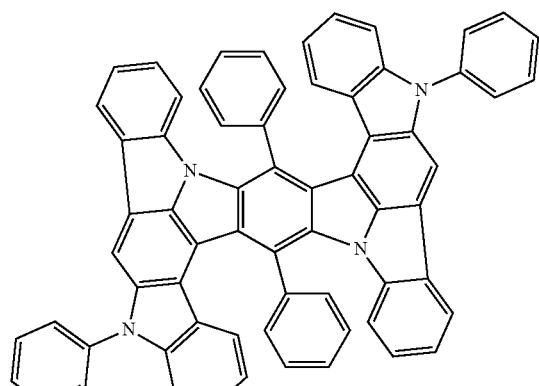
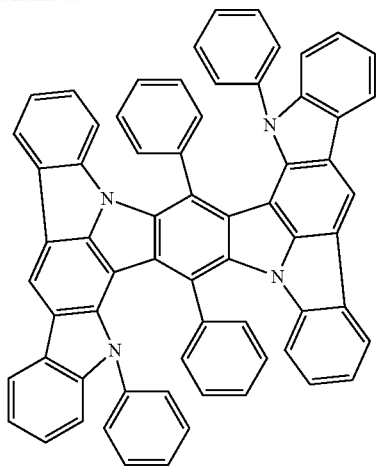
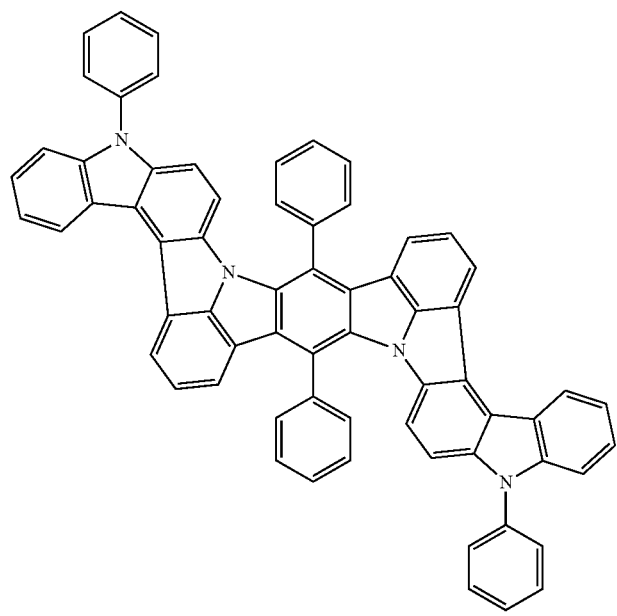
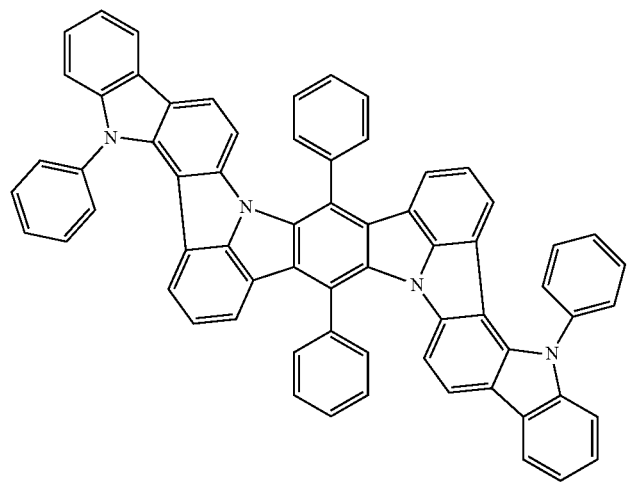
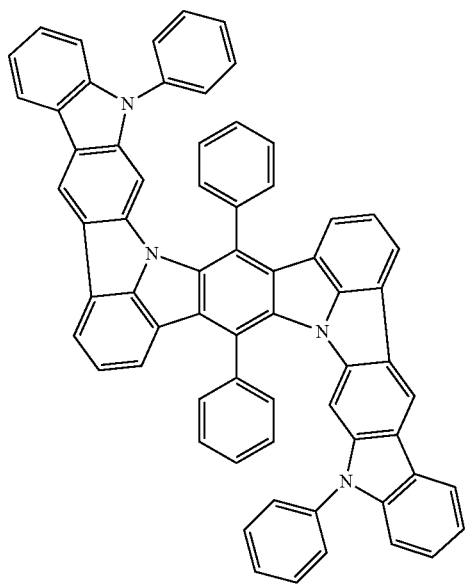

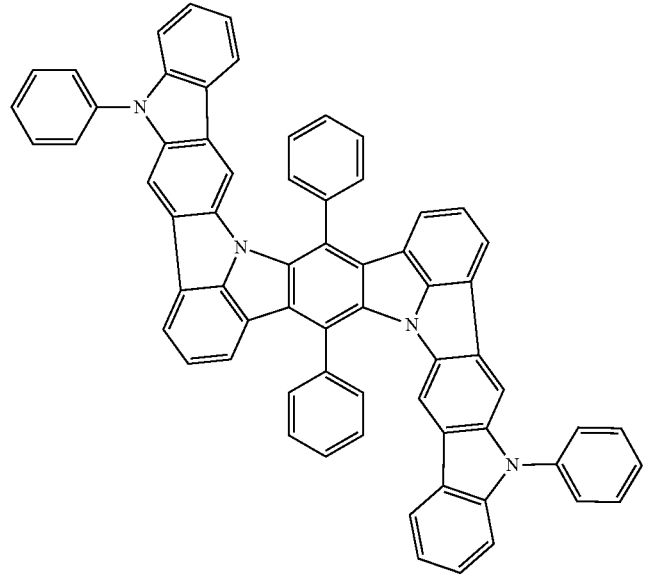
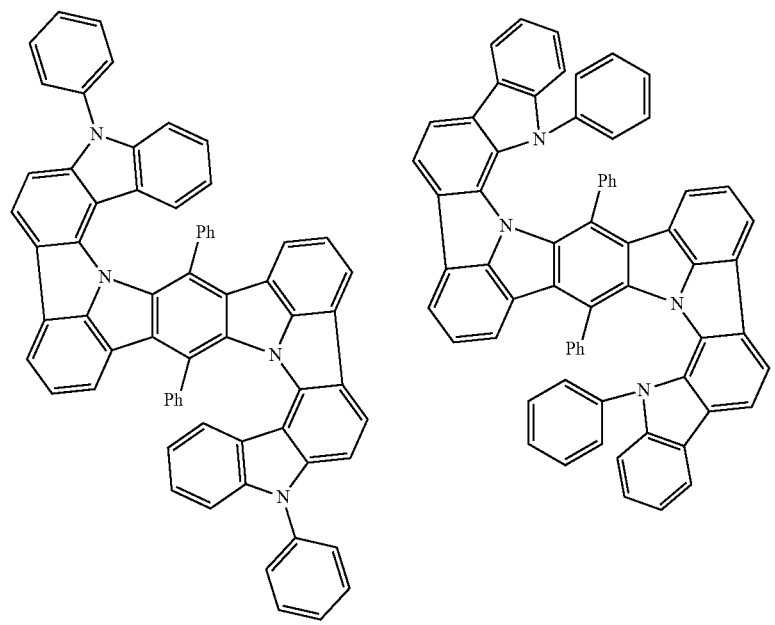
(In the formulas, Ph represents a phenyl group.)
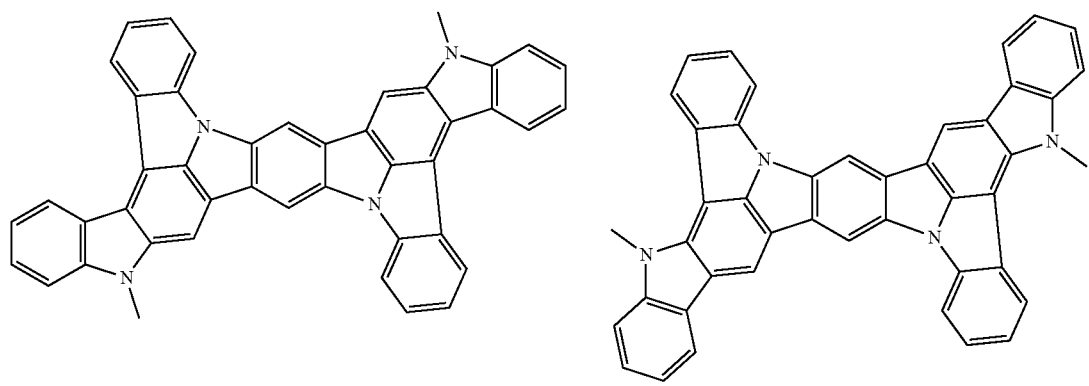

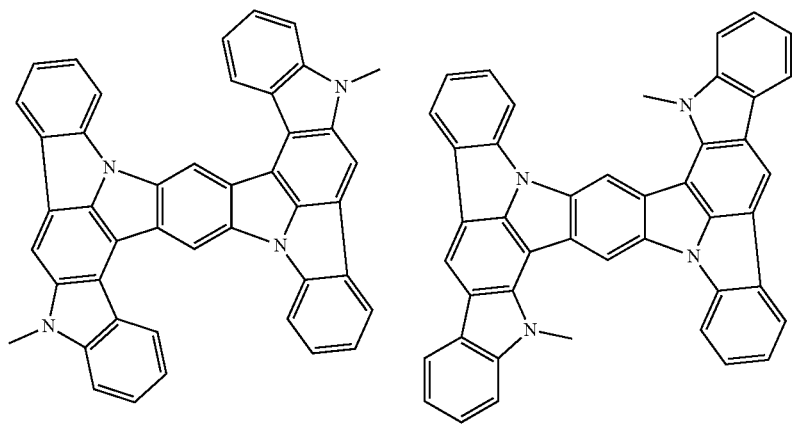
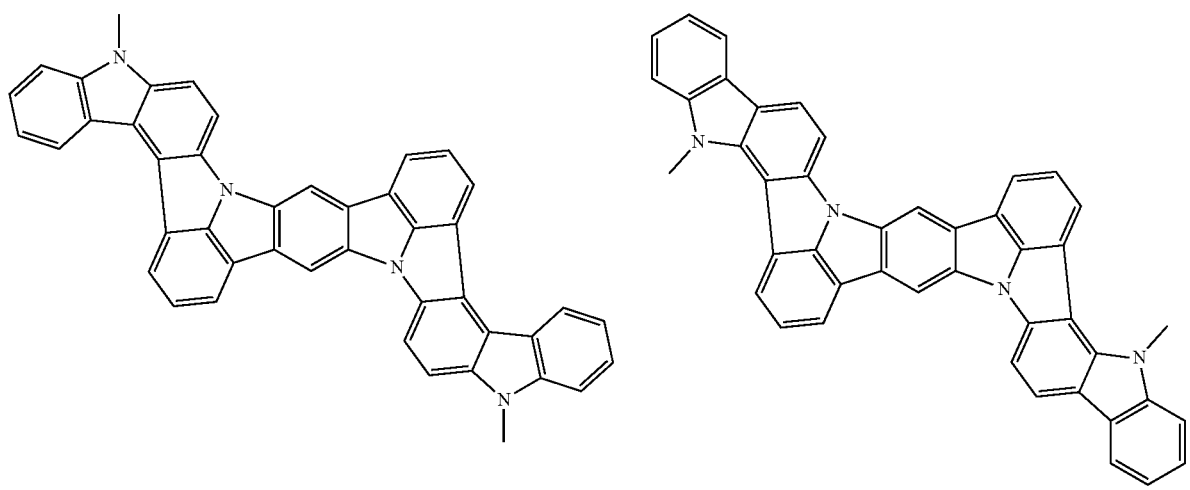
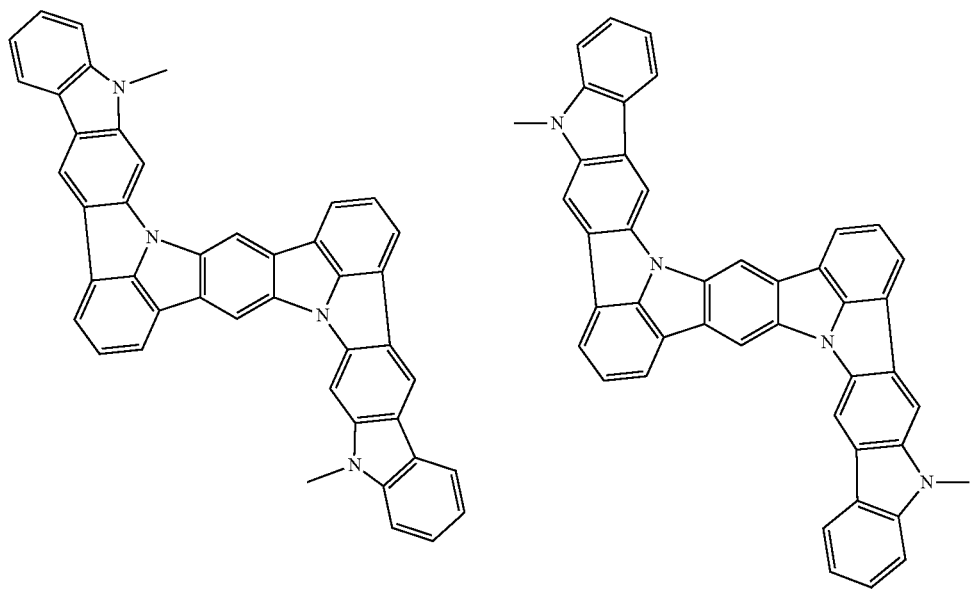

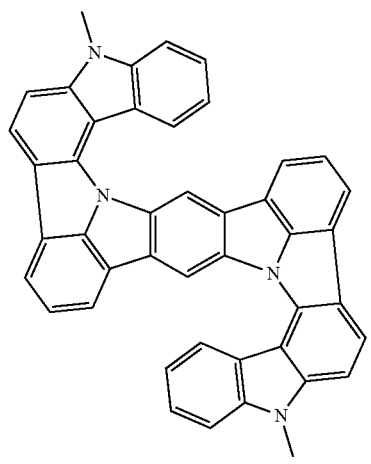
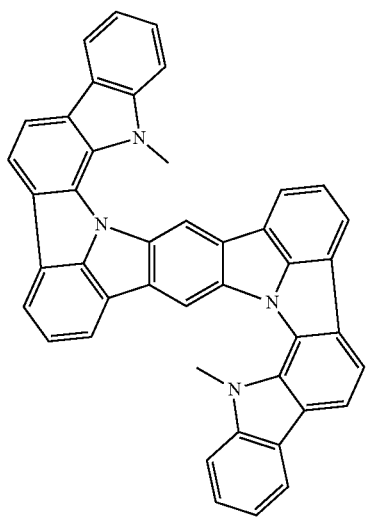
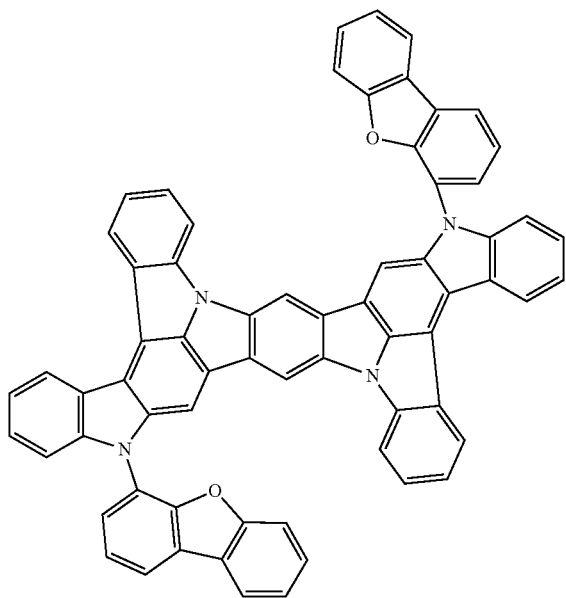
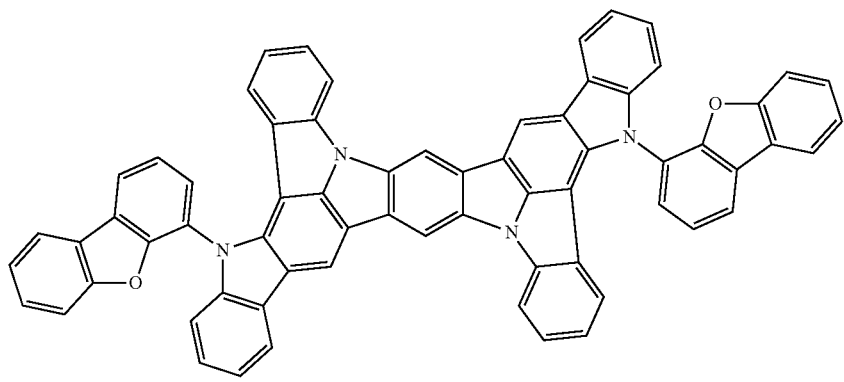

-continued
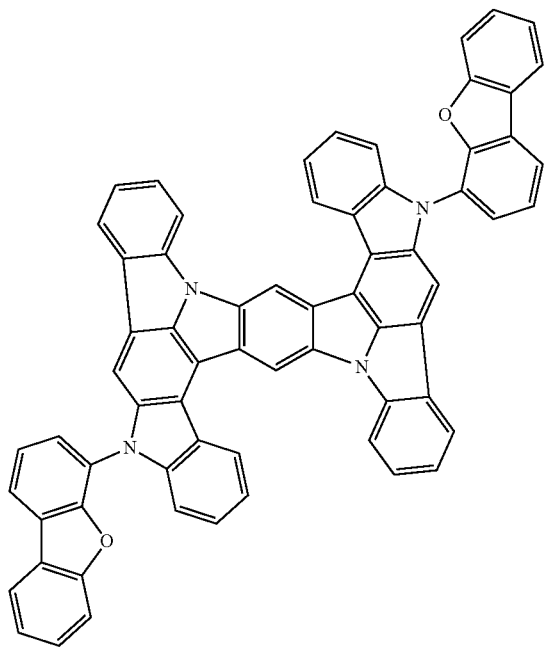
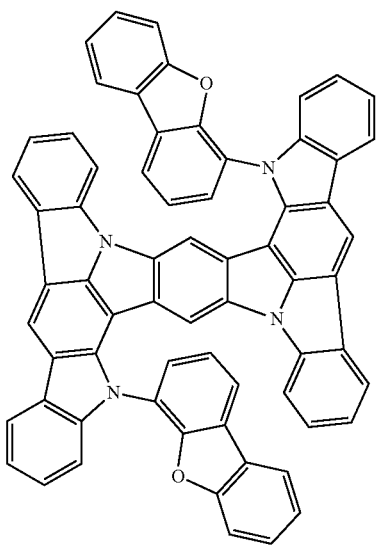
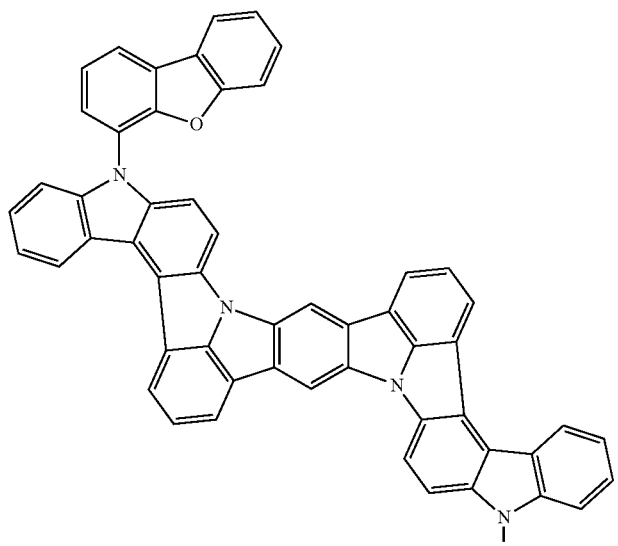
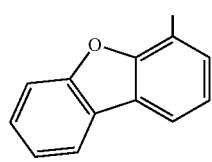

-continued
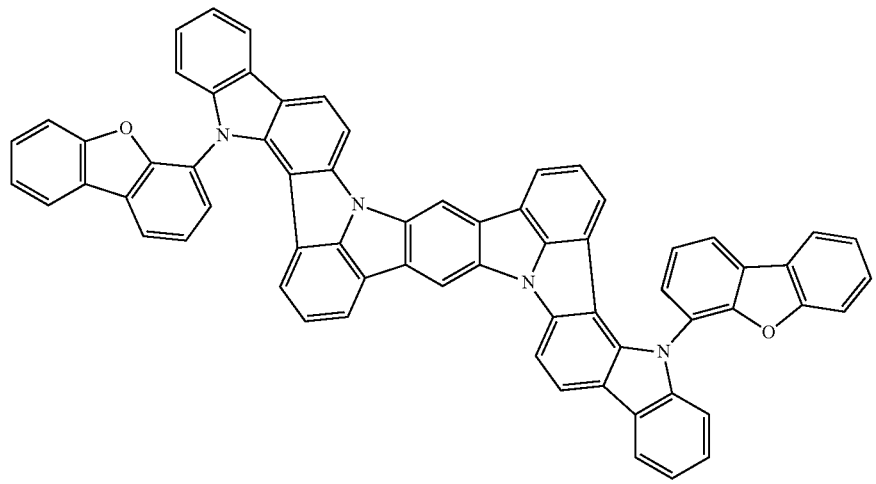
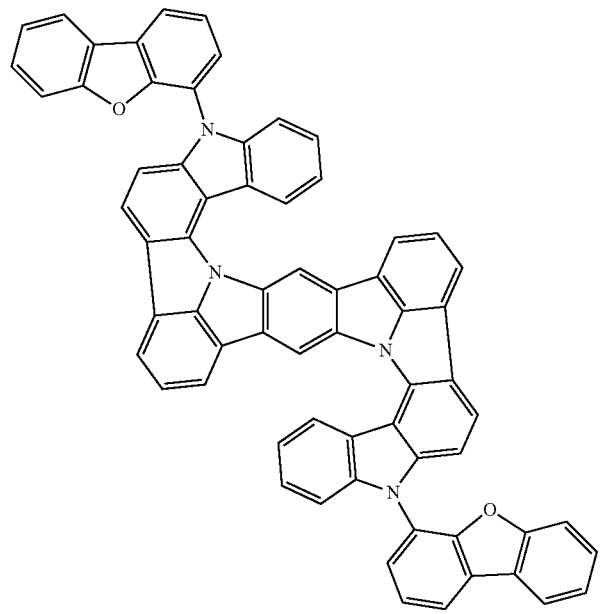
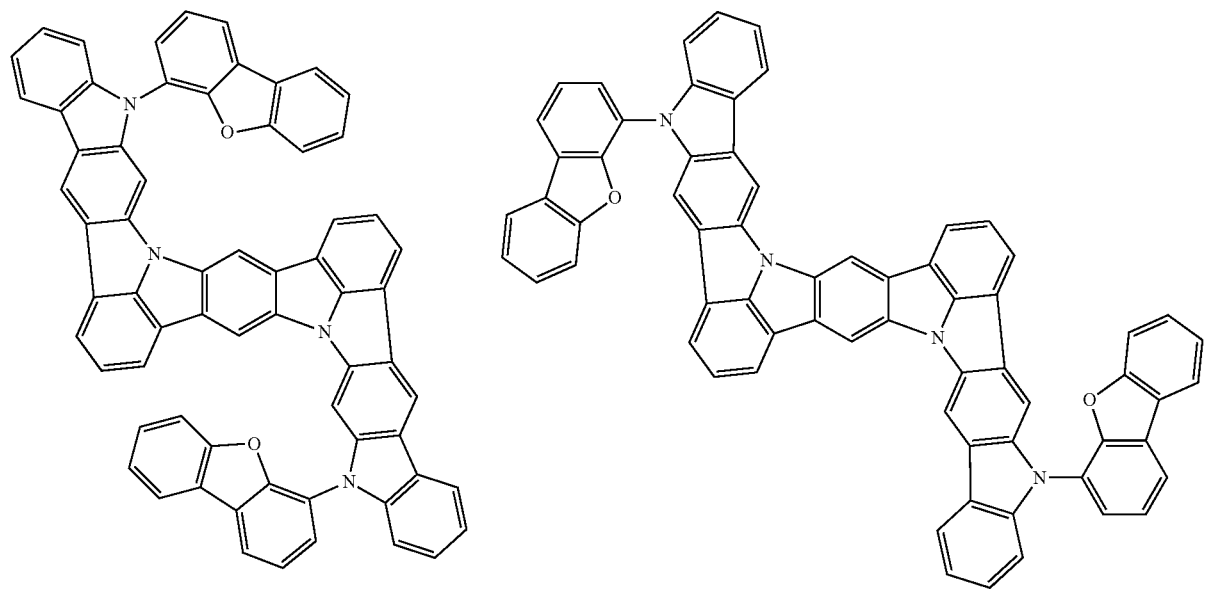
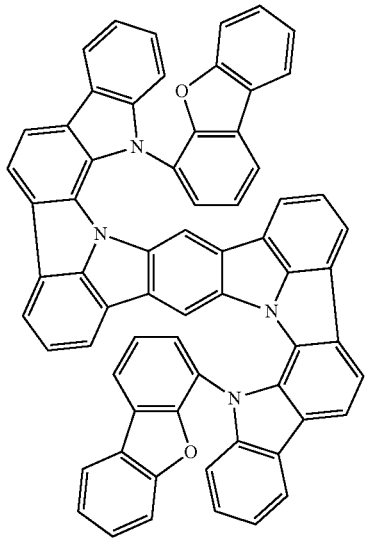

-continued
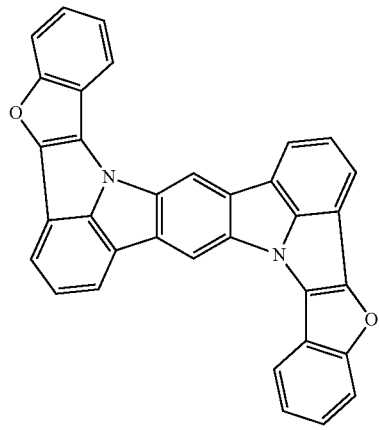
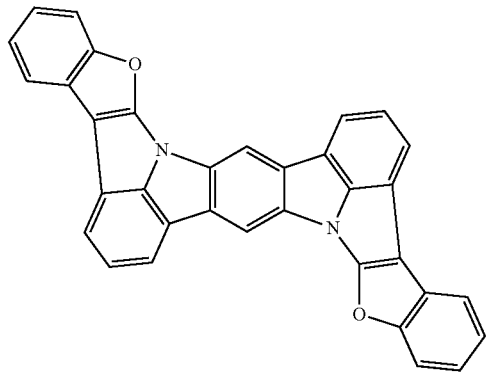
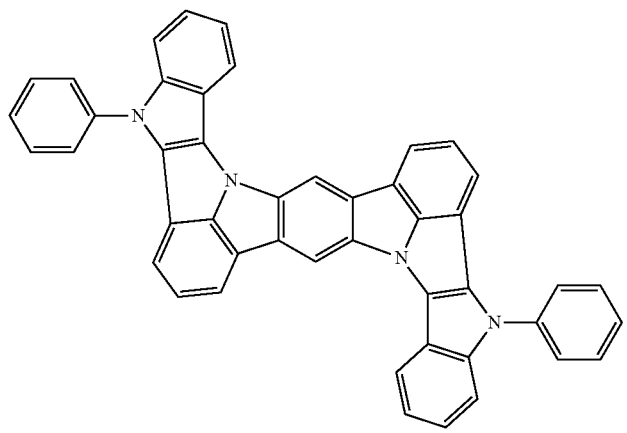
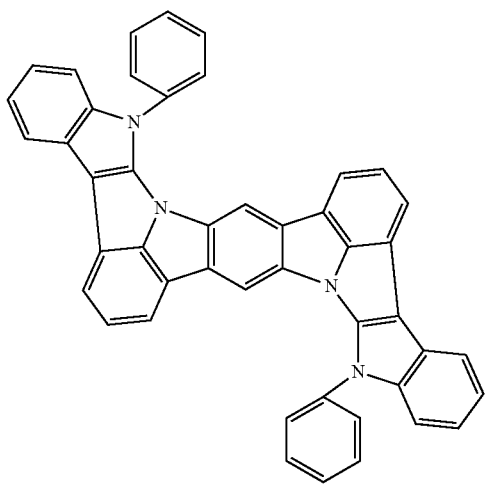
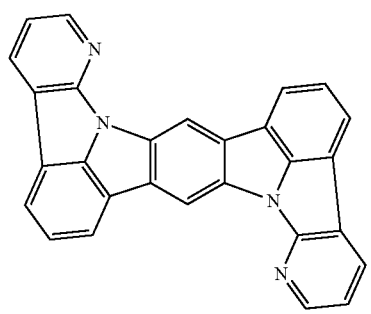
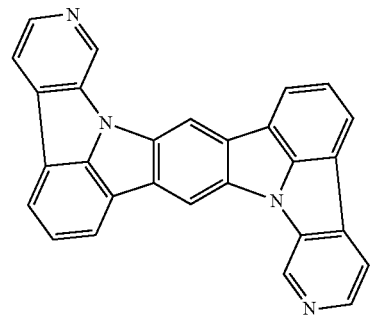
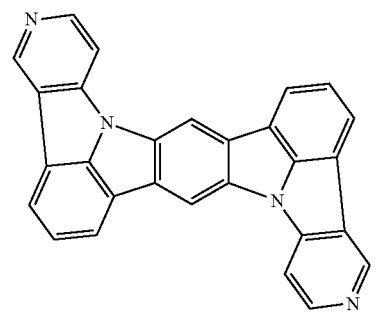
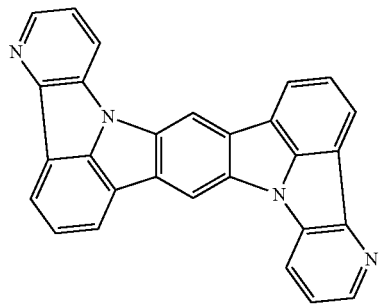
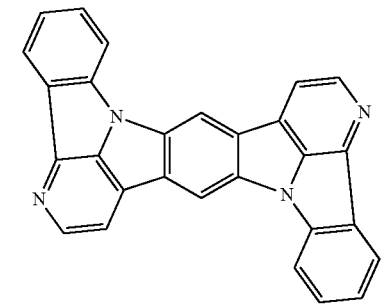
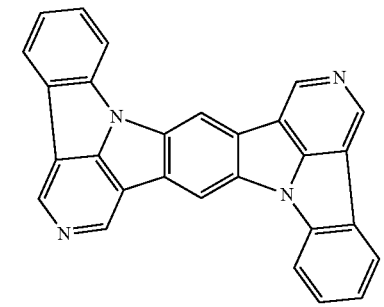

-continued
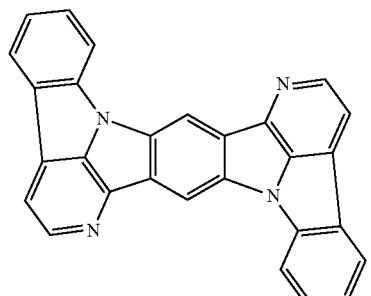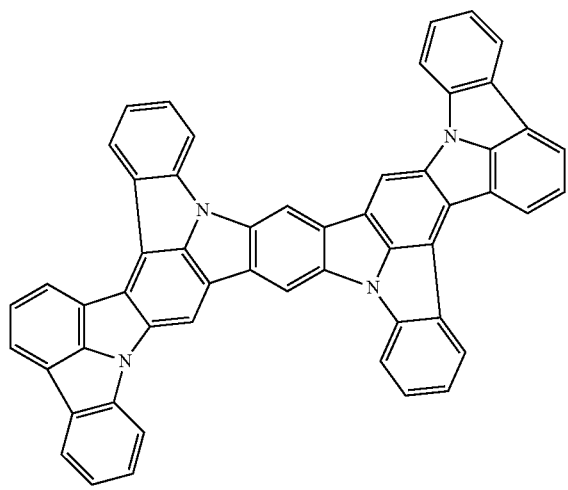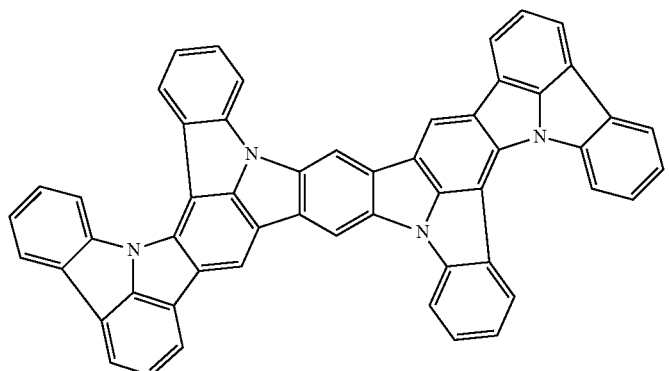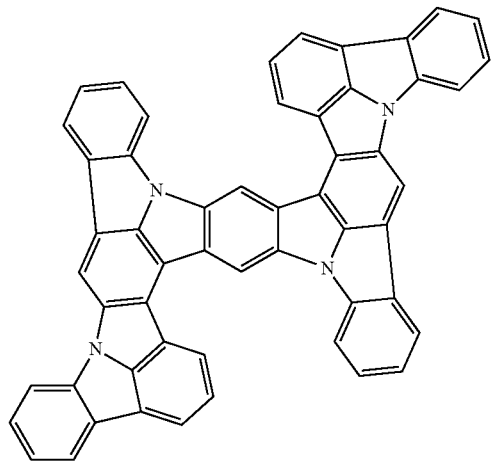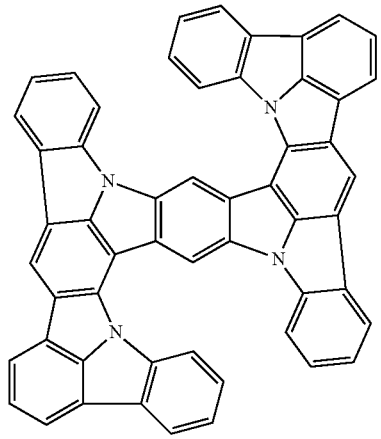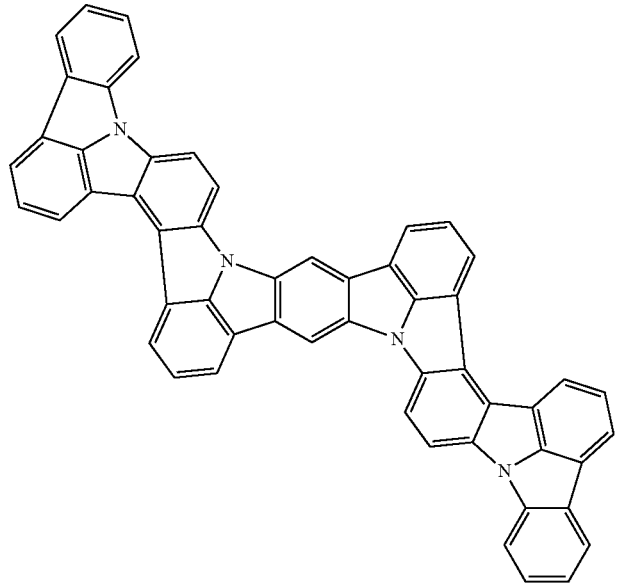

-continued
73
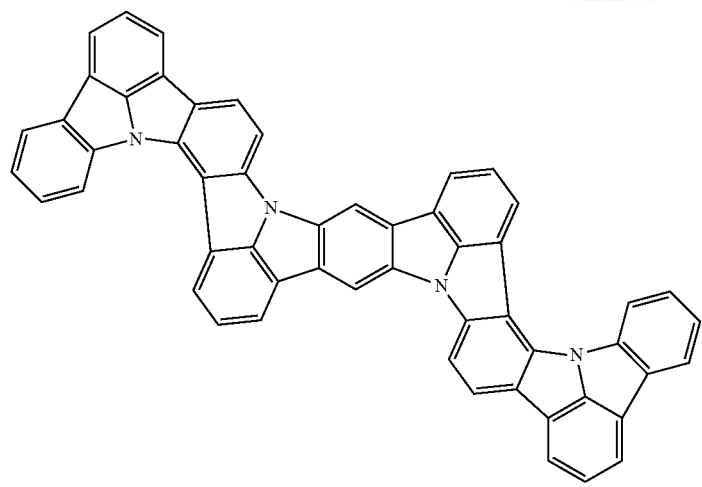
74
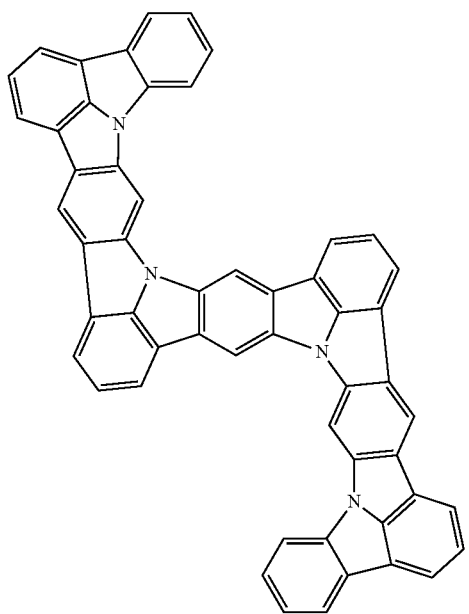
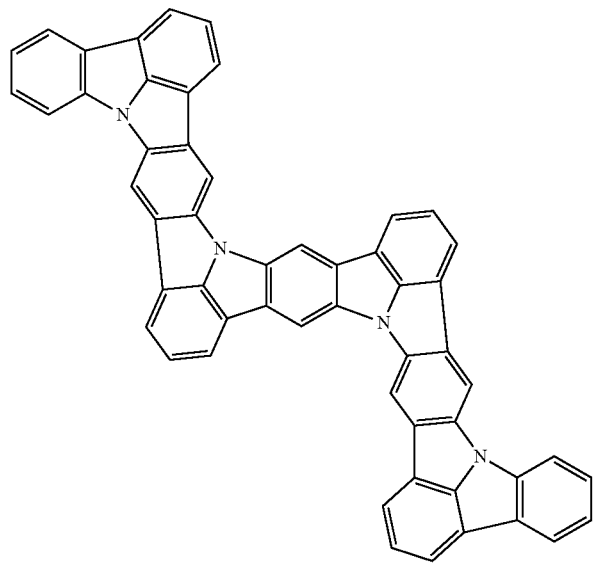
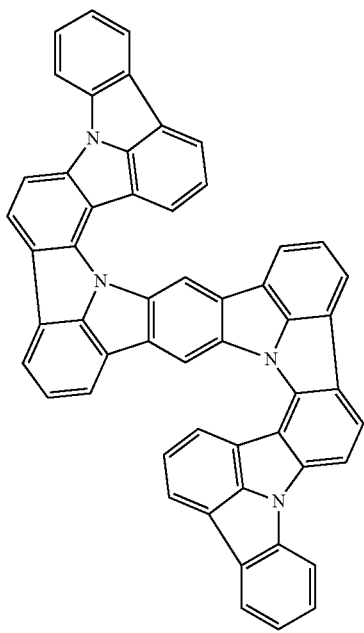

-continued
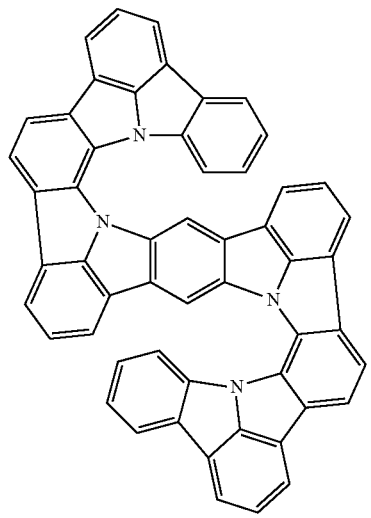
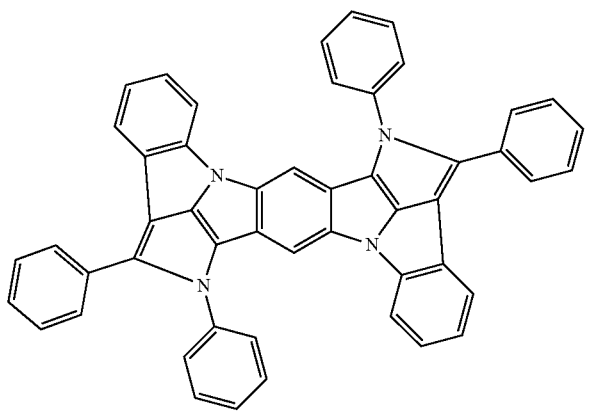
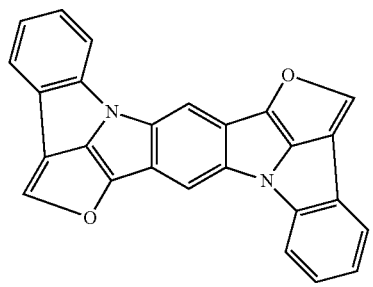
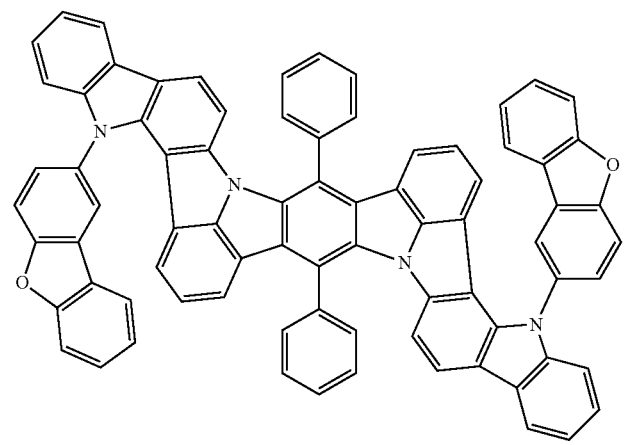
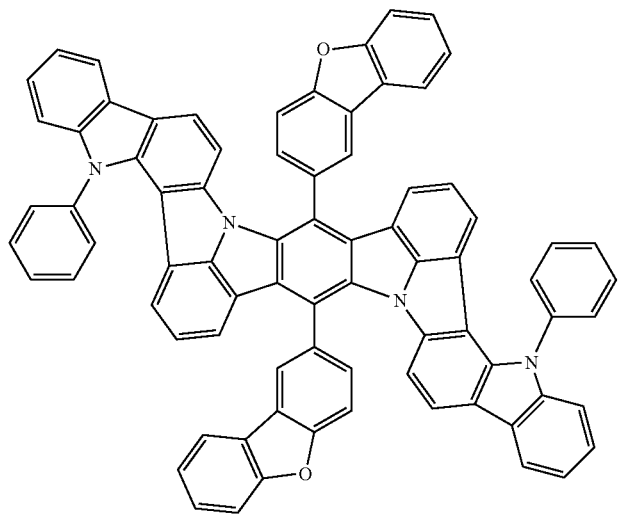
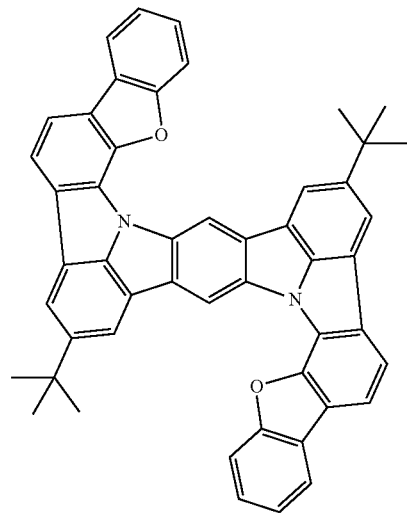

-continued

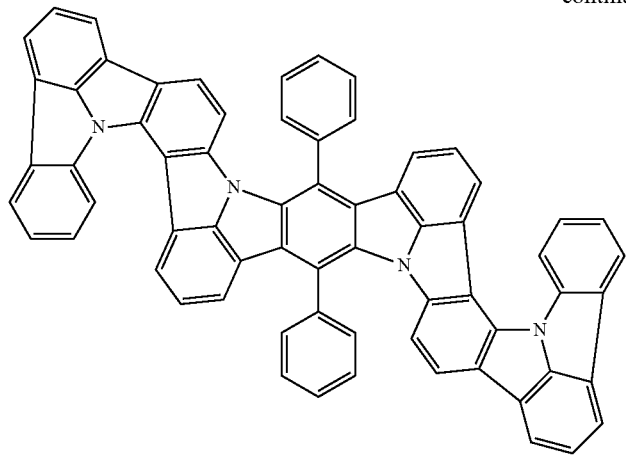

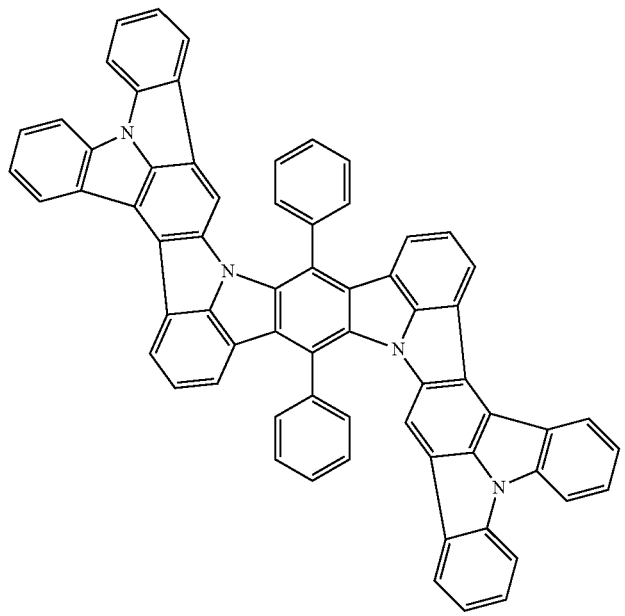 [SMILES: c1ccc(-c2c3c4cccc5c6c7c8ccccc8n8c9ccccc9c(cc6n(c3c(-c3ccccc3)c3c6cccc9c%10c%11c%12ccccc%12n%12c%13ccccc%13c(cc%10n(c23)c69)c%11%12)c45)c78)cc1]

The compound according to the present aspect is useful as a material for an organic EL device.

The compound according to the present aspect is useful as a material of an emitting layer of the organic EL device, and particularly useful as a fluorescent emitting material (also referred to as a fluorescent dopant) of the emitting layer.

The compound according to the present aspect can cause improvement in luminous efficiency of the organic EL device.

[Organic Electroluminescence Device]

An organic electroluminescence device according to another aspect of the invention has a cathode, an anode and one or more organic layers arranged between the cathode and the anode. Then, at least one layer of the one or more organic layers includes the compound according to one aspect of the invention described above, and a compound represented by the following formula (10).

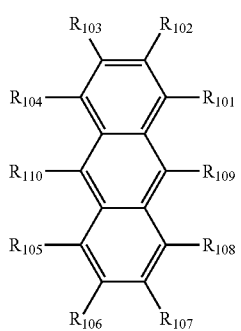

In the formula (10), at least one of $R_{101}$ to $R_{110}$ is a group represented by the following formula (31). When two or more groups represented by the following formula (31) exist, the two or more groups represented by the following formula (31) may be the same with or different from each other.

$$-L_{101}-Ar_{101} \quad (31)$$

In the formula (31), $L_{101}$ is a single bond, a substituted or unsubstituted arylene group having 6 to 30 ring carbon atoms, or a substituted or unsubstituted divalent heterocyclic group having 5 to 30 ring atoms.

$Ar_{101}$ is a substituted or unsubstituted aryl group having 6 to 50 ring carbon atoms, or a substituted or unsubstituted monovalent heterocyclic group having 5 to 50 ring atoms.

One or more sets of two or more adjacent to each other among $R_{101}$ to $R_{110}$ that are not the group represented by the formula (31) form a substituted or unsubstituted and saturated or unsaturated ring, or do not form the ring.

$R_{101}$ to $R_{110}$ that are neither the group represented by the formula (31) nor form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—$O$—$(R_{904})$,

—$S$—$(R_{905})$,

—$N(R_{906})(R_{907})$, a substituted or unsubstituted aryl group having 6 to 50 ring carbon atoms, or a substituted or unsubstituted monovalent heterocyclic group having 5 to 50 ring atoms.

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms. When two or more of $R_{901}$ to $R_{907}$ exist, two or more of $R_{901}$ to $R_{907}$ may be the same with or different from each other.

In one embodiment, the compound (10) is a compound represented by the following formula (10-1).

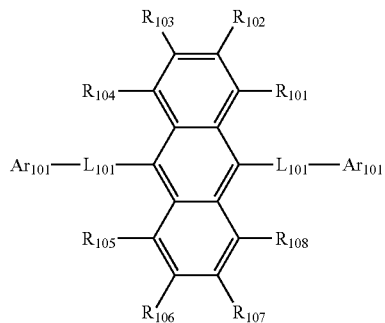

(10-1)

In the formula (10-1), $R_{101}$ to $R_{108}$, and $L_{101}$ and $Ar_{101}$ are as defined in the formula (10).

In one embodiment, the compound (10) is a compound represented by the following formula (10-2).

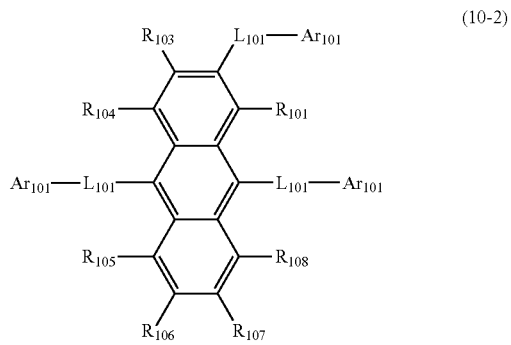

(10-2)

In the formula (10-2), $R_{101}$, $R_{103}$ to $R_{108}$, and $L_{101}$ and $Ar_{101}$ are as defined in the formula (10).

In one embodiment, the compound (10) is a compound represented by the following formula (10-3).

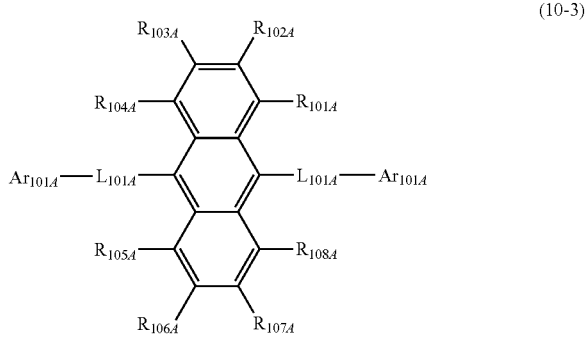

(10-3)

In the formula (10-3), $R_{101A}$ to $R_{108A}$ are independently a hydrogen atom, or a substituted or unsubstituted aryl group having 6 to 50 ring carbon atoms.

$L_{101A}$ is a single bond, or a substituted or unsubstituted arylene group having 6 to 30 ring carbon atoms. Two of $L_{101A}$ may be the same with or different from each other.

$Ar_{101A}$ is a substituted or unsubstituted aryl group having 6 to 50 ring carbon atoms. Two of $Ar_{101A}$ may be the same with or different from each other.

In one embodiment, the compound (10) is a compound represented by the following formula (10-4):

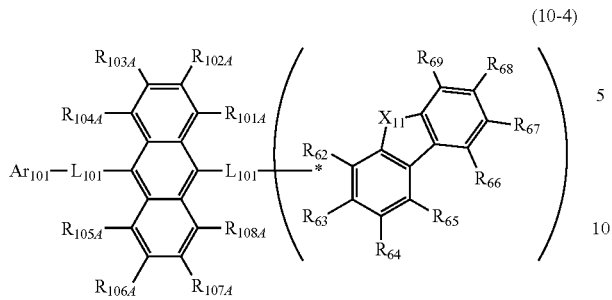

(10-4)

In the formula (10-4), $L_{101}$ and $Ar_{101}$ are as defined in the formula (10).

$R_{101A}$ to $R_{108A}$ are independently a hydrogen atom, or a substituted or unsubstituted aryl group having 6 to 50 ring carbon atoms.

$X_{11}$ is O, S or N($R_{61}$).

$R_{61}$ is a hydrogen atom, a substituted or unsubstituted alkyl group having 1 to 50 carbon atoms, or a substituted or unsubstituted aryl group having 6 to 50 ring carbon atoms.

One of $R_{62}$ to $R_{69}$ is be bonded with $L_{101}$.

One or more sets of two or more adjacent to each other among $R_{62}$ to $R_{69}$ that are not bonded with $L_{101}$ form a substituted or unsubstituted and saturated or unsaturated ring, or do not form the ring.

$R_{62}$ to $R_{69}$ that are neither bonded with $L_{101}$ nor form the ring are independently a hydrogen atom, a substituted or unsubstituted alkyl group having 1 to 50 carbon atoms, or a substituted or unsubstituted aryl group having 6 to 50 ring carbon atoms.

In one embodiment, the compound (10) is a compound represented by the following formula (10-4A).

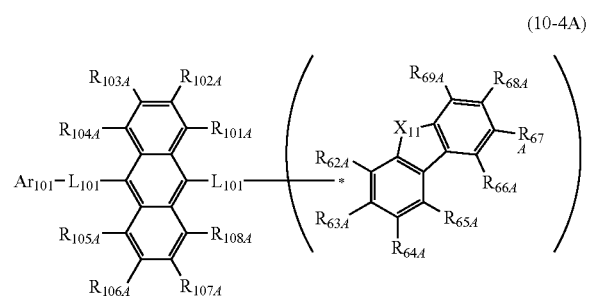

(10-4A)

In the formula (10-4A), $L_{101}$ and $Ar_{101}$ are as defined in the formula (10).

$R_{101A}$ to $R_{108A}$ are independently a hydrogen atom, or a substituted or unsubstituted aryl group having 6 to 50 ring carbon atoms.

$X_{11}$ is O, S or N($R_{61}$).

$R_{61}$ is a hydrogen atom, a substituted or unsubstituted alkyl group having 1 to 50 carbon atoms, or a substituted or unsubstituted aryl group having 6 to 50 ring carbon atoms.

Any of one set of two groups adjacent to each other among $R_{62A}$ to $R_{69A}$ forms a ring represented by the following formula (10-4A-1).

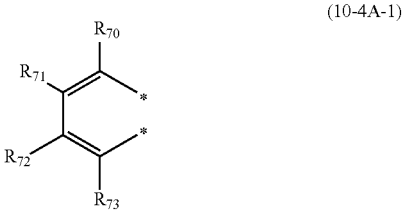

(10-4A-1)

In the formula (10-4A-1), two of * are bonded with two adjacent to each other among $R_{62A}$ to $R_{69A}$, respectively.

One of $R_{70}$ to $R_{73}$ is bonded with $L_{101}$.

$R_{70}$ to $R_{73}$ that are not bonded with $L_{101}$ are independently a hydrogen atom, a substituted or unsubstituted alkyl group having 1 to 50 carbon atoms, or a substituted or unsubstituted aryl group having 6 to 50 ring carbon atoms.

One or more sets of two or more adjacent to each other among $R_{62A}$ to $R_{69A}$ that do not form the ring represented by the formula (10-4A-1) form a substituted or unsubstituted and saturated or unsaturated ring, or do not form the ring.

$R_{62A}$ to $R_{69A}$ that do not form the ring represented by the formula (10-4A-1) and the substituted or unsubstituted and saturated or unsaturated ring are independently a hydrogen atom, a substituted or unsubstituted alkyl group having 1 to 50 carbon atoms, or a substituted or unsubstituted aryl group having 6 to 50 ring carbon atoms.

In one embodiment, the compound (10) is a compound represented by the following formula (10-6).

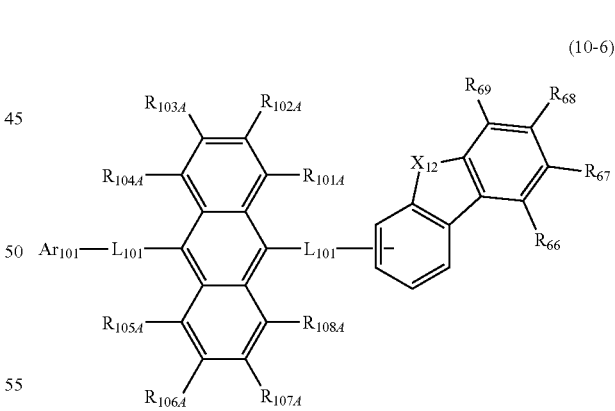

(10-6)

In the formula (10-6), $L_{101}$ and $Ar_{101}$ are as defined in the formula (10).

$R_{101A}$ to $R_{108A}$ are as defined in the formula (10-4).

$R_{66}$ to $R_{69}$ are as defined in the formula (10-4).

$X_{12}$ is O or S.

In one embodiment, the compound represented by the formula (10-6) is a compound represented by the following formula (10-6H).

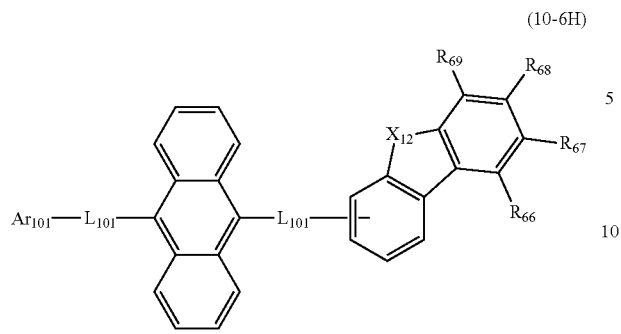

(10-6H)

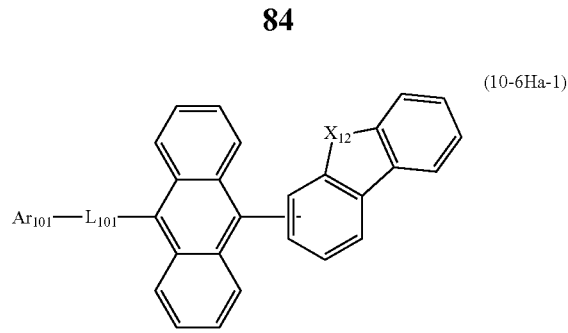

(10-6Ha-1)

In the formula (10-6H), $L_{101}$ and $Ar_{101}$ are as defined in the formula (10).

$R_{66}$ to $R_{69}$ are as defined in the formula (10-4).

$X_{12}$ is O or S.

In one embodiment, the compounds represented by the formulas (10-6) and (10-6H) each are a compound represented by the following formula (10-6Ha).

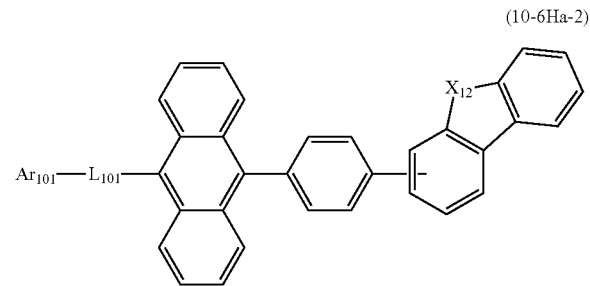

(10-6Ha-2)

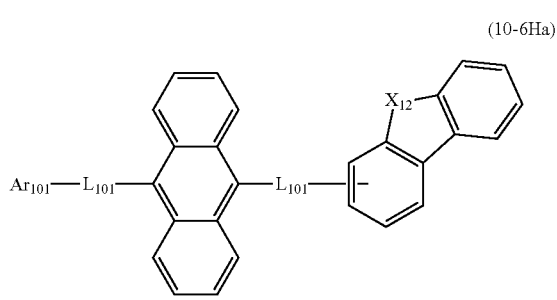

(10-6Ha)

In the formula (10-6Ha-1) and (10-6Ha-2), $L_{101}$ and $Ar_{101}$ are as defined in the formula (10).

$X_{12}$ is O or S.

In one embodiment, the compound (10) is a compound represented by the following formula (10-7).

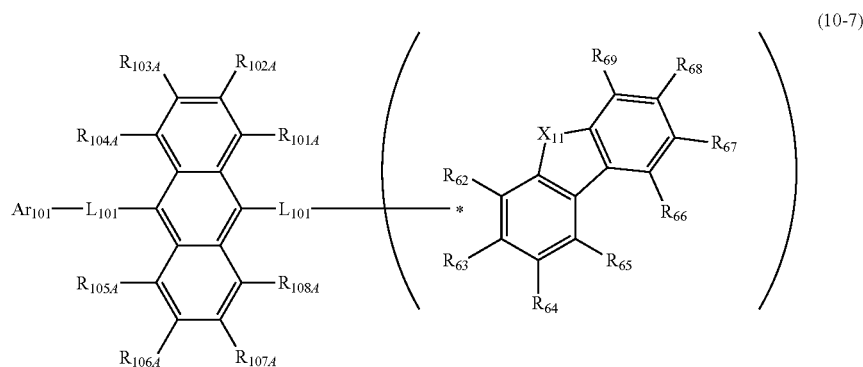

(10-7)

In the formula (10-6Ha), $L_{101}$ and $Ar_{101}$ are as defined in the formula (10).

$X_{12}$ is O or S.

In one embodiment, the compounds represented by the formulas (10-6), (10-6H) and (10-6Ha) each are a compound represented by the following formula (10-6Ha-1) or (10-6Ha-2).

In the formula (10-7), $L_{101}$ and $Ar_{101}$ are as defined in the formula (10).

$R_{101A}$ to $R_{108A}$ are as defined in the formula (10-4).

$X_{11}$ is as defined in the formula (10-4).

$R_{62}$ to $R_{69}$ are as defined in the formula (10-4). However, any of one set of $R_{66}$ and $R_{67}$, $R_{67}$ and $R_{68}$, and $R_{68}$ and $R_{69}$ is bonded with each other to form a substituted or unsubstituted and saturated or unsaturated ring.

In one embodiment, the compound (10) is a compound represented by the following formula (10-7H).

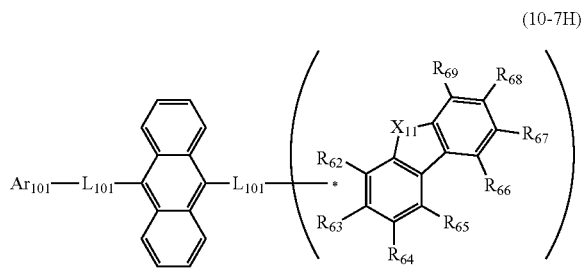

(10-7H)

In the formula (10-7H), $L_{101}$ and $Ar_{101}$ are as defined in the formula (10).

$X_{11}$ is as defined in the formula (10-4).

$R_{62}$ to $R_{69}$ are as defined in the formula (10-4). However, any of one set of $R_{66}$ and $R_{67}$, $R_{67}$ and $R_{68}$, and $R_{68}$ and $R_{69}$ is bonded with each other to form a substituted or unsubstituted and saturated or unsaturated ring.

In one embodiment, the compound (10) is a compound represented by the following formula (10-8).

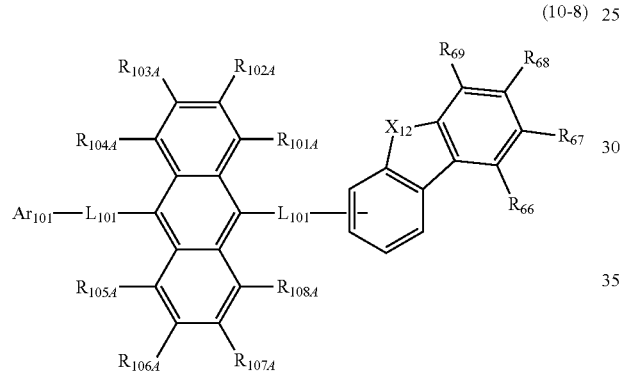

(10-8)

In the formula (10-8), $L_{101}$ and $Ar_{101}$ are as defined in the formula (10).

$R_{101A}$ and $R_{108A}$ are as defined in the formula (10-4).

$X_{12}$ is O or S.

$R_{66}$ to $R_{69}$ are as defined in the formula (10-4), in which any of one set of $R_{66}$ and $R_{67}$, $R_{67}$ and $R_{68}$, and $R_{68}$ and $R_{69}$ is bonded with each other to form a substituted or unsubstituted and saturated or unsaturated ring.

In one embodiment, the compound represented by the formula (10-8) is a compound represented by the following formula (10-8H).

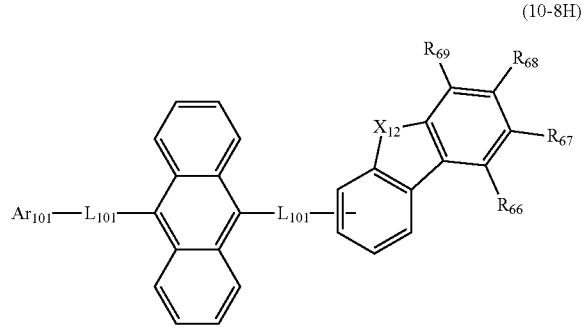

(10-8H)

In the formula (10-8H), $L_{101}$ and $Ar_{101}$ are as defined in the formula (10).

$R_{66}$ to $R_{69}$ are as defined in the formula (10-4), in which any of one set of $R_{66}$ and $R_{67}$, $R_{67}$ and $R_{68}$, and $R_{68}$ and $R_{69}$ is bonded with each other to form a substituted or unsubstituted and saturated or unsaturated ring. $R_{66}$ and $R_{67}$, $R_{67}$ and $R_{68}$, or $R_{68}$ and $R_{69}$ are preferably bonded with each other to form an unsubstituted benzene ring.

$X_{12}$ is O or S.

In one embodiment, in the compound represented by the formula (10-7), (10-8) or (10-8H), any of one set of $R_{66}$ and $R_{67}$, $R_{67}$ and $R_{68}$, and $R_{68}$ and $R_{69}$ is bonded with each other to form a ring represented by the following formula (10-8-1) or (10-8-2), and $R_{66}$ to $R_{69}$ that do not form the ring represented by the formula (10-8-1) or (10-8-2) do not form a substituted or unsubstituted and saturated or unsaturated ring.

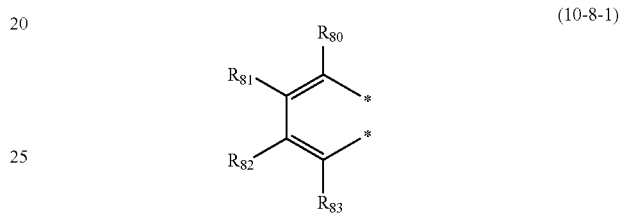

(10-8-1)

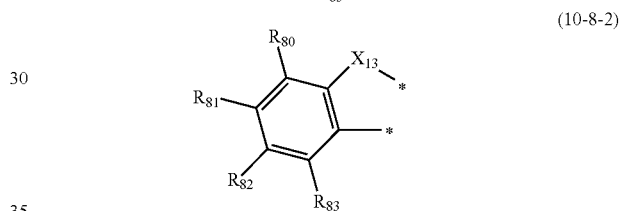

(10-8-2)

In the formulas (10-8-1) and (10-8-2), two of * are bonded with any of one set of $R_{66}$ and $R_{67}$, $R_{67}$ and $R_{68}$, and $R_{68}$ and $R_{69}$, respectively.

$R_{80}$ to $R_{83}$ are independently a hydrogen atom, a substituted or unsubstituted alkyl group having 1 to 50 carbon atoms, or a substituted or unsubstituted aryl group having 6 to 50 ring carbon atoms.

$X_{13}$ is O or S.

In one embodiment, the compound (10) is a compound represented by the following formula (10-9).

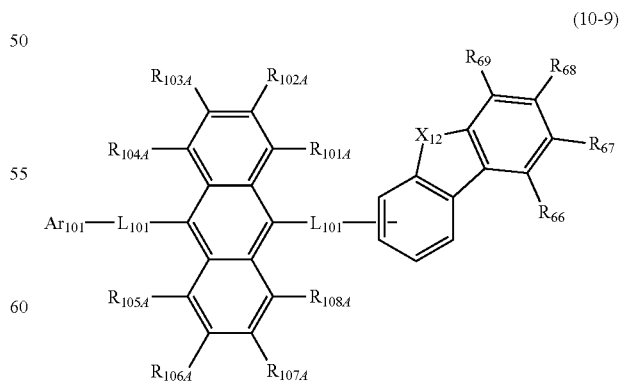

(10-9)

In the formula (10-9), $L_{101}$ and $Ar_{101}$ are as defined in the formula (10).

$R_{101A}$ to $R_{108A}$ are as defined in the formula (10-4).

$R_{66}$ to $R_{69}$ are as defined in the formula (10-4), in which both of $R_{66}$ and $R_{67}$, $R_{67}$ and $R_{68}$, and $R_{68}$ and $R_{69}$ are neither bonded with each other nor form a substituted or unsubstituted and saturated or unsaturated ring.

$X_{12}$ is O or S.

In one embodiment, the compound (10) is selected from the group consisting of compounds represented by the following formulas (10-10-1) to (10-10-4).

In the formulas (10-10-1) to (10-10-4), $L_{101A}$, $Ar_{101A}$ and $R_{101A}$ to $R_{108A}$ are as defined in the formula (10-3).

In one embodiment, the compounds represented by the formulas (10-10-1) to (10-10-4) are compounds represented by the following formulas (10-10-1H) to (10-10-4H).

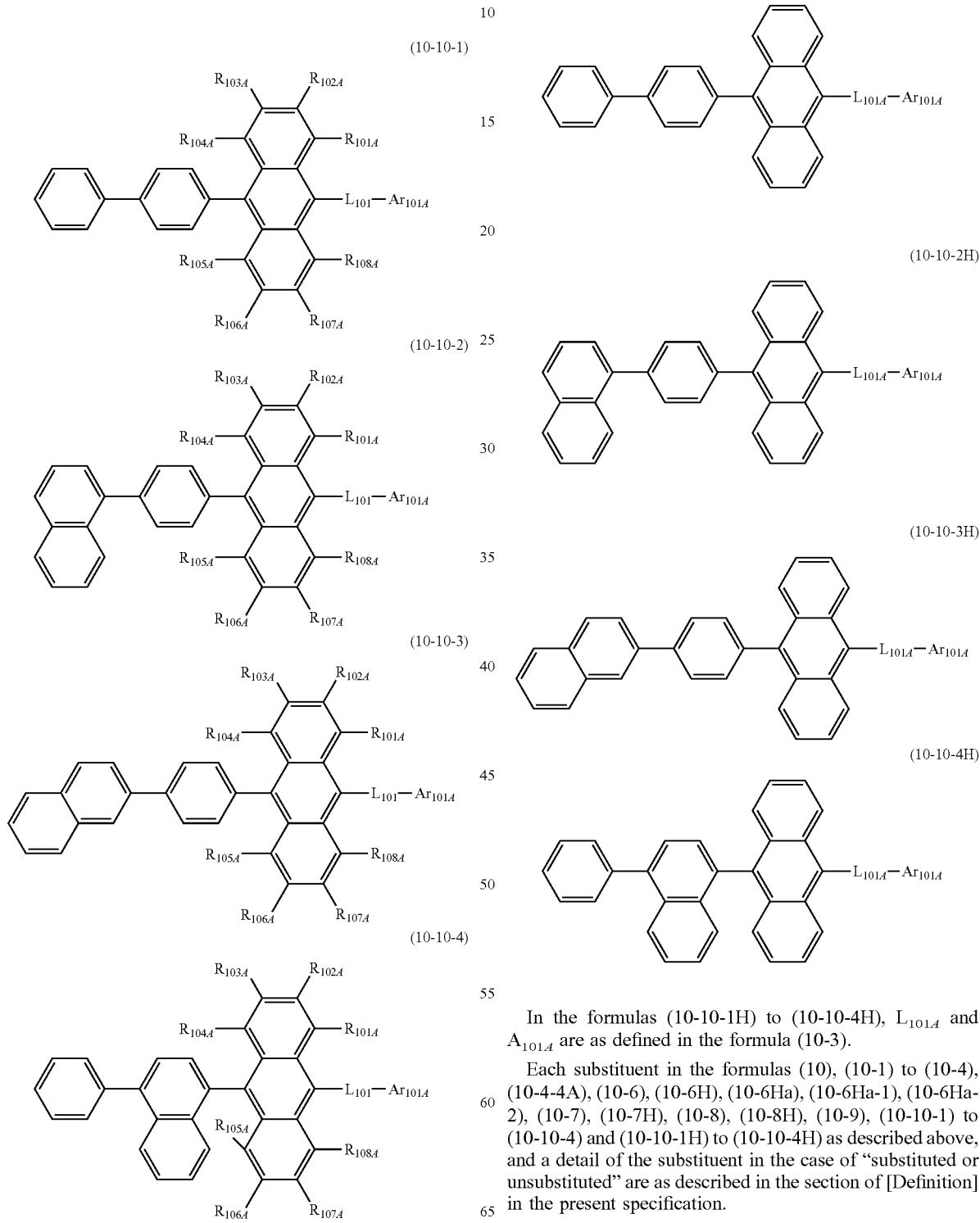

In the formulas (10-10-1H) to (10-10-4H), $L_{101A}$ and $A_{101A}$ are as defined in the formula (10-3).

Each substituent in the formulas (10), (10-1) to (10-4), (10-4-4A), (10-6), (10-6H), (10-6Ha), (10-6Ha-1), (10-6Ha-2), (10-7), (10-7H), (10-8), (10-8H), (10-9), (10-10-1) to (10-10-4) and (10-10-1H) to (10-10-4H) as described above, and a detail of the substituent in the case of "substituted or unsubstituted" are as described in the section of [Definition] in the present specification.

Specific examples of the compound represented by the formula (10) include compounds shown below.

89	90
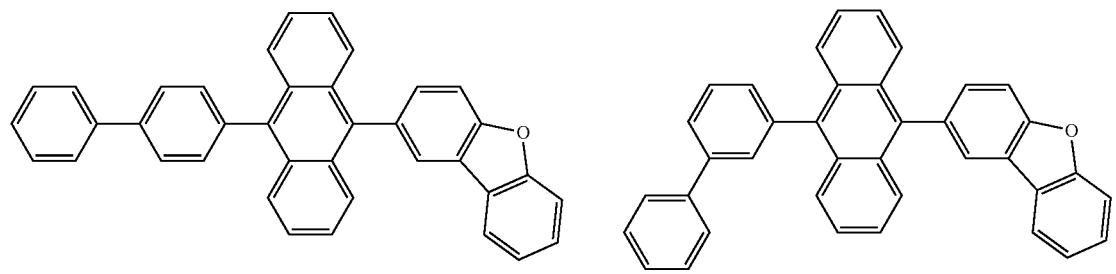
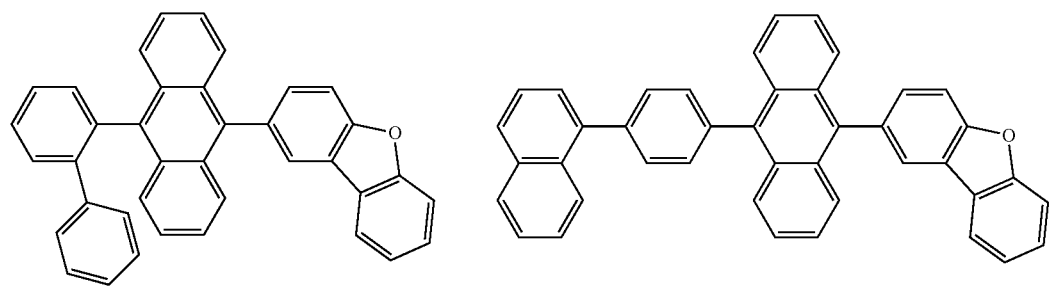
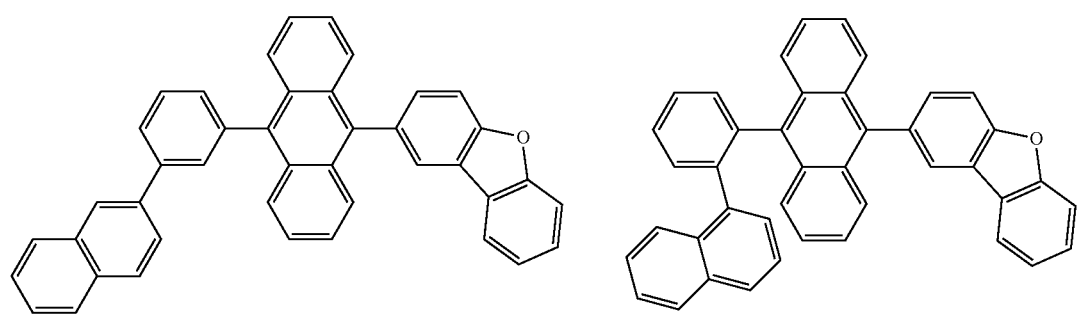
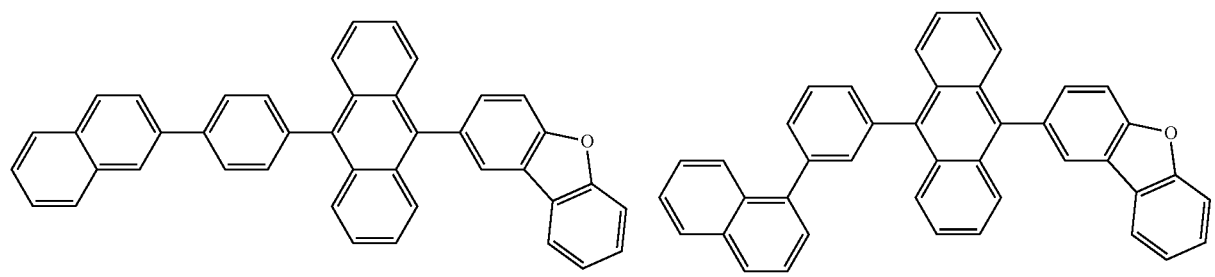
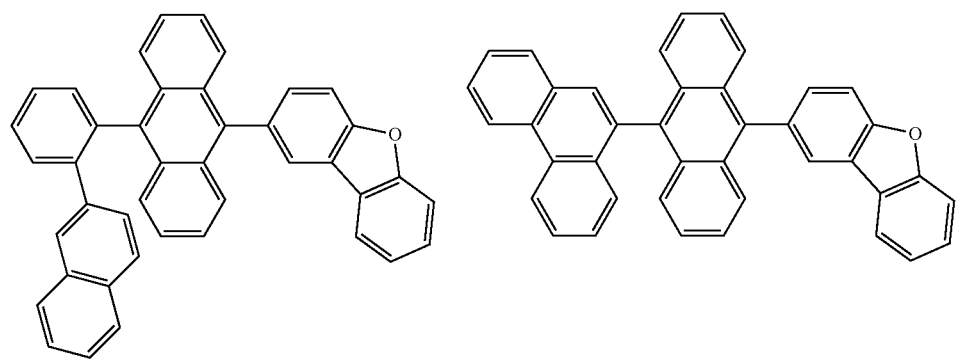

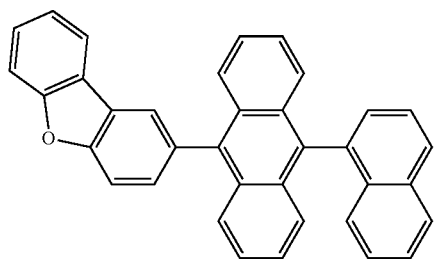
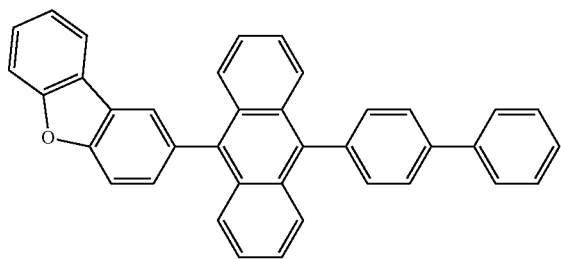
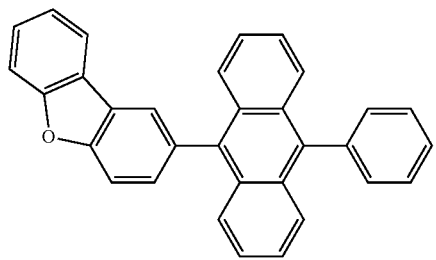
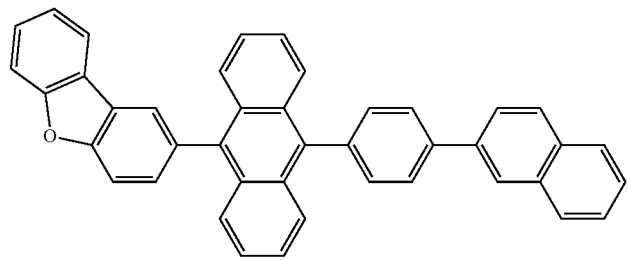
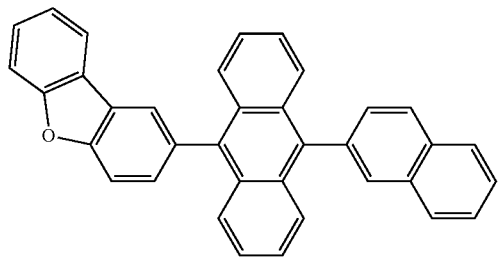
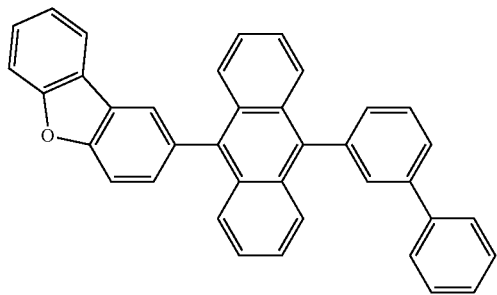
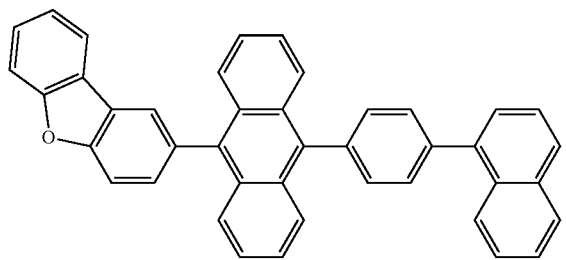
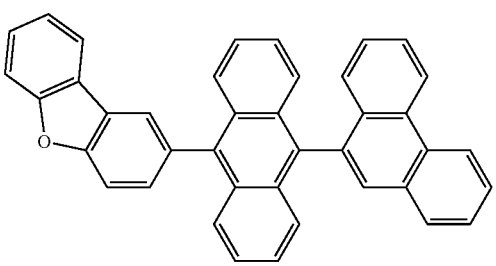
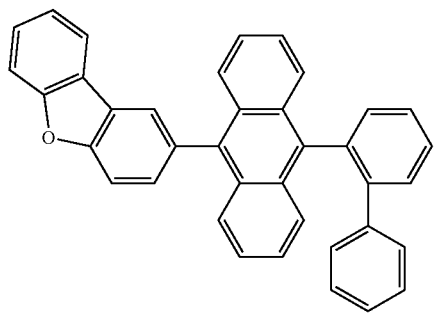
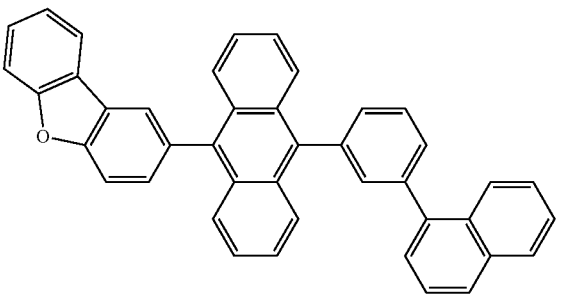

-continued
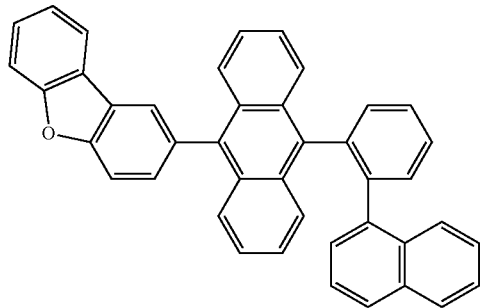
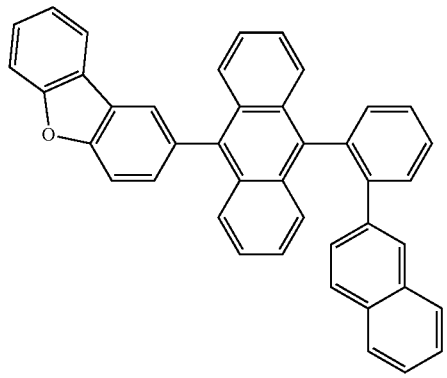
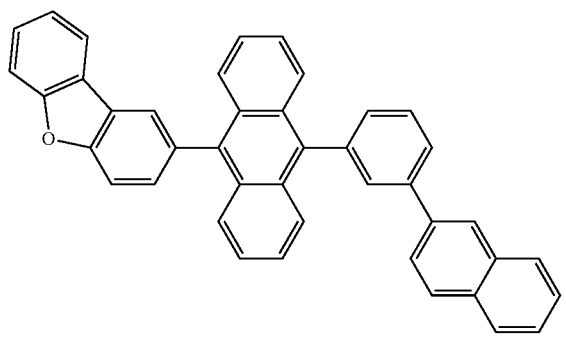
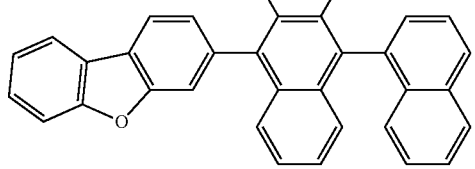
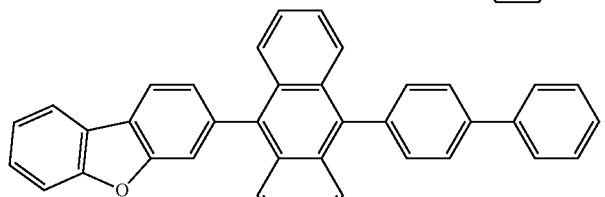
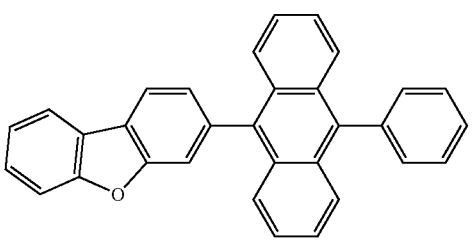
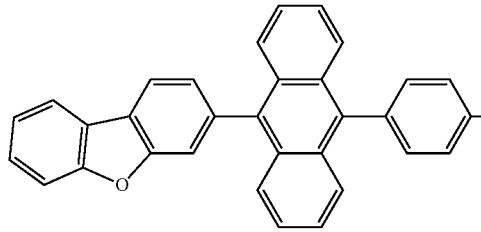
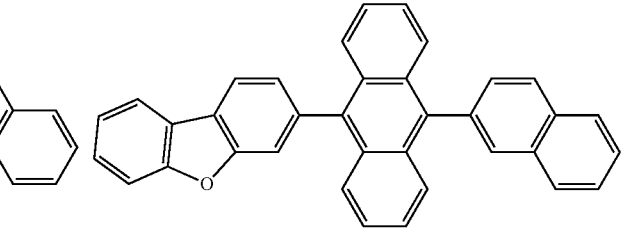
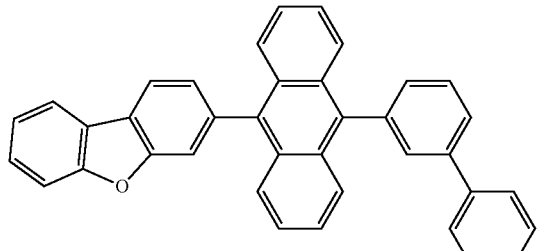
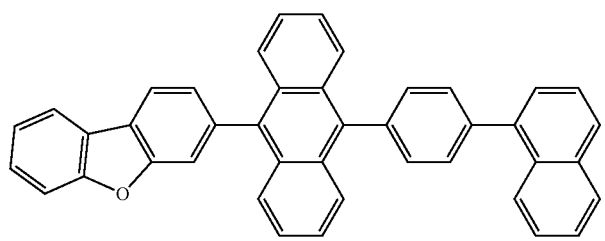
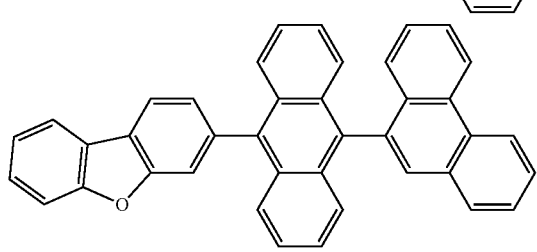
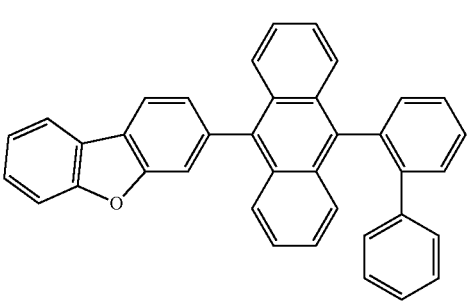

95 96
-continued
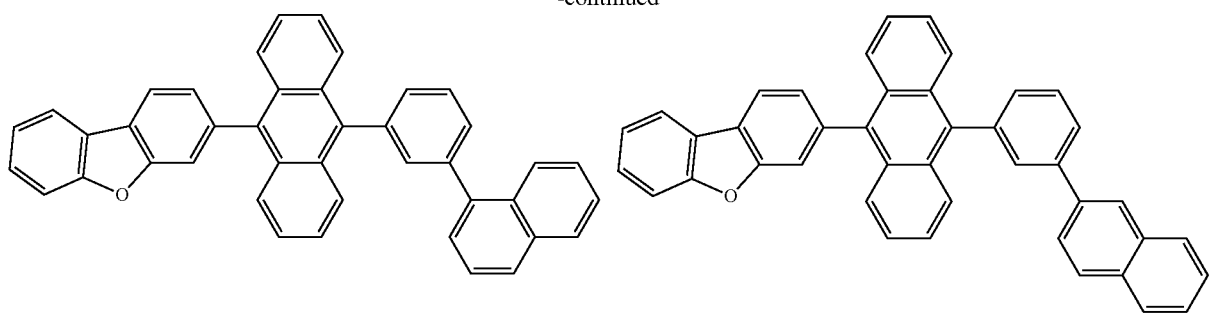
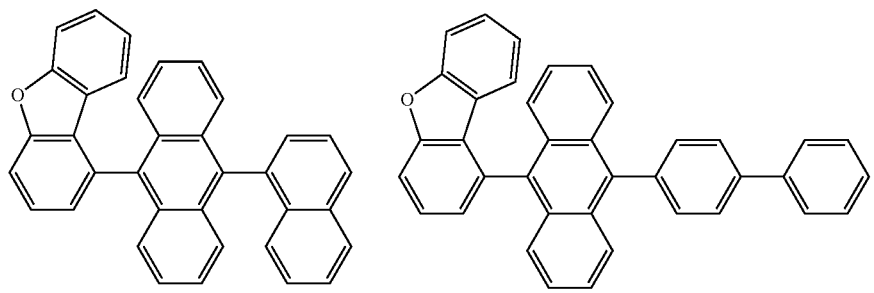
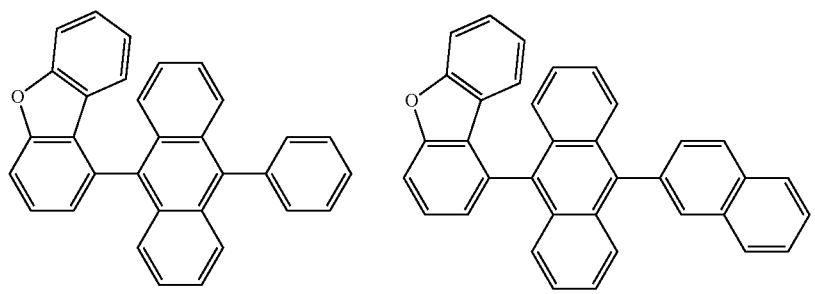
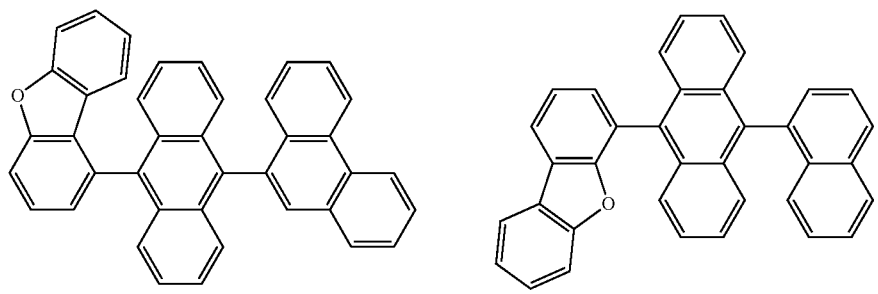
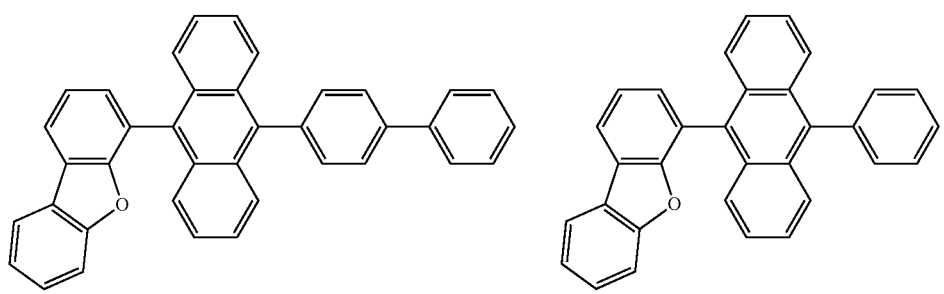

-continued
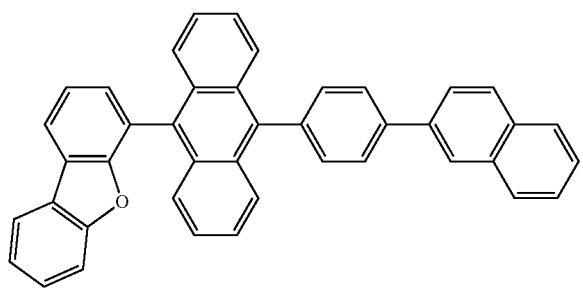
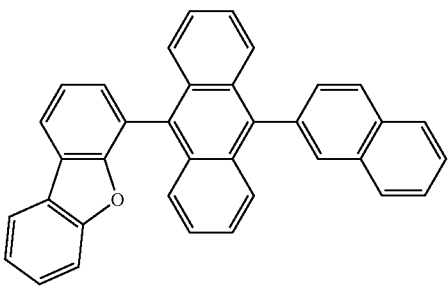
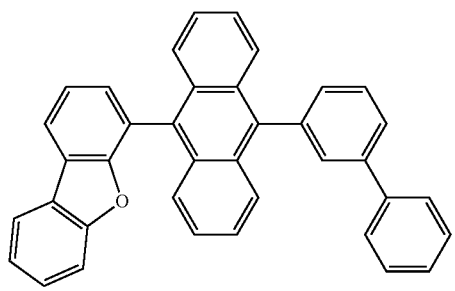
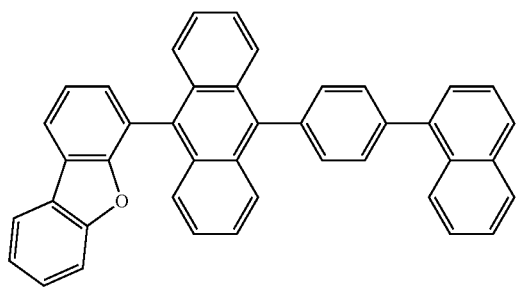
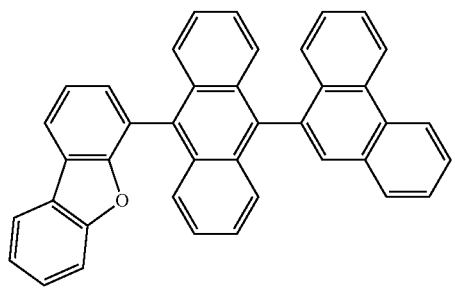
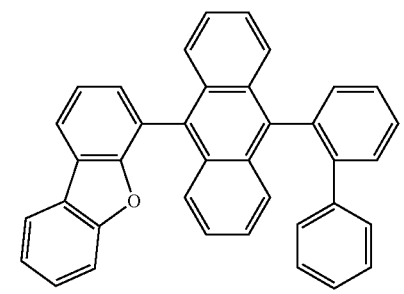
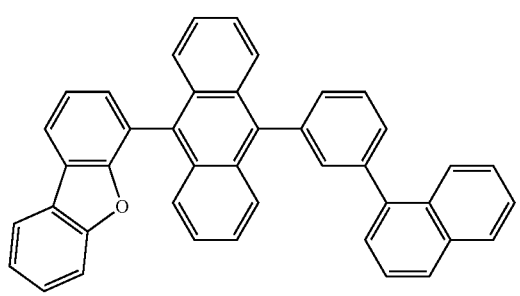
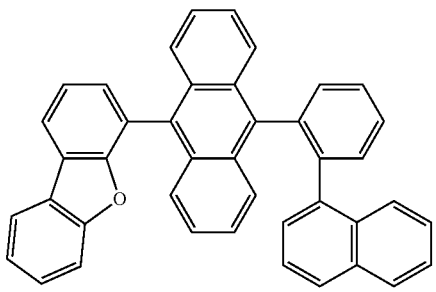
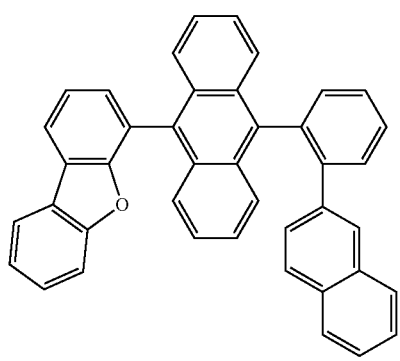
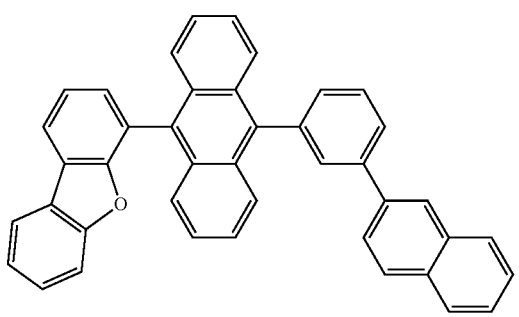

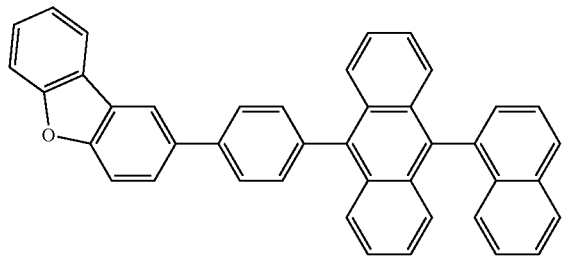
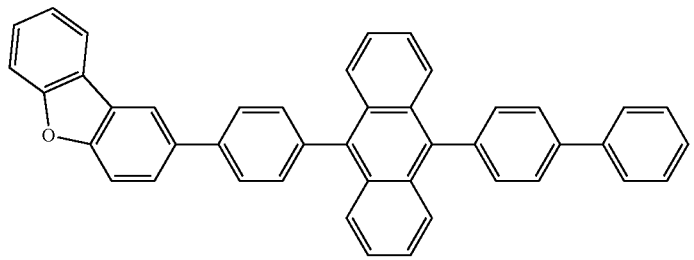
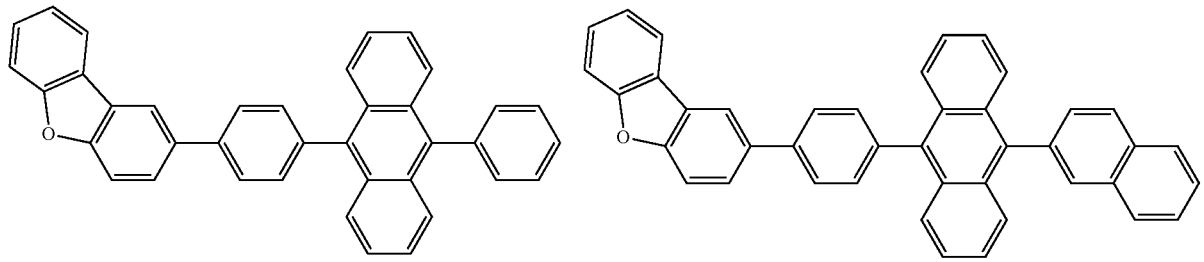
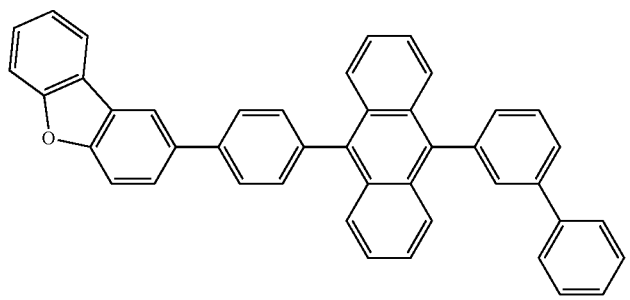
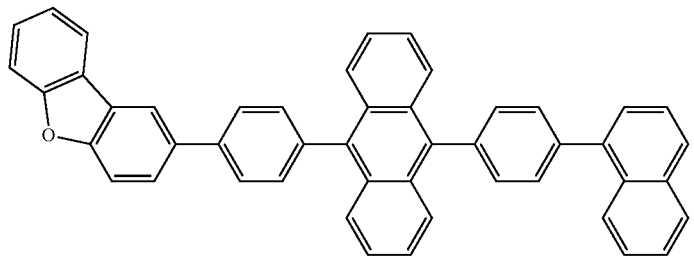
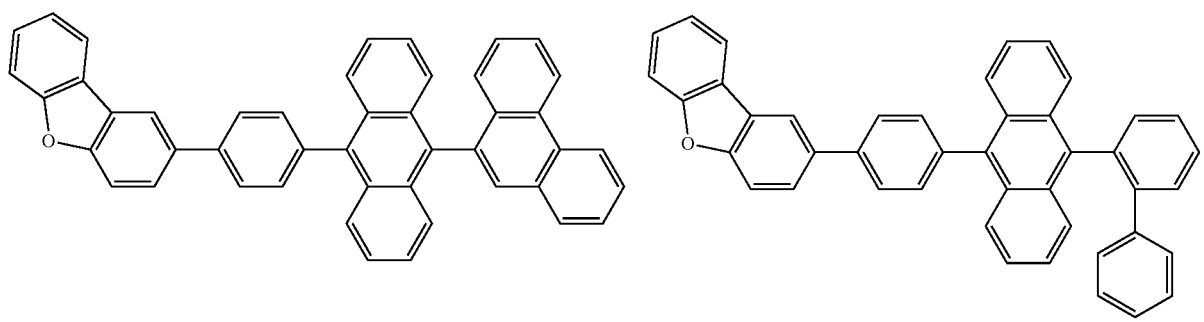

-continued
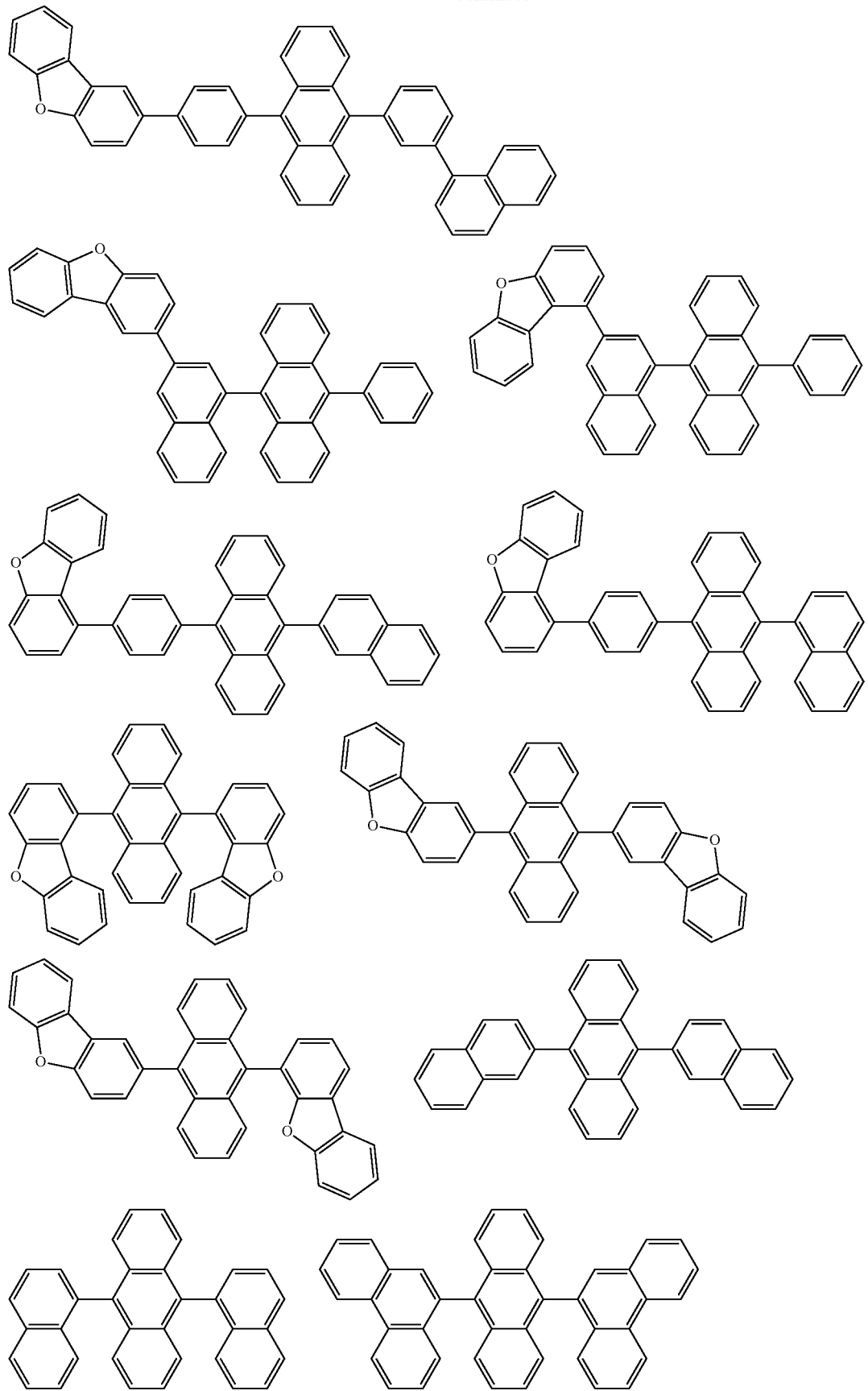

-continued
| 103 | 104 |
|---|---|
| 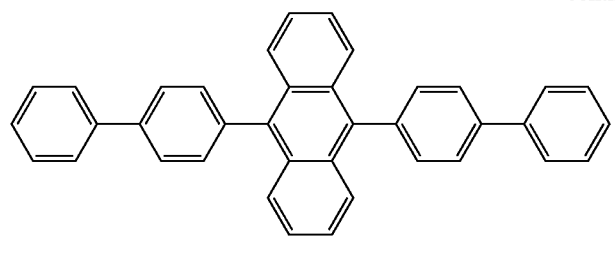 | 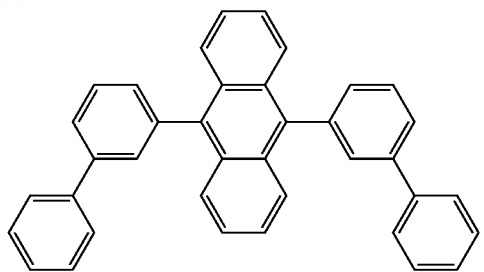 |
| 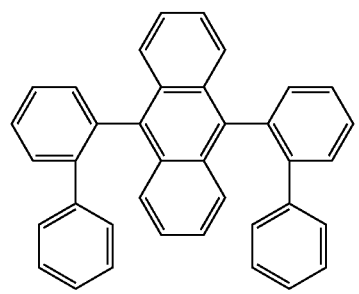 | 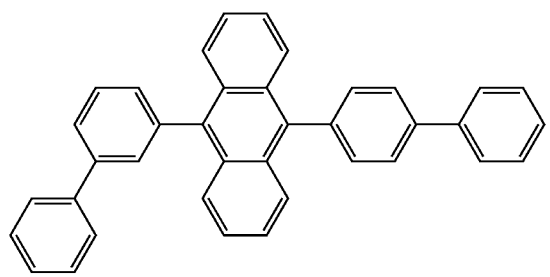 |
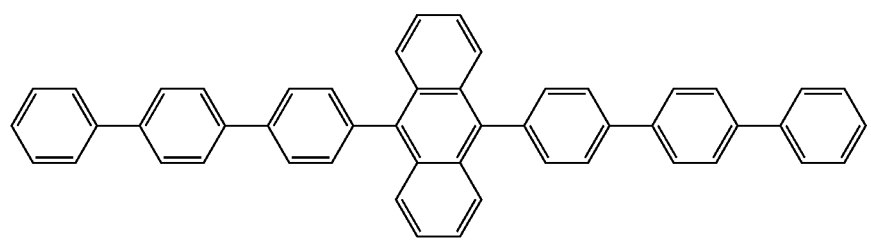
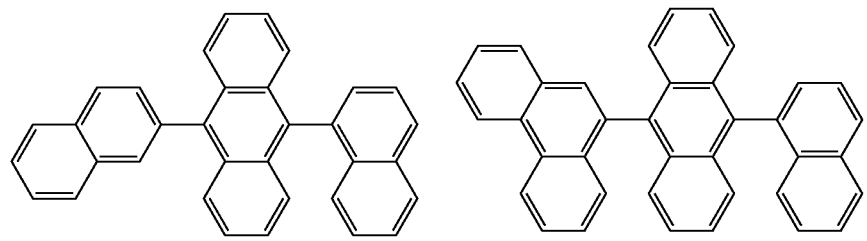
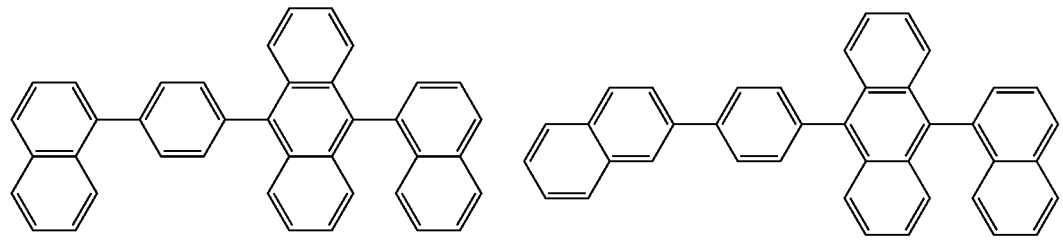
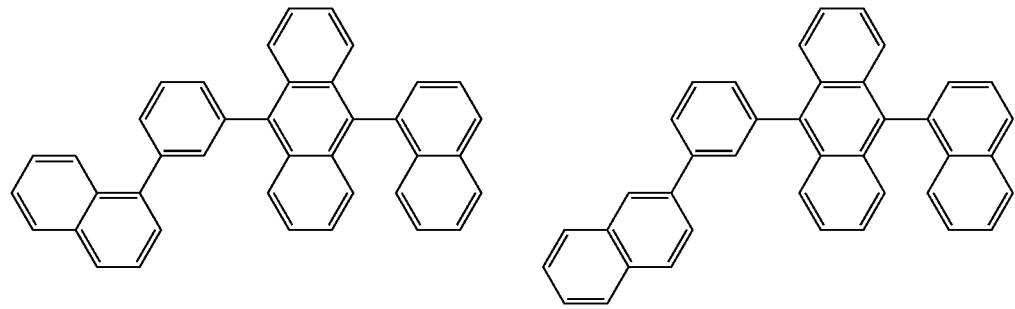

-continued
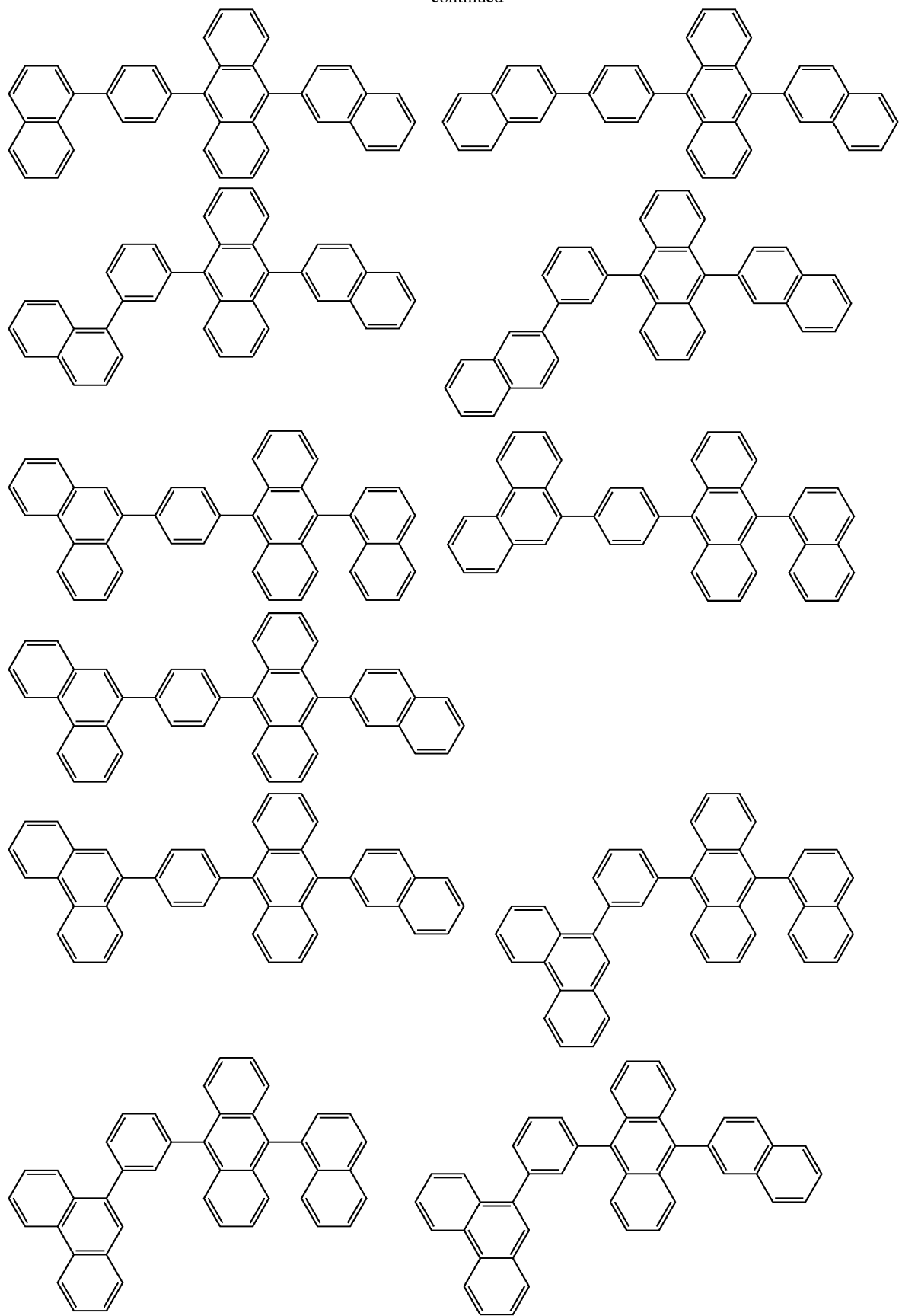

107 108
-continued
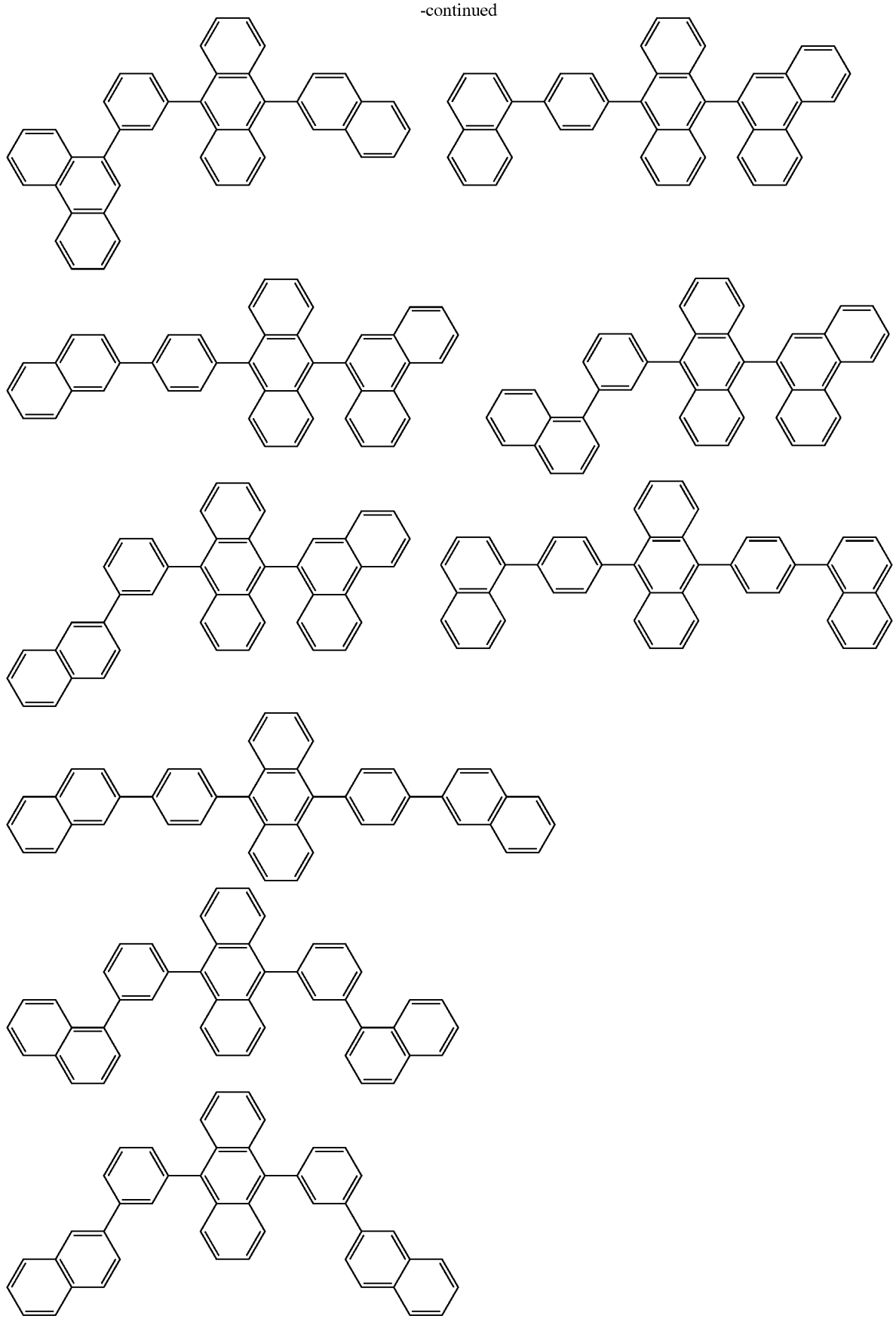

-continued
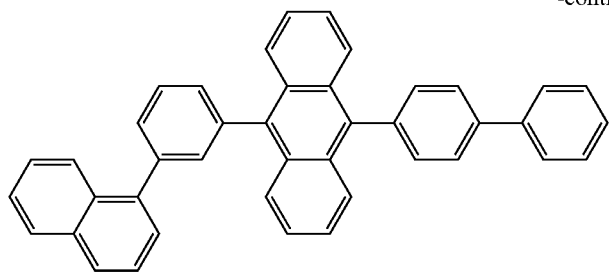
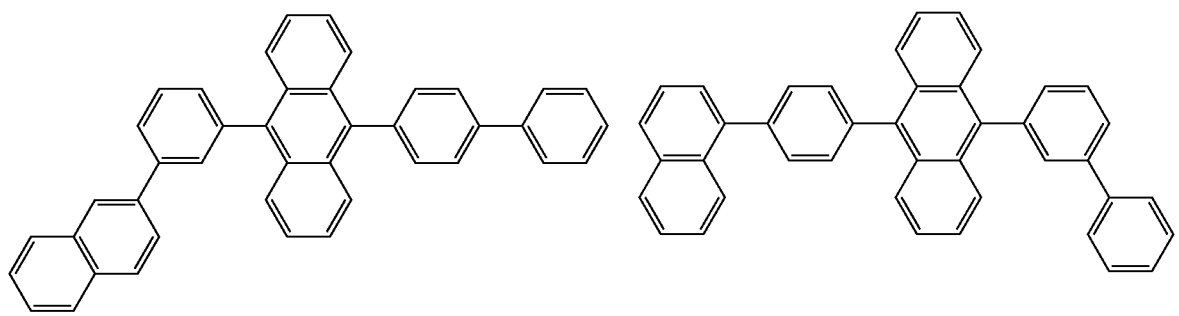
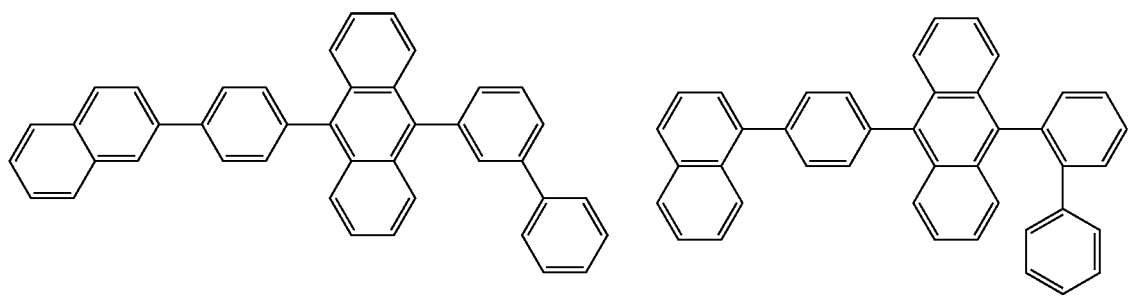
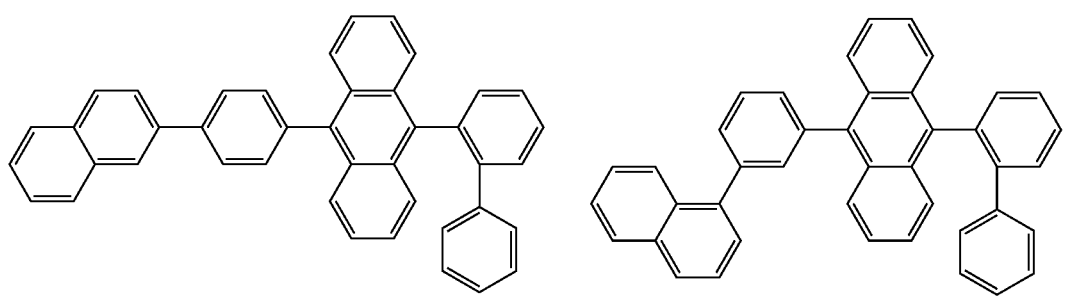
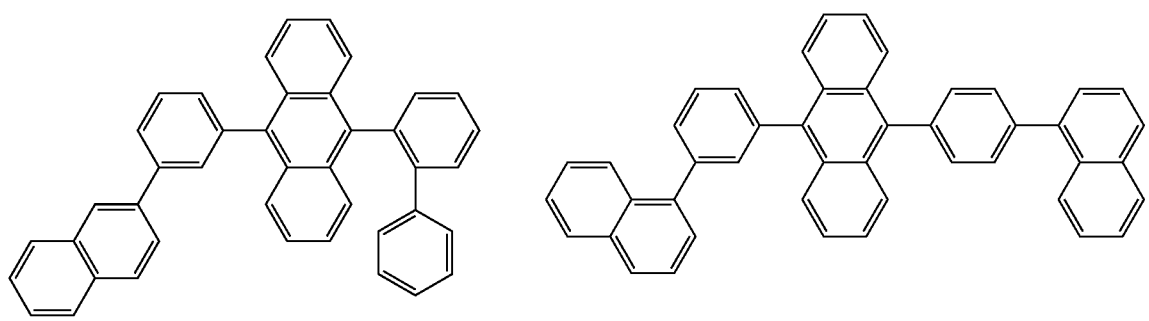

-continued
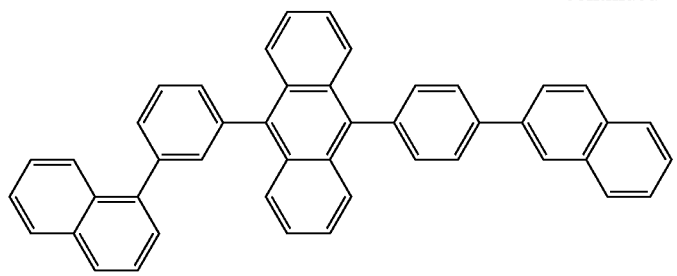
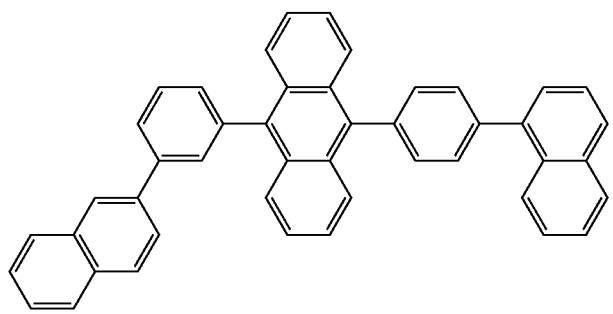
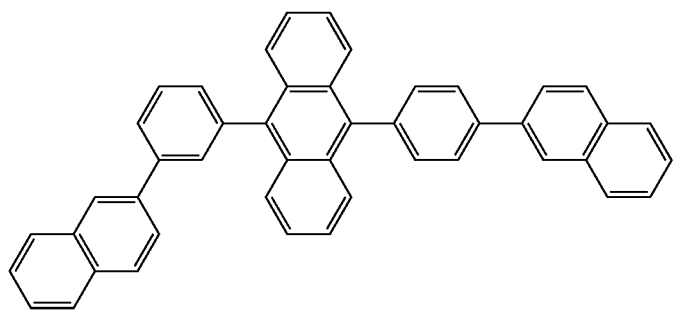
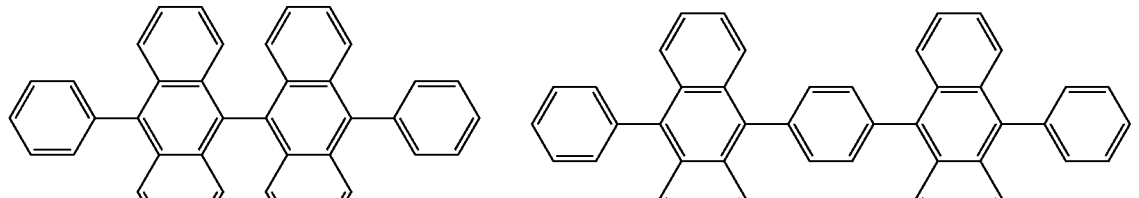
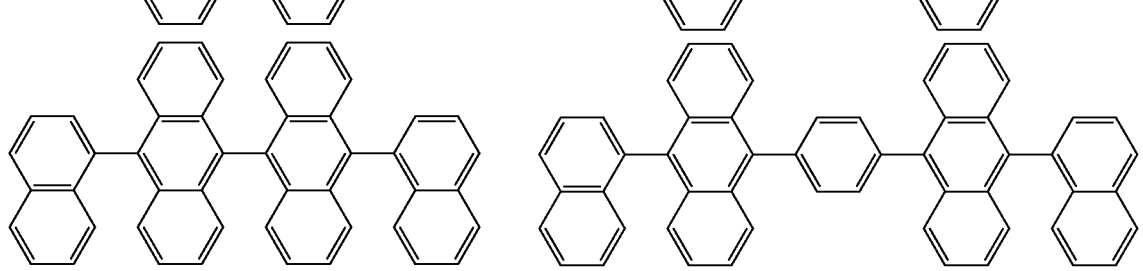
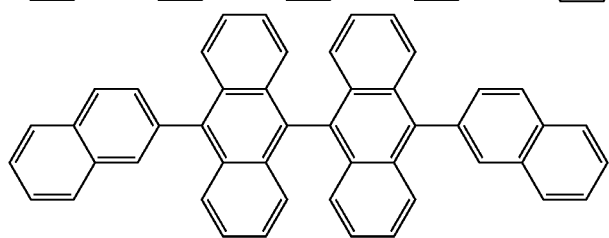

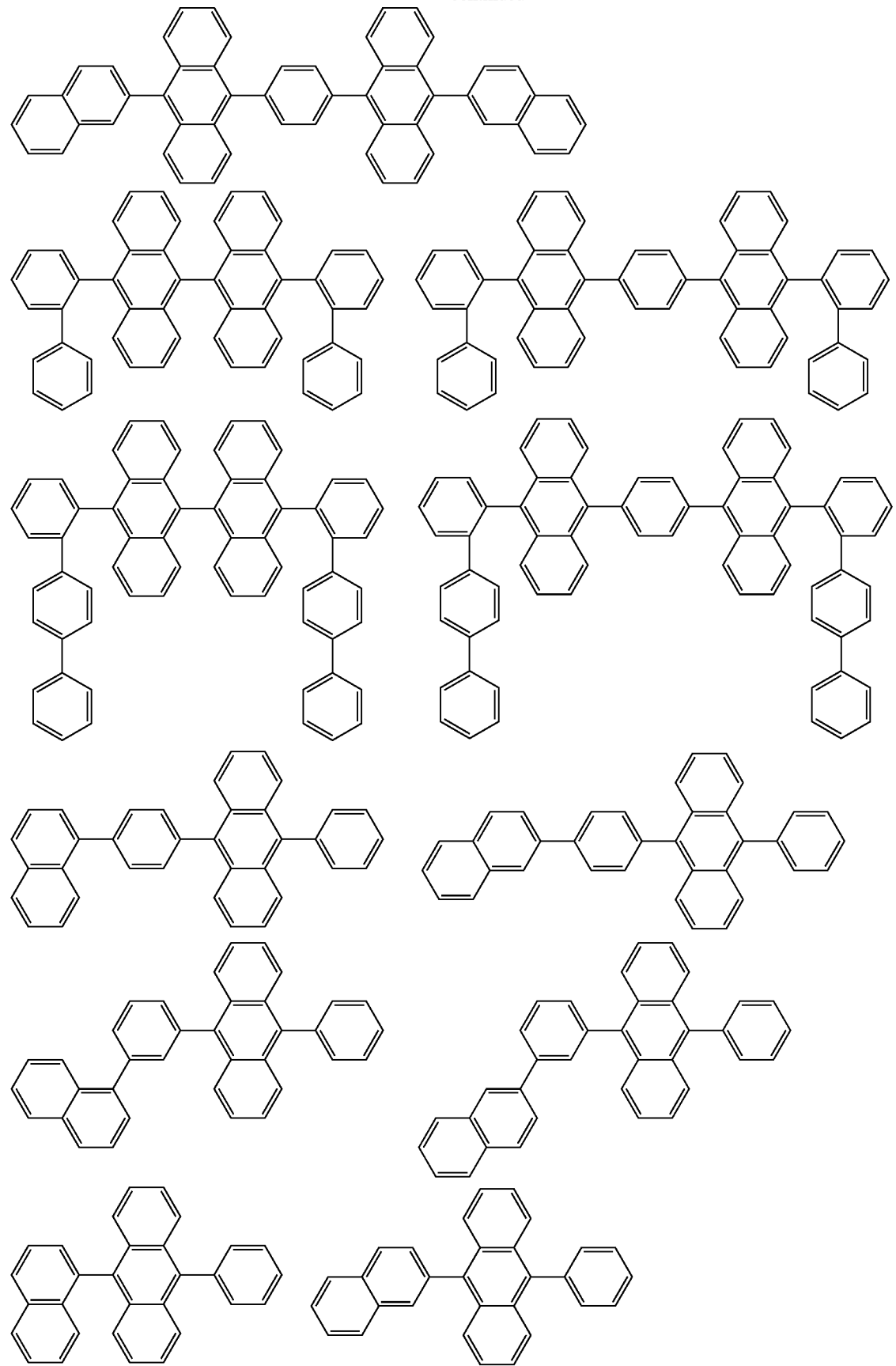
-continued

-continued
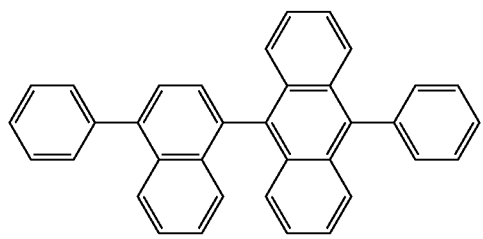
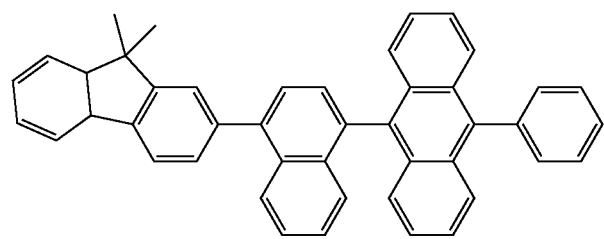
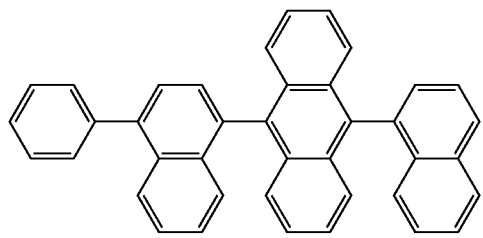
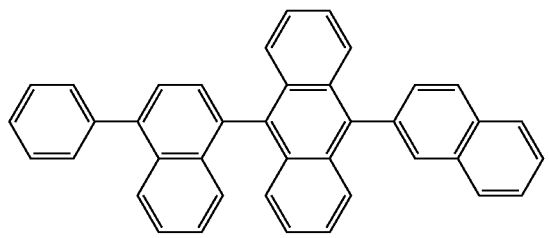
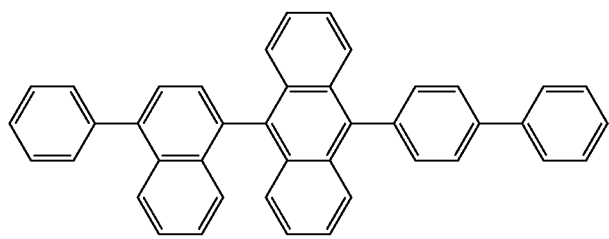
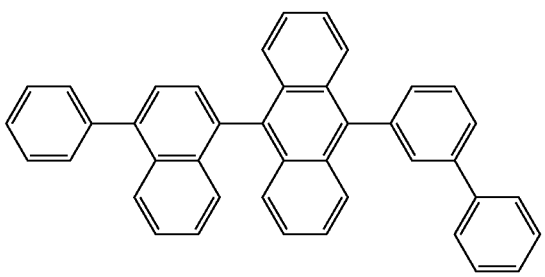
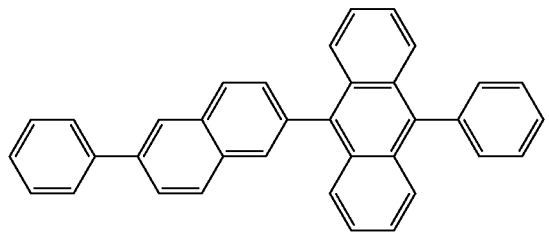
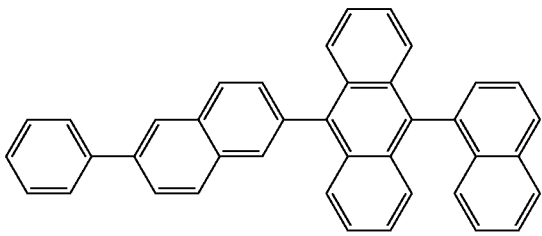
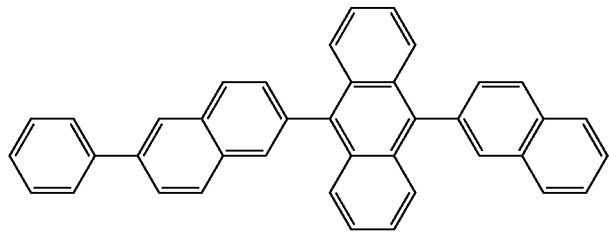
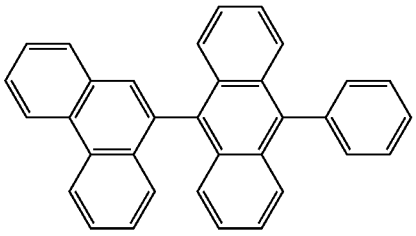
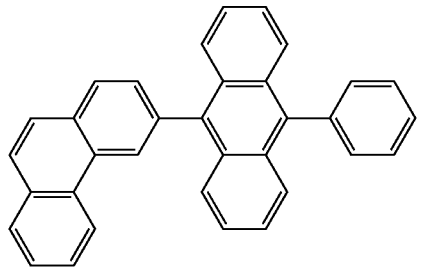
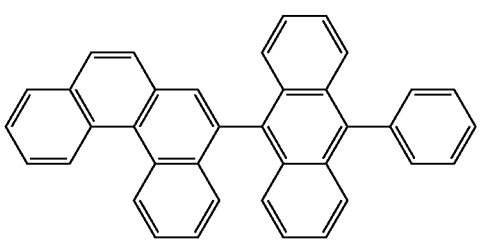

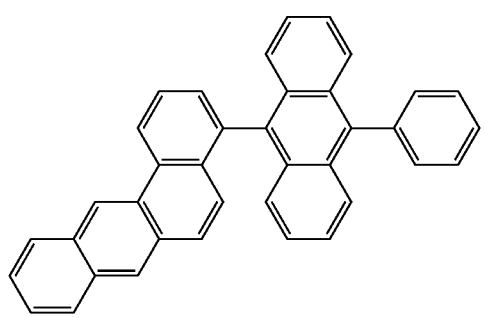
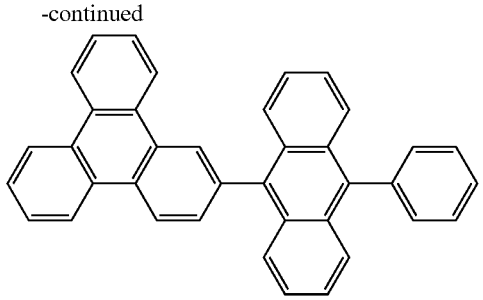
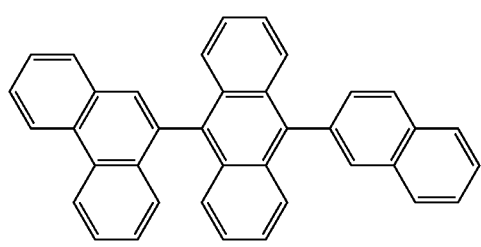
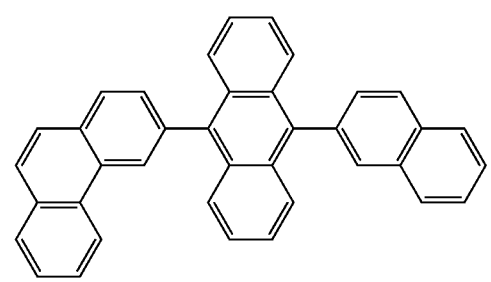
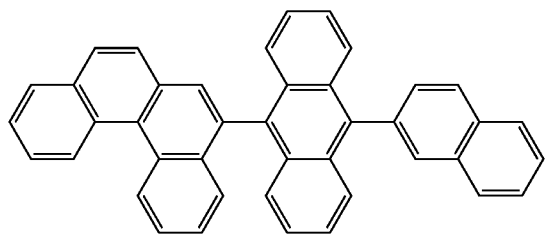
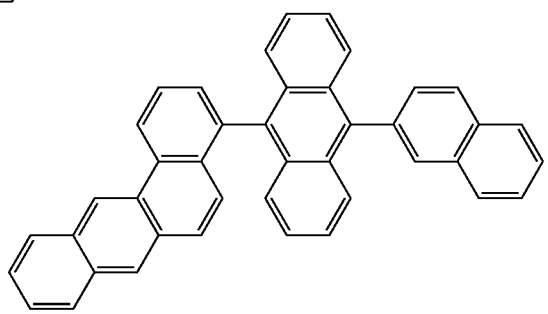
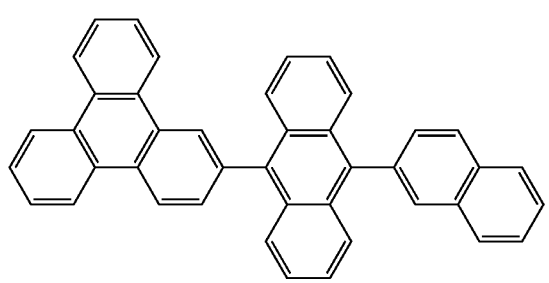
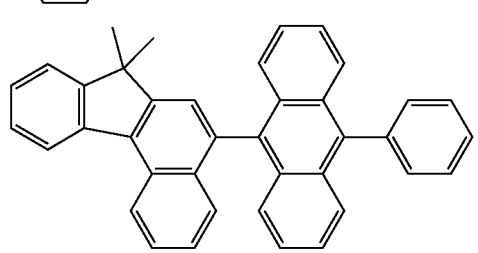
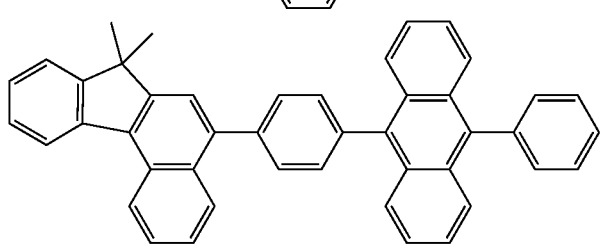
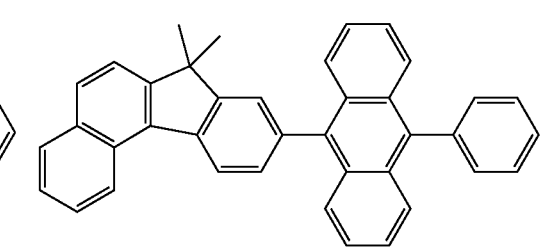
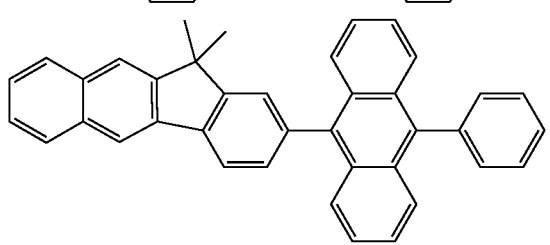
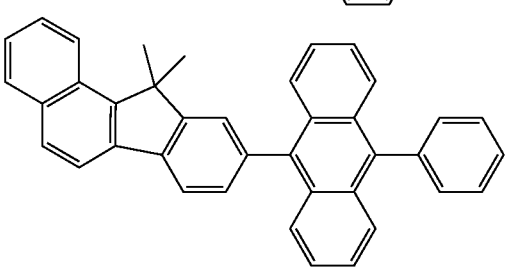

119
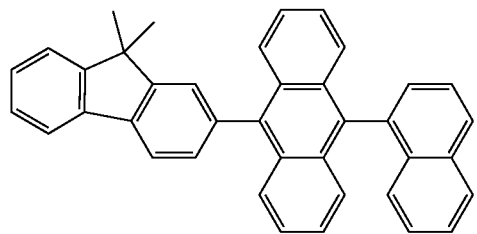
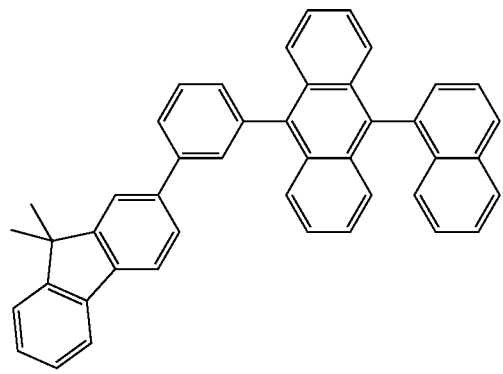
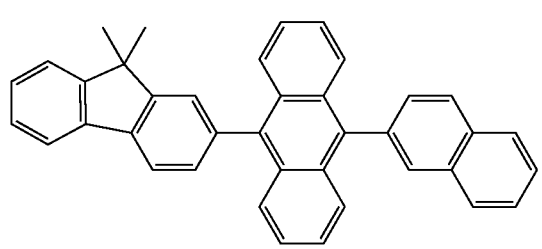
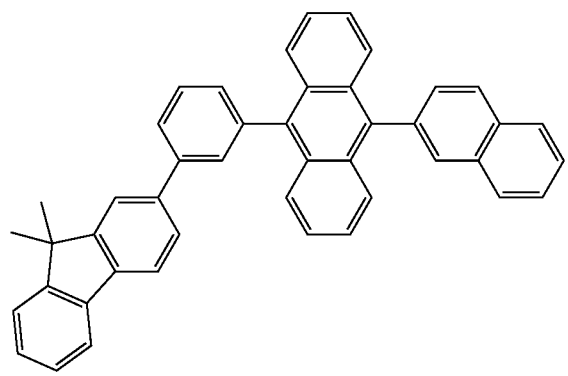
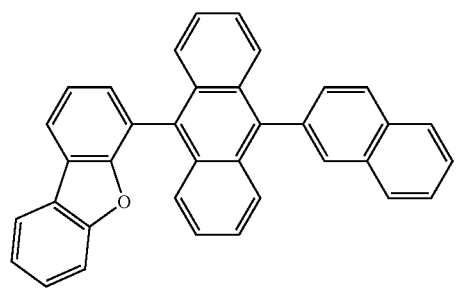
120
-continued
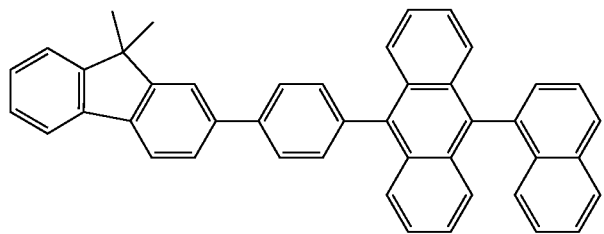
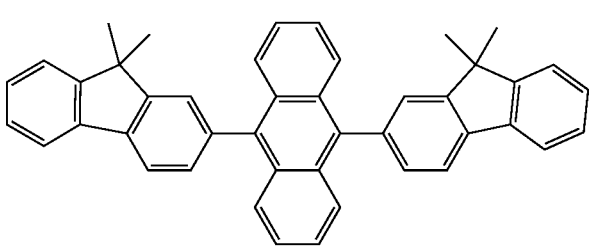
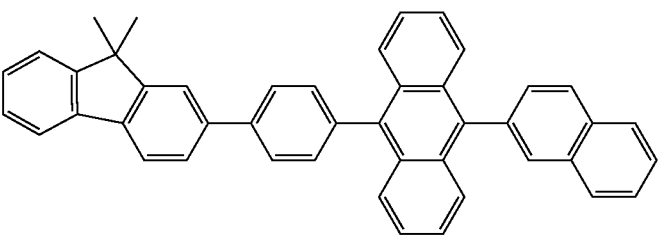
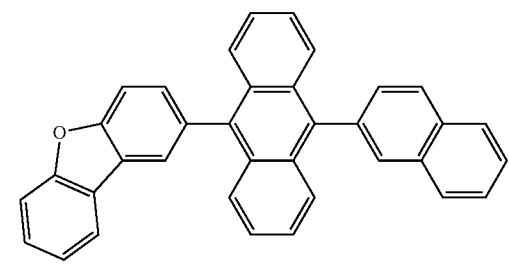
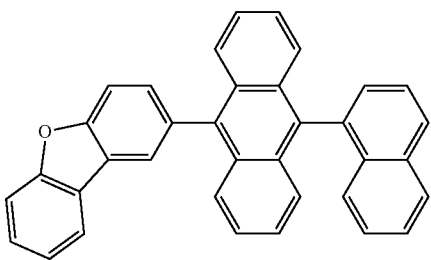

-continued
| 121 | 122 |
|---|---|
| 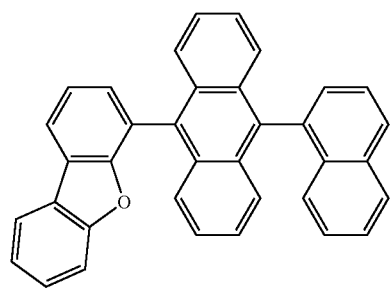 | 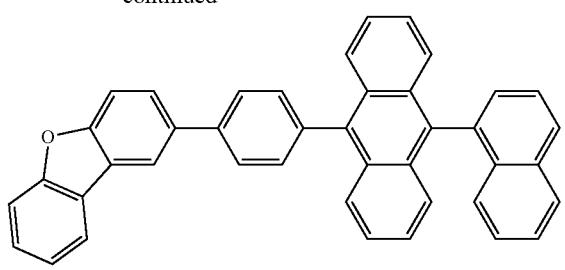 |
| 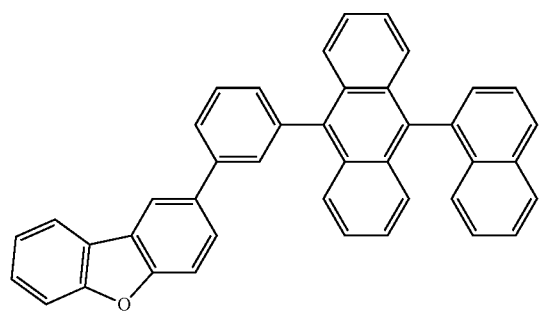 | 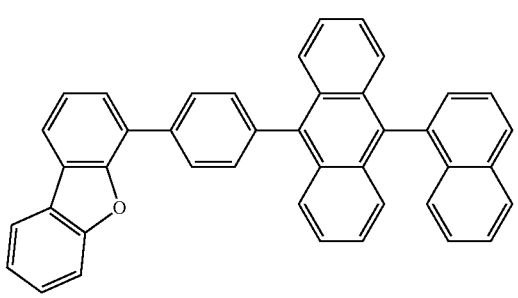 |
| 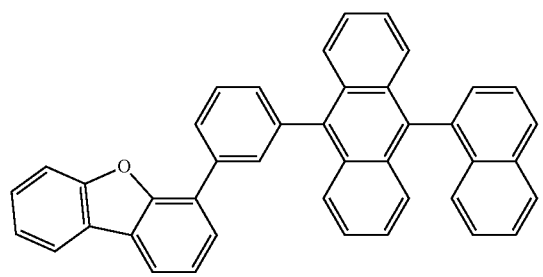 | 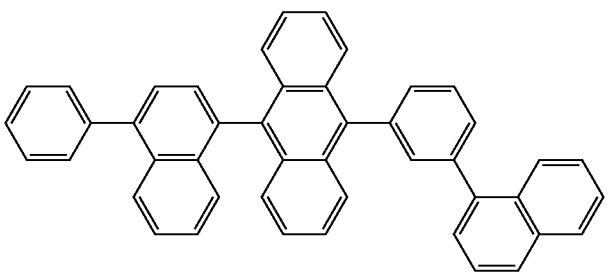 |
| 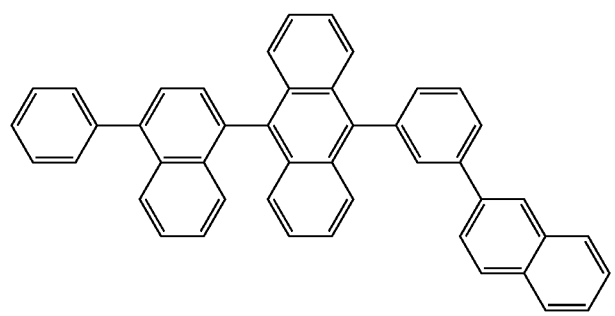 | |
| 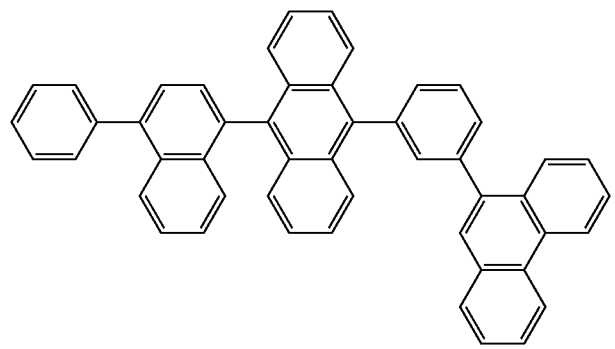 | |

-continued
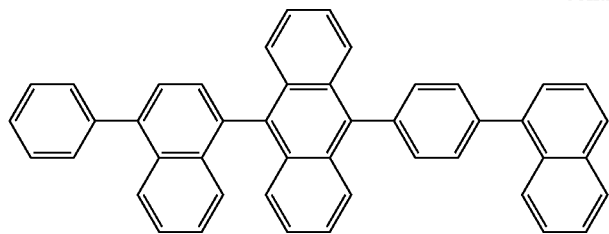
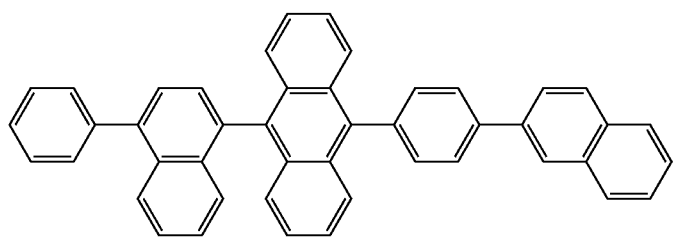
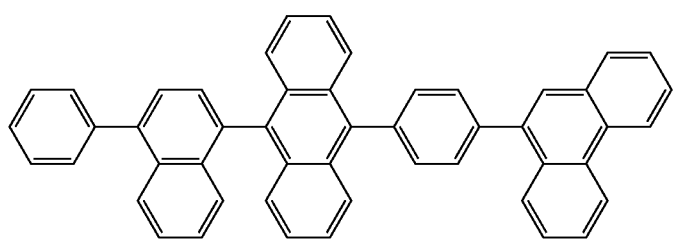
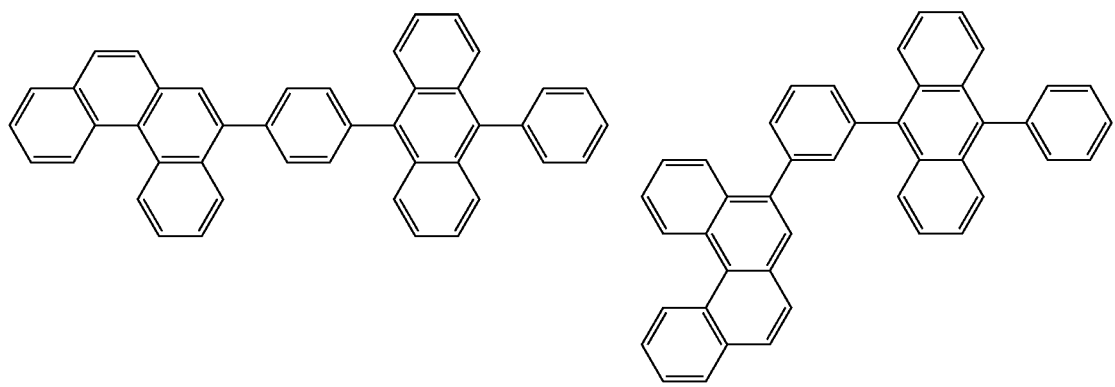
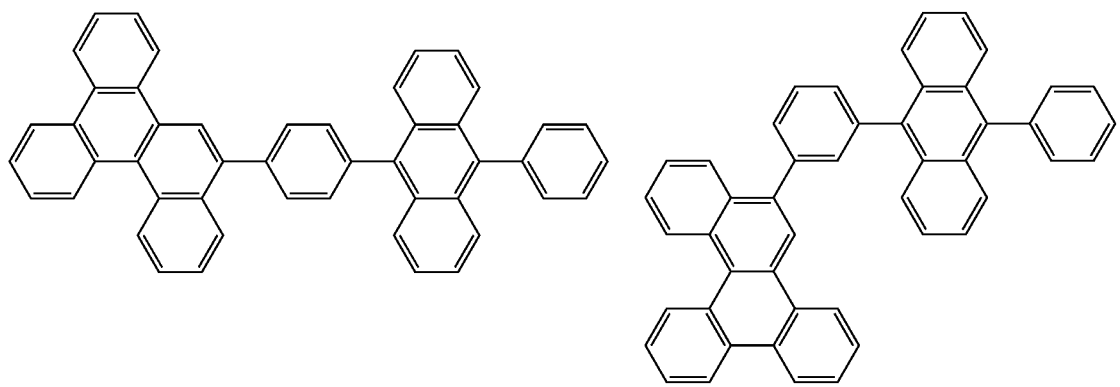

125
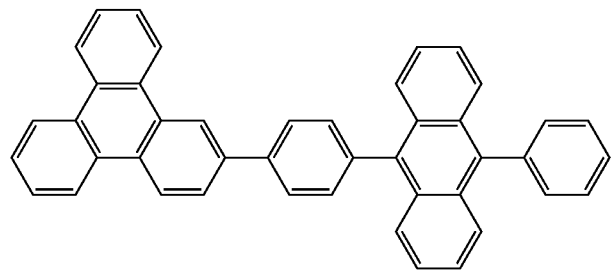
126
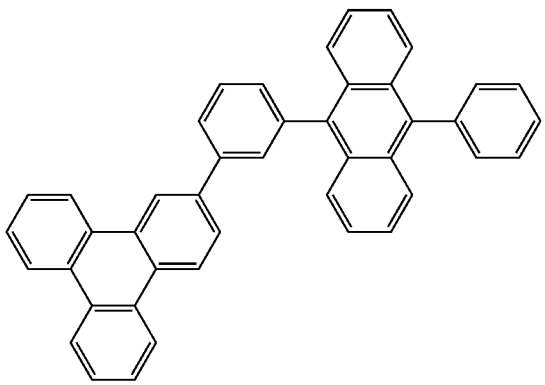
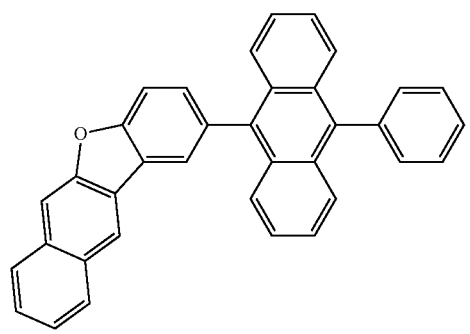
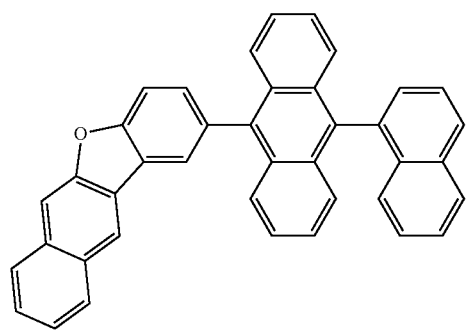
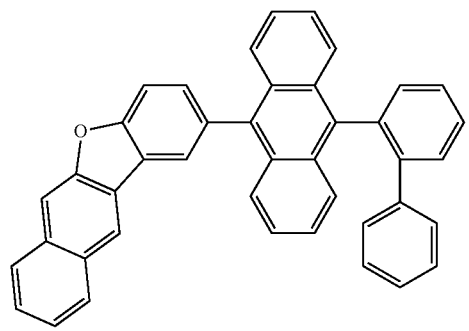
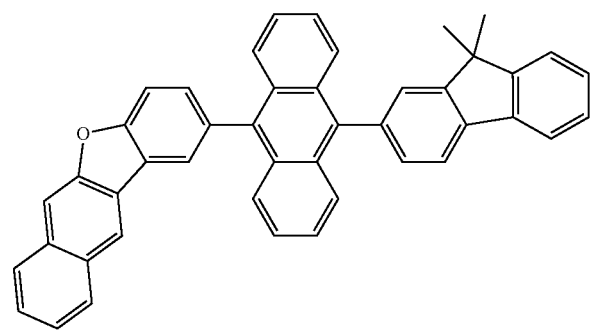
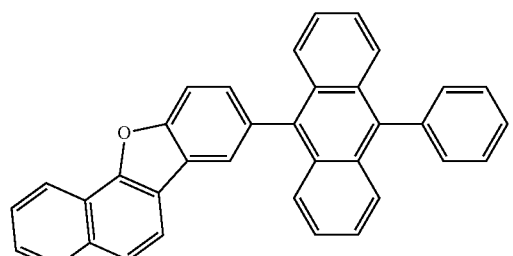
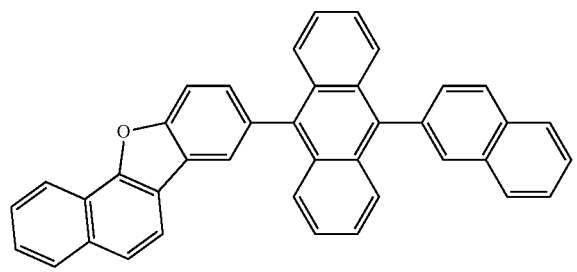
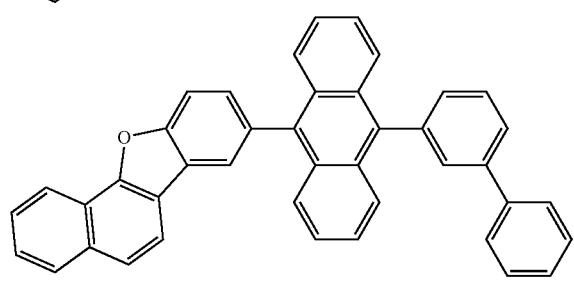
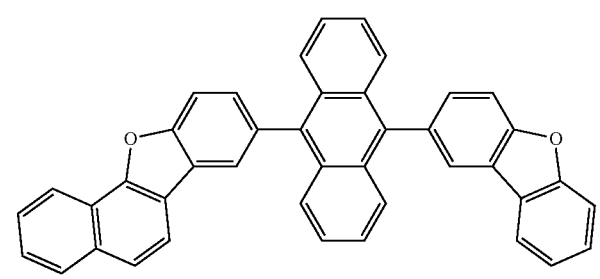

127
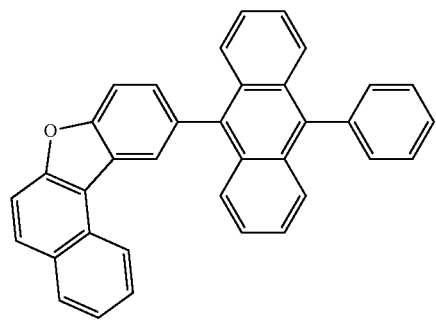
128
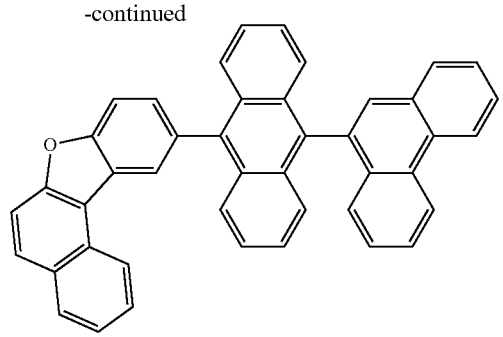
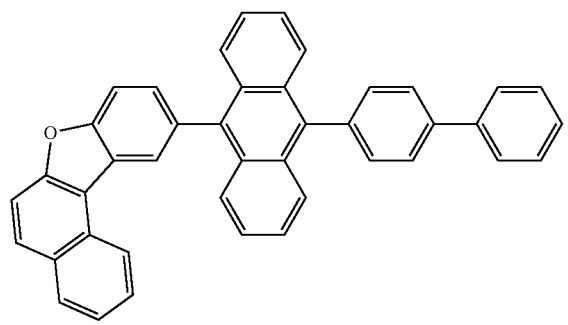
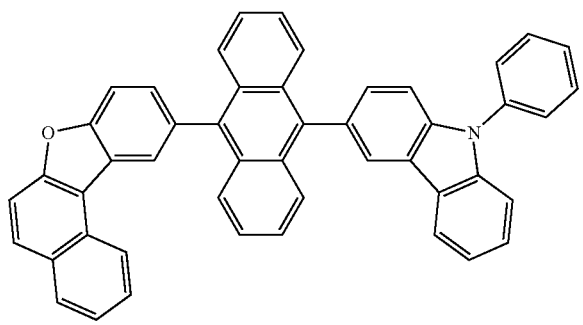
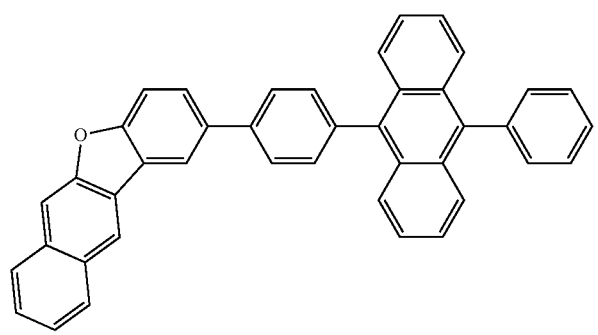
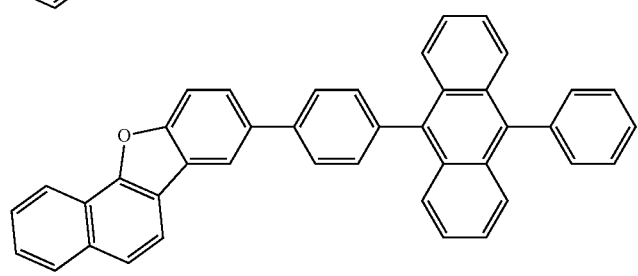
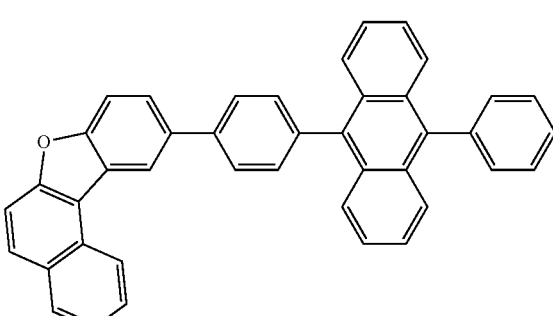
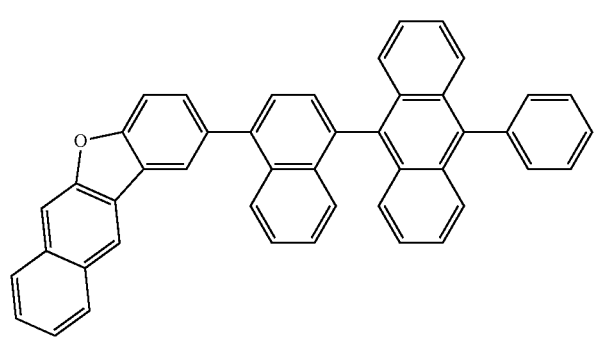
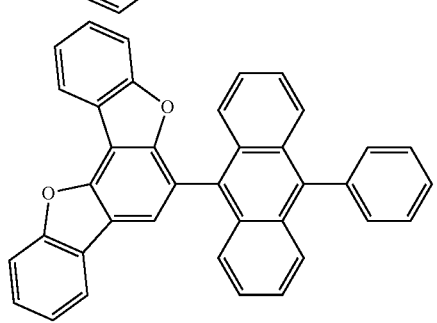

-continued
129
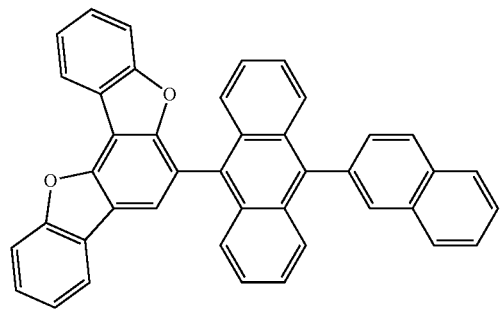
130
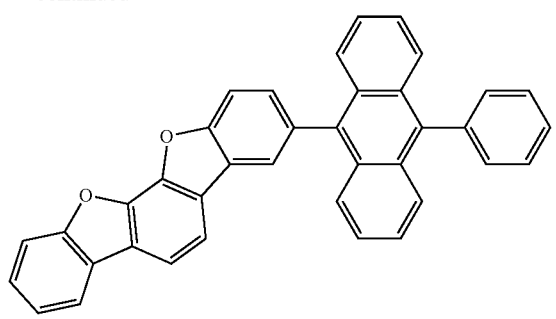
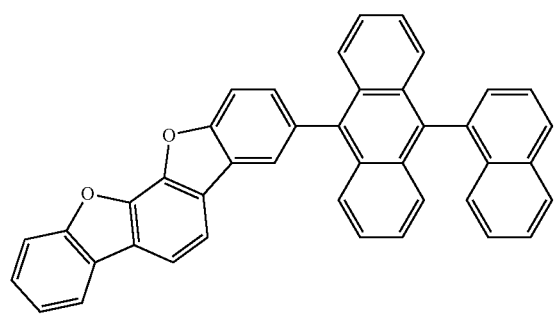
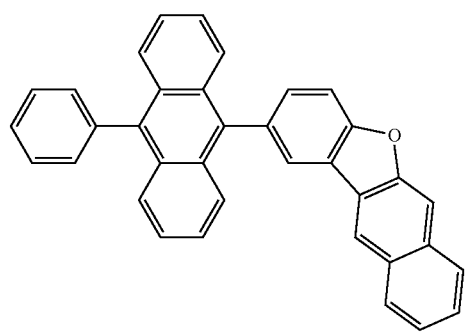
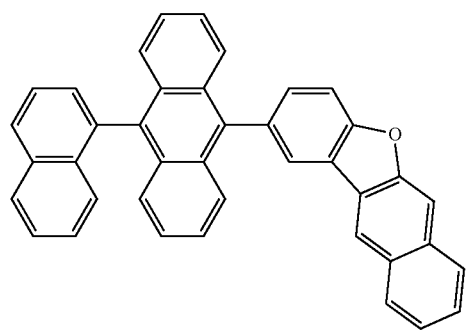
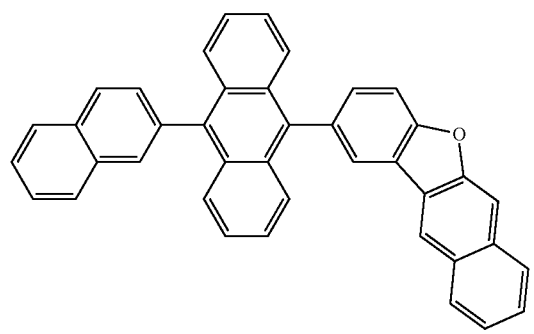
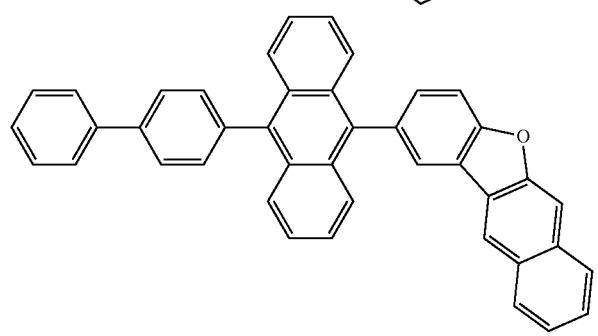
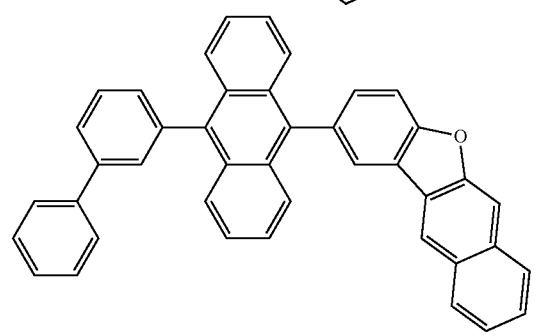
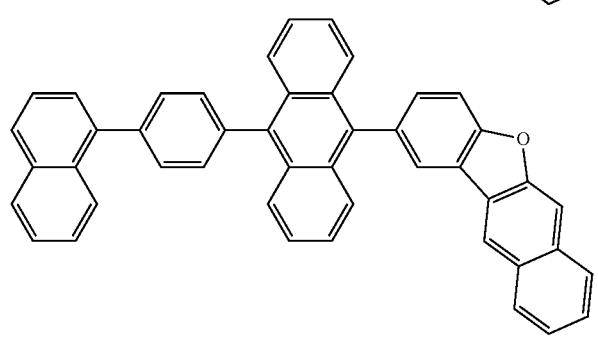
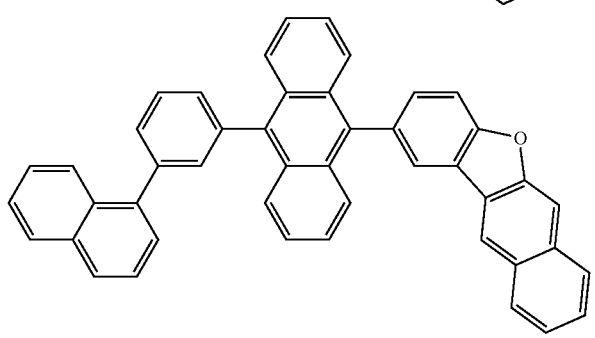

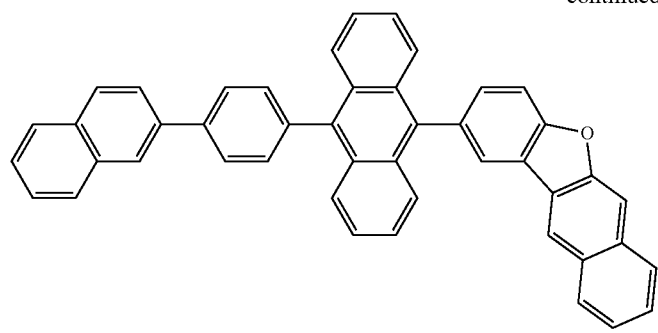
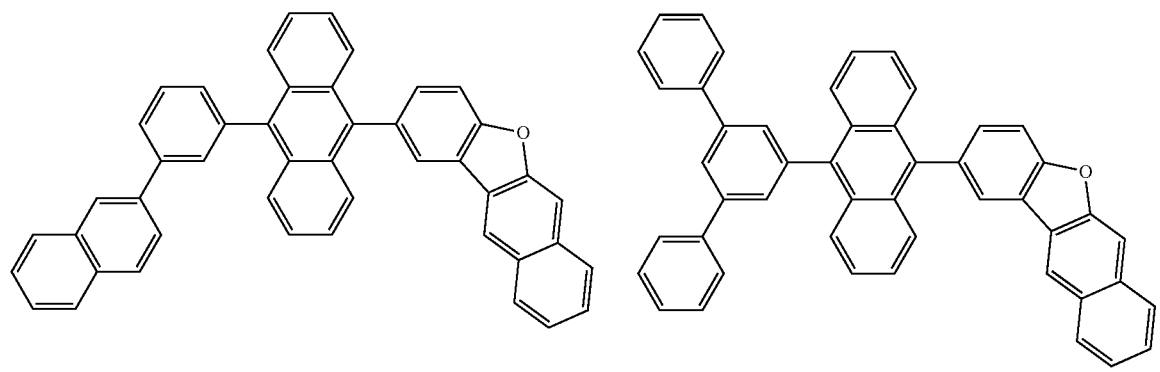
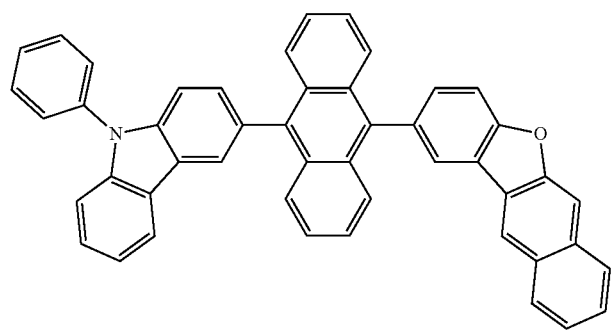
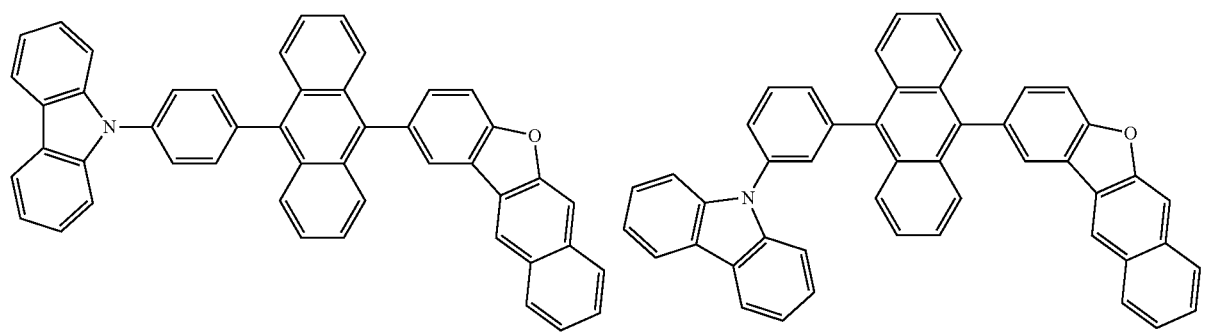
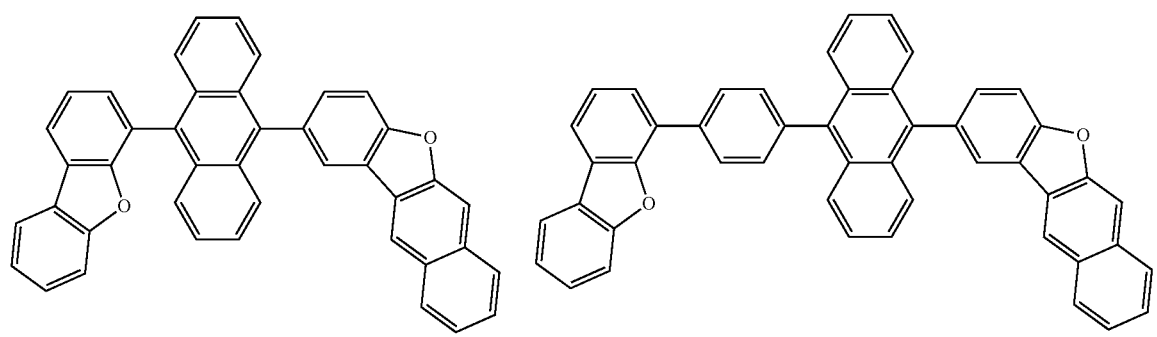

133
134
-continued
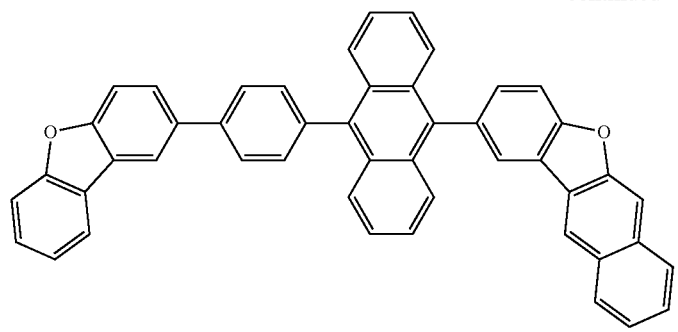
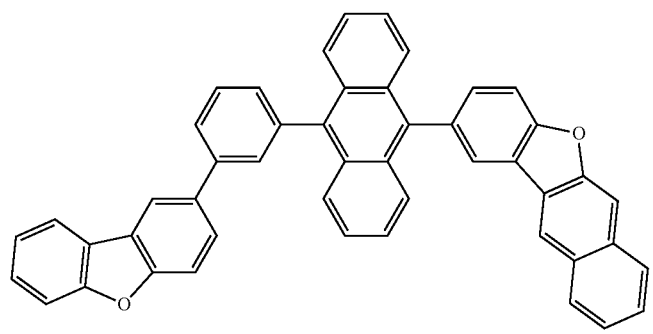
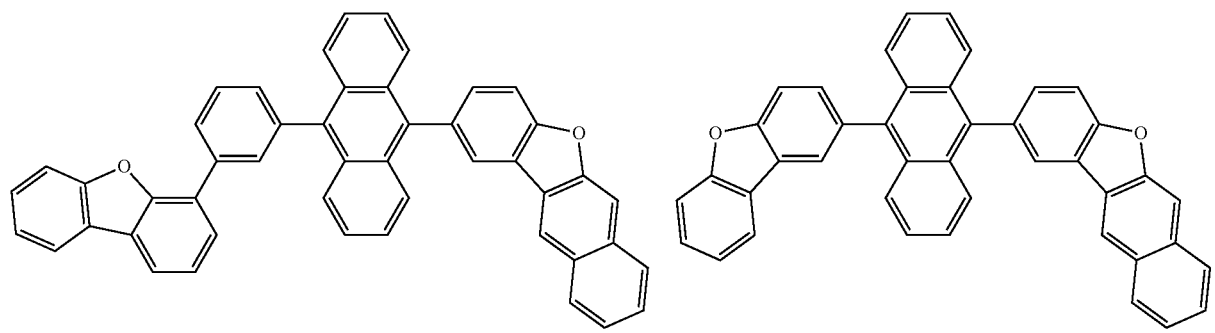
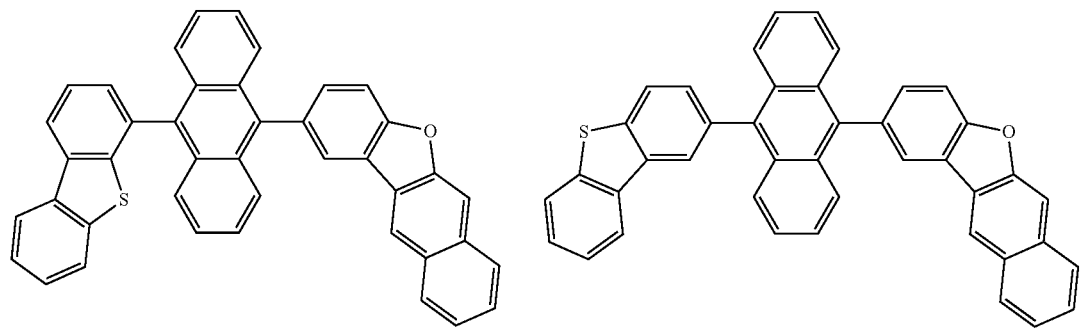
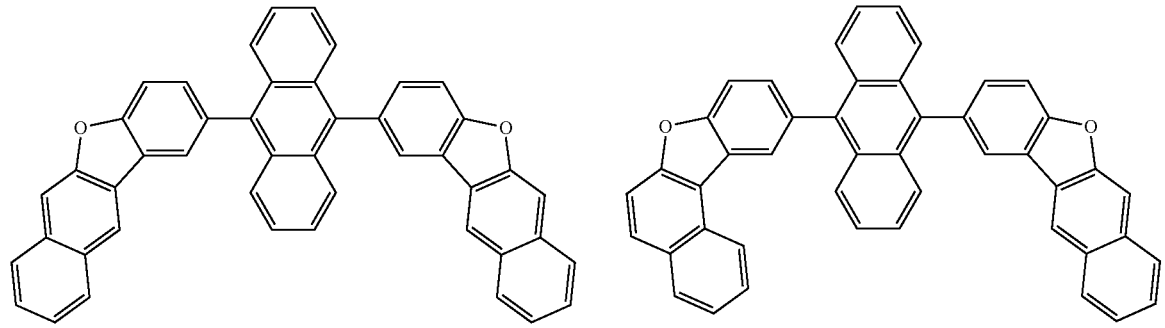

-continued
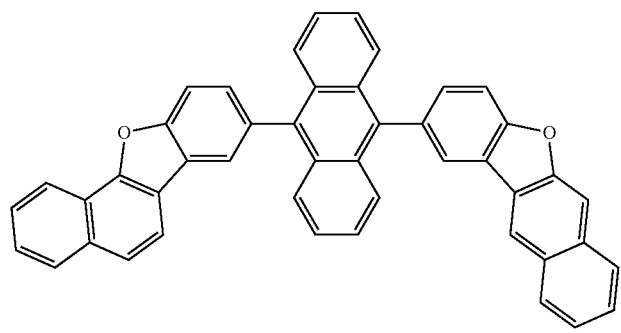
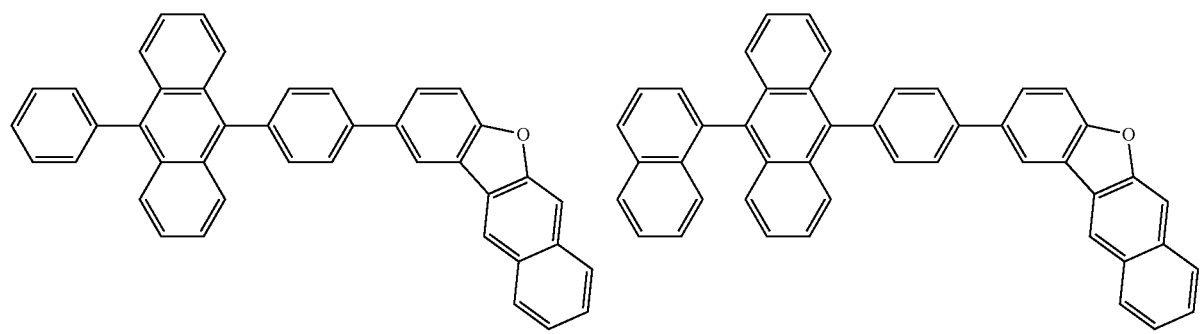
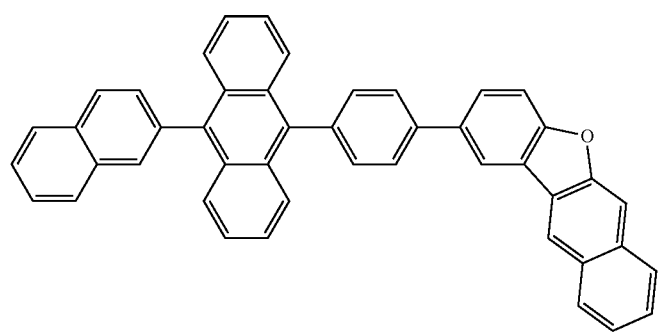
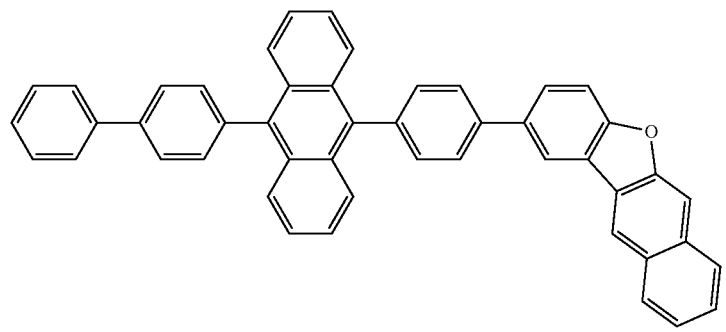
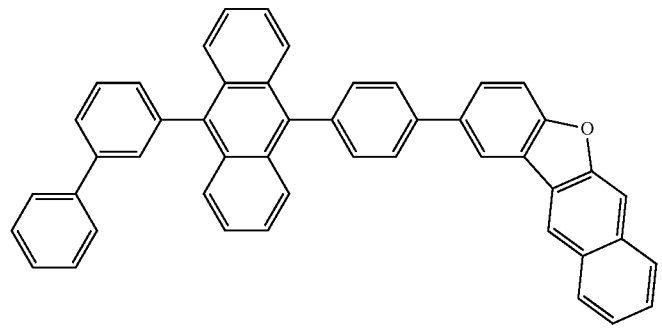

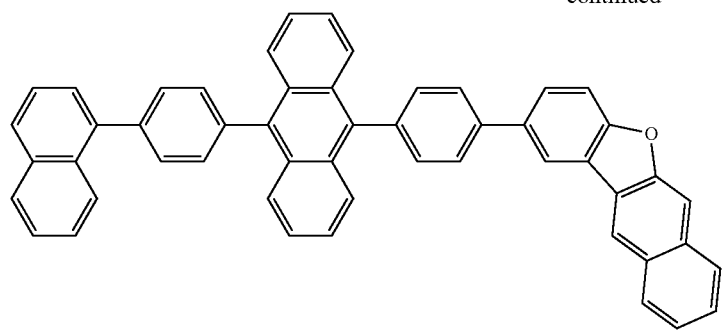

-continued
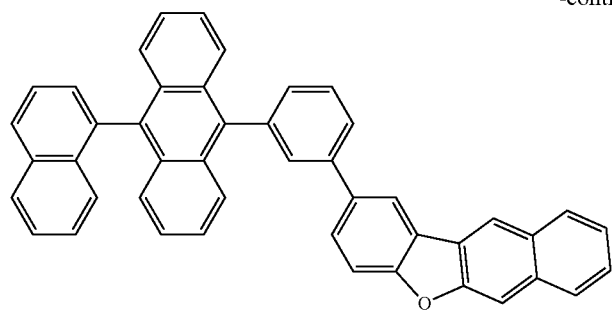
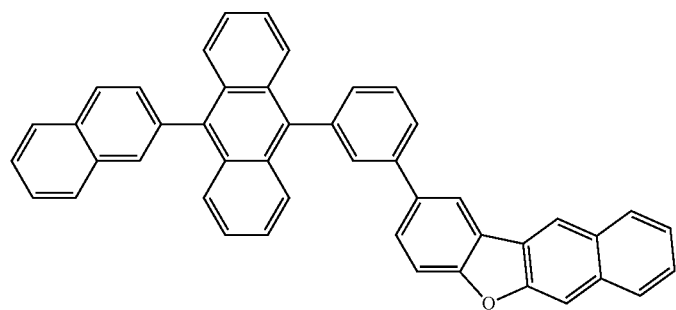
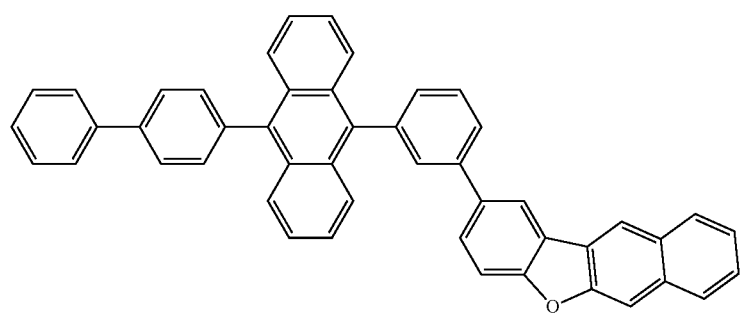
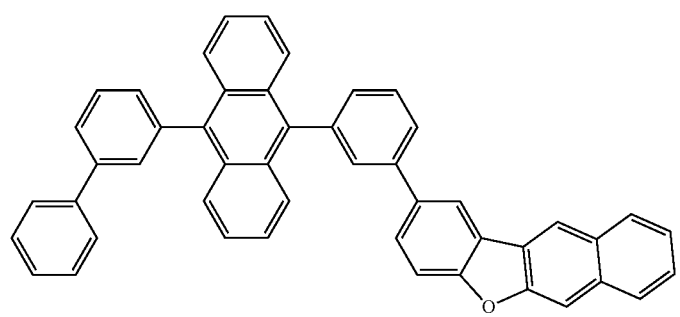
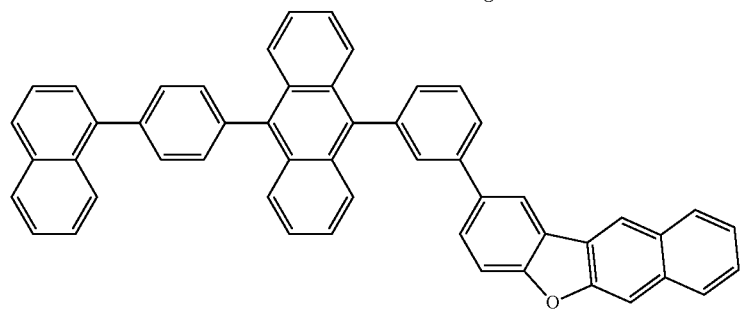

-continued
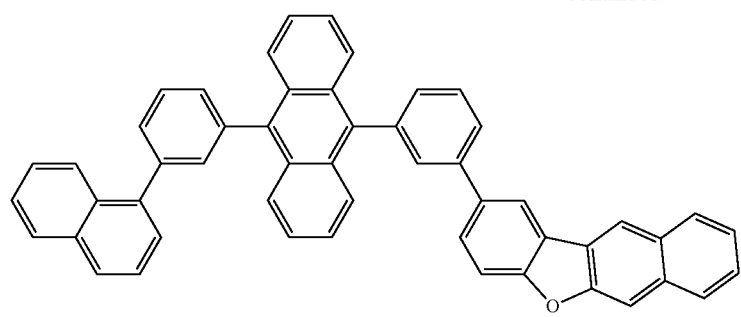
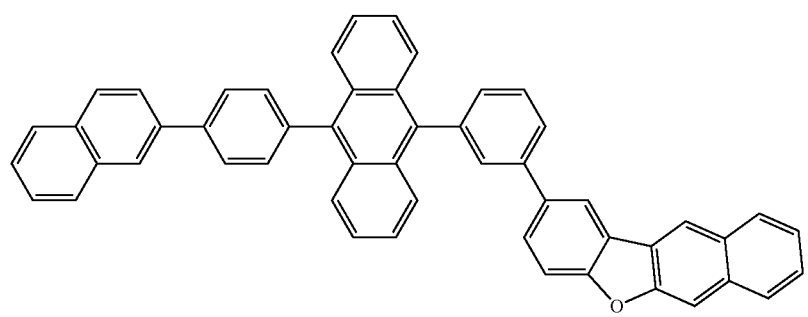
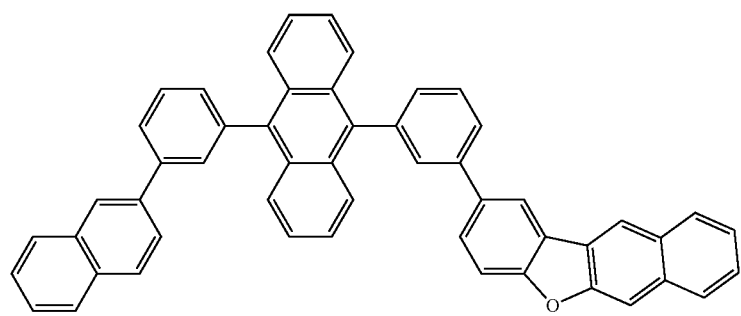
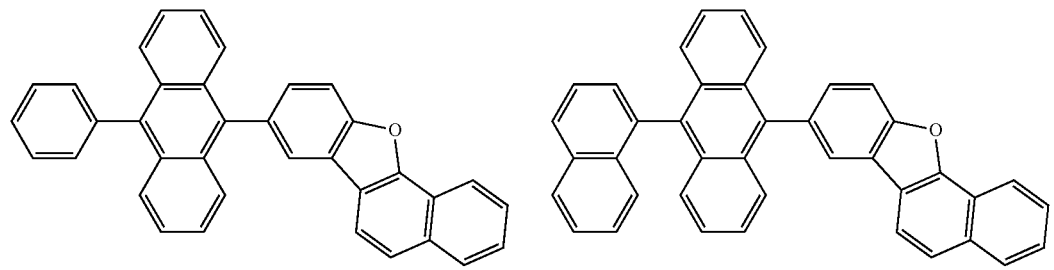
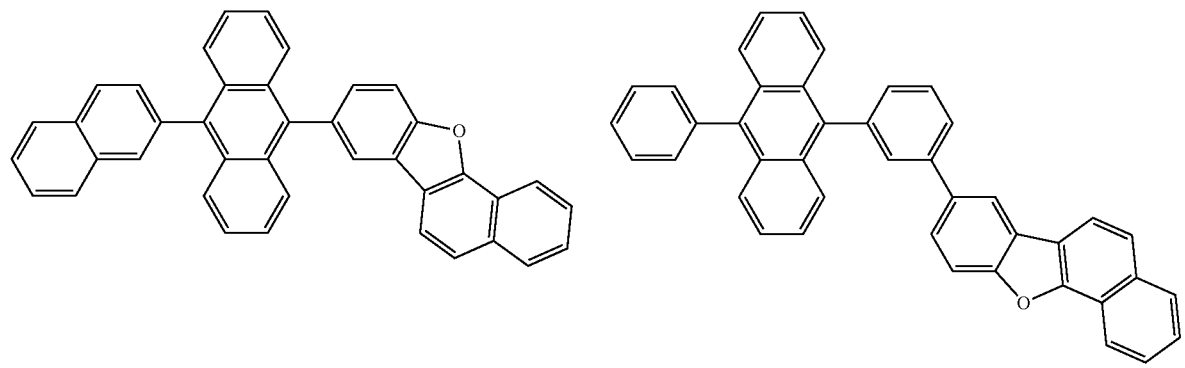

-continued
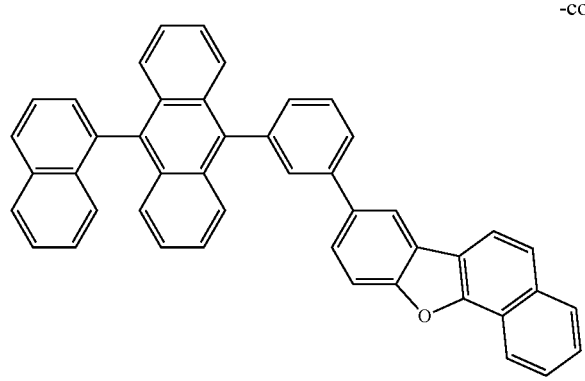
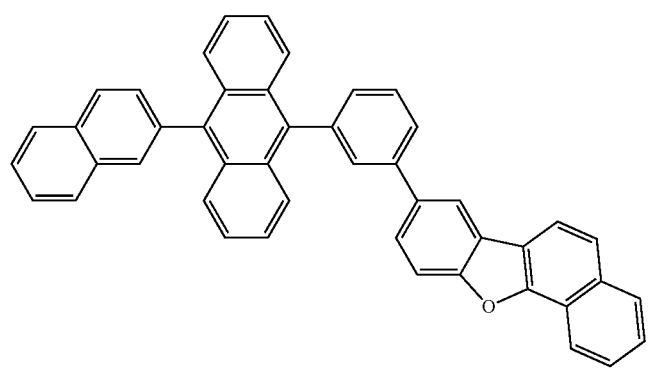
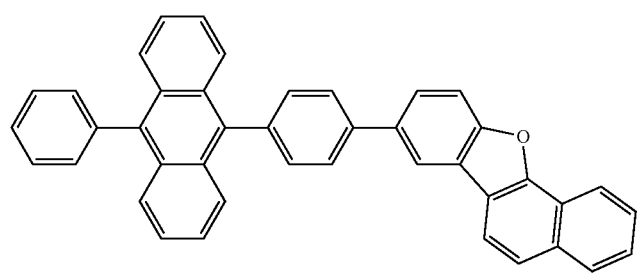
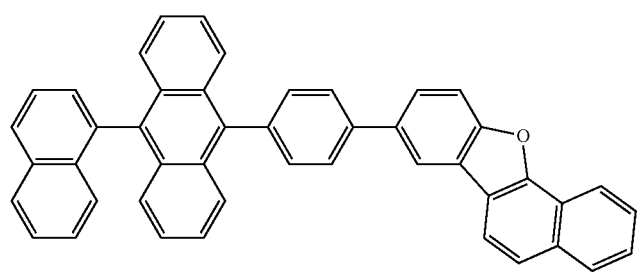
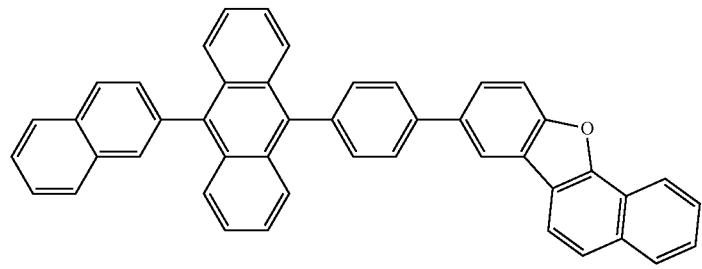

145 146
-continued
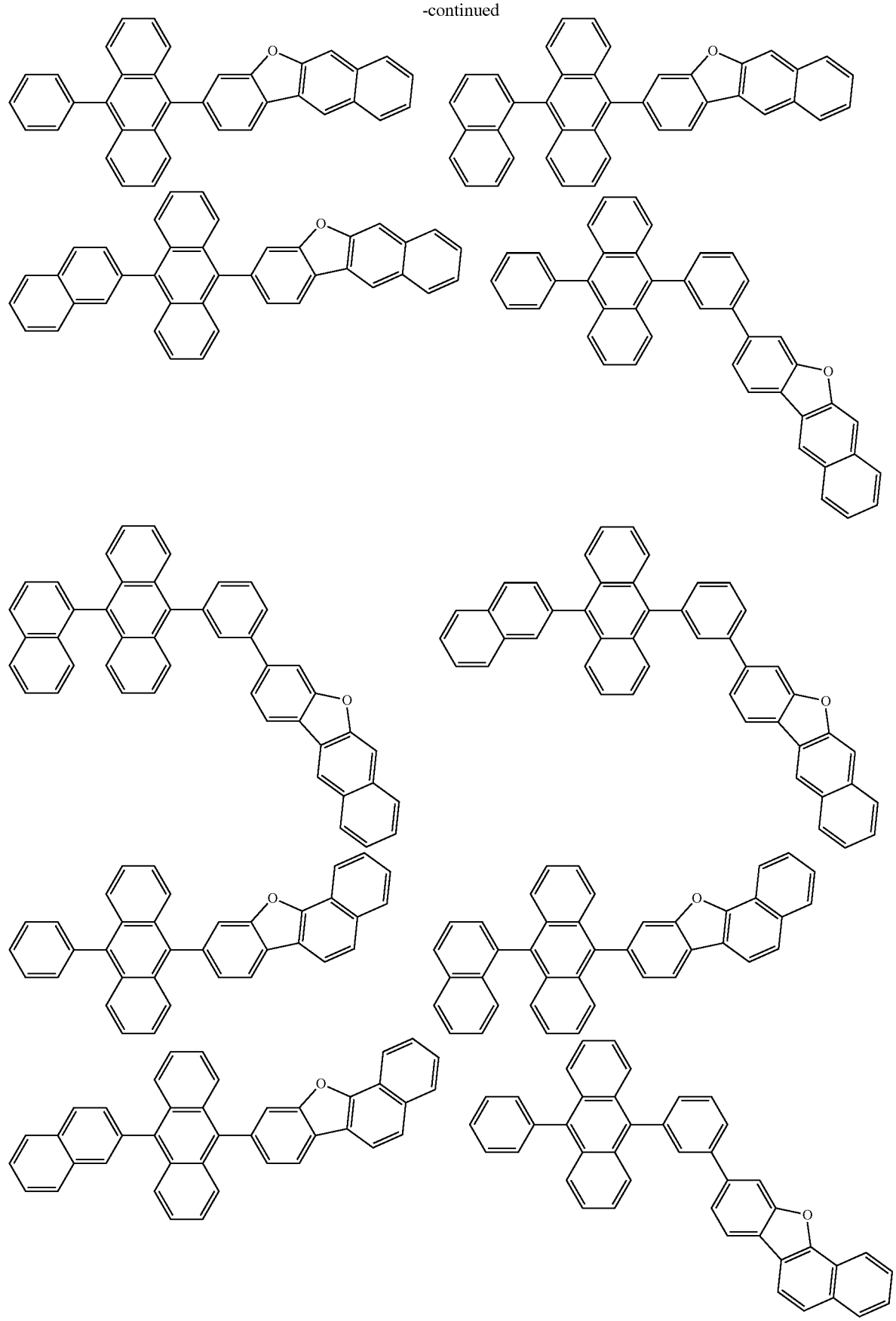

-continued
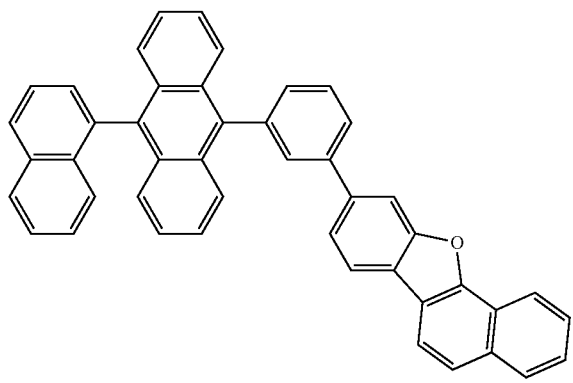
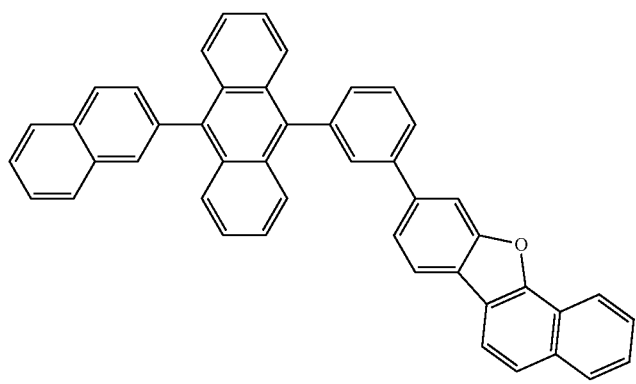
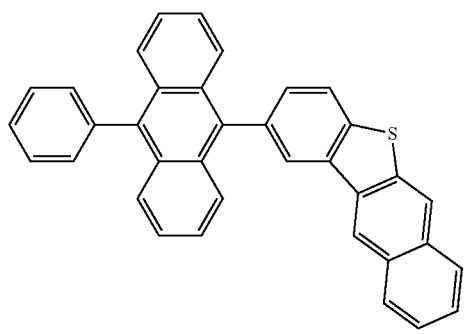
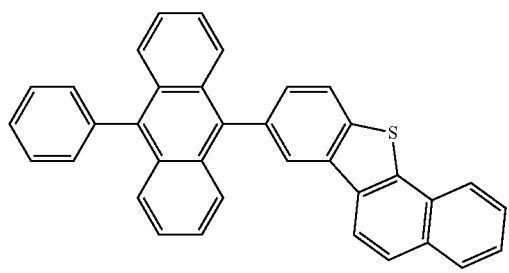
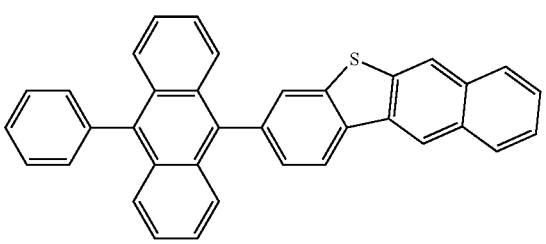
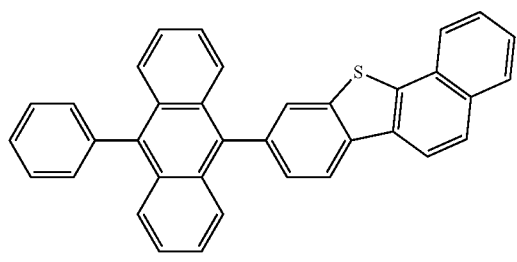
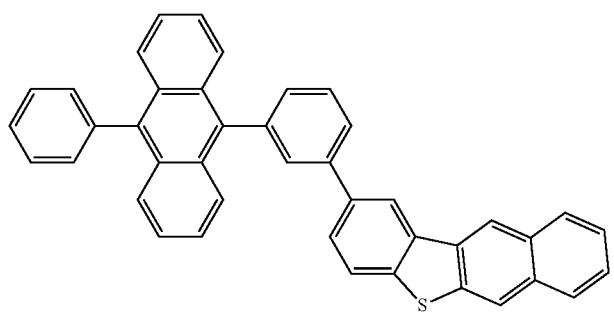
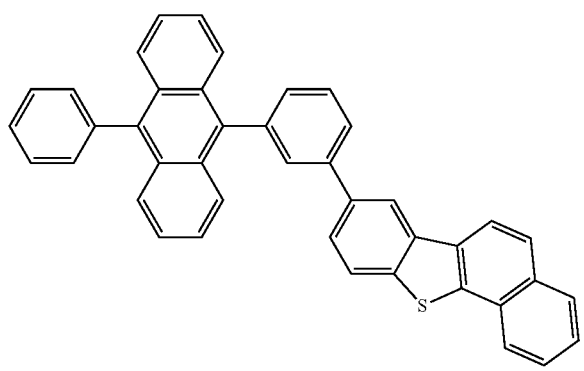
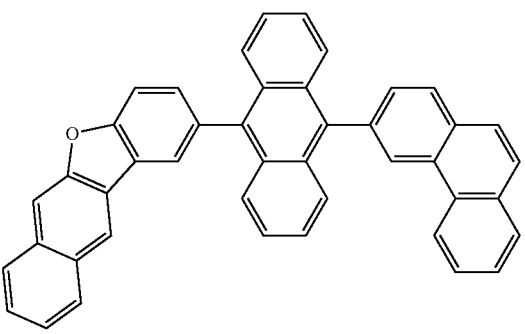

-continued
| 149 | 150 |
|---|---|
| 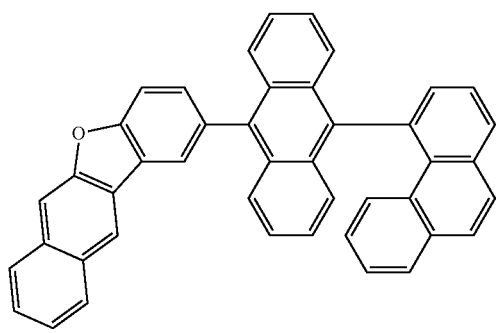 | 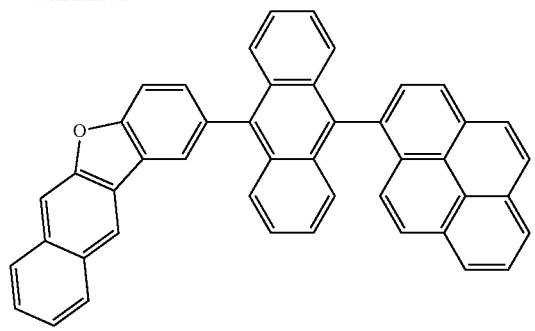 |
| 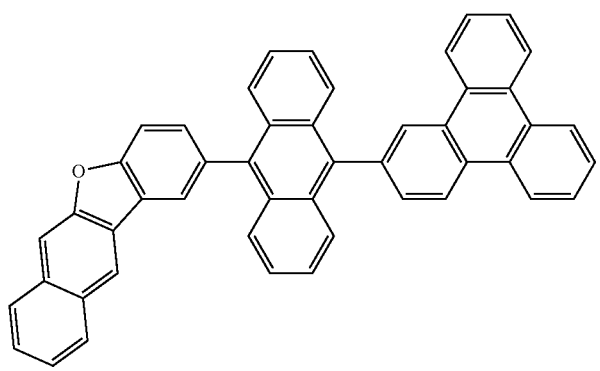 | 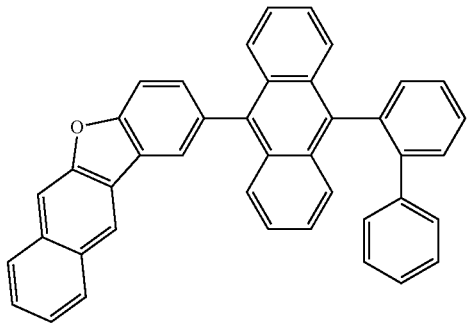 |
| 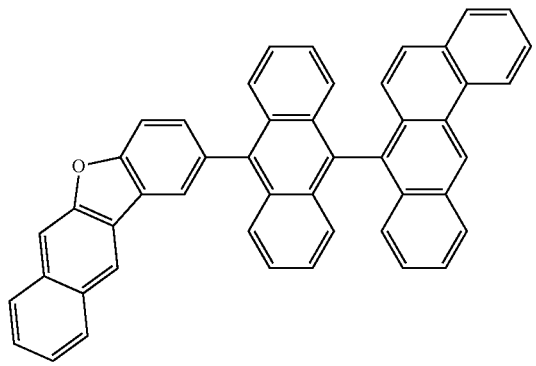 | 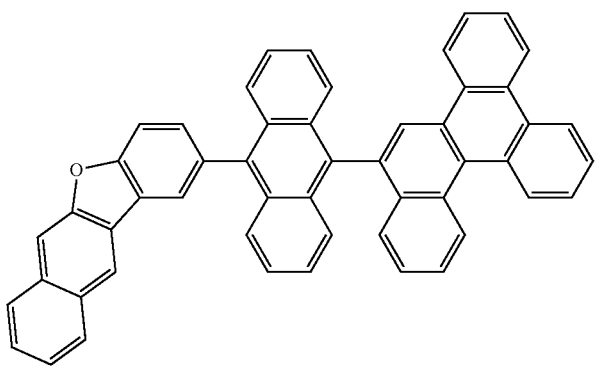 |
| 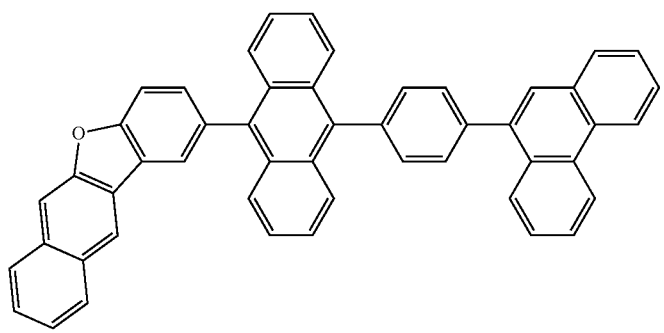 | |

-continued
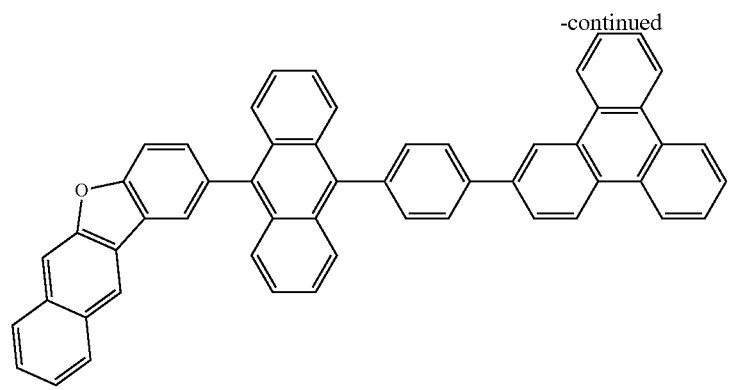
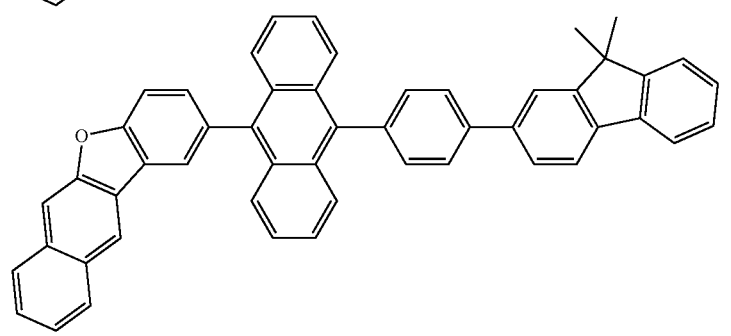
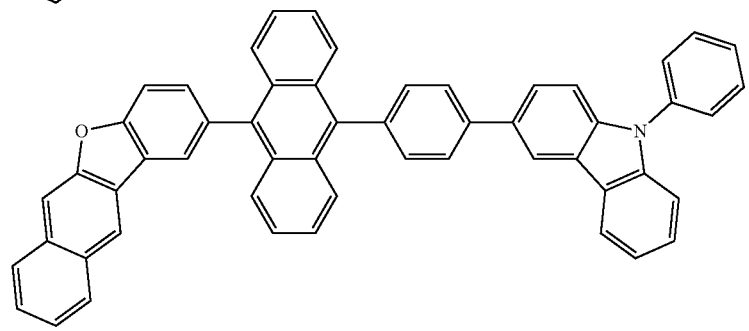
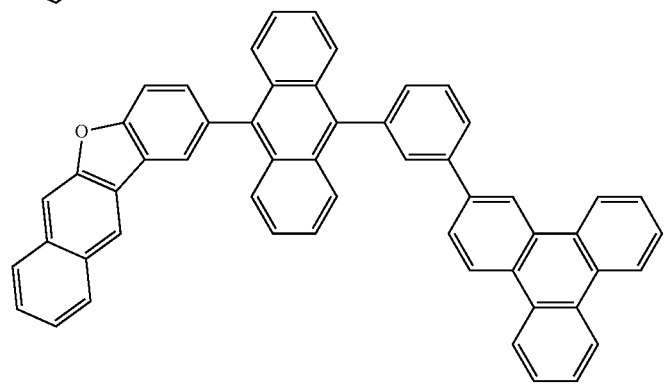
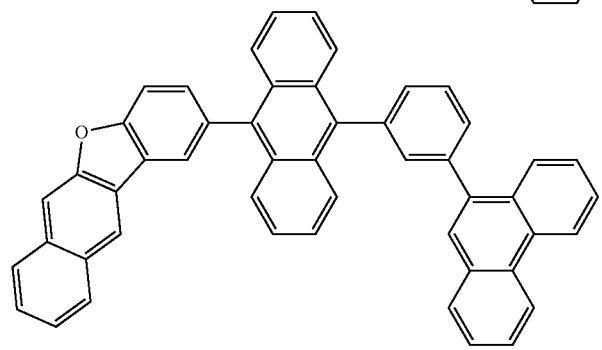

-continued
153
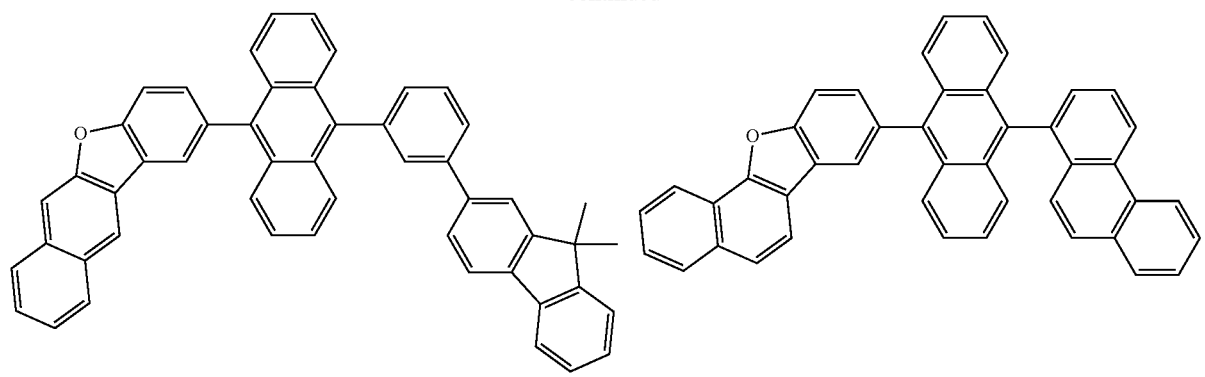
154
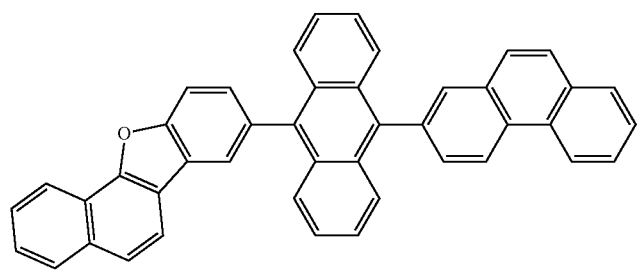
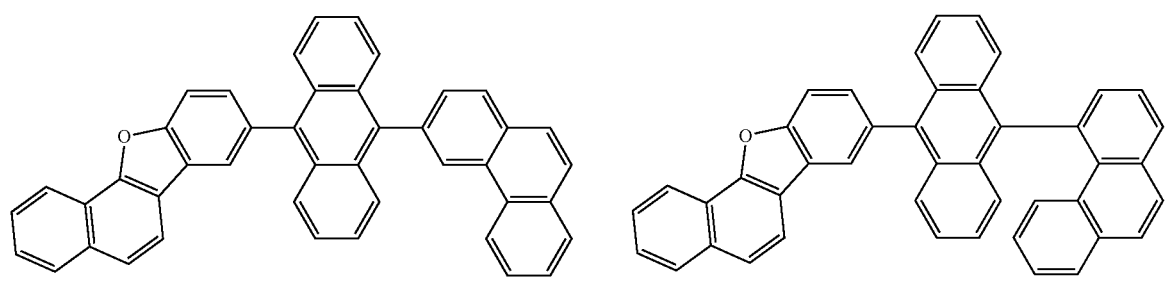
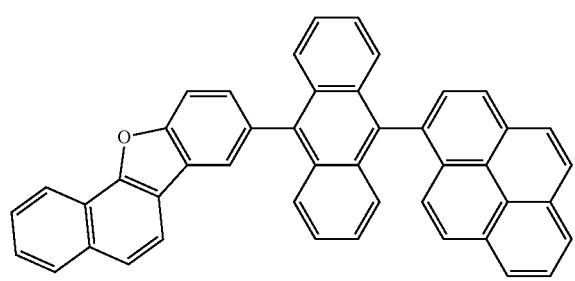
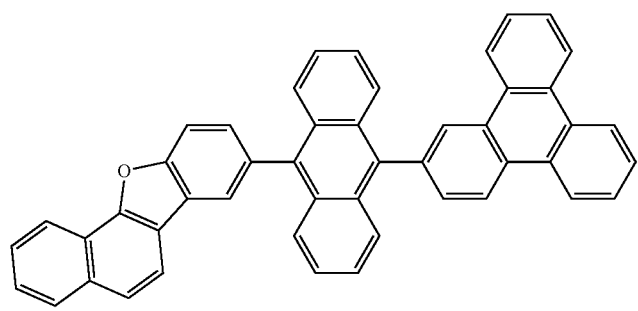

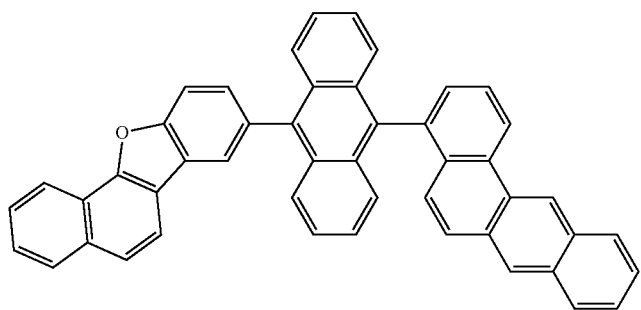
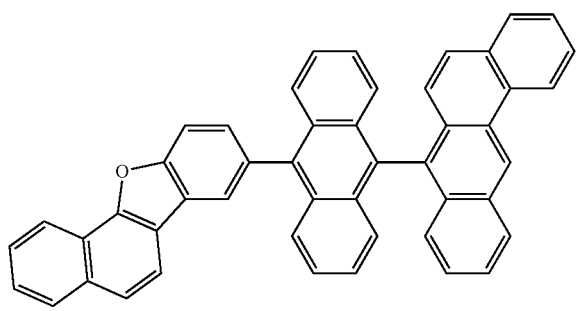
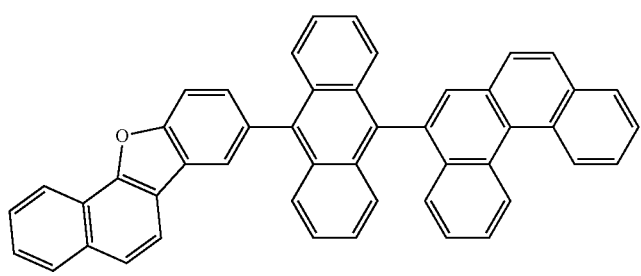
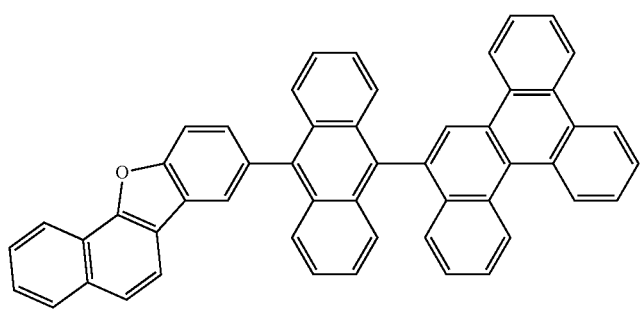
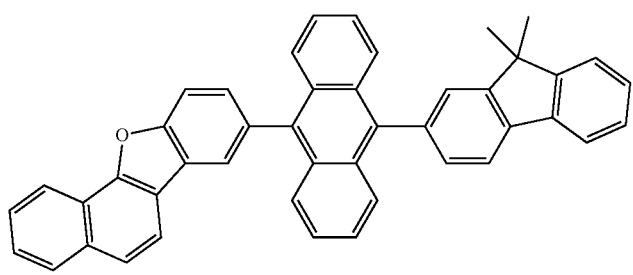

-continued
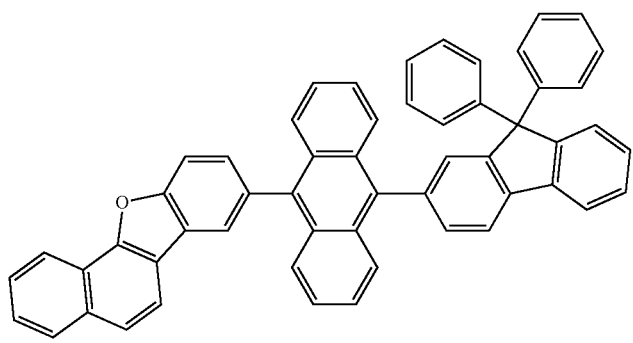
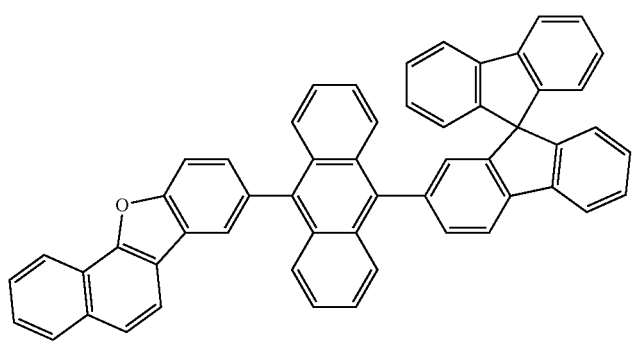
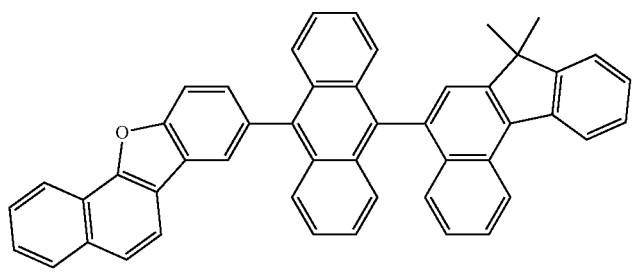
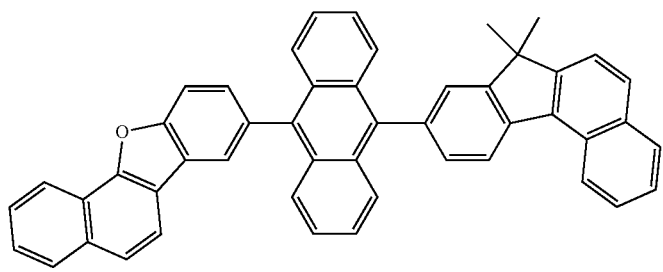
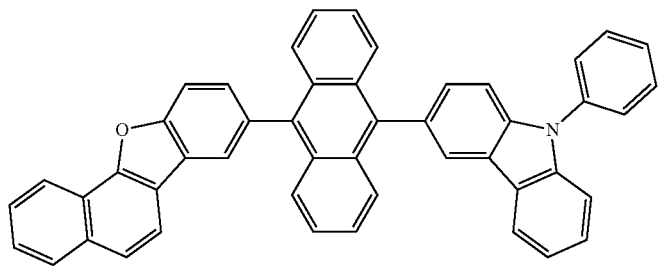

159 160
-continued
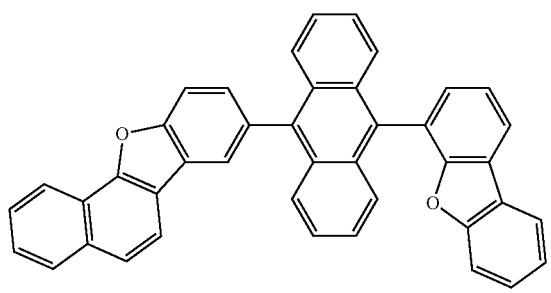
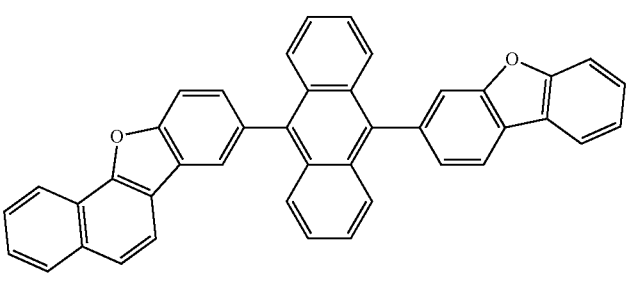
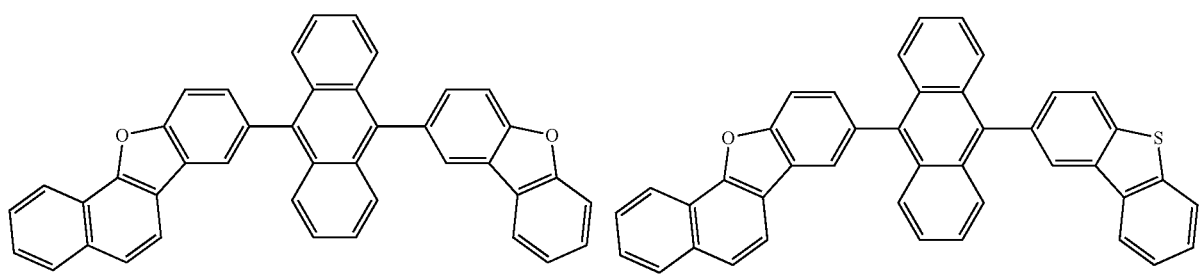
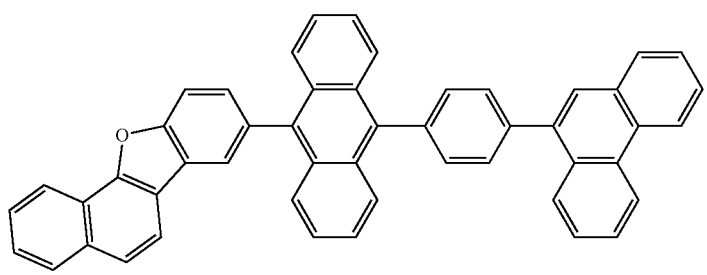
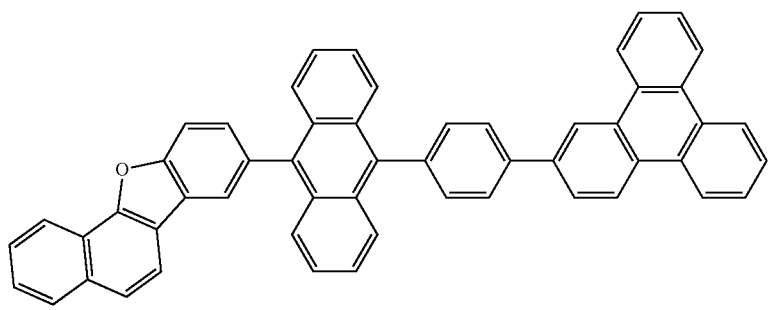
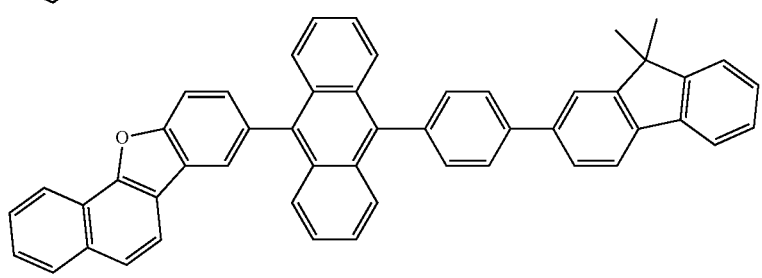
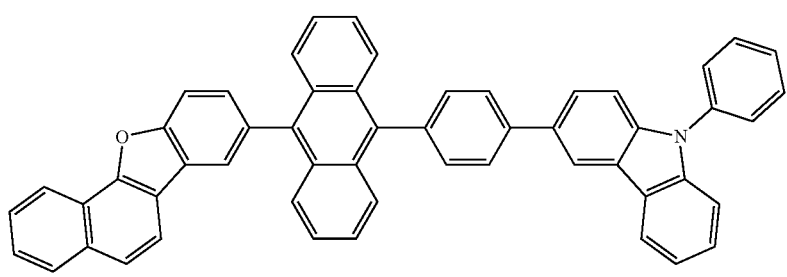

-continued
161 162
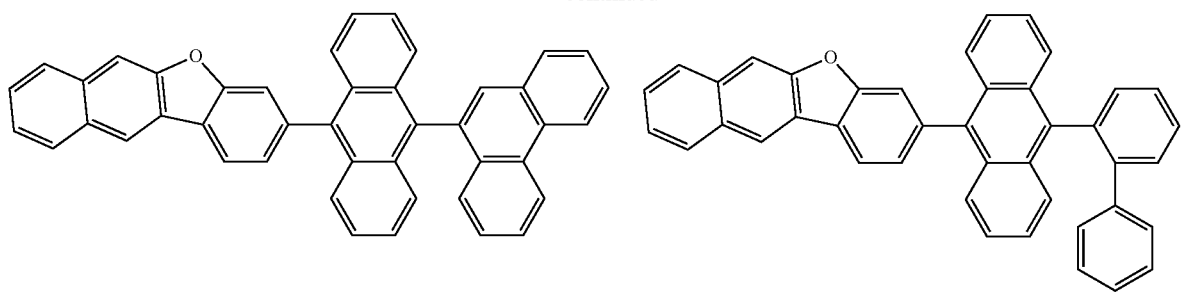
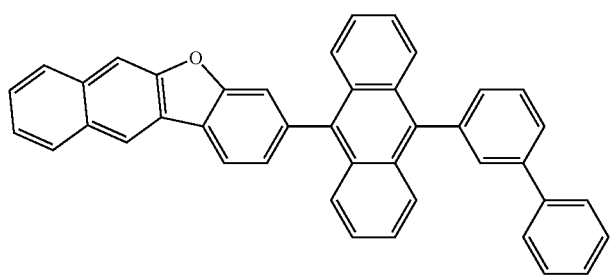
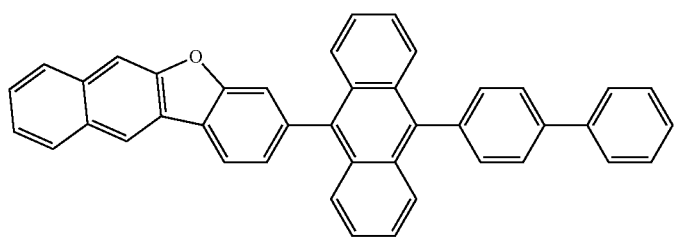
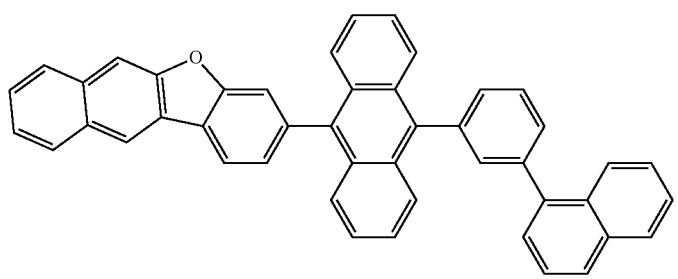
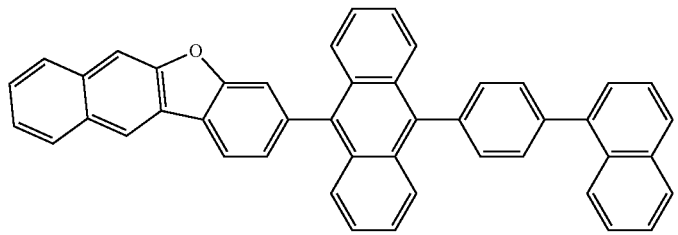
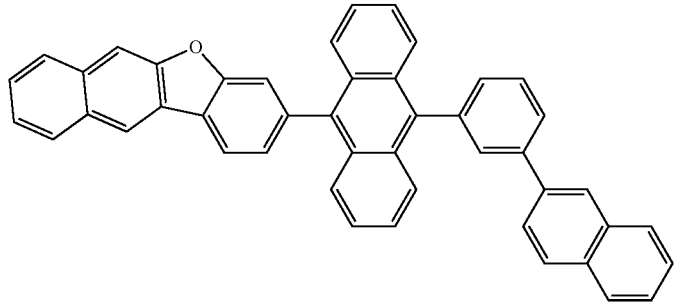

-continued
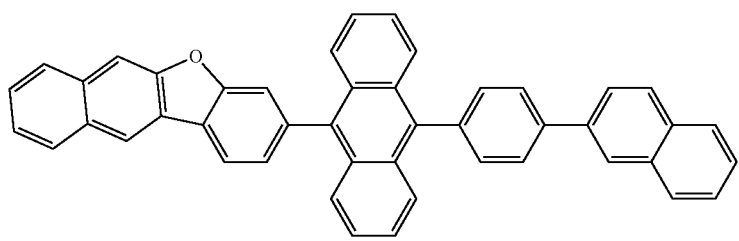
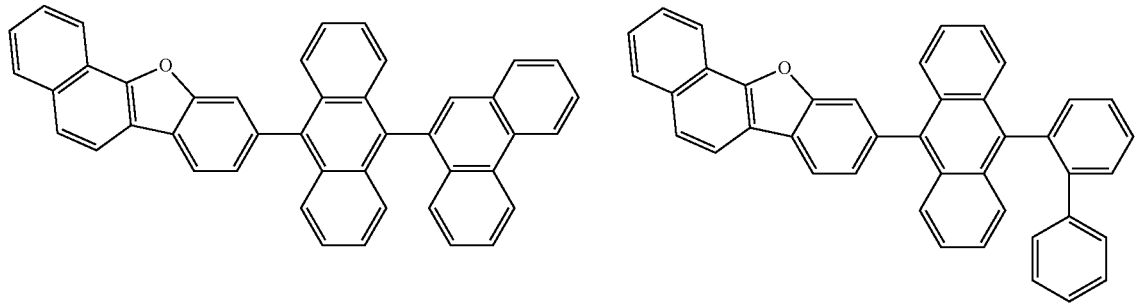
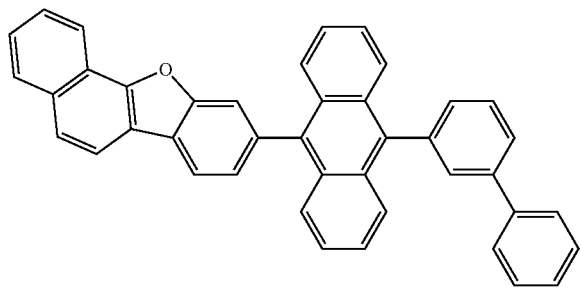
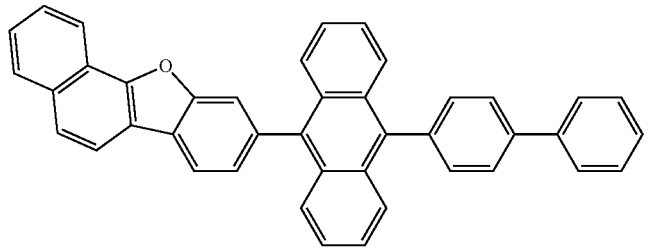
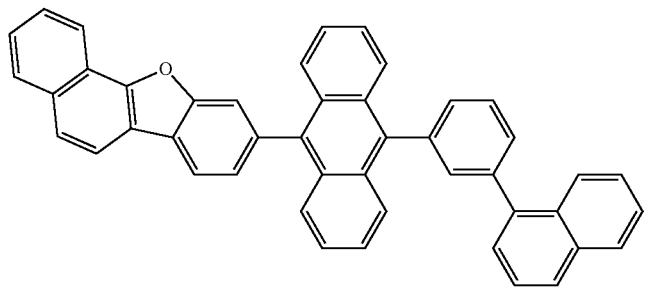
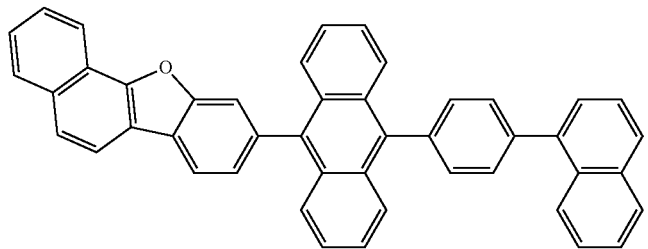

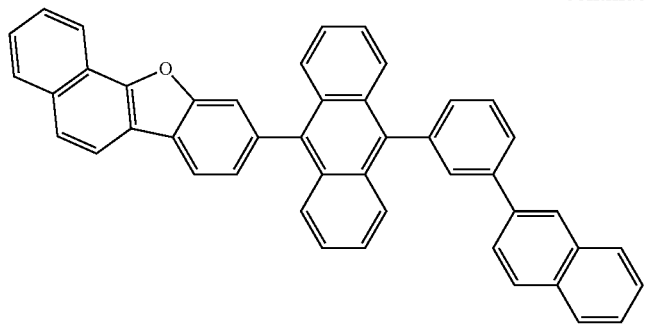
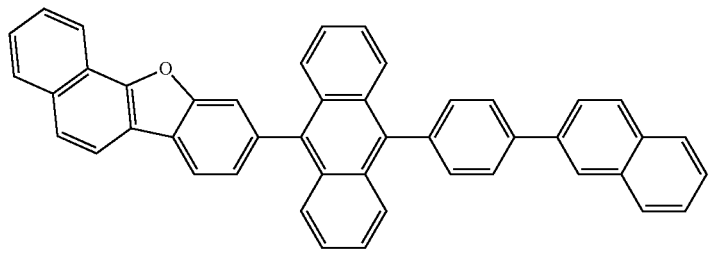
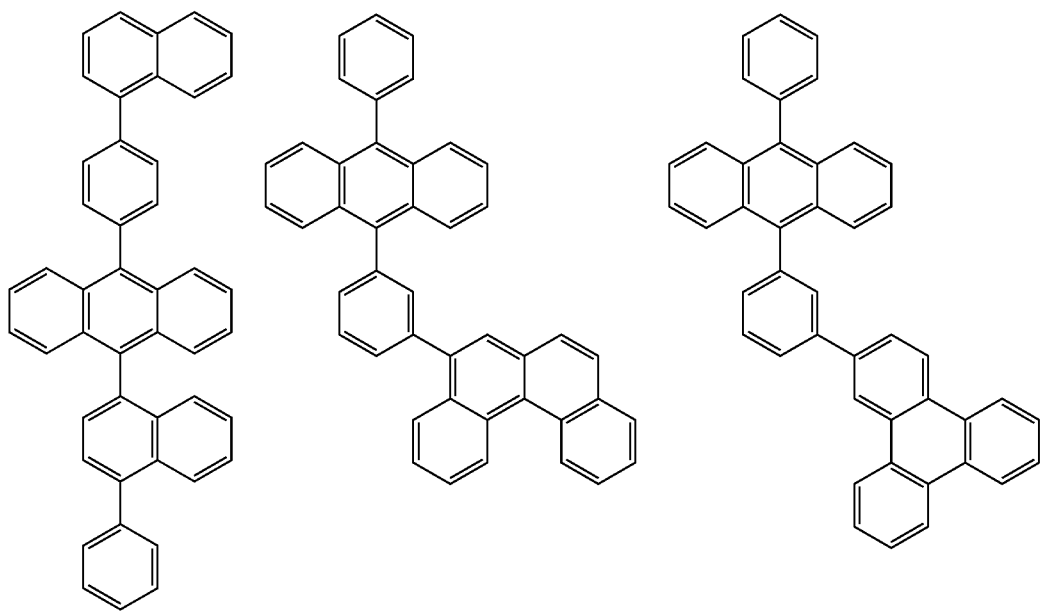

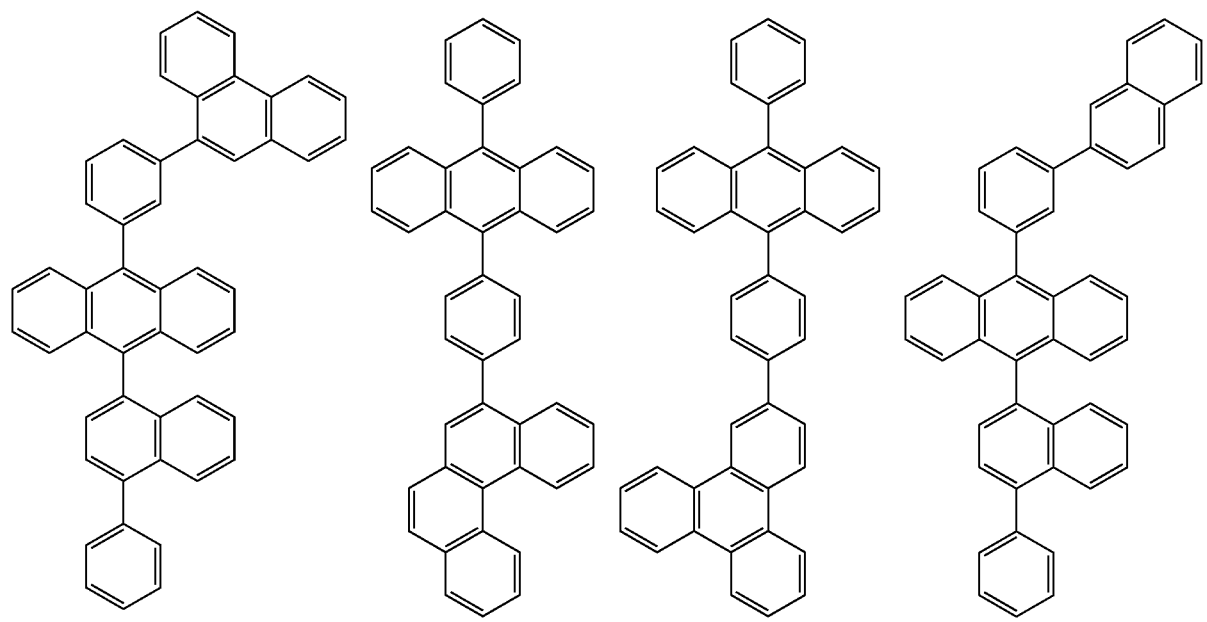
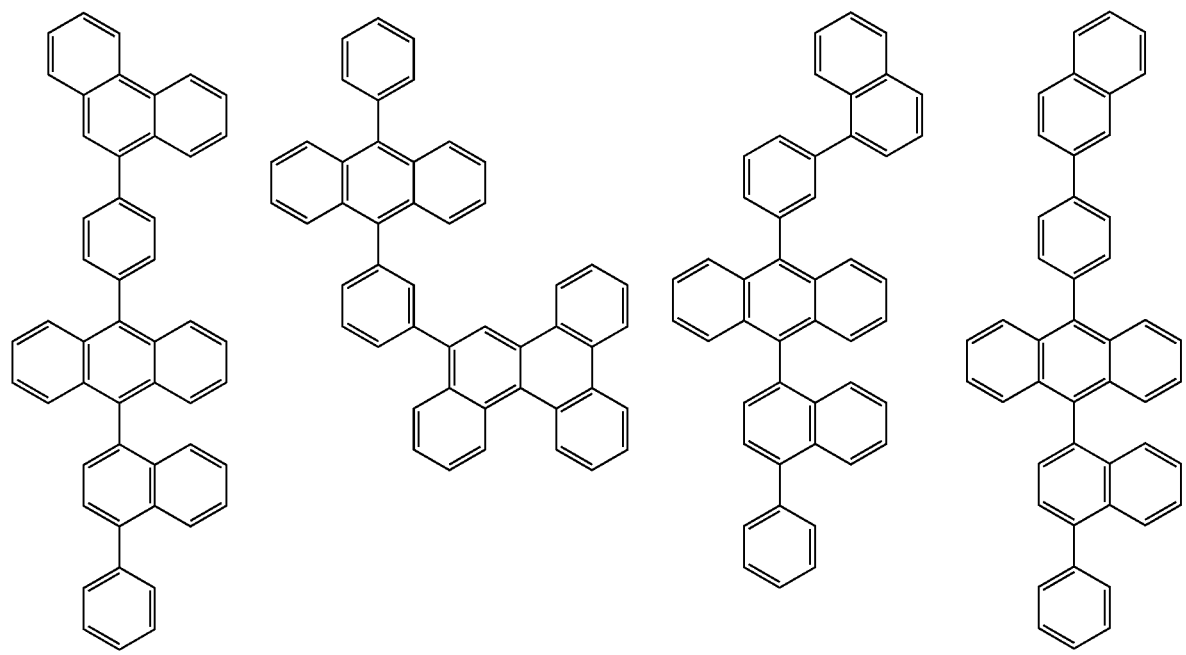

169
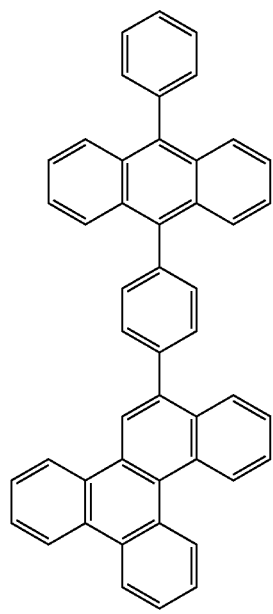
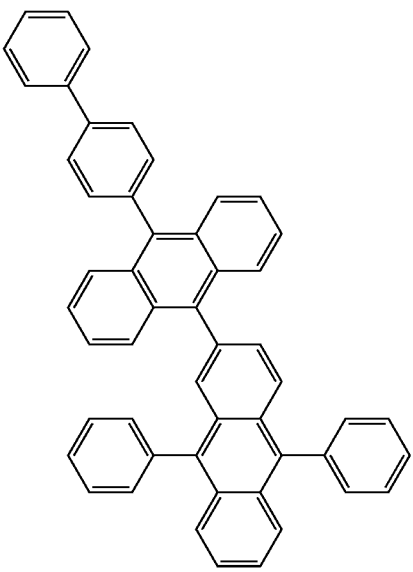
170
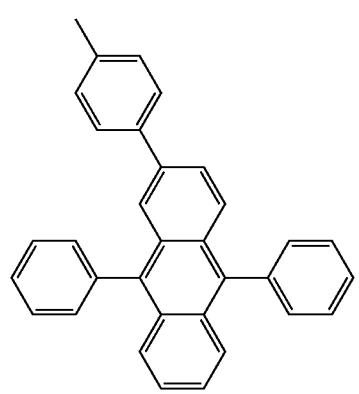
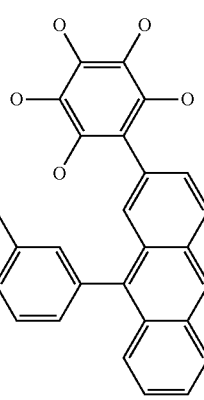
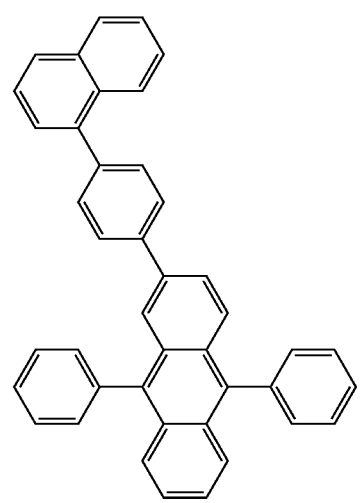

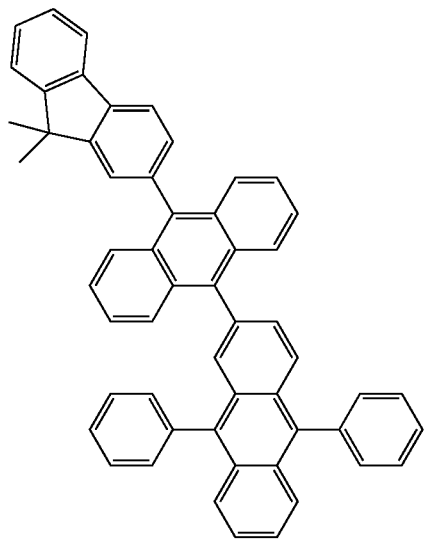
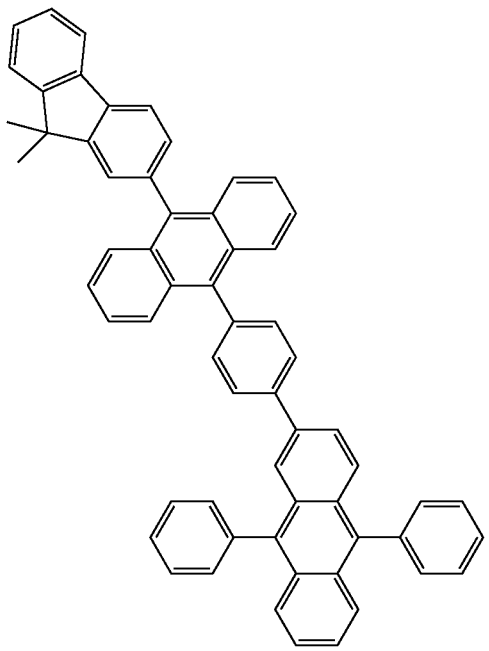
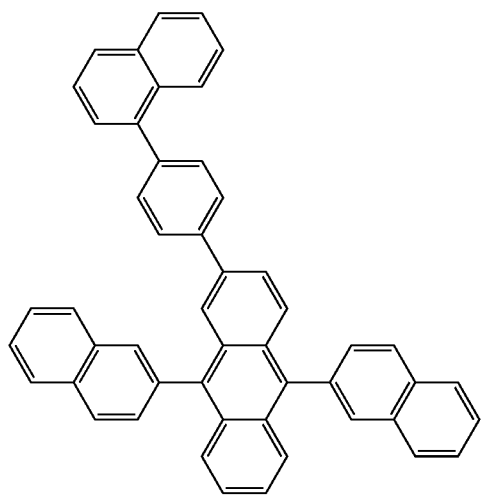
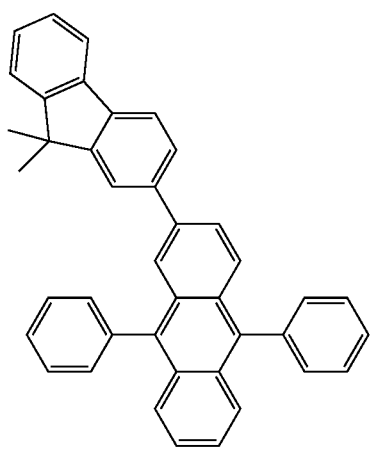
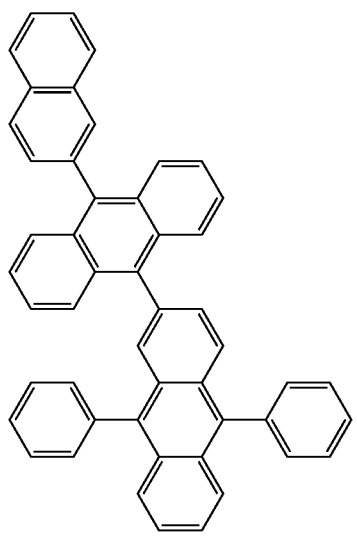
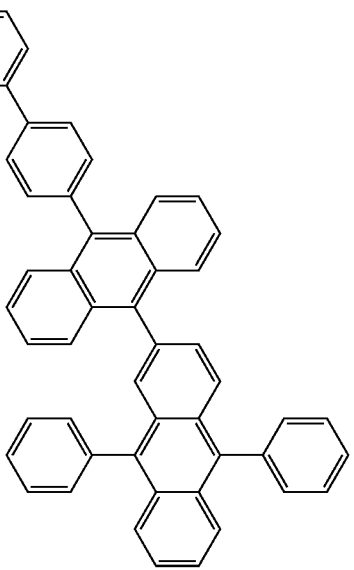

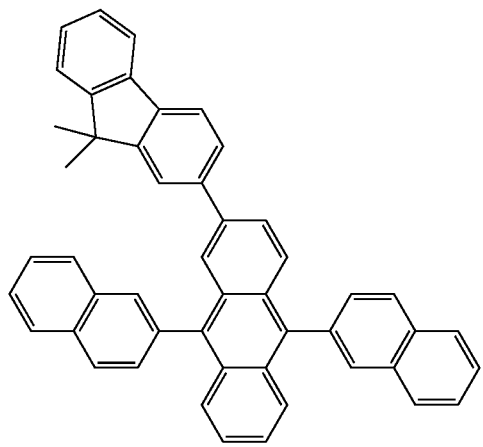
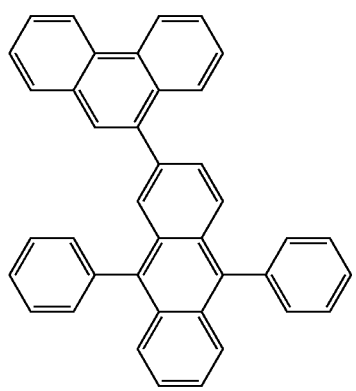
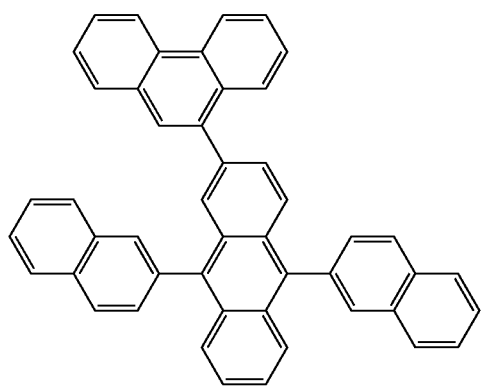
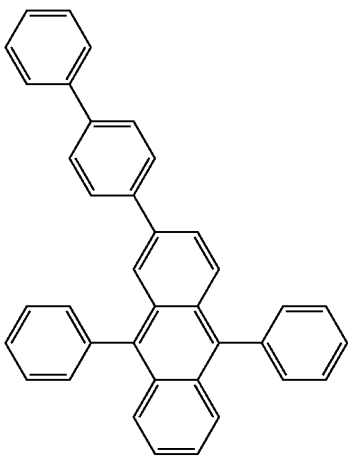
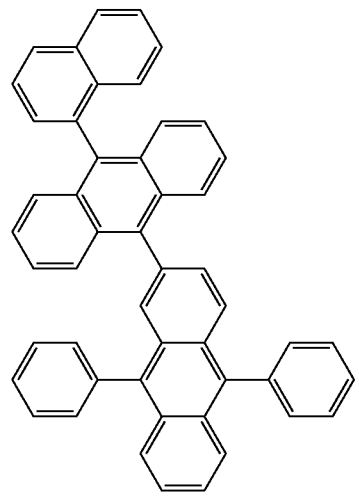
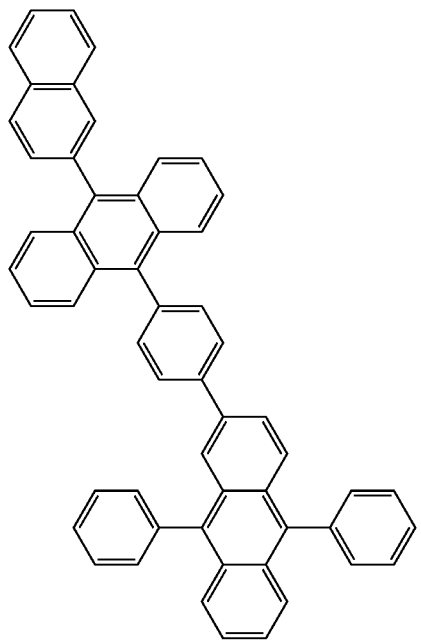
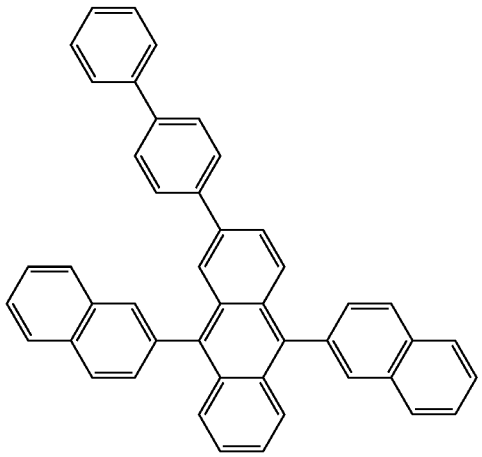

-continued
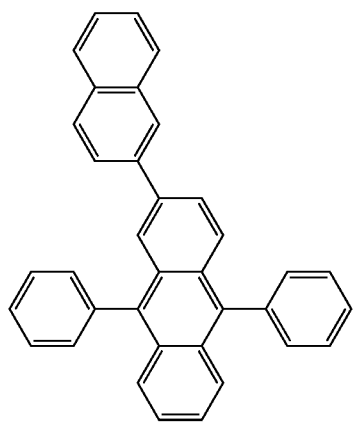
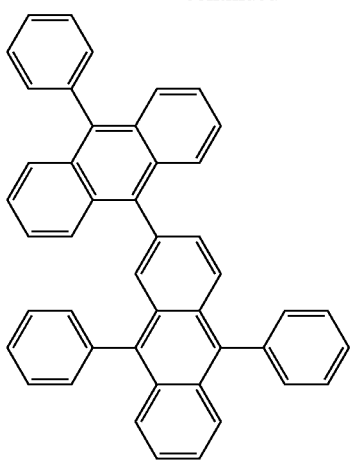
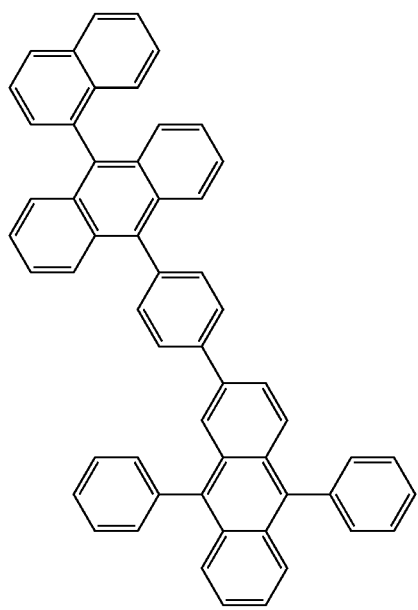
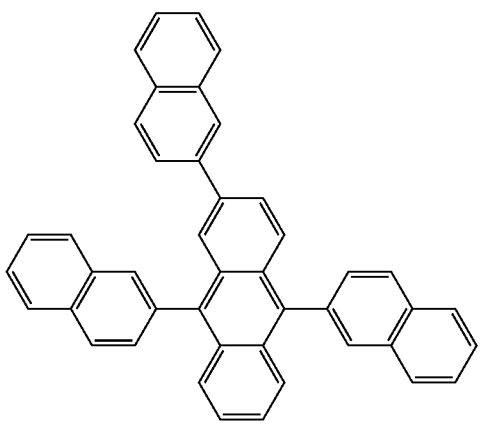
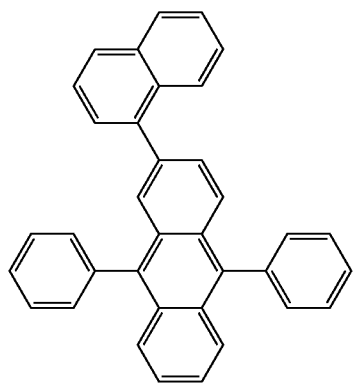
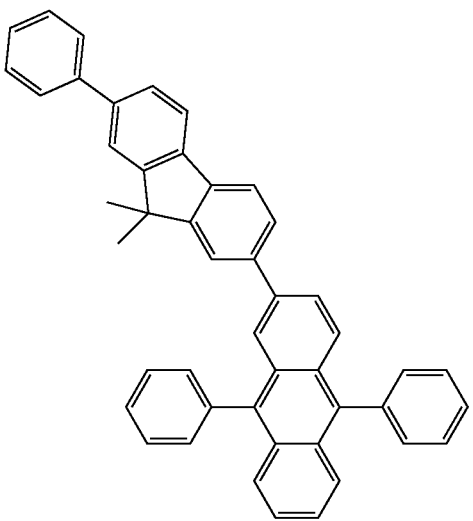

-continued
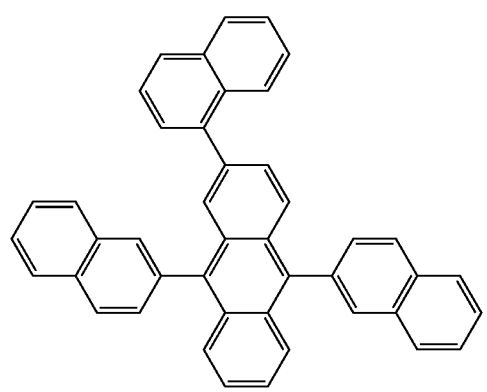
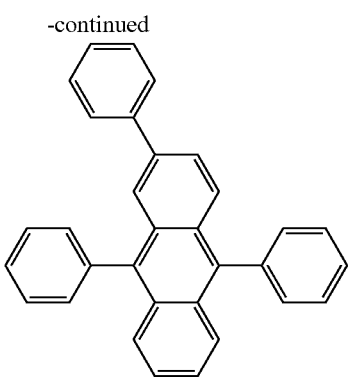
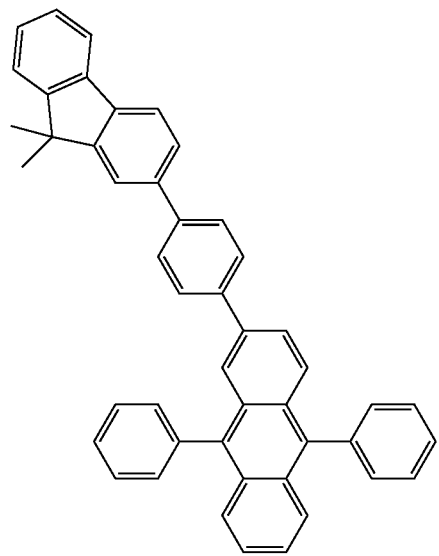
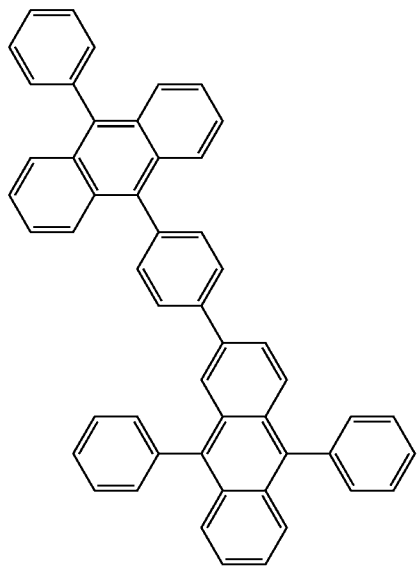
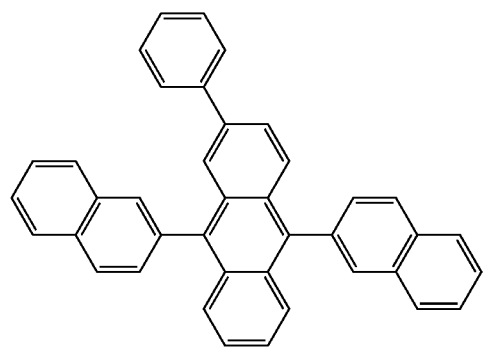
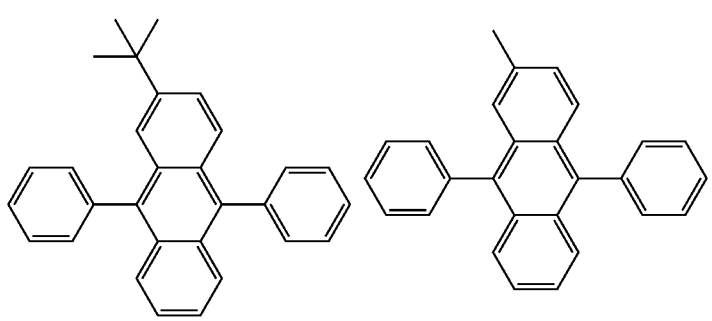

-continued
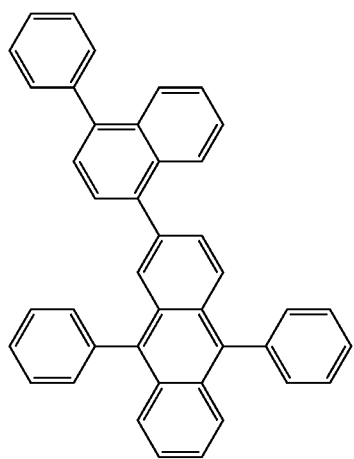

-continued
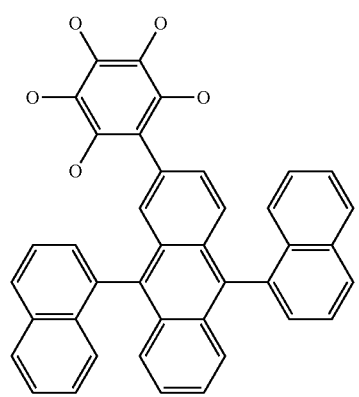
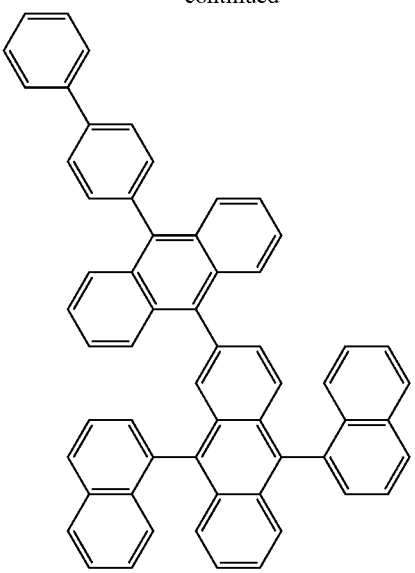
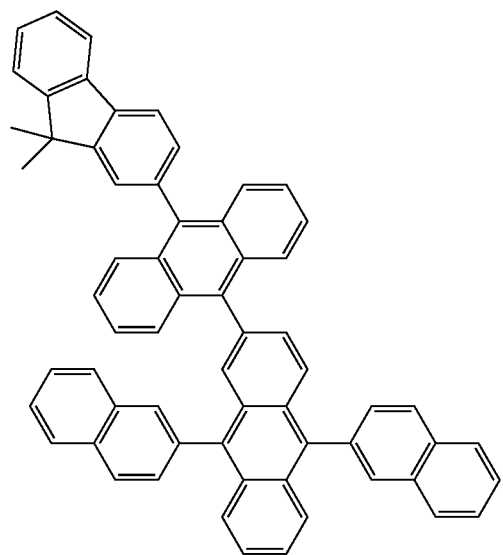

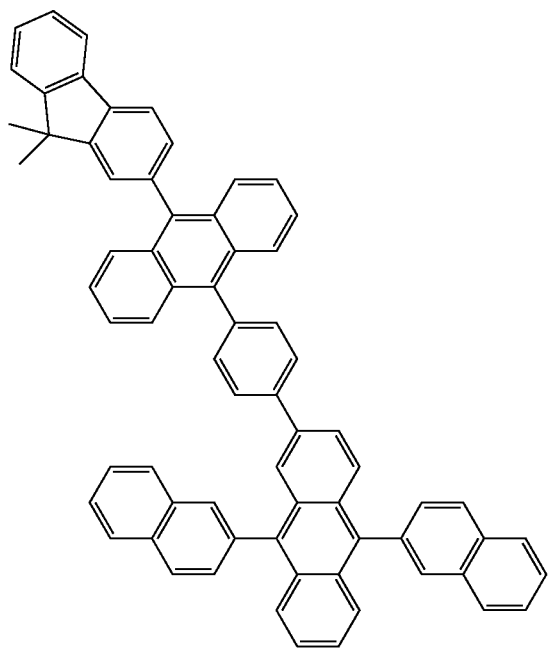
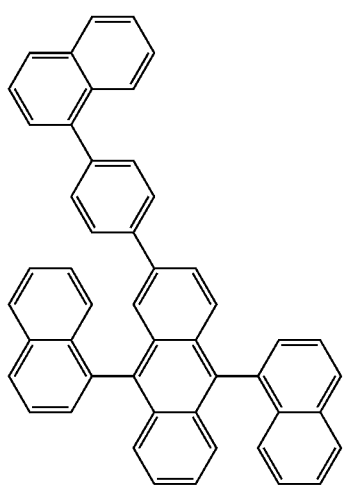
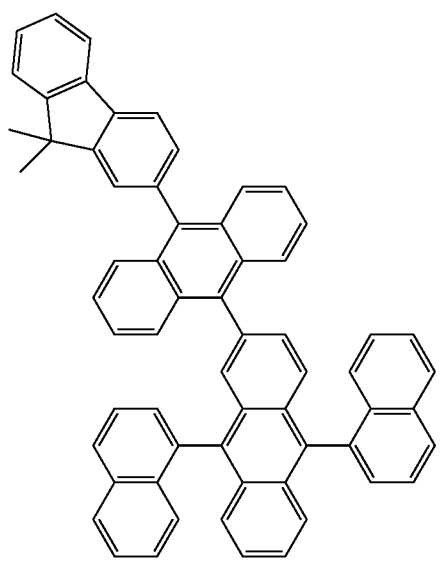
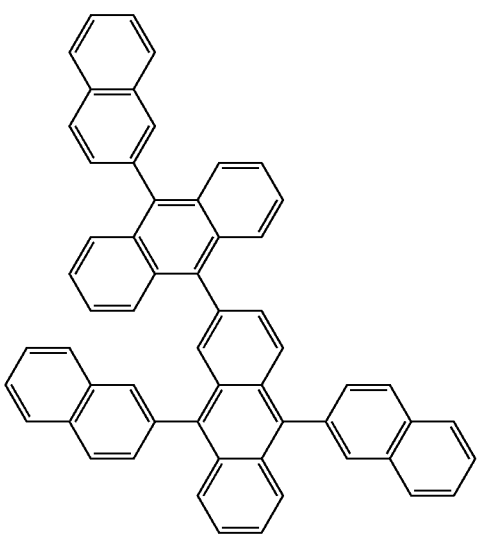

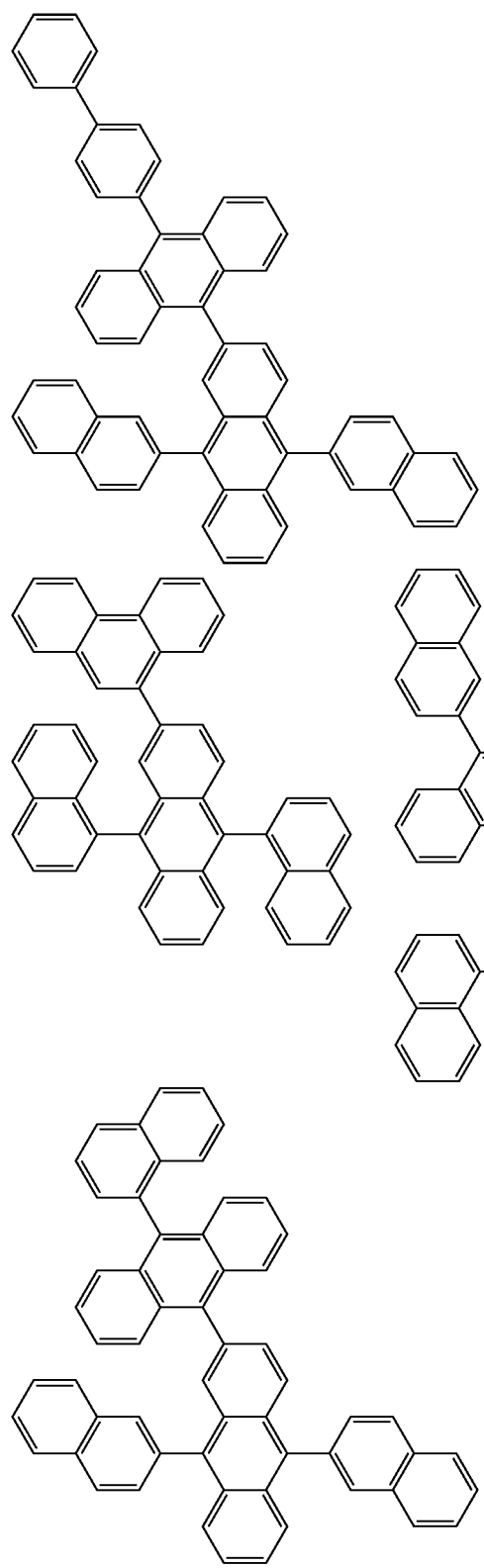
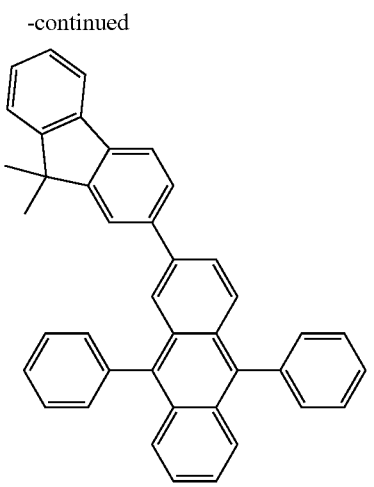
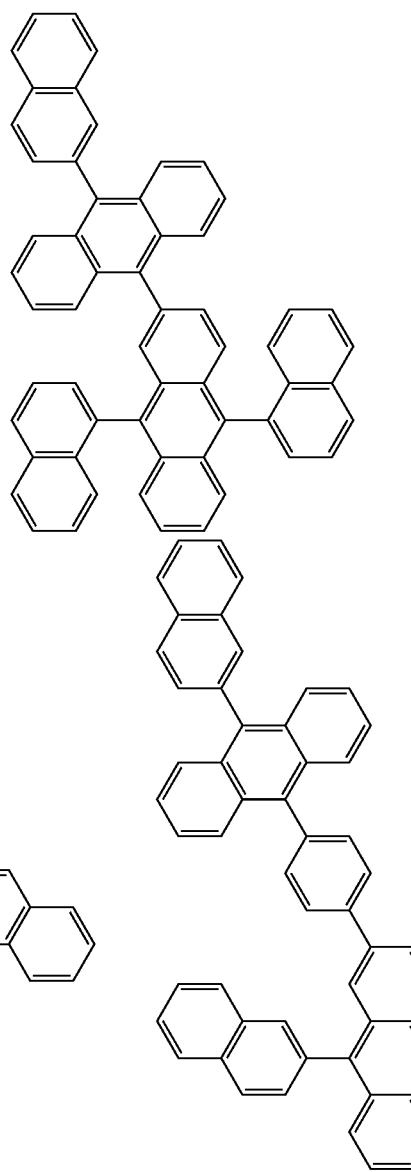

-continued
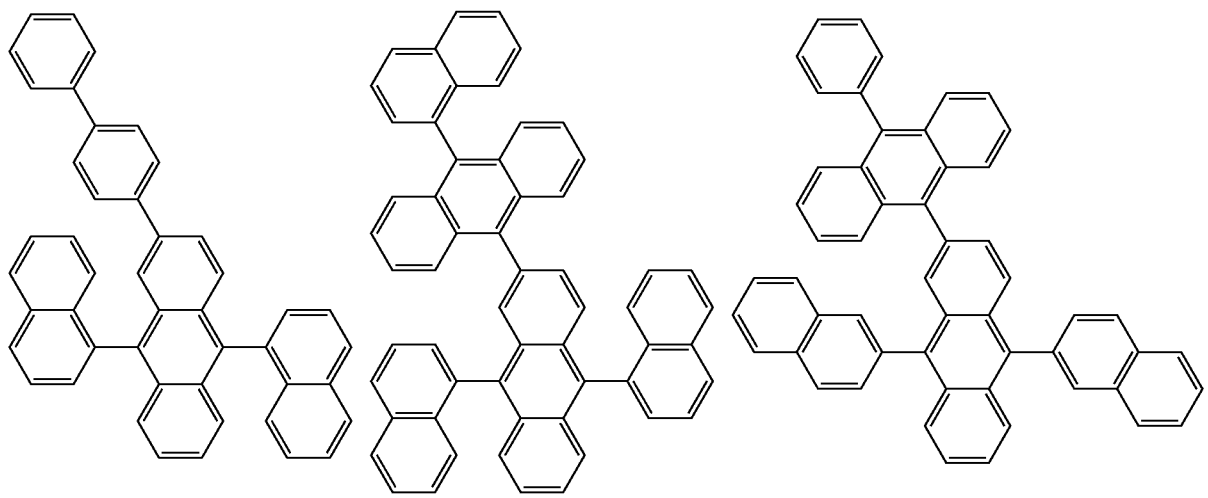
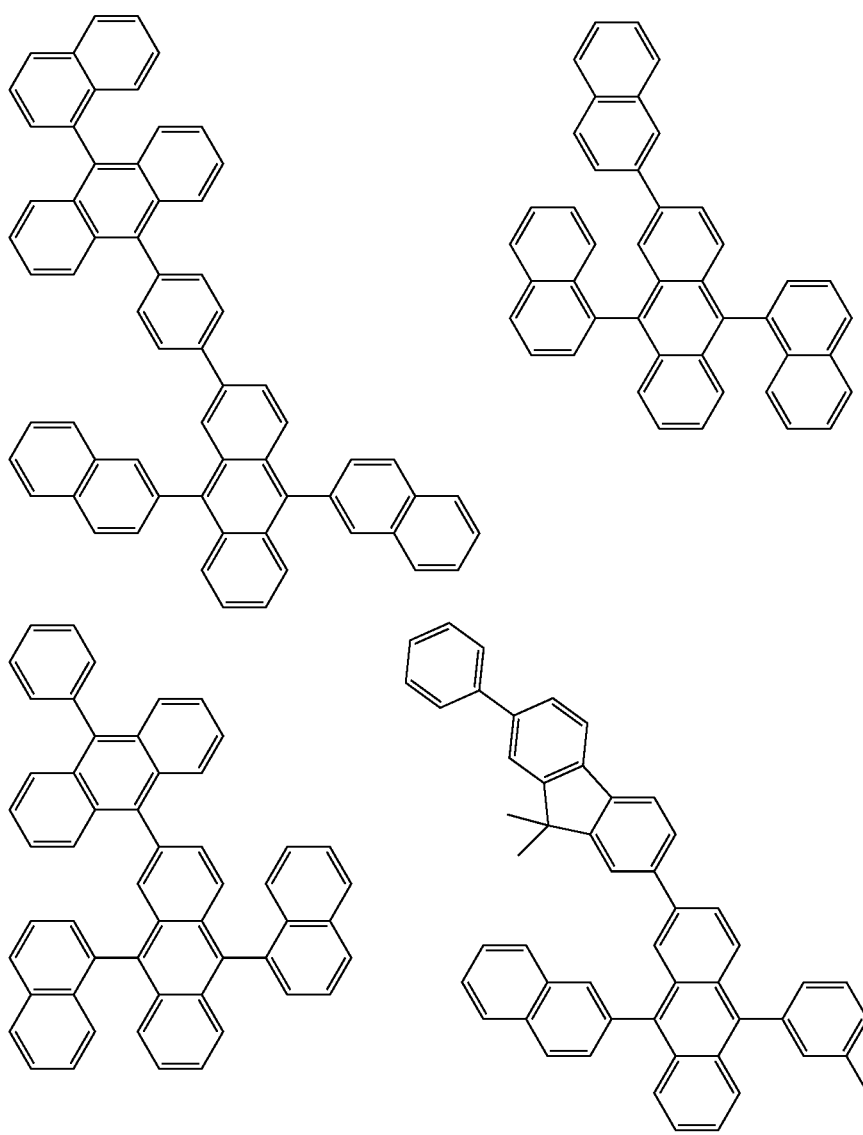

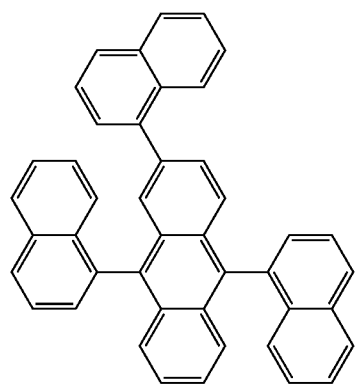
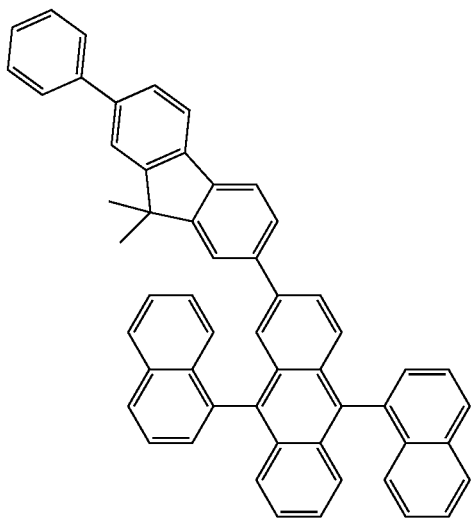
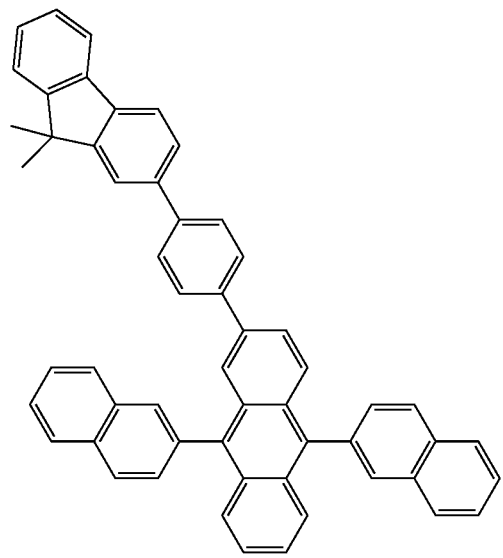
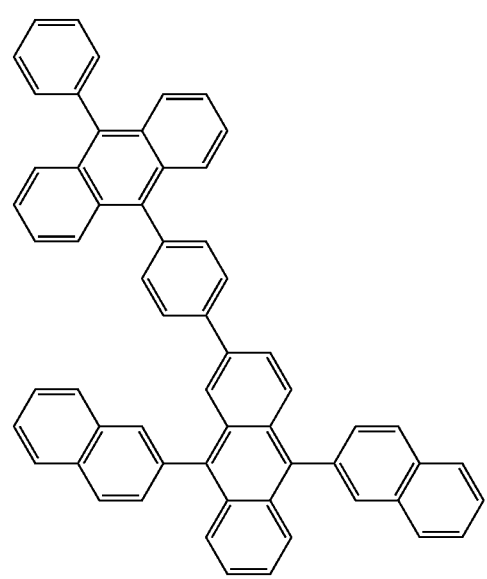
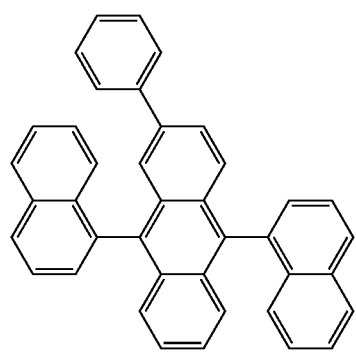
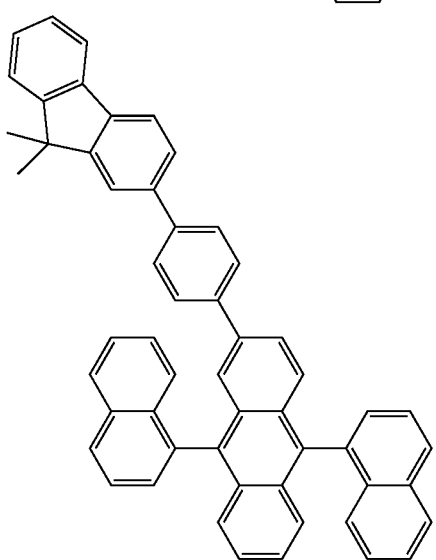

191
192
-continued
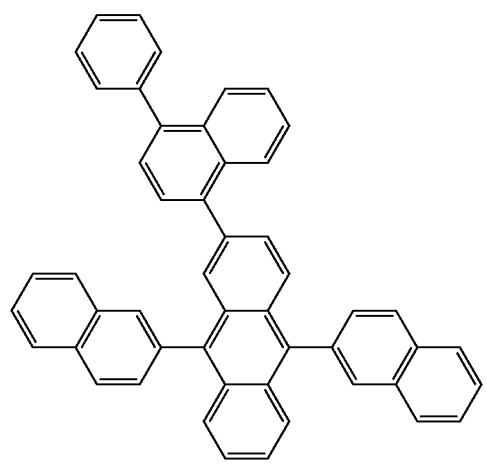
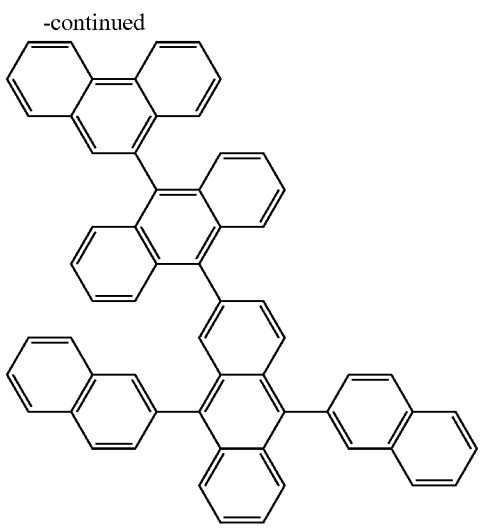
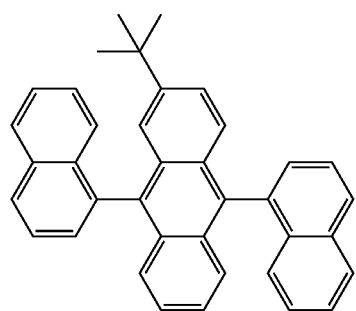
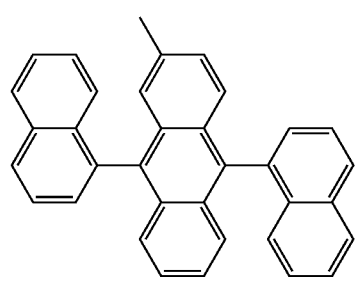
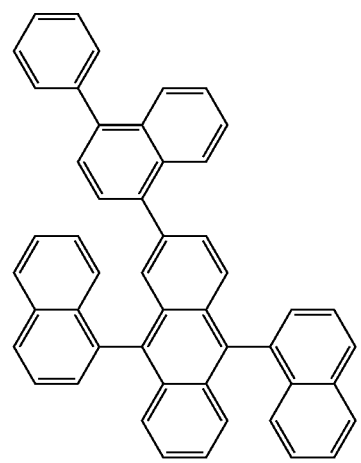
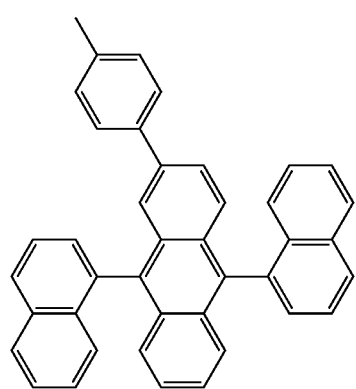
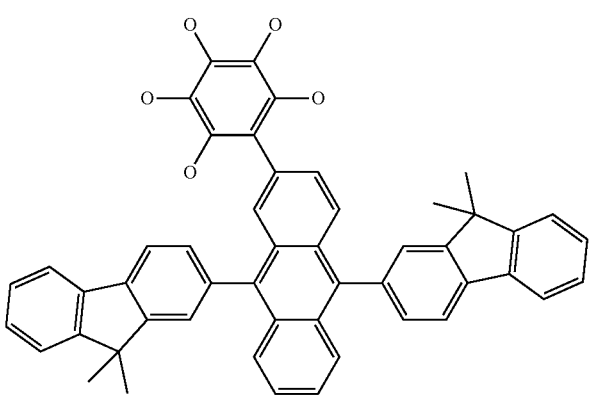

193
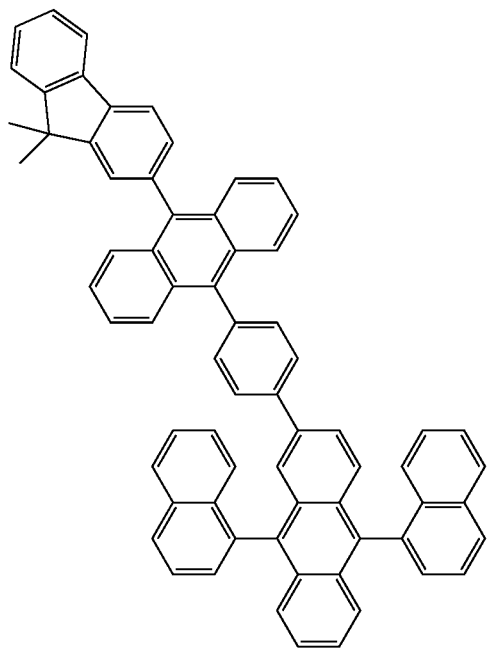
194
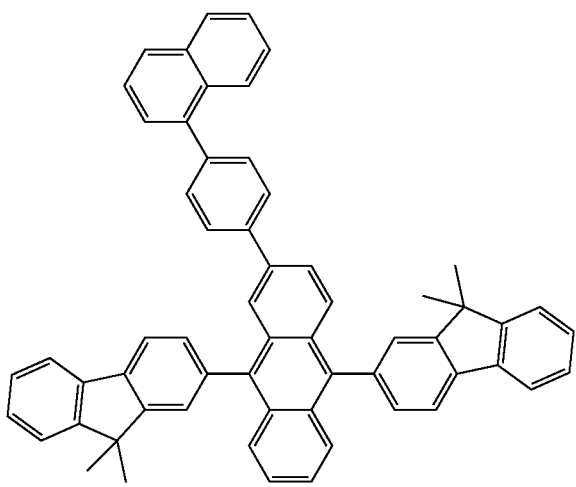
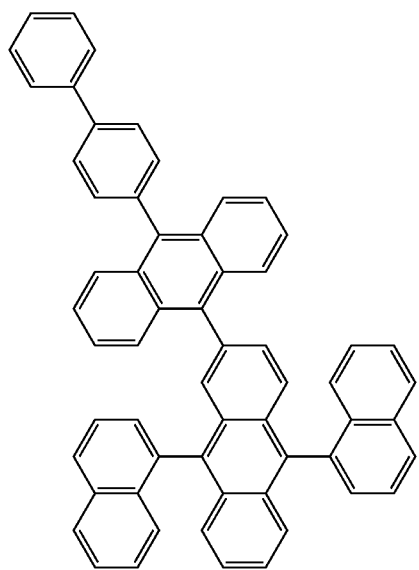
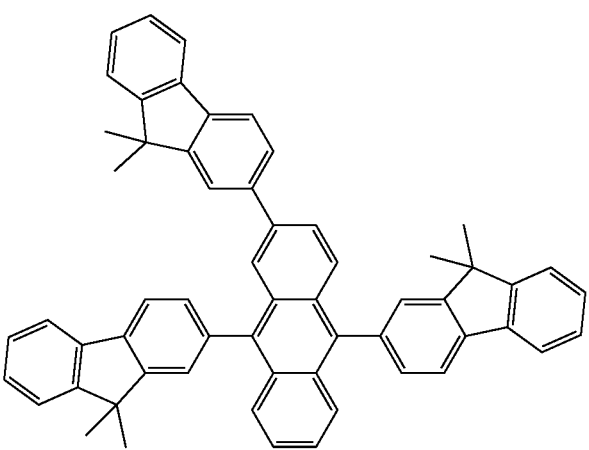

-continued
| 195 | 196 |
|---|---|
| 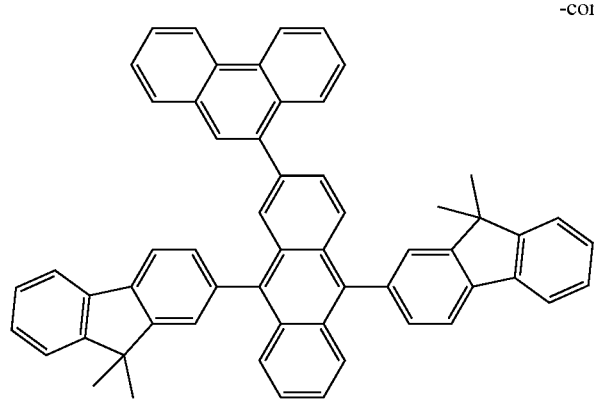 | 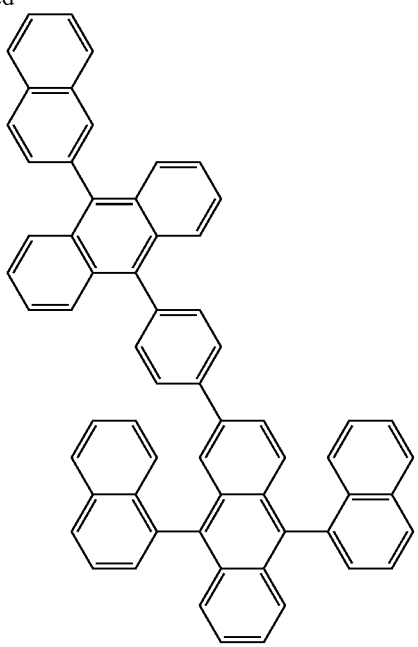 |
| 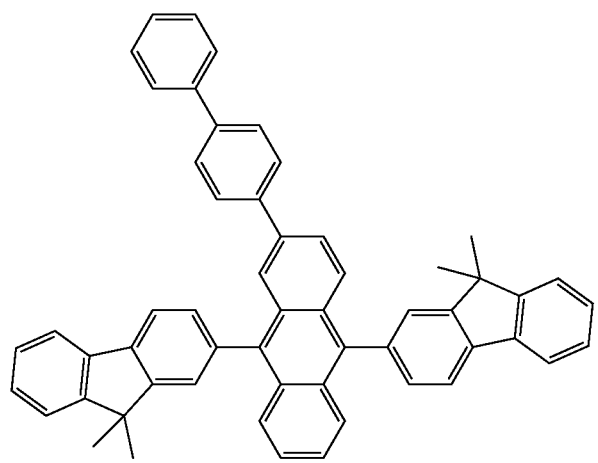 | 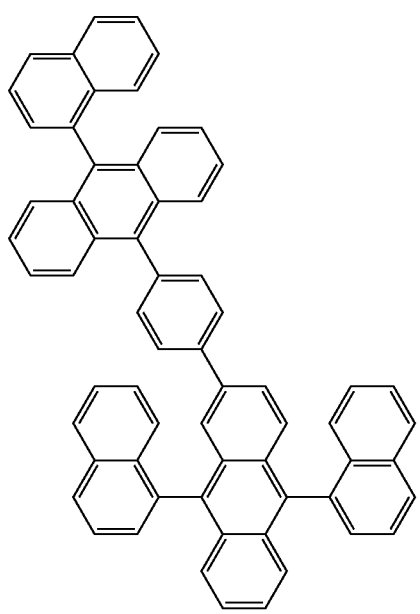 |
| 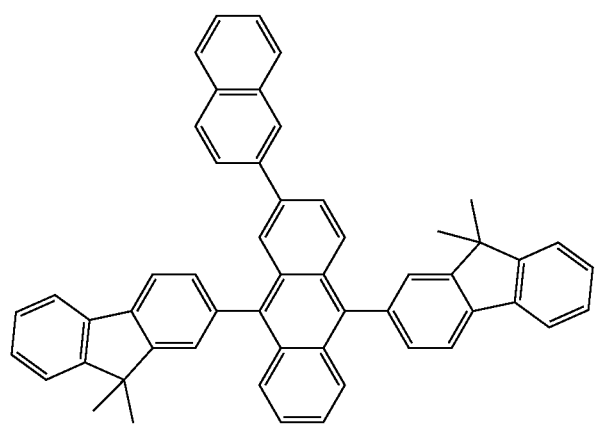 | 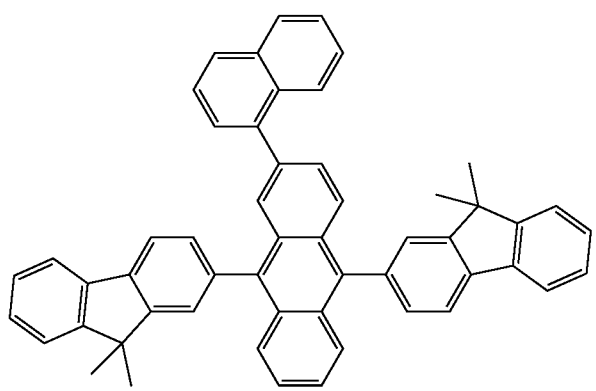 |

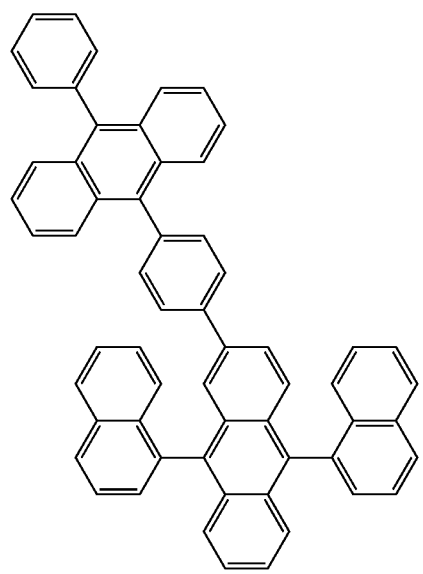
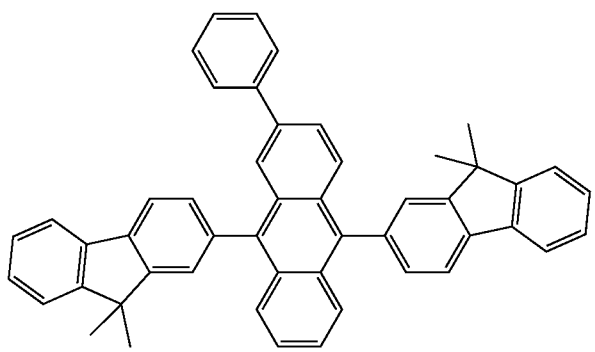
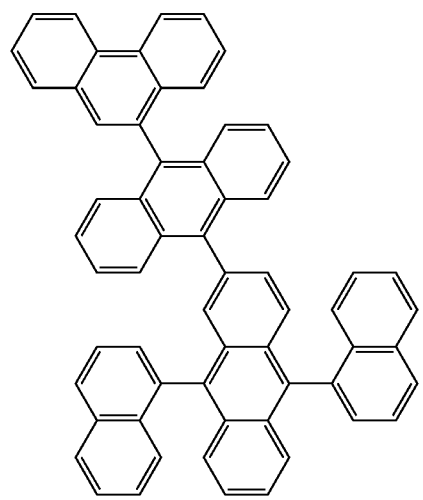
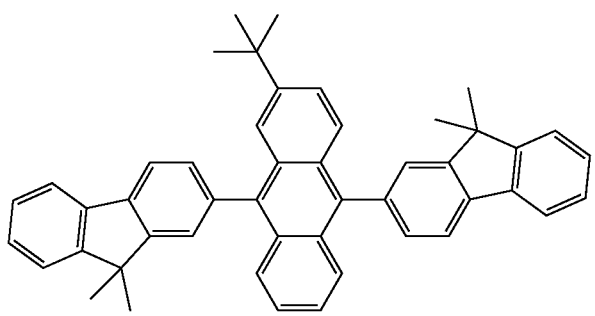
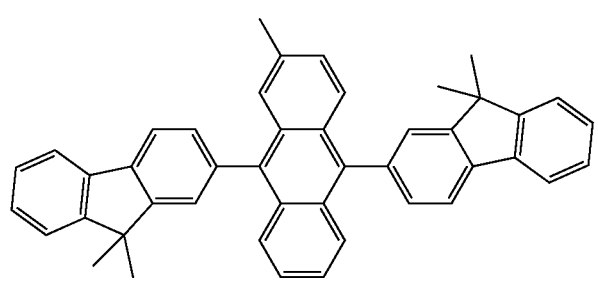
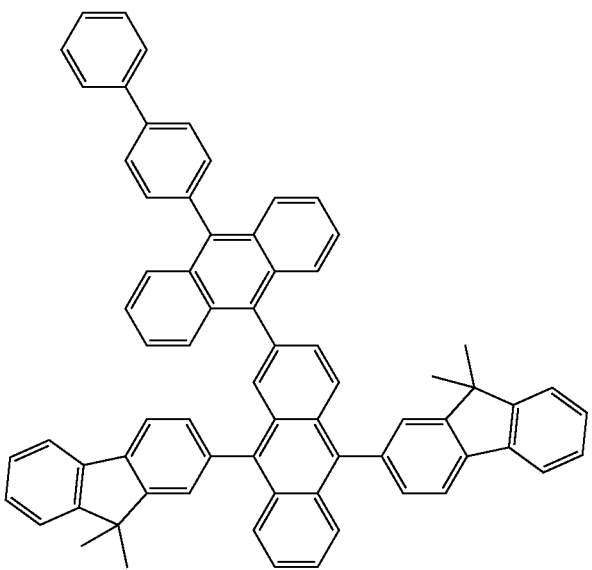

199
200
-continued
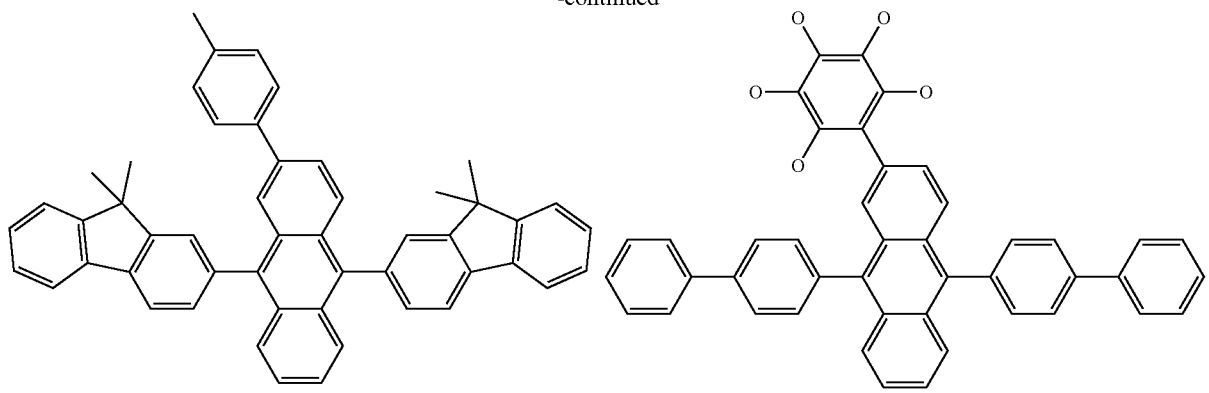
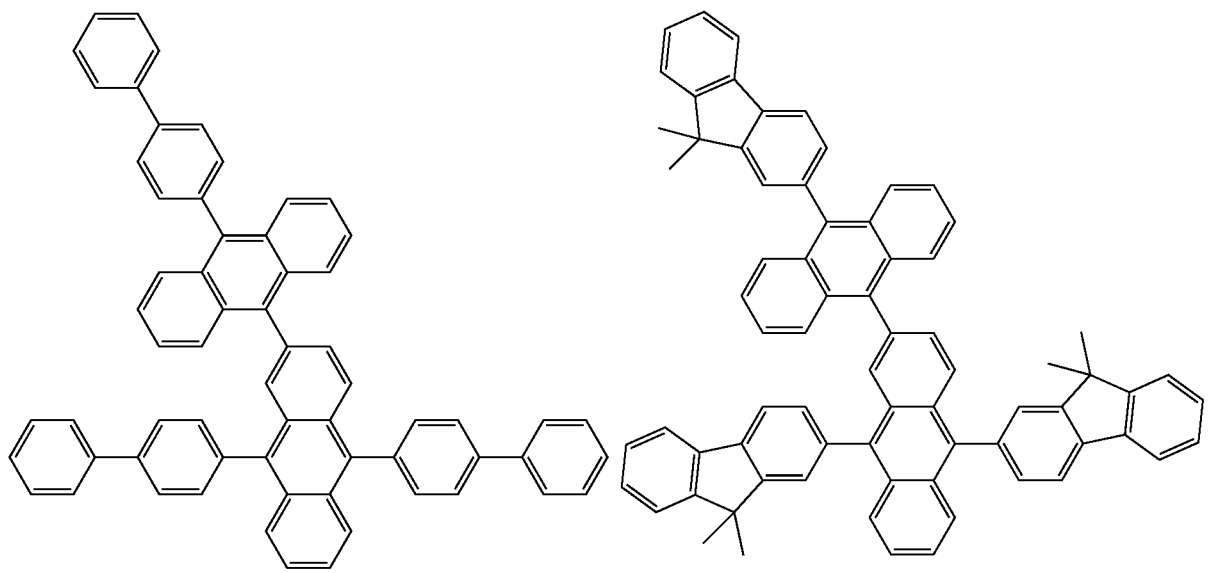
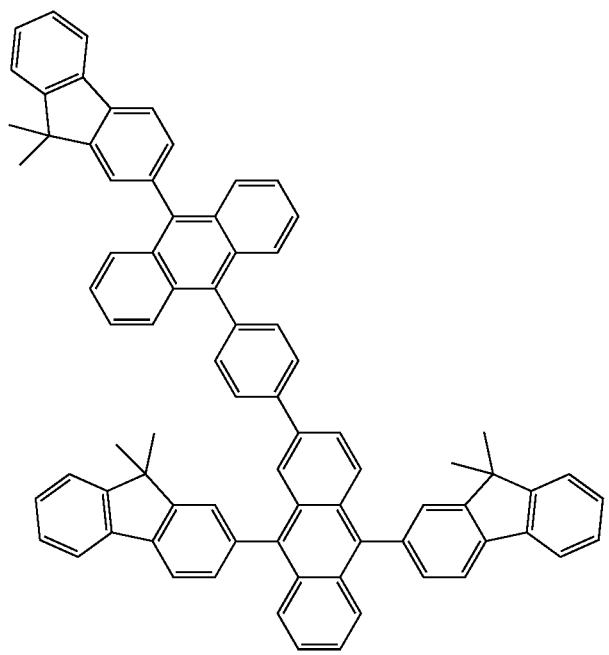

-continued
201
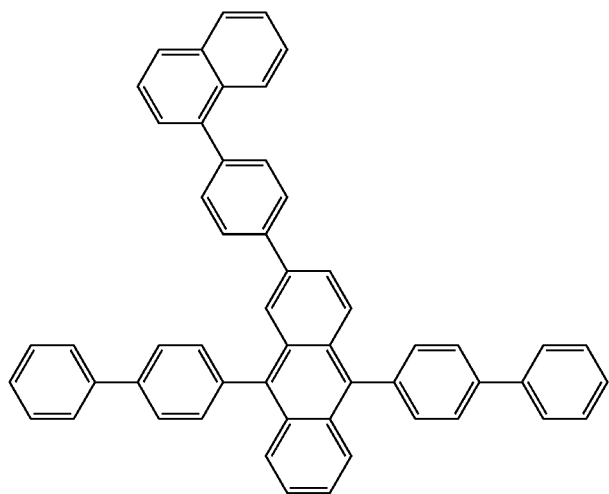
202
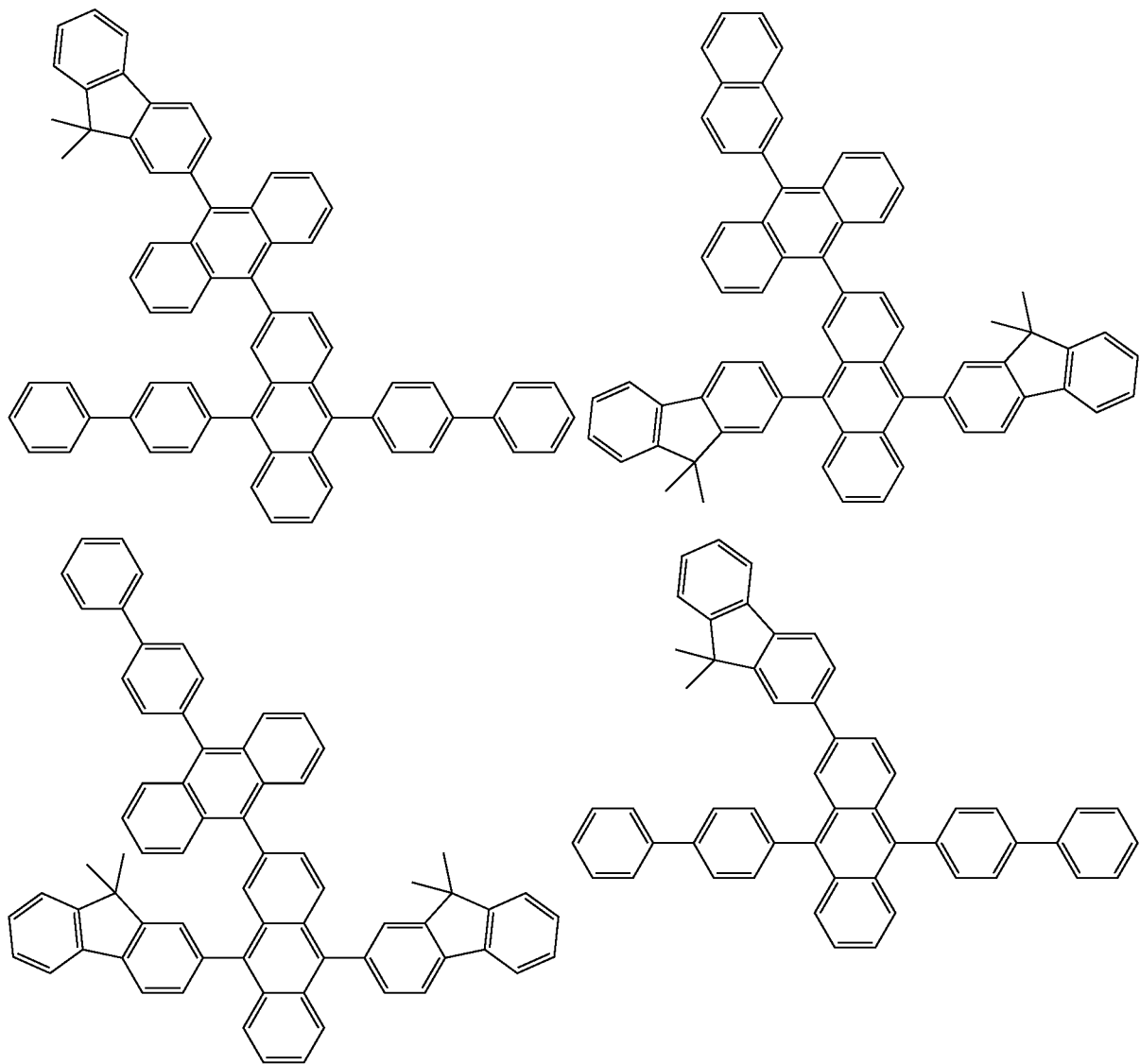

203
204
-continued
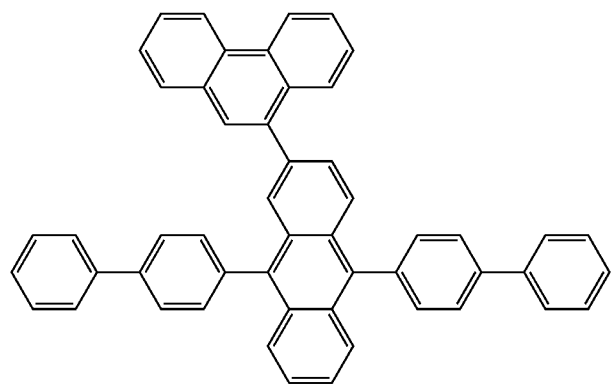
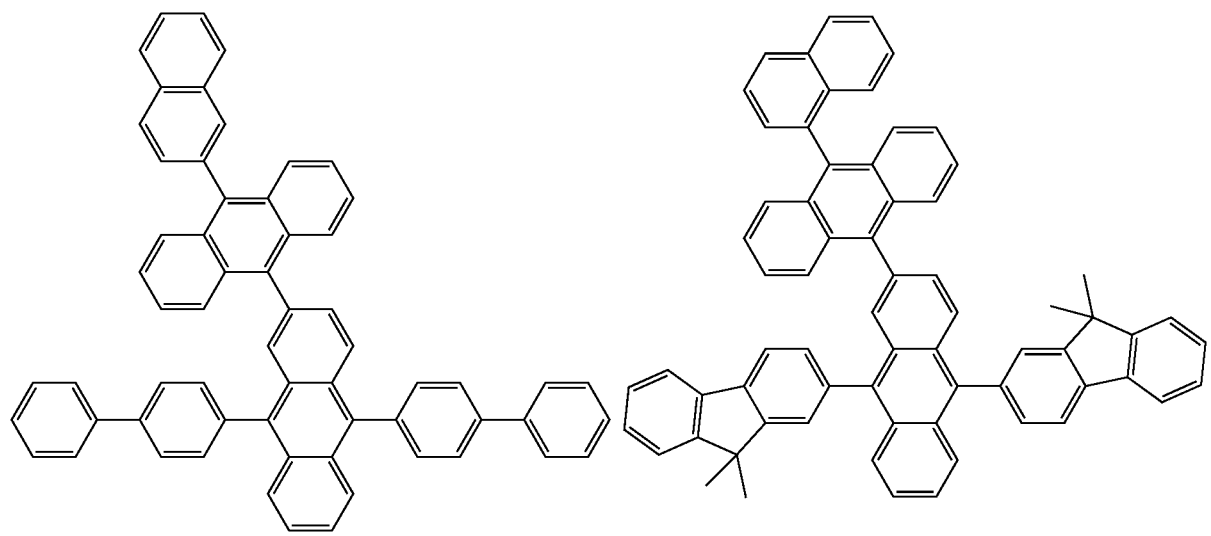
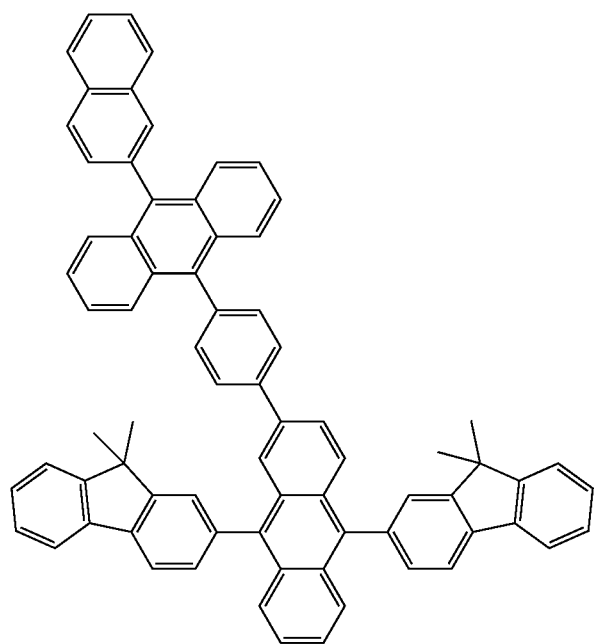
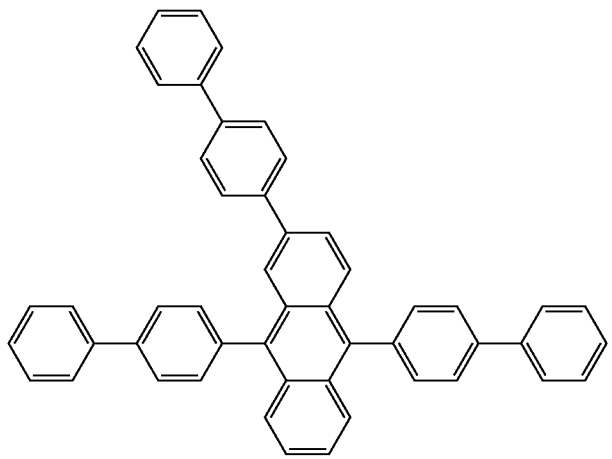

-continued
205
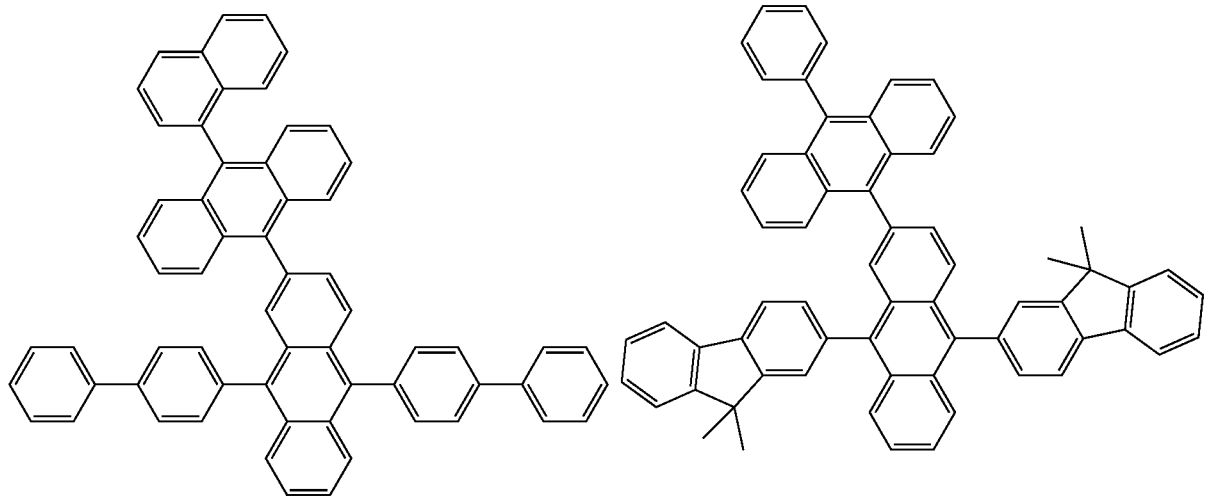
206
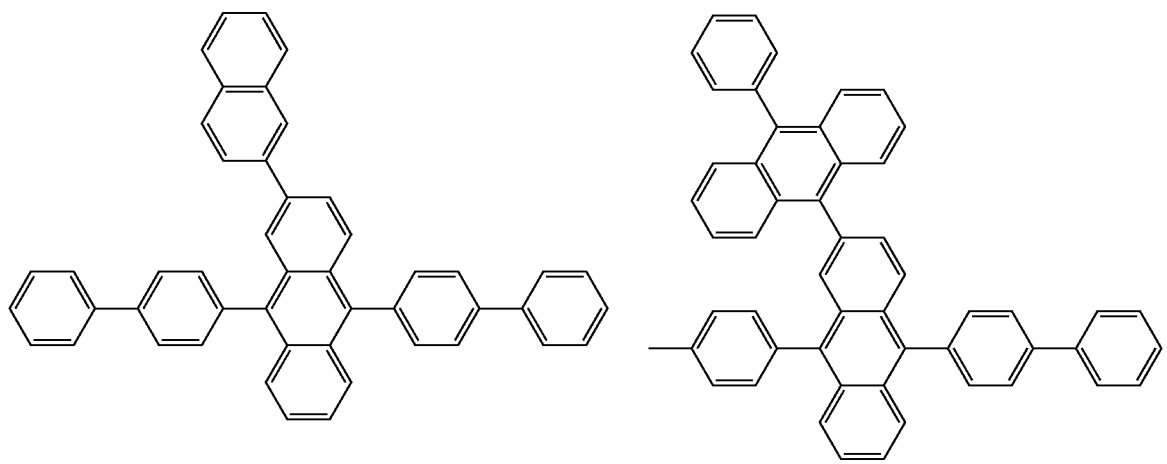
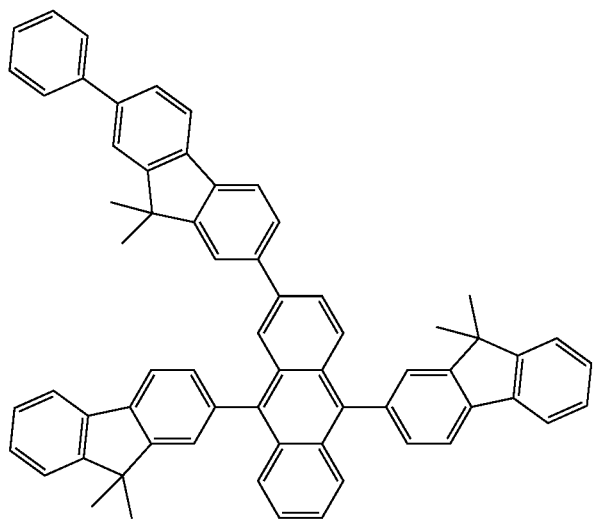

207 208
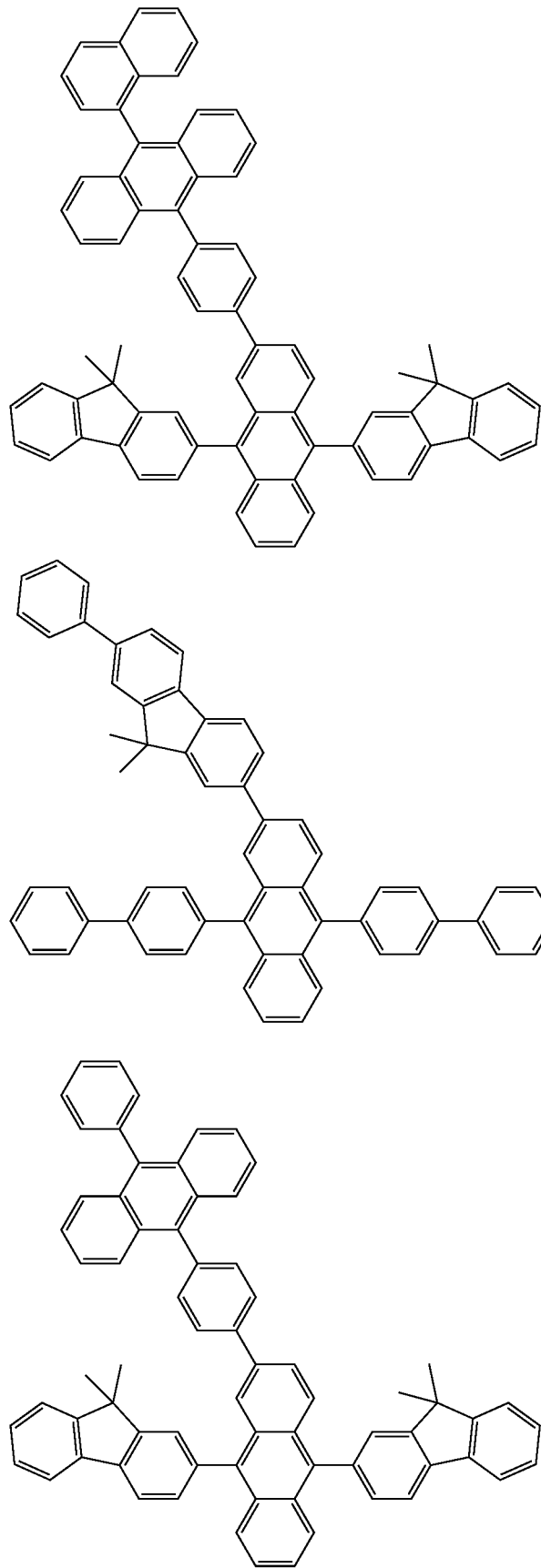
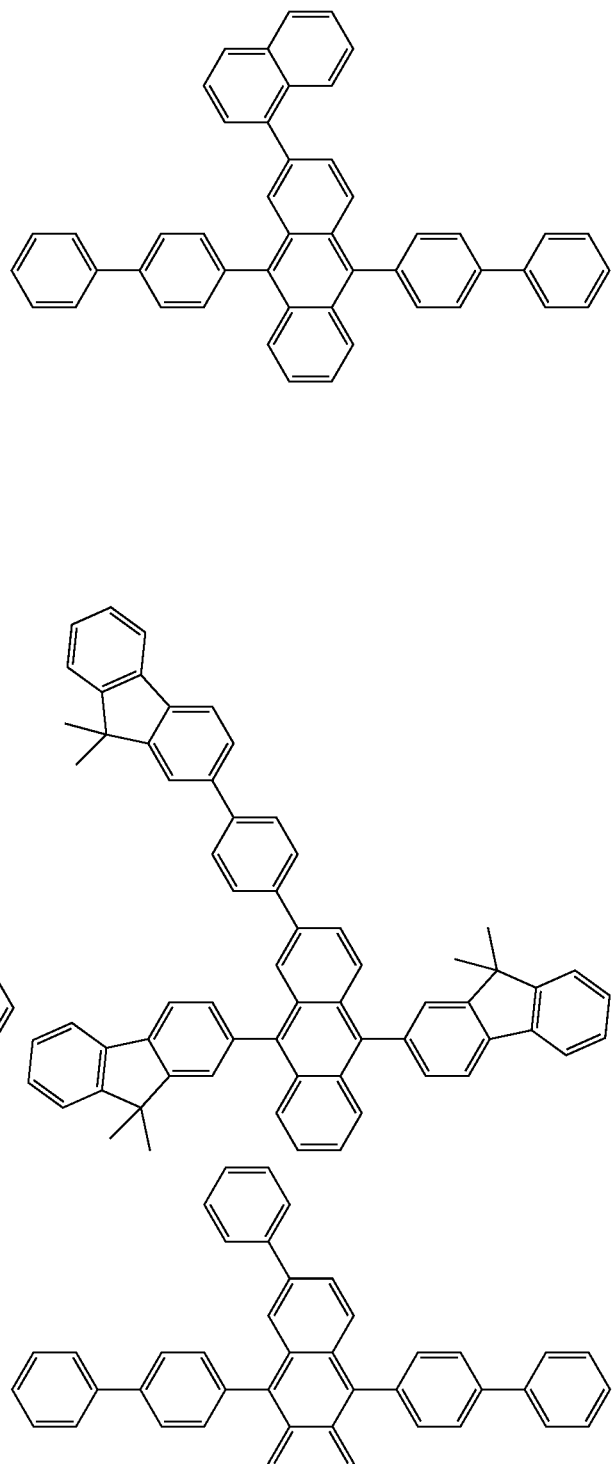

209
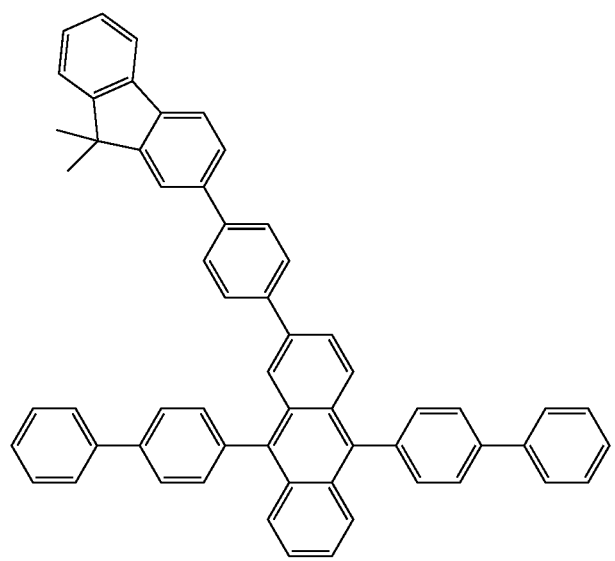
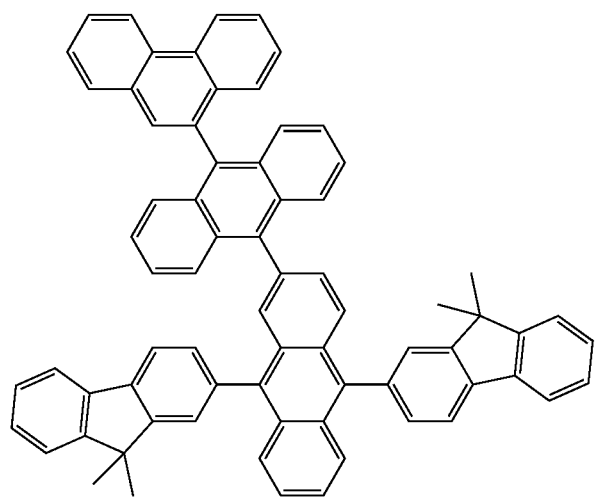
210
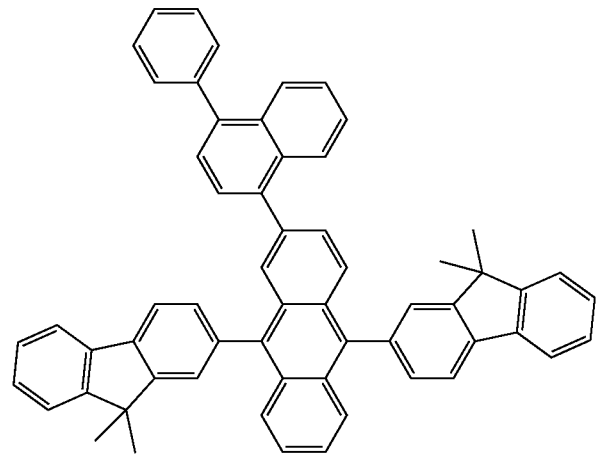
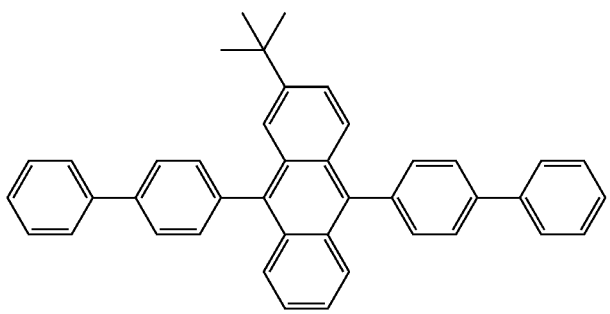
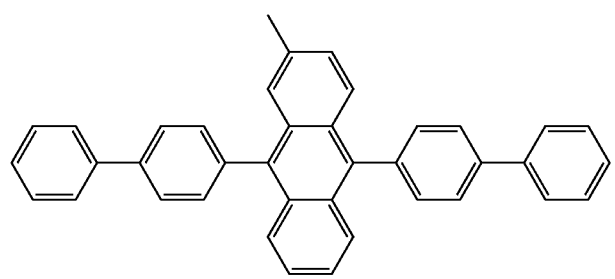

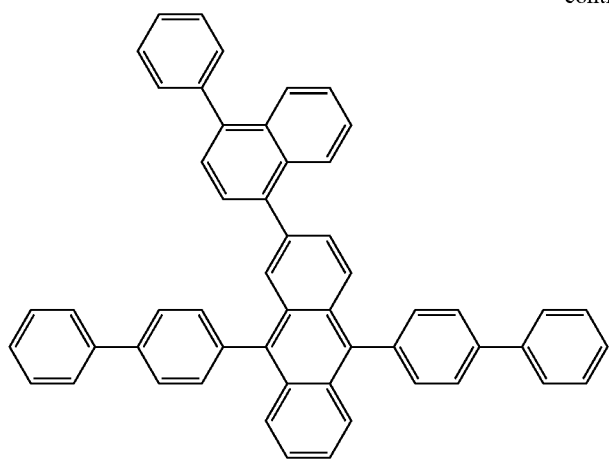
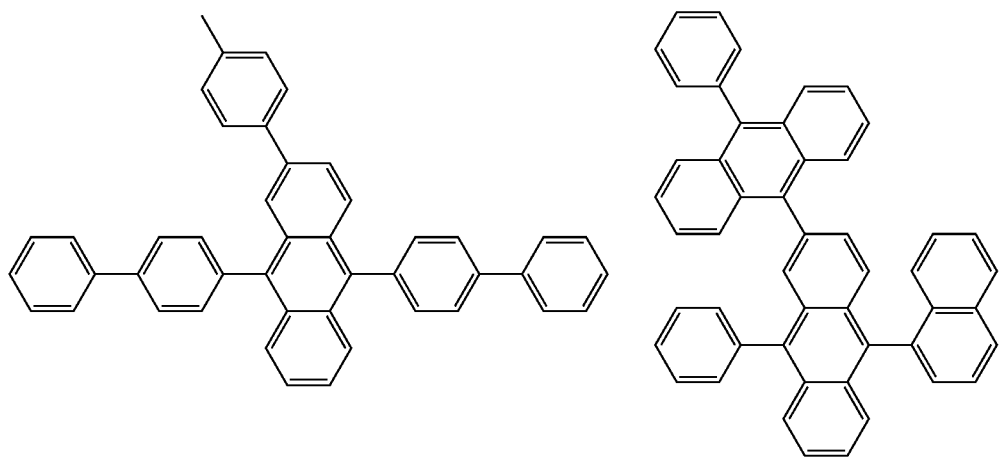
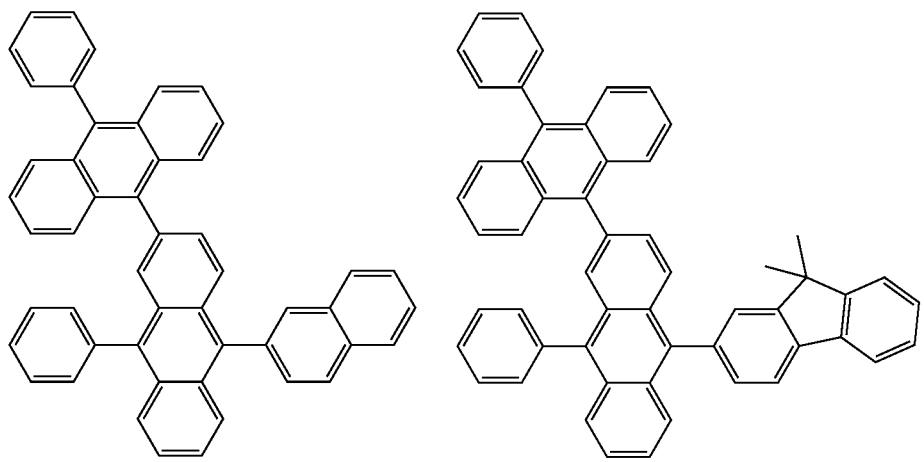

213
214
-continued
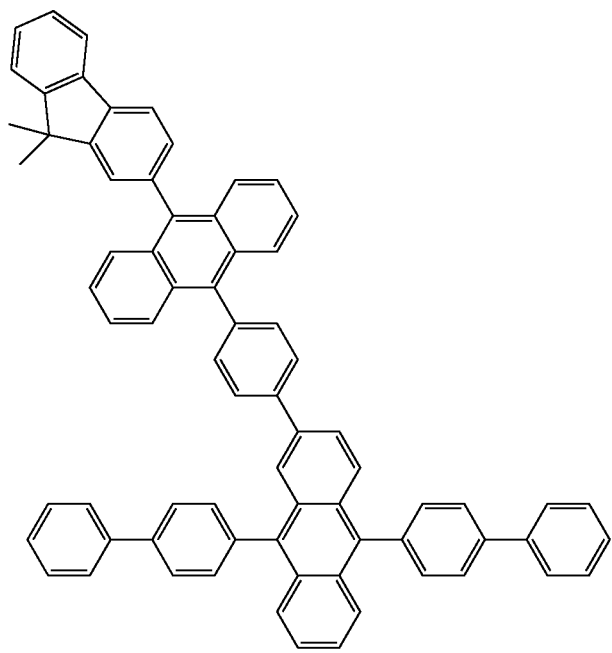
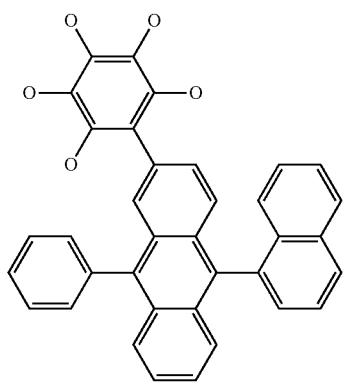
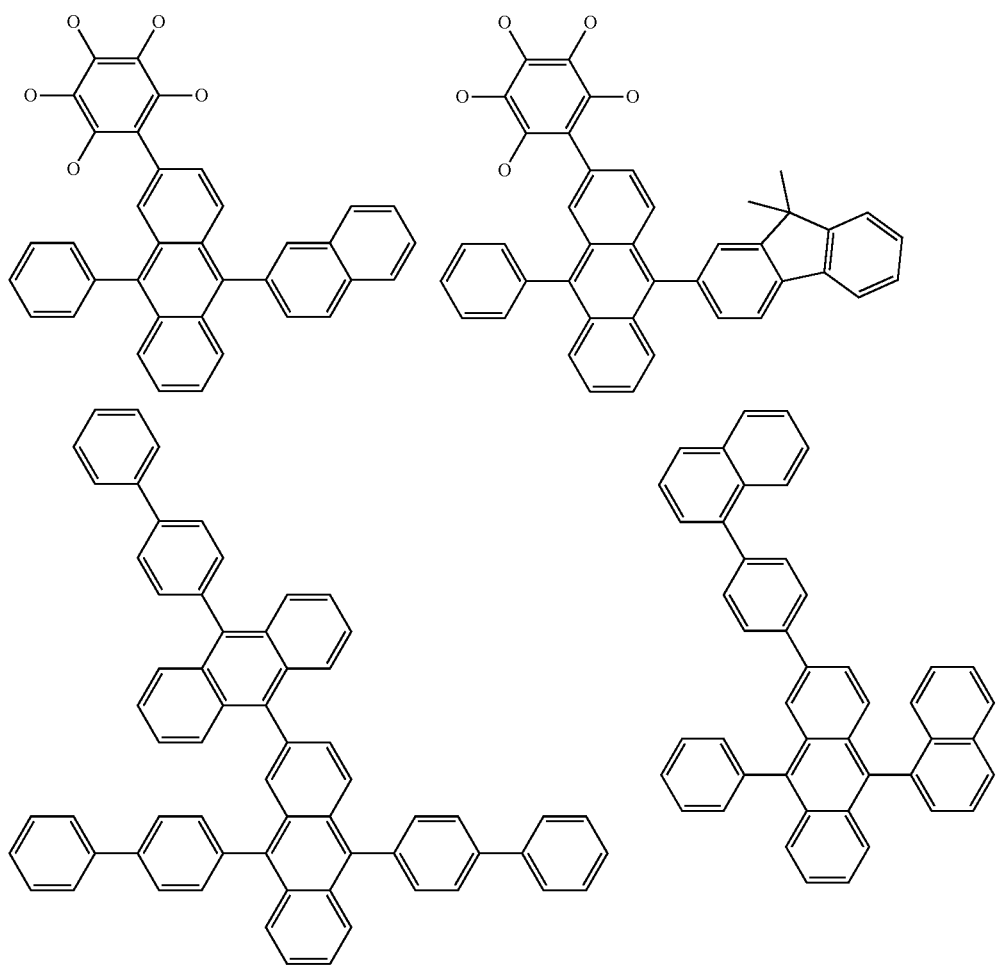

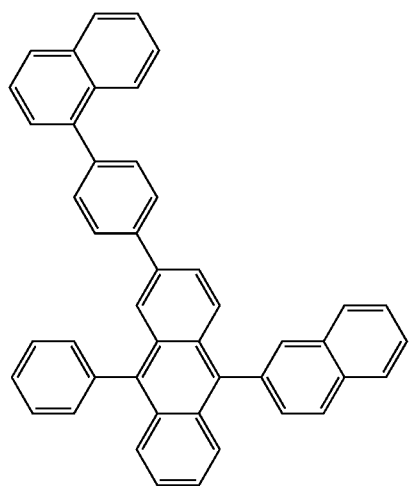
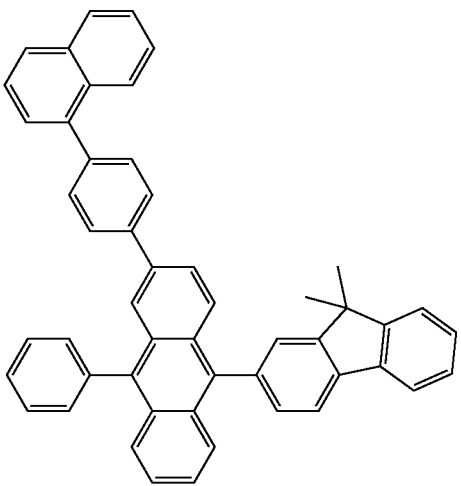
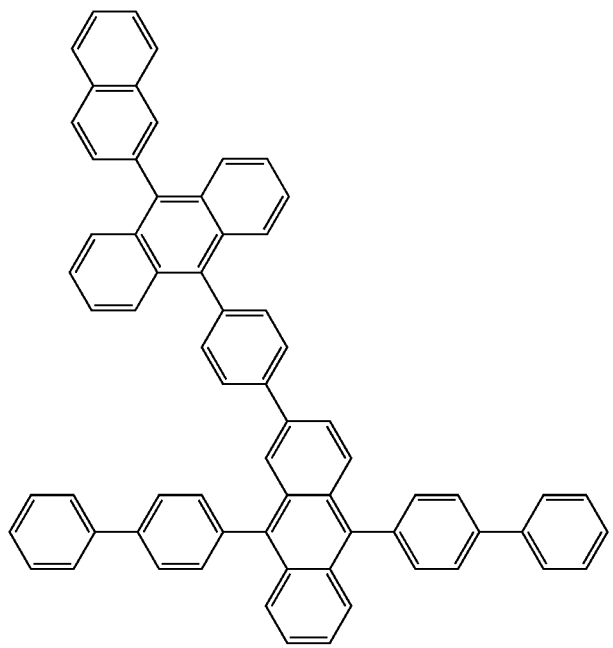
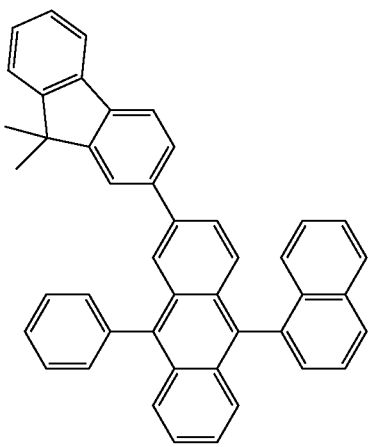
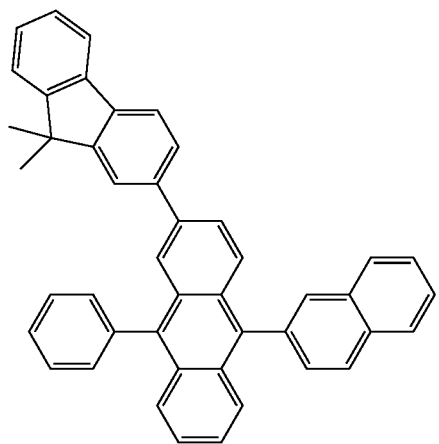
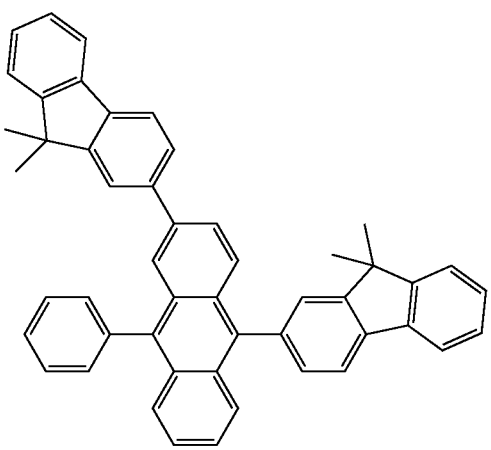

-continued
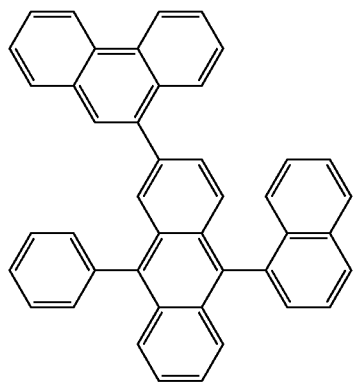
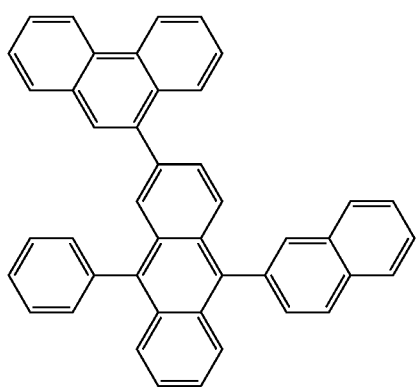
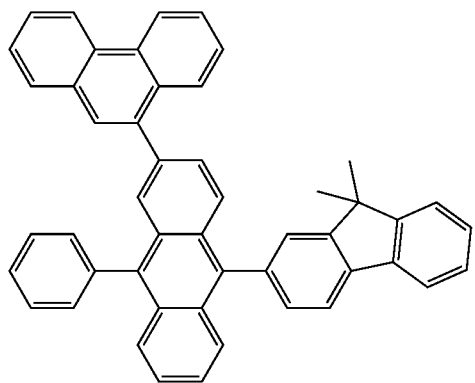
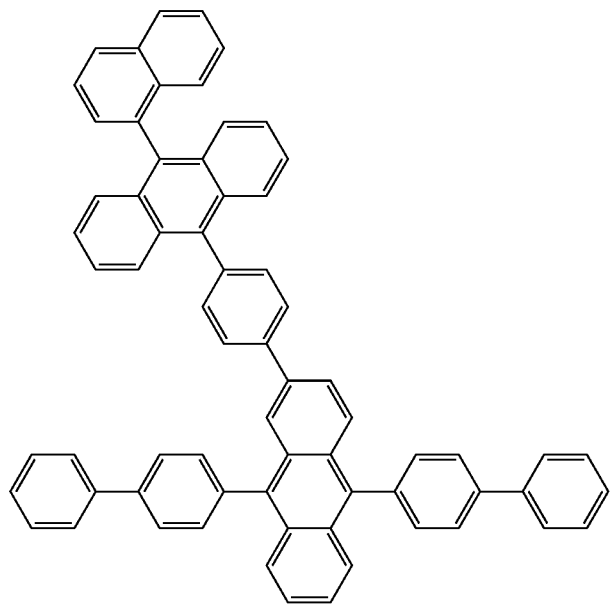
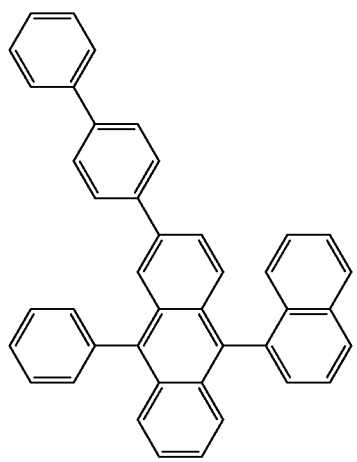
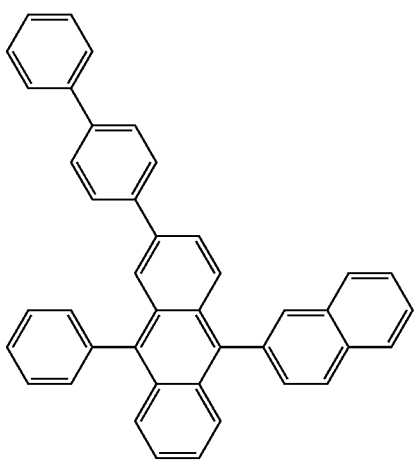

-continued
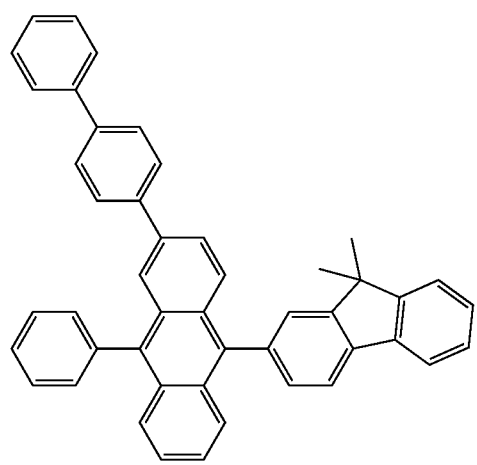
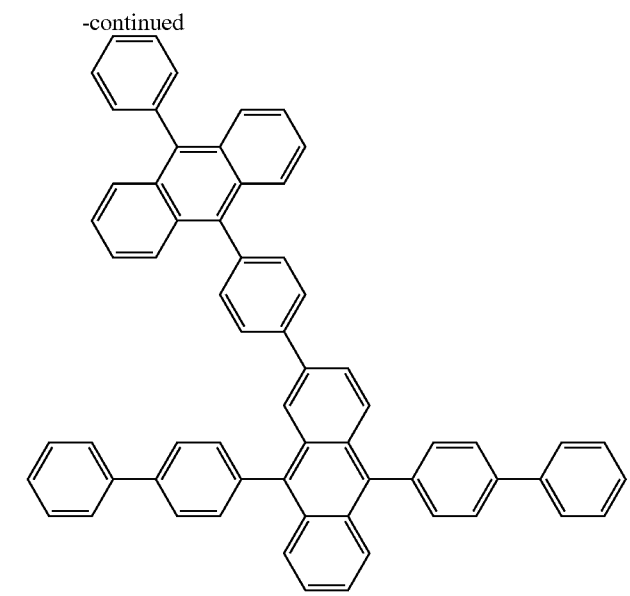
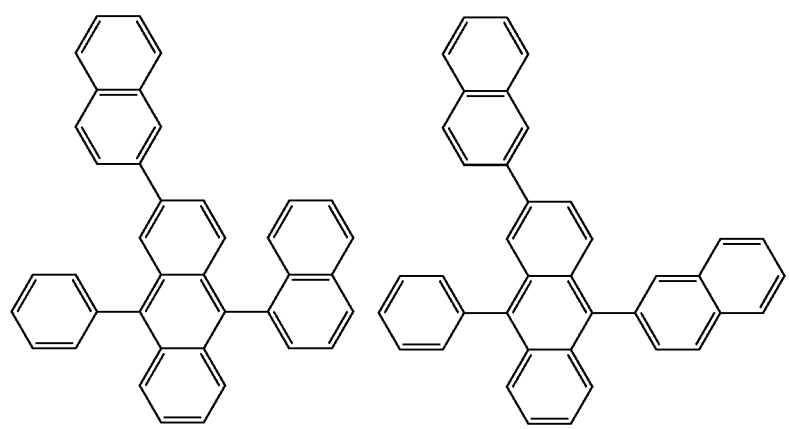
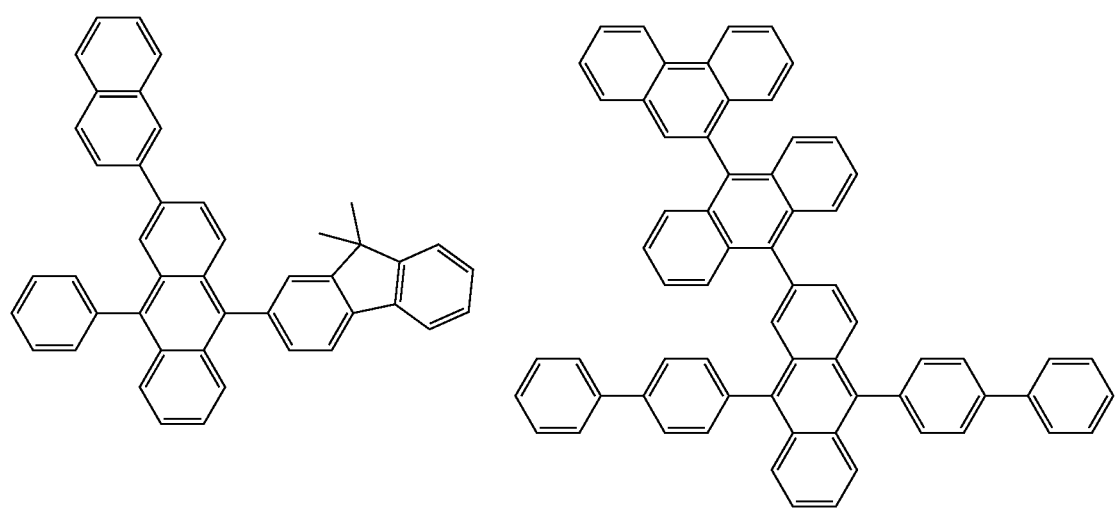

-continued
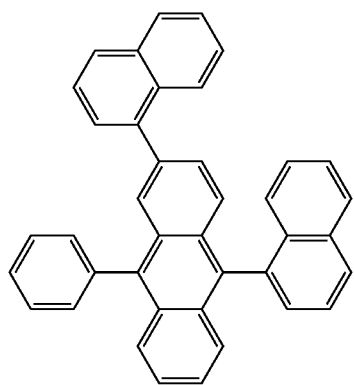
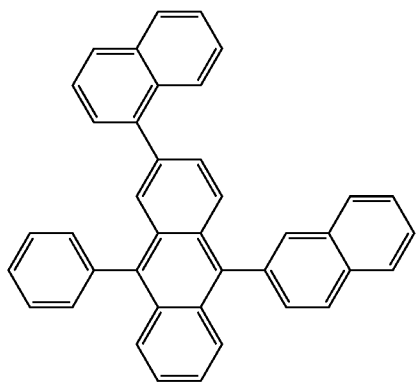
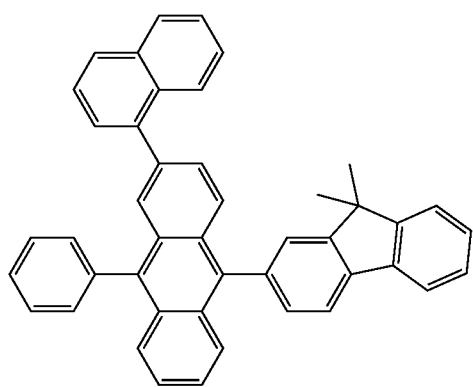
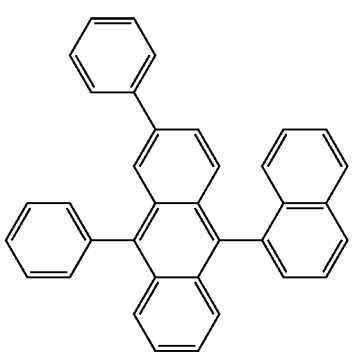
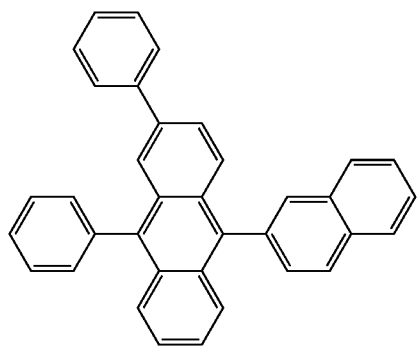
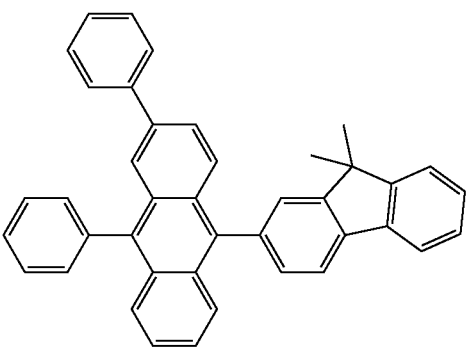
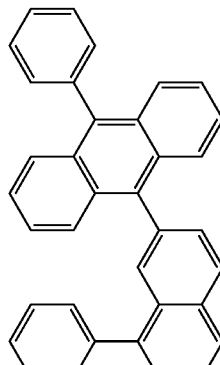
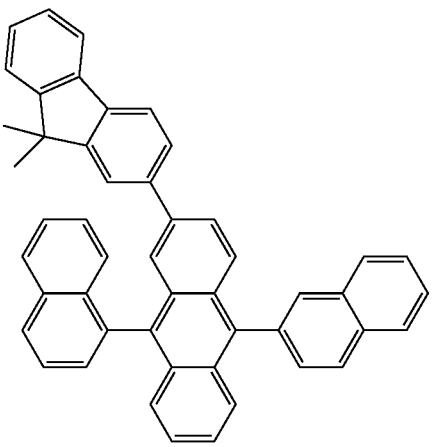

-continued
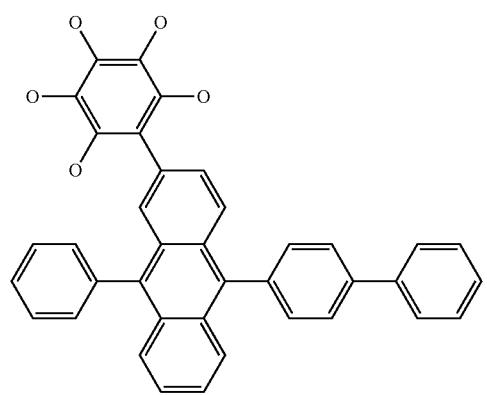
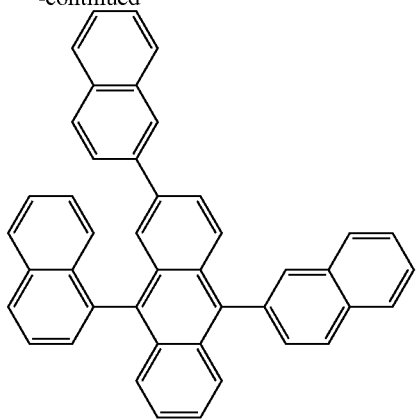
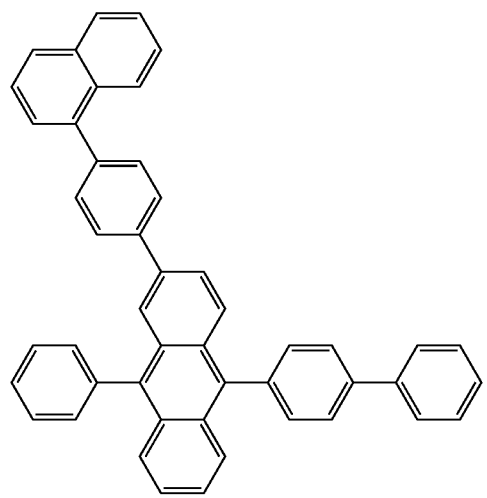
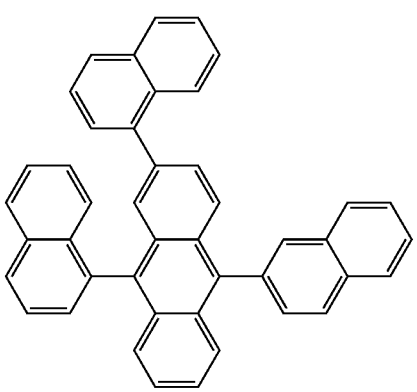
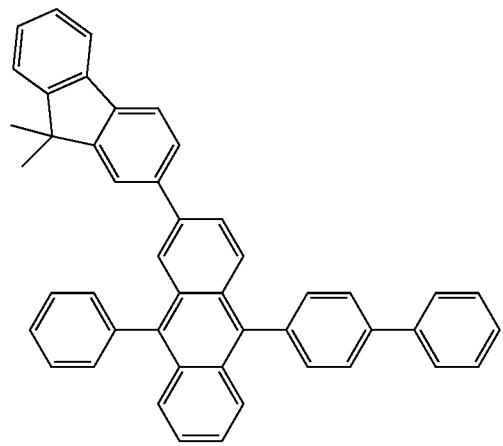
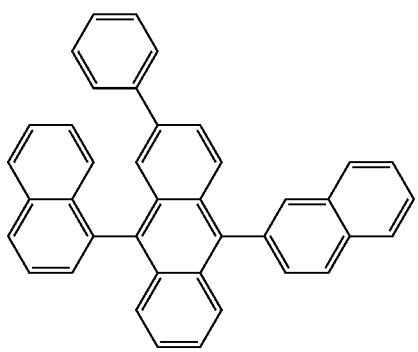

-continued
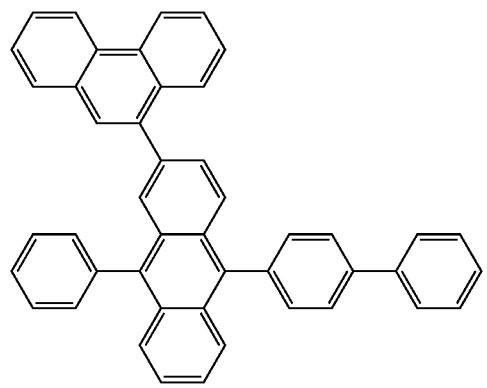
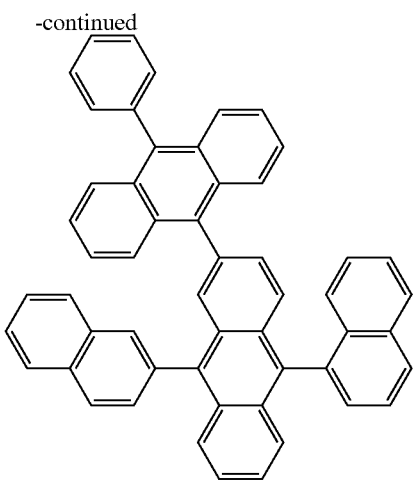
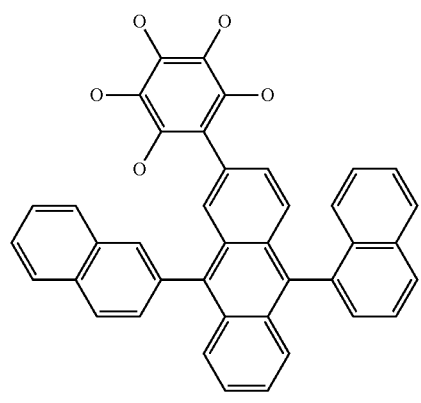
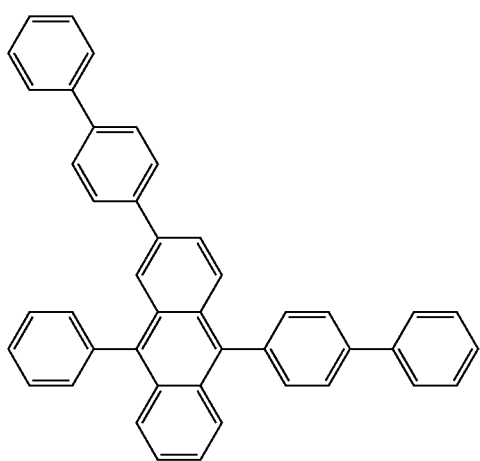
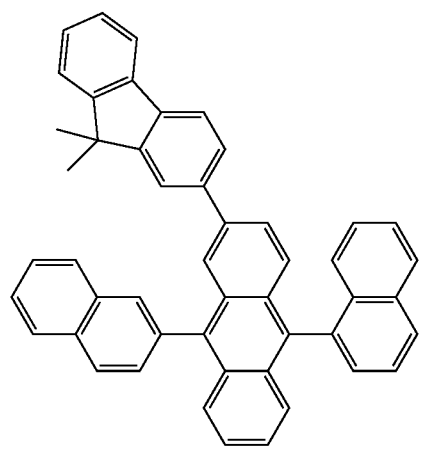
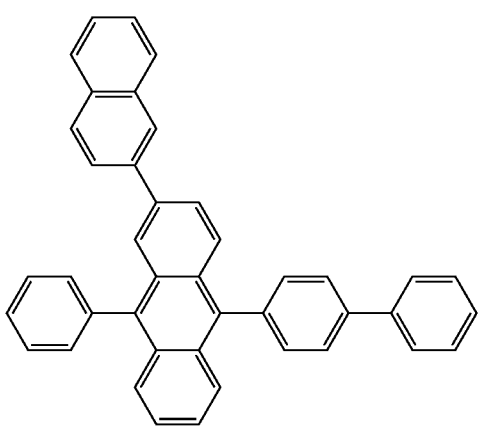

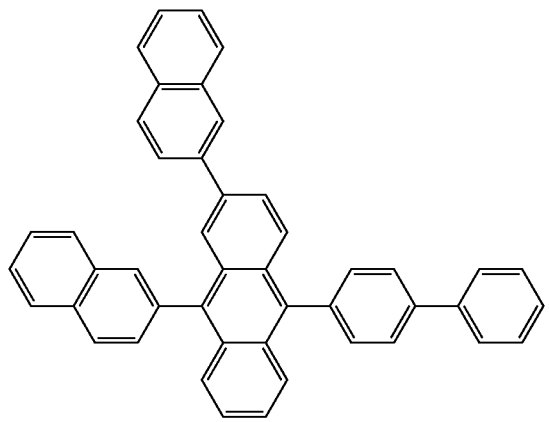
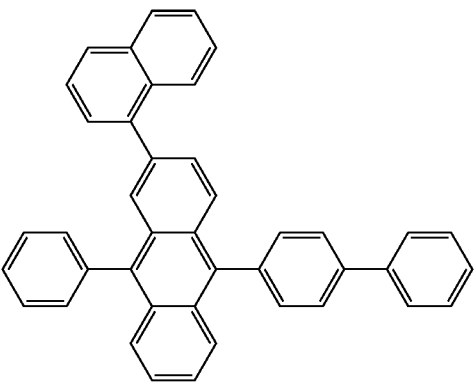
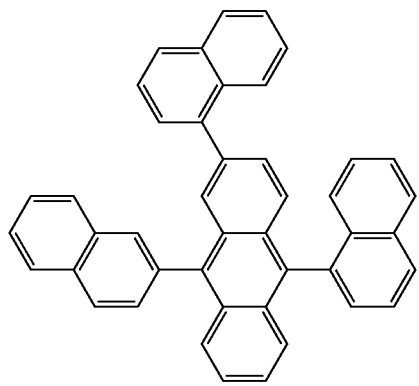
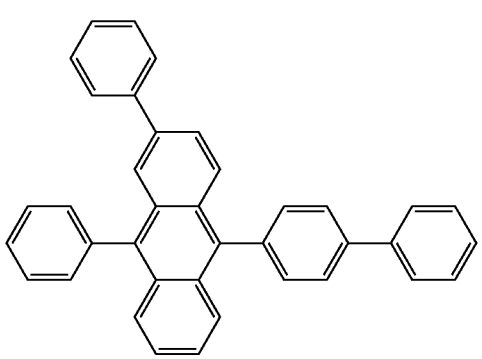
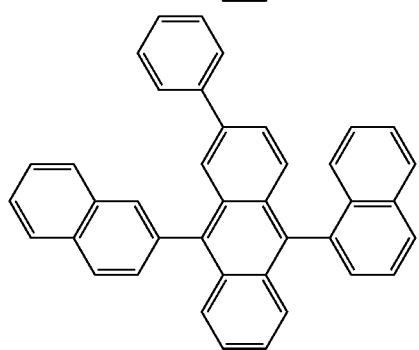
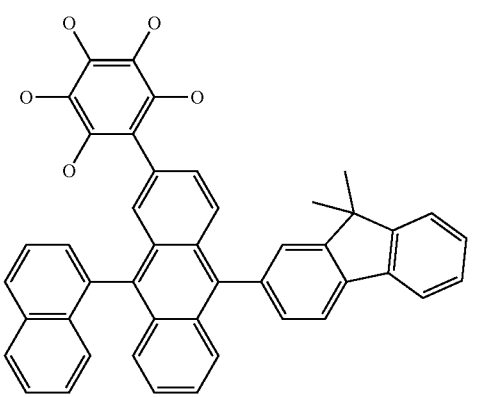
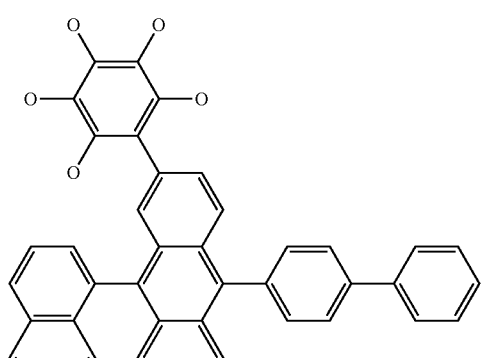
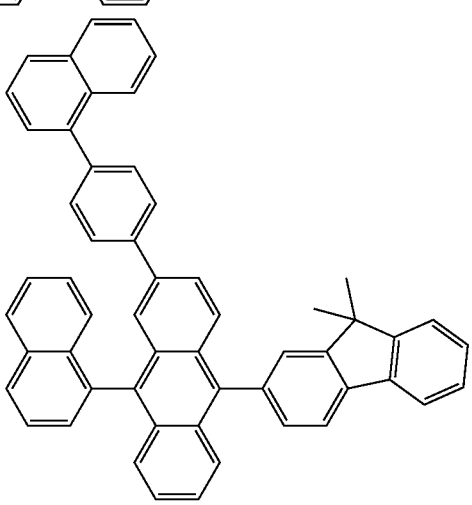

-continued
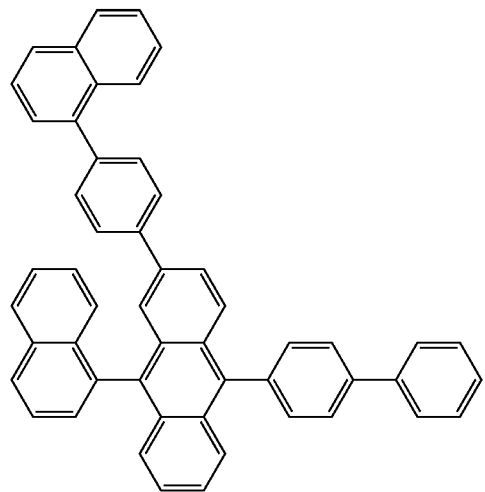
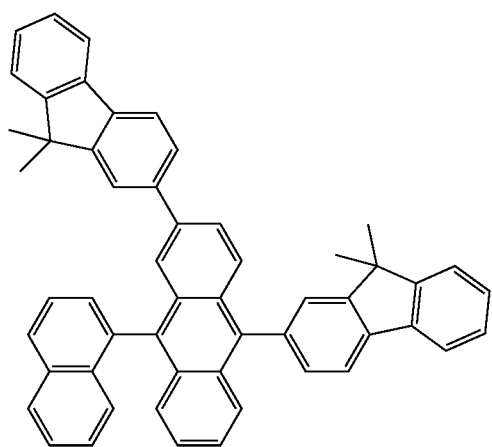
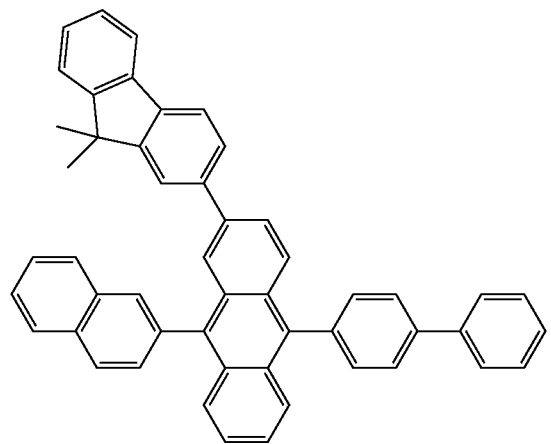
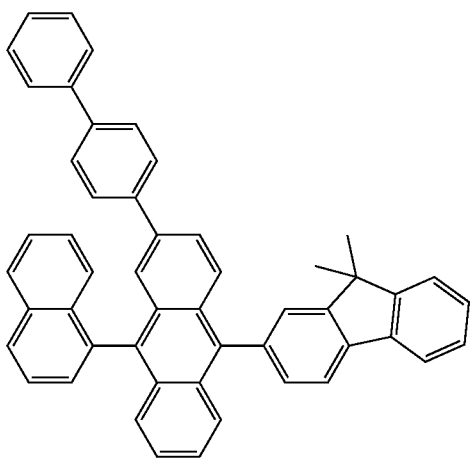
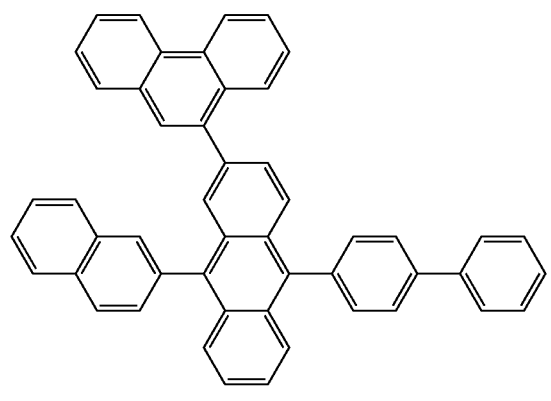
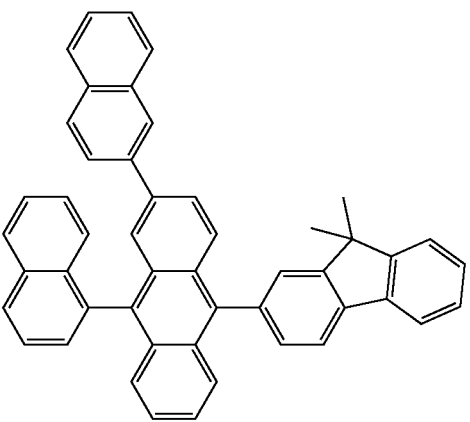

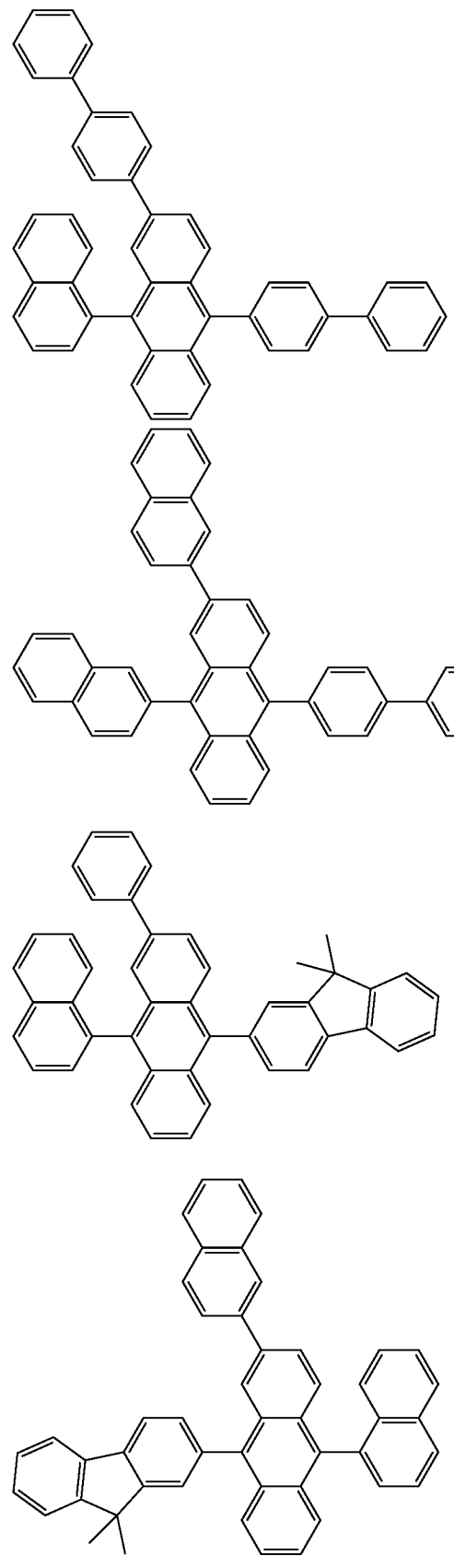
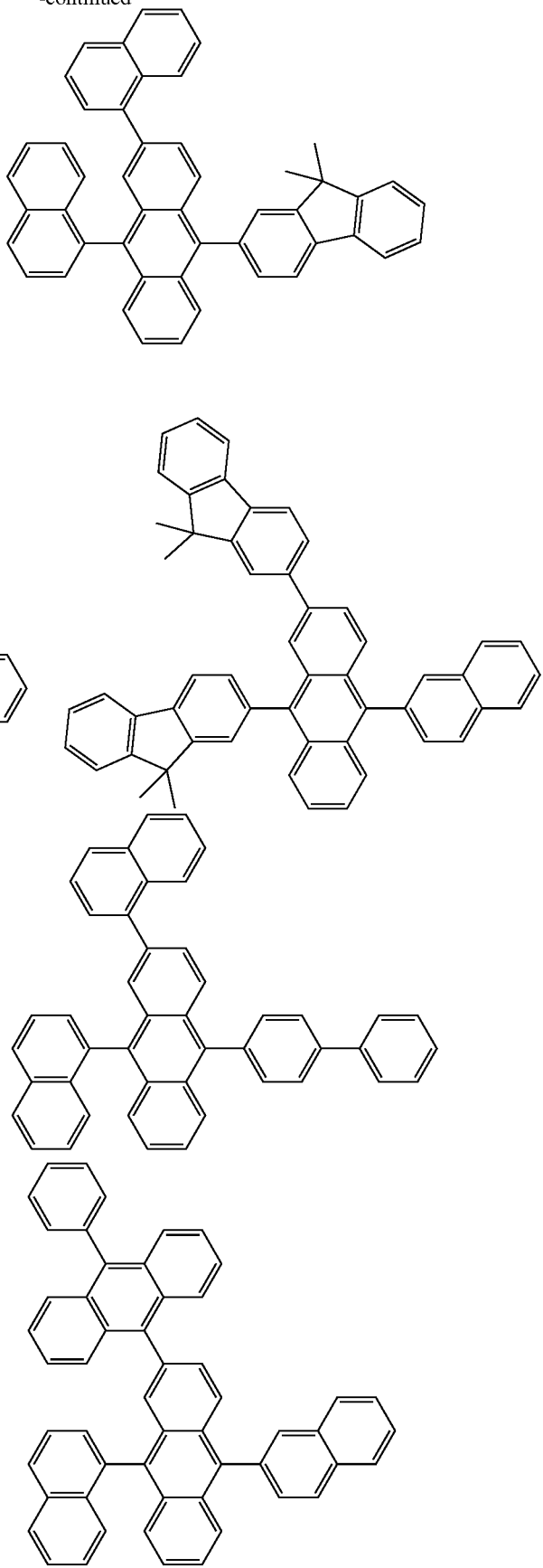

-continued
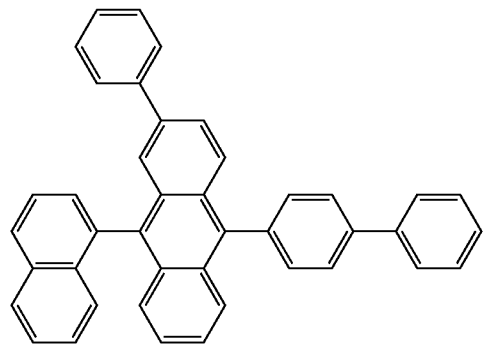
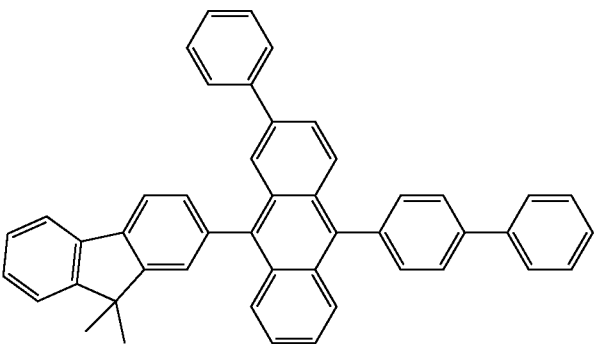
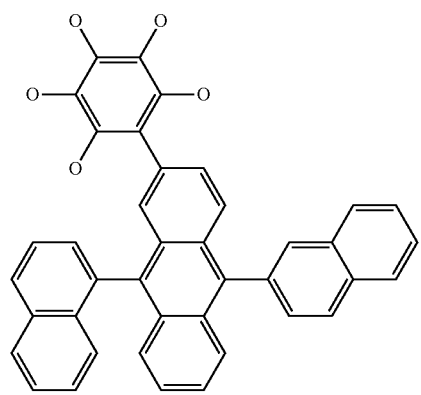
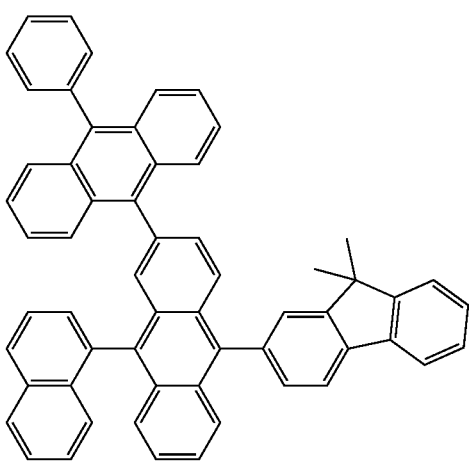
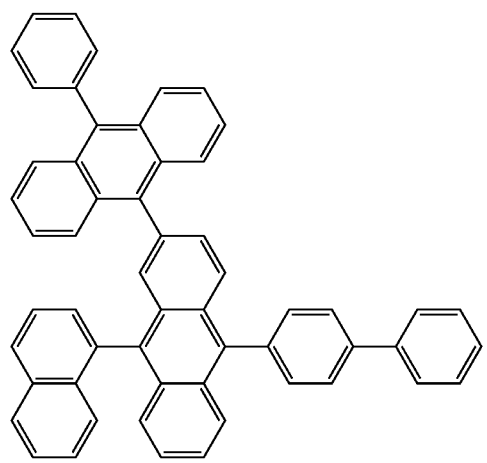
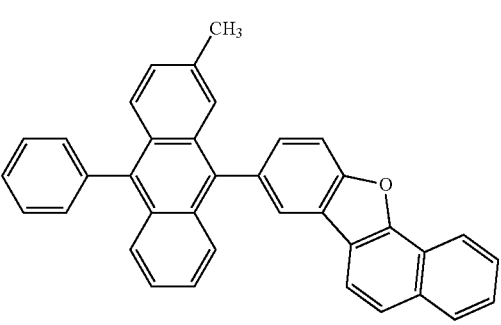
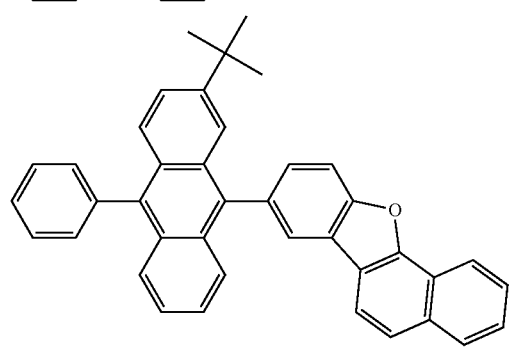
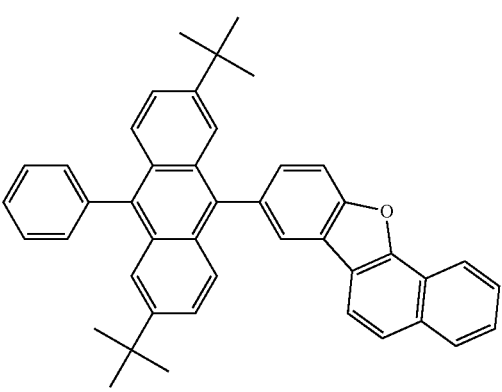

-continued
235
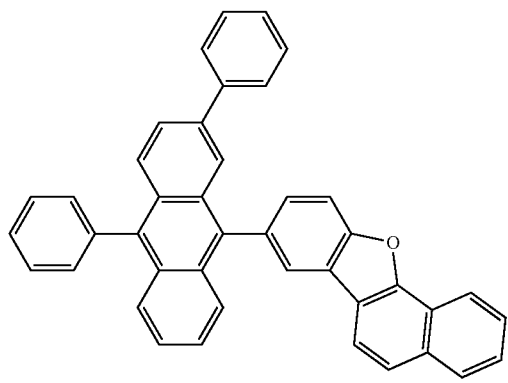
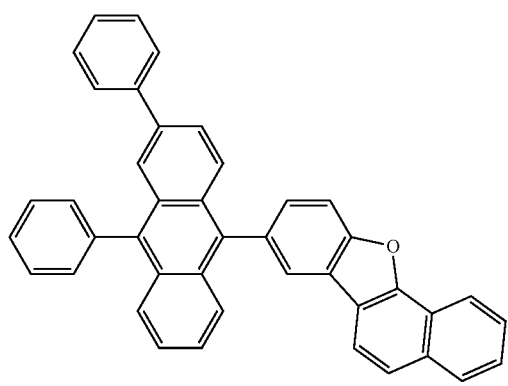
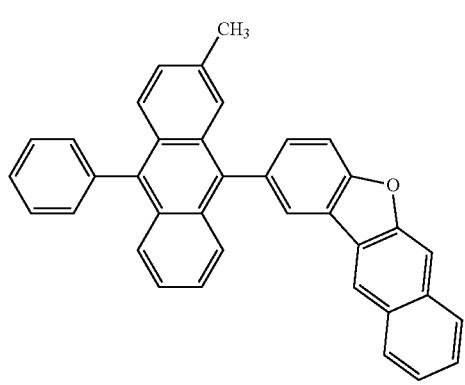
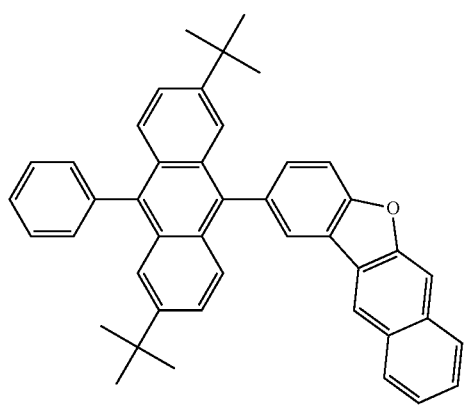
236
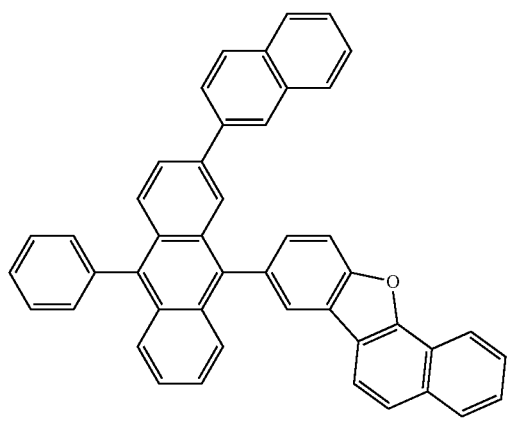
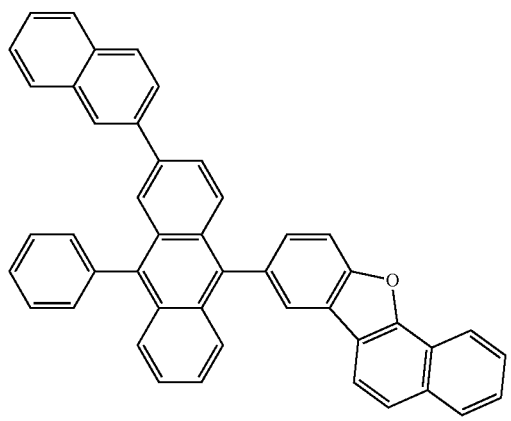
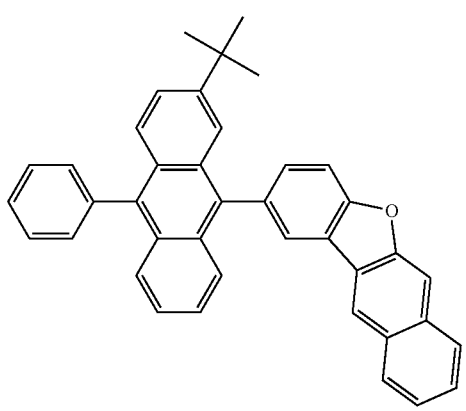
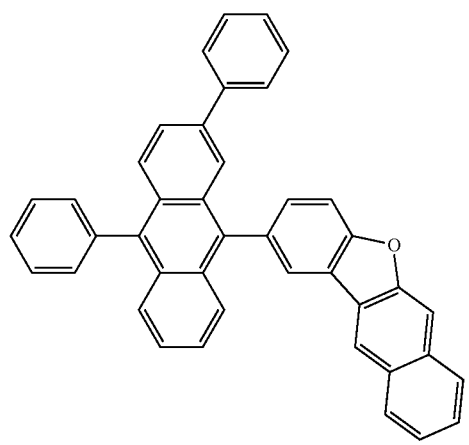

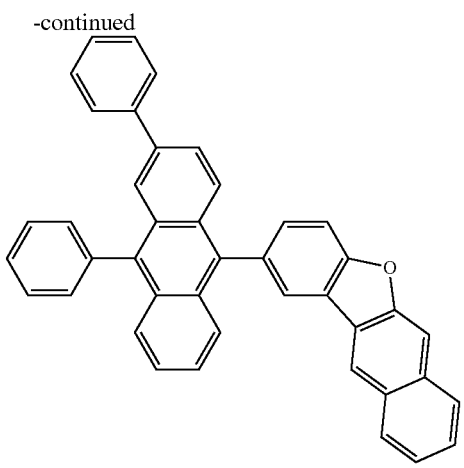

-continued

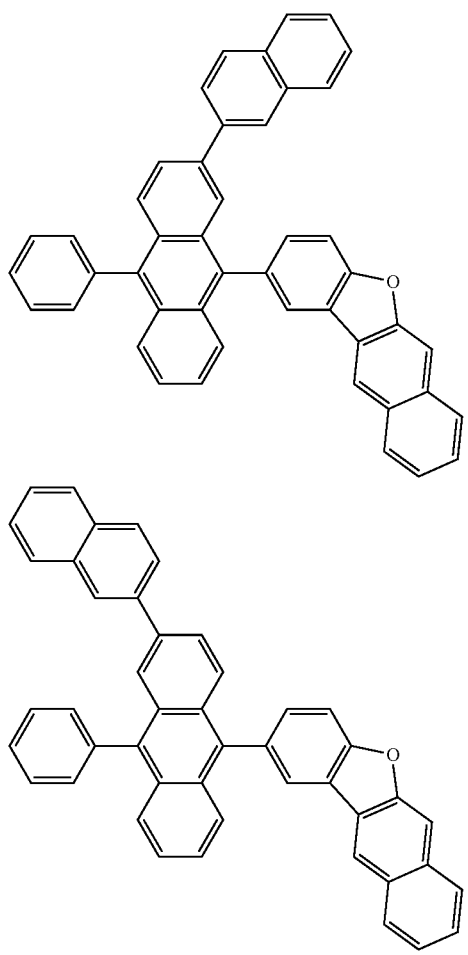

Hereinafter, a layer configuration of the organic EL device according to another aspect of the invention will be described.

The organic EL device according to another aspect of the invention has an organic layer between a pair of electrodes formed of the cathode and the anode. The organic layer includes at least one layer composed of an organic compound. Alternatively, the organic layer is formed by stacking a plurality of layers composed of the organic compound. The organic layer may further contain an inorganic compound in addition to the organic compound.

In one embodiment, at least one layer of the organic layers is the emitting layer.

In one embodiment, when the emitting layer contains the compound represented by the formula (1-1) and the compound represented by the formula (10), a content of the compound represented by the formula (1-1) is preferably 1 mass % or more and 20 mass % or less based on a total mass of the emitting layer.

Further, in one embodiment, when the emitting layer contains the compound represented by the formula (1-1) and the compound represented by the formula (10), a content of the compound represented by the formula (10) is preferably 80 mass % or more and 99 mass % or less based on the total mass of the emitting layer.

The organic layer may be formed, for example, as one layer of the emitting layer, or may include other layers which can be adopted in the layer configuration of the organic EL device. The layer that can be adopted in the layer configuration of the organic EL device is not particularly limited, but specific examples thereof include a hole-transporting zone (a hole-transporting layer, a hole-injecting layer, an electron-blocking layer, an exciton-blocking layer or the like) provided between the anode and the emitting layer, an emitting layer, a space layer, and an electron-transporting zone (an electron-transporting layer, an electron-injecting layer, a hole-blocking layer or the like) provided between the cathode and the emitting layer.

One embodiment of the organic EL device preferably has the hole-transporting layer between the anode and the emitting layer.

One embodiment of the organic EL device preferably has the electron-transporting layer between the cathode and the emitting layer.

Specific examples of a typified device configuration of the organic EL device of the invention include structures such as
(1) an anode/an emitting layer/a cathode,
(2) an anode/a hole-injecting layer/an emitting layer/a cathode,
(3) an anode/an emitting layer/an electron-injecting-transporting layer/a cathode,
(4) an anode/a hole-injecting layer/an emitting layer/an electron-injecting-transporting layer /a cathode,
(5) an anode/an organic semiconductor layer/an emitting layer/a cathode, (6) an anode/an organic semiconductor layer/an electron barrier layer/an emitting layer/a cathode,
(7) an anode/an organic semiconductor layer/an emitting layer/an adhesion improving layer /a cathode,
(8) an anode/a hole-injecting-transporting layer/an emitting layer/an electron-injecting-transporting layer/a cathode,
(9) an anode/an insulating layer/an emitting layer/an insulating layer/a cathode,
(10) an anode/an inorganic semiconductor layer/an insulating layer/an emitting layer/an insulating layer/a cathode,
(11) an anode/an organic semiconductor layer/an insulating layer/an emitting layer/an insulating layer/a cathode,
(12) an anode/an insulating layer/a hole-injecting-transporting layer/an emitting layer/an insulating layer/a cathode, and
(13) an anode/an insulating layer/a hole-injecting-transporting layer/an emitting layer/an electron-injecting-transporting layer/a cathode.

Among the above-described structures, a configuration of (8) is preferably used, but the configuration is not limited thereto.

Further, the emitting layer may be a phosphorescent emitting layer or a fluorescent emitting layer, and may include a plurality of emitting layers. When the organic EL device has the plurality of emitting layers, the organic EL device may have a space layer between the respective emitting layers for the purpose of preventing excitons generated in the phosphorescent emitting layer from diffusing into the fluorescent emitting layer.

The FIGURE shows a schematic configuration of one example of the organic EL device in an embodiment of the invention.

An organic EL device 1 has a transparent substrate 2, an anode 3, a cathode 4, and an organic layer 10 arranged between the anode 3 and the cathode 4.

The organic layer 10 has an emitting layer 5 described above, and may have a hole-injecting-transporting layer 6 or the like between the emitting layer 5 and the anode 3, and an electron-injecting-transporting layer 7 or the like between the emitting layer 5 and the cathode 4.

Further, the electron barrier layer may be provided on a side of the anode 3 of the emitting layer 5, and a hole barrier layer may be provided on a side of the cathode 4 of the emitting layer 5, respectively.

Accordingly, electrons or holes can be confined in the emitting layer 5 to enhance generation probability of the excitons in the emitting layer 5.

Moreover, the "hole-injecting-transporting layer" herein means "at least one of the hole-injecting layer and the hole-transporting layer", and the "electron-injecting-transporting layer" herein means "at least one of the electron-injecting layer and the electron-transporting layer".

The compound represented by the formula (1-1) and the compound represented by the formula (10), to be contained in the above-described emitting layer 5, may have one kind alone, or two or more kinds thereof, respectively.

A substrate is used as a support of an emitting device. As the substrate, glass, quartz, plastics or the like can be used, for example. Further, a flexible substrate may be used. A term "flexible substrate" means a bendable (flexible) substrate, and specific examples thereof include a plastic substrate formed of polycarbonate or polyvinyl chloride.

For the anode formed on the substrate, metal, alloy, an electrically conductive compound, a mixture thereof or the like, each having a large work function (specifically 4.0 eV or more), is preferably used. Specific examples thereof include indium oxide-tin oxide (ITO: Indium Tin Oxide), silicon or silicon oxide-containing indium oxide-tin oxide, indium oxide-zinc oxide, tungsten oxide, zinc oxide-containing indium oxide, and graphene. In addition thereto, specific examples thereof include gold (Au), platinum (Pt), or nitride of a metallic material (for example, titanium nitride).

The hole-injecting layer is a layer containing a material having high hole-injection properties. As the material having high hole-injection properties, such a material can be used as molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a ladder-type compound such as a fluorene derivative, or a polymer compound (an oligomer, a dendrimer, a polymer or the like).

The hole-transporting layer is a layer containing a material having high hole-transporting properties. For the hole-transporting layer, an aromatic amine compound, a carbazole derivative, an anthracene derivative, or the like can be used. A polymer compound such as poly(N-vinylcarbazole) (abbreviation: PVK) and poly(4-vinyltriphenylamine) (abbreviation: PVTPA) can also be used. However, a material other than the above-described materials may be used as long as the material has higher transporting properties of holes in comparison with electrons. It should be noted that the layer containing the material having high hole-transporting properties may be formed into not only a monolayer, but also a layer in which two or more layers formed of the above-described materials are stacked.

The electron-transporting layer is a layer containing a substance having high electron-transporting properties. For the electron-transporting layer, such a material can be used as 1) a metal complex such as a lithium complex, an aluminum complex, a beryllium complex and a zinc complex; 2) a heteroaromatic compound such as an imidazole derivative, a benzimidazole derivative, an azine derivative, a carbazole derivative and a phenanthroline derivative; and 3) a polymer compound.

The electron-injecting layer is a layer containing a material having high electron-injection properties. For the electron-injecting layer, such a material can be used as alkali metal, alkaline earth metal or a compound thereof, such as lithium (Li), a lithium complex, lithium fluoride (LiF), cesium fluoride (CsF), calcium fluoride ($CaF_2$) and lithium oxide (LiOx).

For the cathode, metal, alloy, an electrically conductive compound, a mixture thereof, or the like, each having a small work function (specifically, 3.8 eV or less) is preferably used. Specific examples of such a cathode material include an element belonging to group 1 or group 2 of the periodic table of the elements, namely, alkali metal such as lithium (Li) and cesium (Cs), alkaline earth metal such as magnesium (Mg), and alloy containing the metal thereof (for example, MgAg and AlLi).

In one embodiment of the organic EL device of the invention, a method for forming each layer is not limited. A conventionally-known method for forming each layer according to a vacuum deposition process, a spin coating process or the like can be used. Each layer such as the emitting layer can be formed by a known method such as a vacuum deposition process, a molecular beam deposition process (MBE process), or an application process such as a dipping process, a spin coating process, a casting process, a bar coating process and a roll coating process, using a solution prepared by dissolving the material in the solvent.

In one embodiment of the organic EL device of the invention, a film thickness of each layer is not particularly

EXAMPLES

Example 1

(1) Synthesis of Compound BD-1

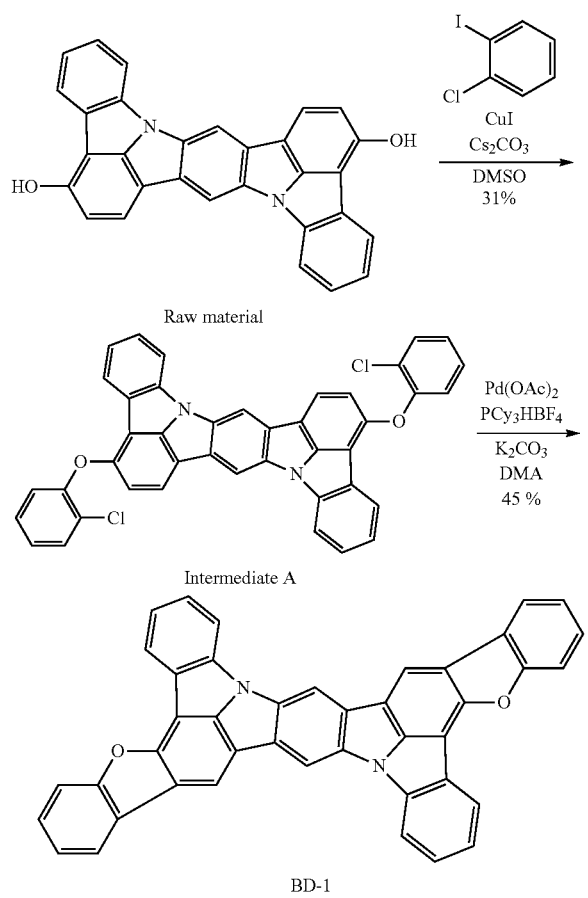

(A) Synthesis of Intermediate A

Under an argon atmosphere, a raw material (5.0 g, 11.5 mmol), 2-chloro-iodobenzene (13.6 g, 57.3 mmol), copper (I) iodide (4.36 g, 22.9 mmol) and $Cs_2CO_3$ (18.7 g, 57.3 mmol) were heated and stirred in N,N-dimethyl sulfoxide (100 mL) at 150° C. for 24 hours. After completion of the reaction, water was added thereto, a precipitate was collected by filtration, and the resulting material was washed with methanol. The resulting solid was purified by column chromatography to obtain a light yellow solid (2.3 g, yield: 31%). The obtained solid was an intermediate A, which was an intended product, and the results of mass spectrometric analysis were: m/e=658 for a molecular weight of 657.

(B) Synthesis of BD-1

Under an argon atmosphere, the intermediate A (2.30 g, 3.50 mmol), $Pd(OAc)_2$ (79 mg, 0.35 mmol), tricyclohexylphosphoniumtetrafluoroborate (258 mg, 0.70 mmol) and potassium carbonate (1.93 g, 14.0 mmol) were dissolved in N,N-dimethylacetamide (80 mL), and the resulting solution was refluxed for 12 hours. After completion of the reaction, water was added thereto, a precipitate was collected by filtration, and the resulting material was washed with methanol. The resulting solid was purified by column chromatography to obtain a yellow solid (920 mg, yield: 45%). The obtained solid was a compound 2, which was an intended product, and the results of mass spectrometric analysis were: m/e=585 for a molecular weight of 584.

(2) Fabrication of Organic EL Device

A 25 mm×75 mm×1.1 mm-thick glass substrate with an ITO transparent electrode (anode) (manufactured by GEO-MATEC Co., Ltd.) was subjected to ultrasonic cleaning in isopropyl alcohol for 5 minutes, and then subjected to UV-ozone cleaning for 30 minutes. A thickness of ITO was adjusted to 130 nm.

The glass substrate with the transparent electrode after being cleaned was mounted onto a substrate holder in a vacuum vapor deposition apparatus. First, a compound HI was deposited on a surface on the side on which the transparent electrode was formed so as to cover the transparent electrode to form a compound HI film having a thickness of 5 nm. The HI film functions as a hole-injecting layer.

Subsequent to formation of the HI film, a compound HT1 was deposited thereon to form an HT1 film having a thickness of 80 nm on the HI film. The HT1 film functions as a first hole-transporting layer.

Subsequent to formation of the HT1 film, a compound HT2 was deposited thereon to form an HT2 film having a thickness of 10 nm on the HT1 film. The HT2 film functions as a second hole-transporting layer.

BH-1 (host material) and BD-1 (dopant material) were co-deposited on the HT2 film to be 4% in a proportion (mass ratio) of the compound BD-1 to form an emitting layer having a thickness of 25 nm.

HBL was deposited on the emitting layer to form an electron-transporting layer having a thickness of 10 nm. ET as an electron-injecting material was deposited on the electron-transporting layer to form an electron-injecting layer having a thickness of 15 nm. LiF was deposited on the electron-injecting layer to form a LiF film having a thickness of 1 nm. Al metal was deposited on the LiF film to form a metal cathode having a thickness of 80 nm.

An organic EL device was fabricated as described above. Compounds used therefor are shown below.

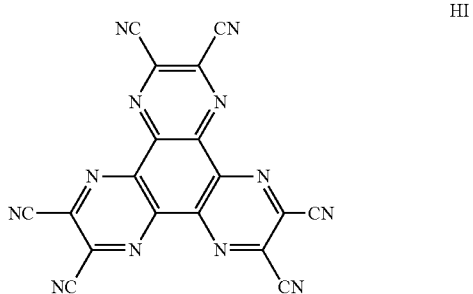

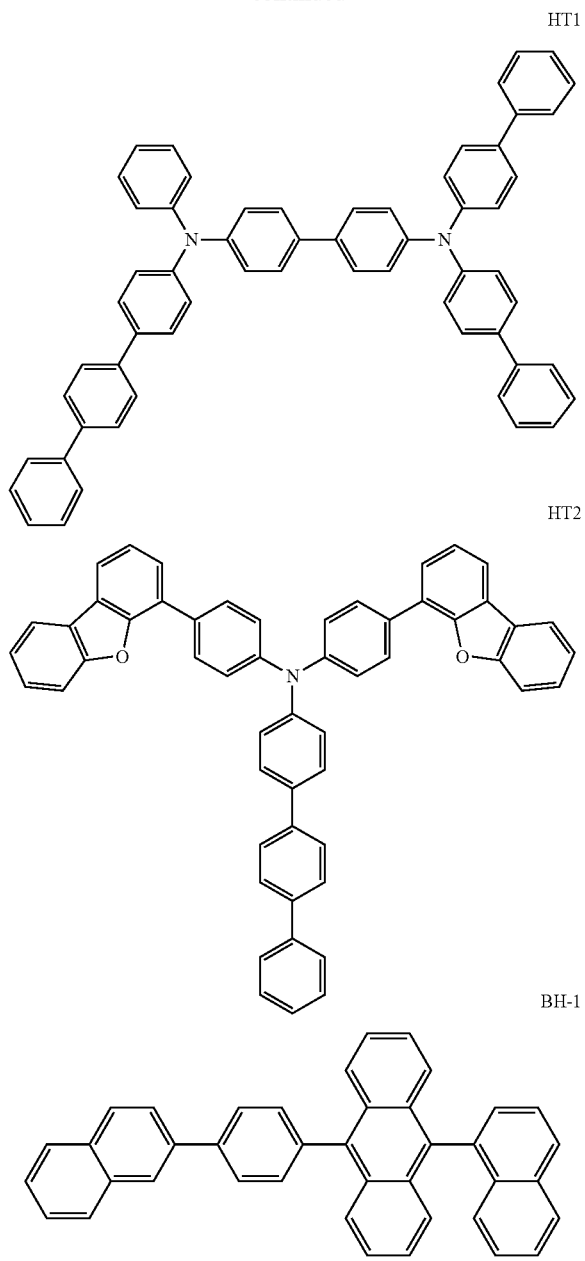

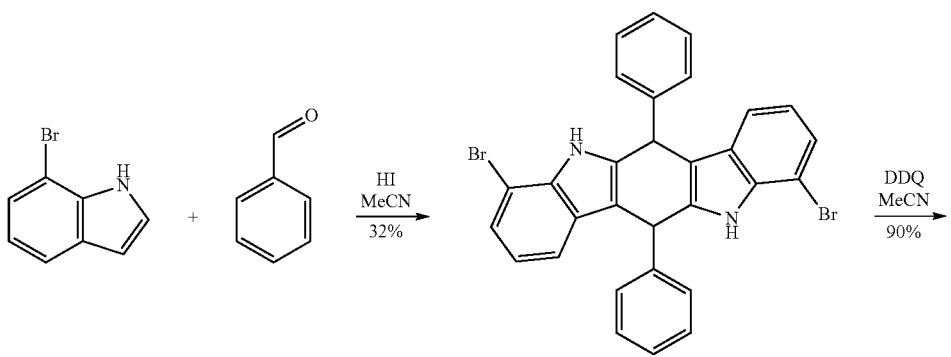

(Evaluation of Organic EL Device)

An initial driving voltage of the obtained organic EL device was measured by driving at a constant current of 10 mA/cm$^2$ of DC (direct current) at room temperature. The measurement results of the voltage are shown in Table 1.

Furthermore, voltage was applied to the organic EL device to be 10 mA/cm$^2$ in current density, thereby measuring an EL emission spectrum by using Spectroradiometer CS-1000 (manufactured by Konica Minolta, Inc.). External quantum efficiency (EQE) (%) was calculated from the resulting spectral radiance spectrum. The results are shown in Table 1.

TABLE 1

| | Host | Dopant | Driving voltage [V] | EQE [%] |
|---|---|---|---|---|
| Example 1 | BH-1 | BD-1 | 3.6 | 7.1 |
| Example 2 | BH-1 | BD-2 | 3.7 | 7.5 |
| Example 3 | BH-1 | BD-3 | 3.7 | 7.2 |
| Com. Example 1 | BH-1 | BD | 3.8 | 6.4 |

Example 2

(1) Synthesis of BD-2

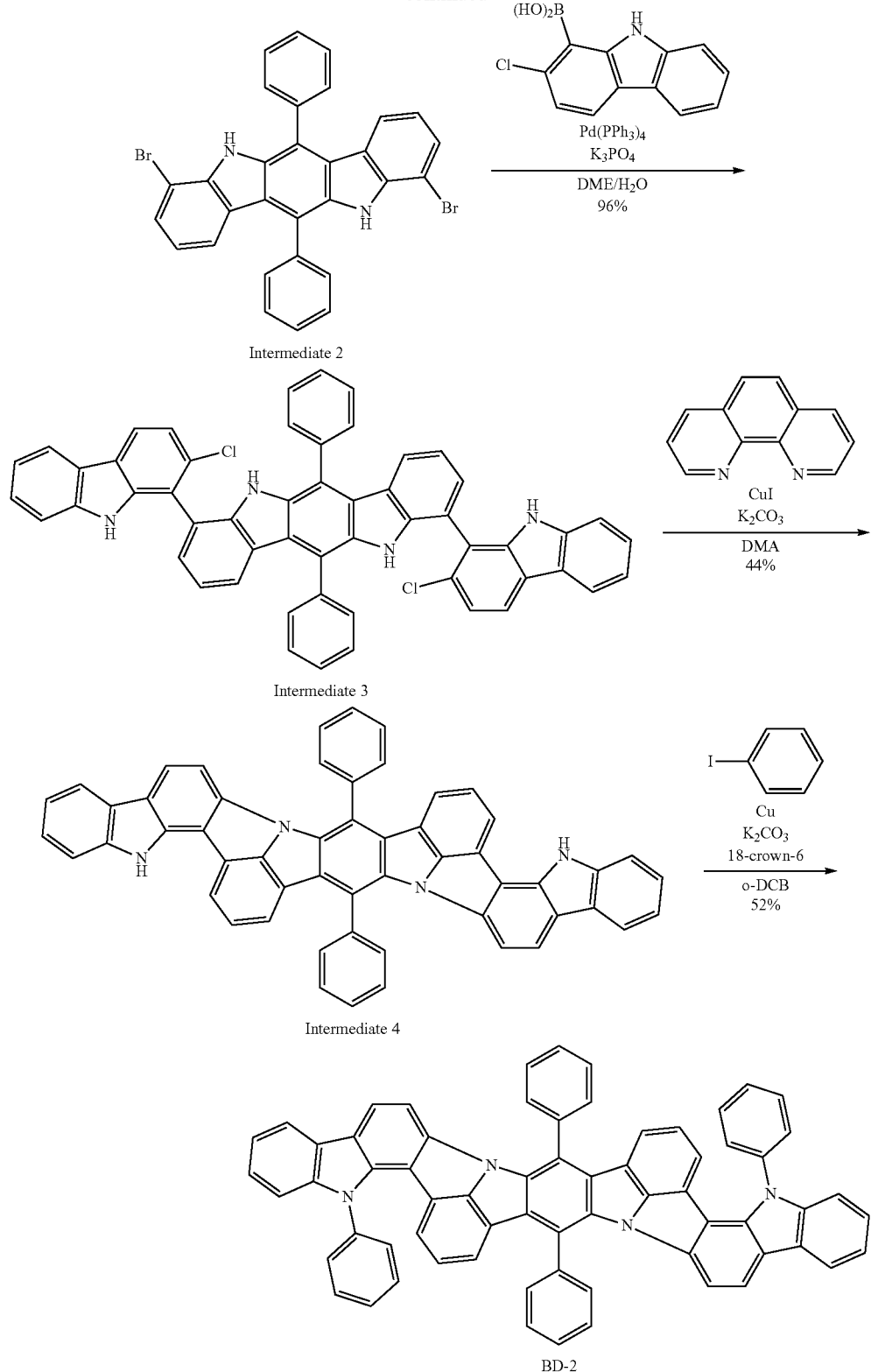

Intermediate 2

Intermediate 3

Intermediate 4

BD-2

(A) Synthesis of Intermediate 1

7-bromo-1H-indole (10.0 g, 51.0 mmol) was dissolved in acetonitrile (200 mL), and benzaldehyde (5.41 g, 51.0 mmol) and 57% hydroiodic acid (2 mL) were added to the resulting solution, and the resulting mixture was stirred at 80° C. for 8 hours. After completion of the reaction, a precipitated solid was collected by filtration, and the resulting material was washed with acetonitrile to obtain a light yellow solid (4.60 g, yield: 32%). The obtained solid was an intermediate 1, which was an intended product, and the results of mass spectrometric analysis were: m/e=569 for a molecular weight of 568.

(B) Synthesis of Intermediate 2

The intermediate 1 (4.5 g, 7.92 mmol) was suspended in acetonitrile (200 mL), and 2,3-dichloro-5,6-dicyano-p-benzoquinone (4.49 g, 19.8 mmol) was added thereto, and the resulting mixture was stirred at 80° C. for 16 hours. After completion of the reaction, a solid was collected by filtration, and the resulting material was washed with acetonitrile to obtain a yellow solid (4.02 g, yield: 90%). The obtained solid was an intermediate 2, which was an intended product, and the results of mass spectrometric analysis were: m/e=567 for a molecular weight of 566.

(C) Synthesis of Intermediate 3

Under an argon atmosphere, 1,2-dimethoxyethane (80 mL) and water (20 mL) were added to the intermediate 2 (3.50 g, 6.18 mmol), 2-chloro-9H-carbazolyl-1-boronic acid (4.55 g, 18.5 mmol), Pd(PPh$_3$)$_4$ (970 mg, 0.839 mmol) and potassium phosphate (7.87 g, 37.1 mmol), and the resulting mixture was stirred at 80° C. for 12 hours. After completion of the reaction, an organic layer was concentrated and a solid was collected by filtration. The resulting material was purified by column chromatography to obtain a yellow solid (4.82 g, yield: 96%). The obtained solid was an intermediate 3, which was an intended product, and the results of mass spectrometric analysis were: m/e=808 for a molecular weight of 807.

(D) Synthesis of Intermediate 4

Under an argon atmosphere, the intermediate 3 (4.00 g, 4.95 mmol), copper(I) iodide (566 mg, 2.97 mmol), 1,10-phenanthroline (535 mg, 2.97 mmol) and potassium carbonate (2.74 g, 19.8 mmol) were suspended in N,N-dimethylacetamide (80 mL), and the resulting suspension was heated and stirred at 160° C. for 8 hours. After completion of the reaction, water was added thereto, and a precipitate was collected by filtration. The resulting material was purified by column chromatography to obtain a yellow solid (1.62 g, yield: 44%). The obtained solid was an intermediate 4, which was an intended product, and the results of mass spectrometric analysis were: m/e=735 for a molecular weight of 734.

(E) Synthesis of BD-2

Under an argon atmosphere, the intermediate 4 (1.00 g, 4.95 mmol), copper powder (346 mg, 5.44 mmol), potassium carbonate (1.5 g, 10.9 mmol) and 18-crown 6-ether (144 mg, 0.544 mmol) were suspended in o-dichlorobenzene (10 mL), and the resulting suspension was heated and stirred at 170° C. for 12 hours. After completion of the reaction, a precipitate was collected by filtration, and the resulting material was passed through short pass column chromatography. The solvent was distilled off to obtain a yellow solid (630 mg, yield: 52%). The obtained solid was BD-2, which was an intended product, and the results of mass spectrometric analysis were: m/e=888 for a molecular weight of 887.

(2) Fabrication of Organic EL Device

An organic EL device was fabricated in a combination of a dopant and a host shown in Table 1, and evaluated, in the same manner as in Example 1. The results are shown in Table 1.

Example 3

(1) Synthesis of BD-3

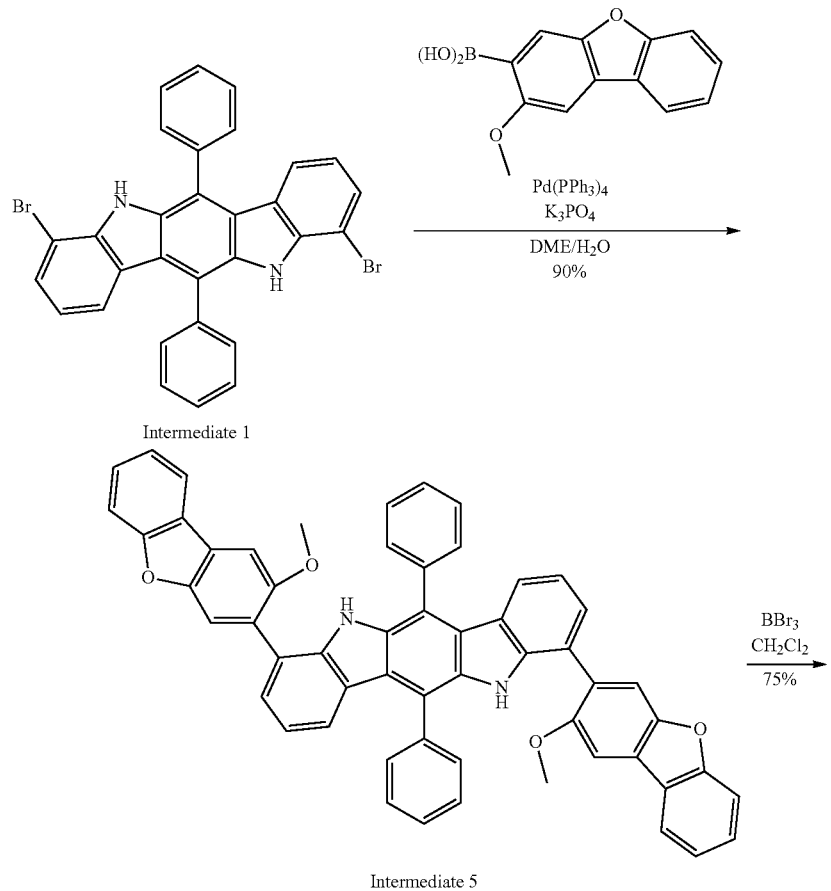

Intermediate 1

Intermediate 5

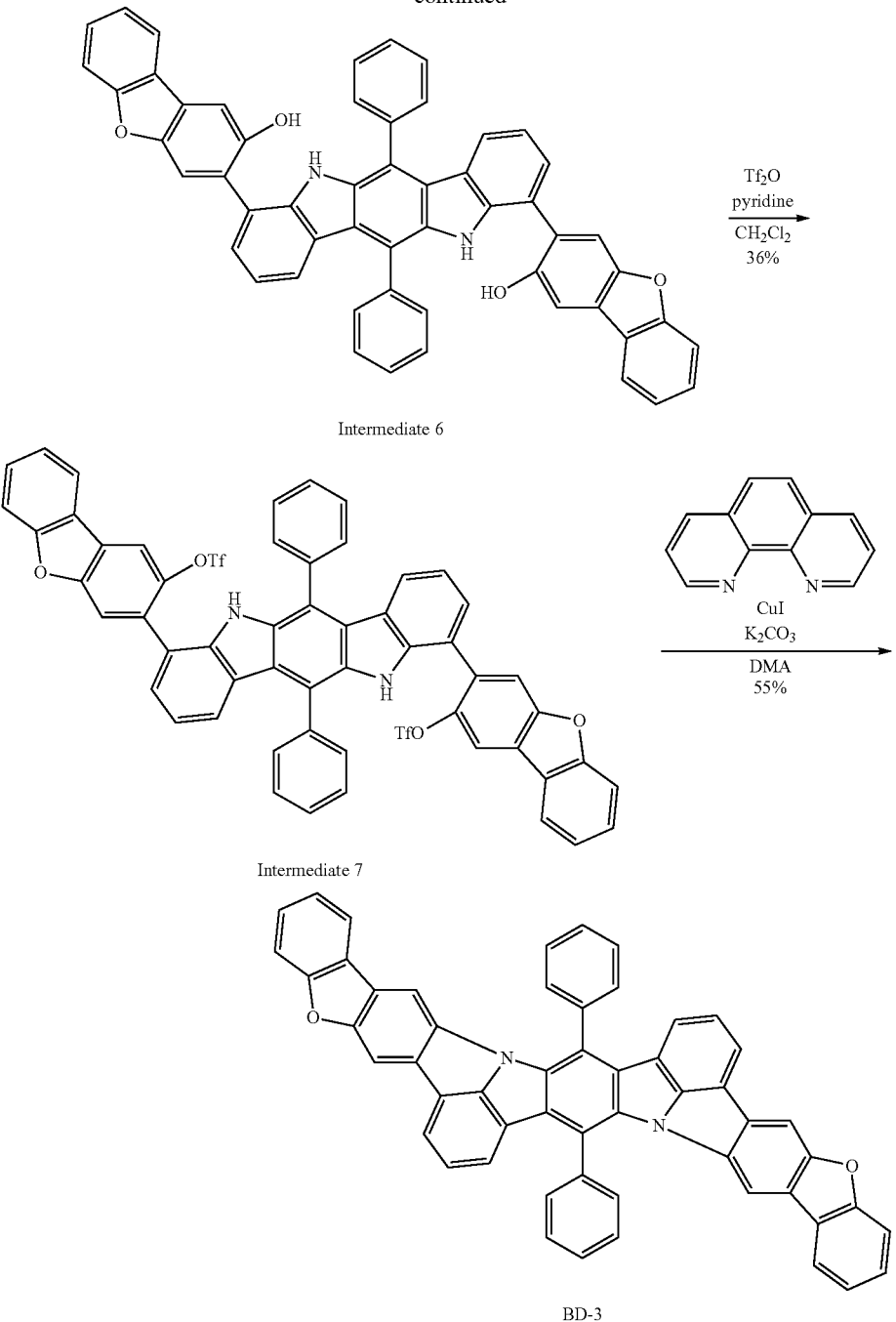

Intermediate 6

Intermediate 7

BD-3

(A) Synthesis of intermediate 5

Under an argon atmosphere, 1,2-dimethoxyethane (80 mL) and water (20 ml) were added to the intermediate 2 (3.00 g, 530 mmol) synthesized in the same manner as in Example 2, 2-methoxydibenzofuranyl-3-boronic acid (3.85 g, 15.9 mmol), Pd(PPh$_3$)$_4$ (918 mg, 0.795 mmol) and potassium phosphate (6.74 g, 31.8 mmol), and the resulting mixture was stirred at 80° C. for 12 hours. After completion of the reaction, an organic layer was concentrated and a solid was collected by filtration. The resulting material was purified by column chromatography 120 column chromatography to obtain a light yellow solid (3.82 g, yield: 90%). The obtained solid was an intermediate 5, which was an intended product, and the results of mass spectrometric analysis were: m/e=802 for a molecular weight of 801.

(B) Synthesis of Intermediate 6

Under an argon atmosphere, the intermediate 5 (3.80 g, 4.74 mmol) was dissolved in dichloromethane (100 mL), and a 1 M BBr$_3$ dichloromethane solution (30 ml) was added thereto, and the resulting mixture was stirred for 24 hours. After completion of the reaction, methanol and water were added thereto, and the resulting mixture was subjected to extraction with ethyl acetate. The solvent was distilled off, and the resulting residue was purified by column chromatography to obtain a light yellow solid (2.74 g, yield: 75%). The obtained solid was an intermediate 6, which was an intended product, and the results of mass spectrometric analysis were: m/e=773 for a molecular weight of 772.

(C) Synthesis of Intermediate 7

Under an argon atmosphere, the intermediate 6 (2.50 g, 3.24 mmol) was suspended in dichloromethane (100 mL), and pyridine (2 mL) and trifluoromethanesulfonic anhydride (2.74 g, 9.72 mmol) were added thereto, and the resulting mixture was stirred for 6 hours. After completion of the reaction, water was added thereto, and only an organic layer was concentrated, and a precipitated solid was collected by filtration. The resulting material was purified by column chromatography to obtain a light yellow solid (1.21 g, yield: 36%). The obtained solid was an intermediate 7, which was an intended product, and the results of mass spectrometric analysis were: m/e=1039 for a molecular weight of 1038.

(D) Synthesis of BD-3

Under an argon atmosphere, the intermediate 7 (1.00 g, 0.963 mmol), copper(I) iodide (92 mg, 0.482 mmol), 1,10-phenanthroline (87 mg, 0.482 mmol) and potassium carbonate (532 mg, 3.85 mmol) were suspended in N,N-dimethylacetamide (20 mL), and the resulting suspension was heated and stirred at 160° C. for 8 hours. After completion of the reaction, water was added thereto, and a precipitate was collected by filtration. The resulting material was purified by column chromatography to obtain a yellow solid (390 mg, yield: 55%). The obtained solid was BD-3, which was an intended product, and the results of mass spectrometric analysis were: m/e=737 for a molecular weight of 736.

(2) Fabrication of Organic EL Device

An organic EL device was fabricated in a combination of a dopant and a host shown in Table 1, and evaluated, in the same manner as in Example 1. The results are shown in Table 1.

Comparative Example 1

An organic EL device was fabricated by using the following compound BD as a dopant, and a host shown in Table 1, and evaluated, in the same manner as in Example 1. The results are shown in Table 1.

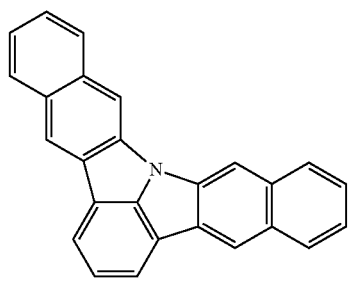

BD

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

EXPLANATION OF NUMERICAL SYMBOLS

1 Organic EL device
2 Substrate
3 Anode
4 Cathode
5 Emitting layer
6 Hole-injecting-transporting layer
7 Electron-injecting-transporting layer
10 Organic layer

The invention claimed is:

1. A compound represented by the following formula (1-5):

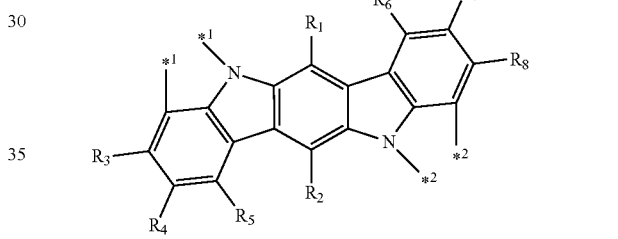

(1-5)

wherein, in the formulas (1-5),
one or more sets of two or more adjacent to each other among $R_1$, $R_2$ and $R_3$ to $R_8$ are bonded with each other to form a substituted or unsubstituted and saturated or unsaturated ring, or do not form the ring;
$R_1$, $R_2$ and $R_3$ to $R_8$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or a substituted or unsubstituted monovalent heterocyclic group having 5 to 50 ring atoms;

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms; when two or more of $R_{901}$ to $R_{907}$ exist, two or more of $R_{901}$ to $R_{907}$ may be the same with or different from each other;

two of *1 are fused with a group represented by the following formula (1A) to form a nitrogen atom-containing five-membered ring;

two of *2 are fused with a group represented by the following formula (1A), which is different from the group bonded with the two of *1, to form a nitrogen atom-containing five-membered ring;

the two groups represented by the following formula (1A) may be the same with or different from each other;

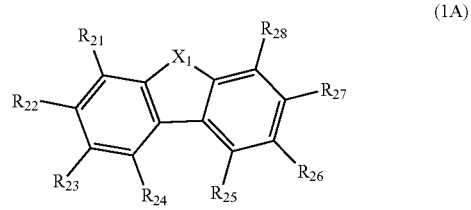

(1A)

wherein, in the formula (1A), one set selected from $R_{21}$ and $R_{22}$, $R_{22}$ and $R_{23}$, $R_{23}$ and $R_{24}$, $R_{25}$ and $R_{26}$, $R_{26}$ and $R_{27}$, and $R_{27}$ and $R_{28}$ is bonded with the two of *1 or the two of *2 in the formula (1-5);

one or more sets of two or more adjacent to each other among $R_{21}$ to $R_{28}$ that are not bonded with the two of *1 or the two of *2 in the formula (1-5) are bonded with each other to from a substituted or unsubstituted and saturated or unsaturated ring, or do not form the ring;

$R_{21}$ to $R_{28}$ that are neither bonded with the two of *1 or the two of *2 in the formula (1-5) nor form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1-5);

$X_1$ is selected from O, S and N($R_{35}$), and two of $X_1$ may be the same with or different from each other;

$R_{35}$ is bonded with either or both of $R_{21}$ and $R_{28}$ to form a substituted or unsubstituted and saturated or unsaturated ring, or does not form the ring; and $R_{35}$ that does not form the ring is a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

2. The compound according to claim 1, which is a compound selected from the compounds represented by the following formulas (1-5-1) to (1-5-6):

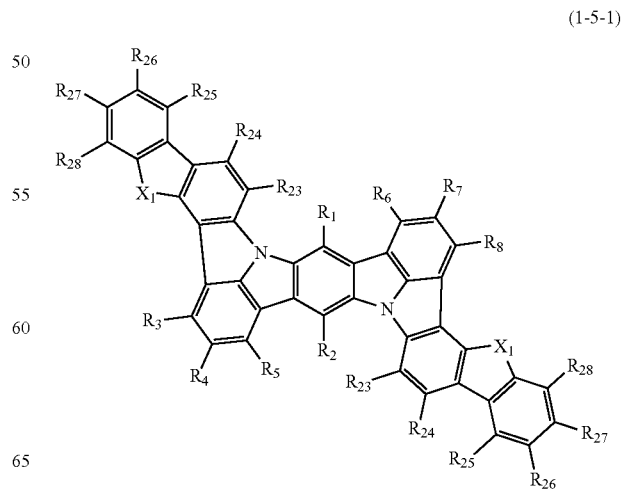

(1-5-1)

(1-5-2)

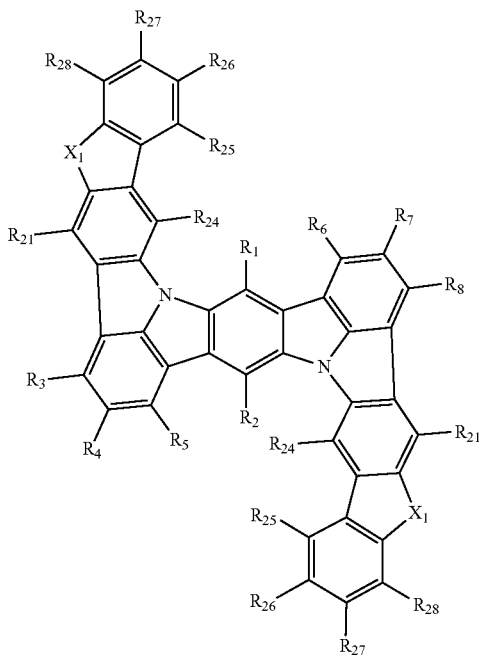

(1-5-3)

(1-5-5)

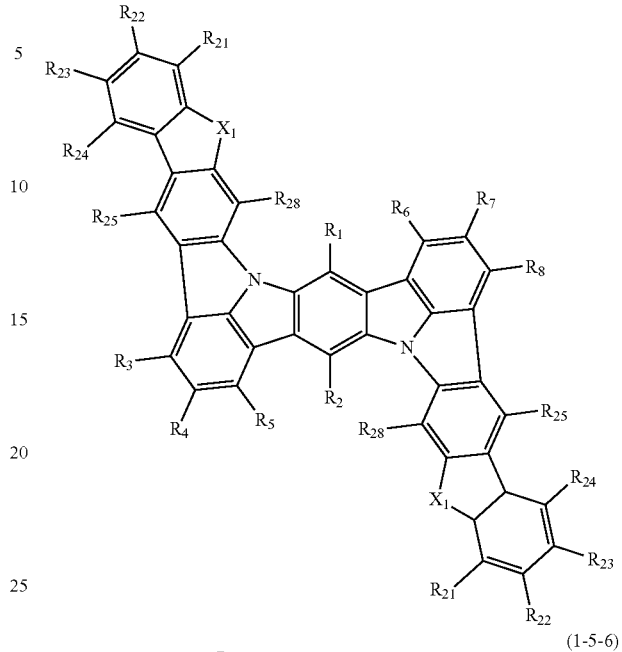

(1-5-6)

(1-5-4)

wherein, in the formulas (1-5-1) to (1-5-6),
$X_1$, $R_1$, $R_2$, $R_3$ to $R_8$ and $R_{21}$ to $R_{28}$ are as defined in the formula (1-5).

3. The compound according to claim 2, represented by the formula (1-5-1) or (1-5-2).

4. The compound according to claim 2, represented by the formula (1-5-1).

5. The compound according to claim 4, wherein $R_1$ and $R_2$ are a phenyl group.

6. The compound according to claim 5, wherein $X_1$ is $N(R_{35})$.

7. The compound according to claim 6, wherein $R_{35}$ is a substituted or unsubstituted aryl group having 6 to 50 ring carbon atoms.

8. The compound according to claim 1, wherein the compound is any of the following compounds:

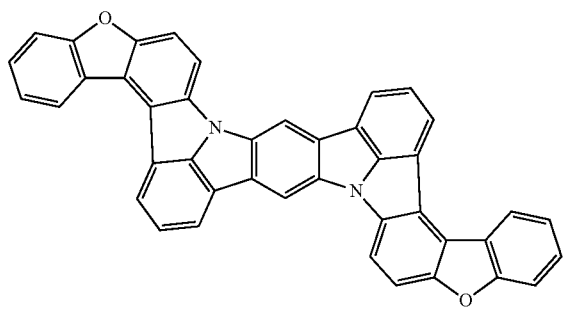
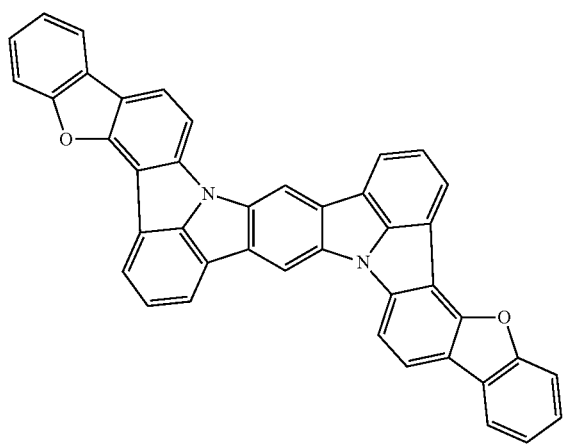
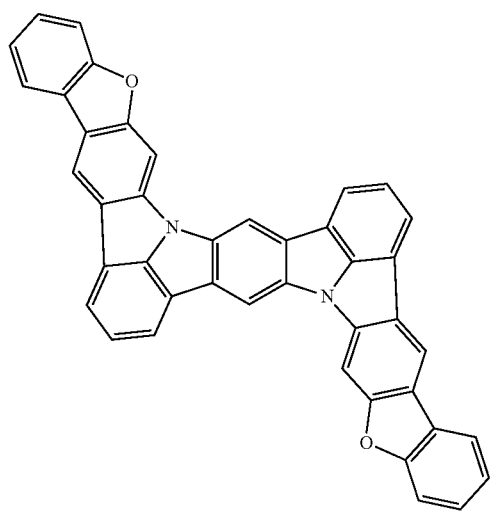

-continued
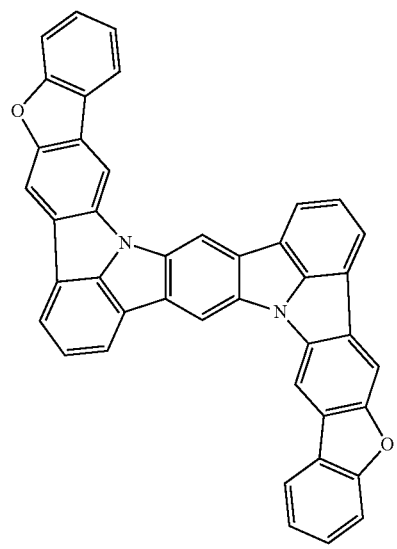
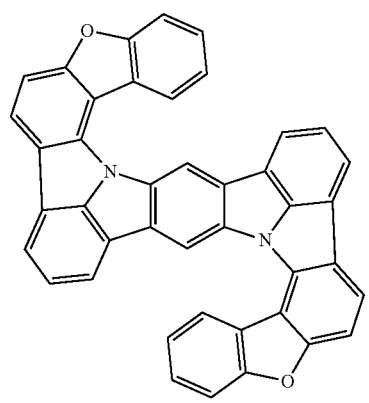
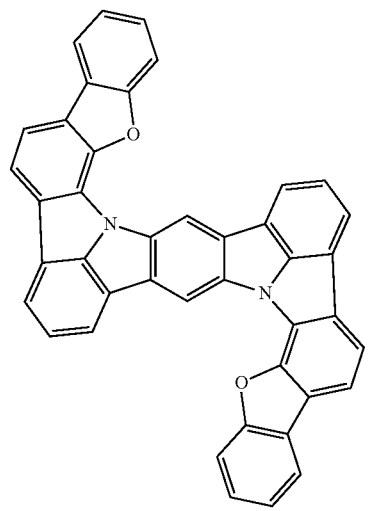

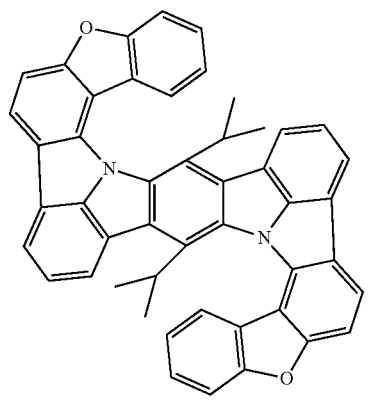
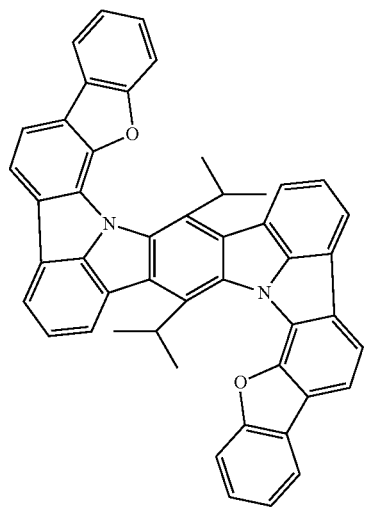
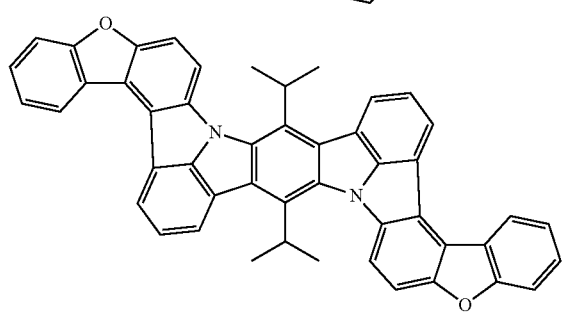
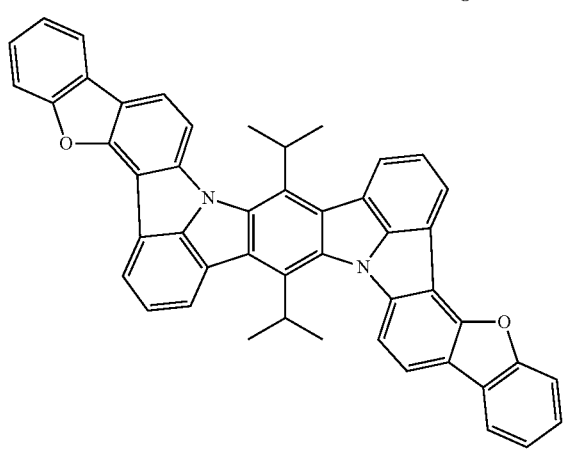

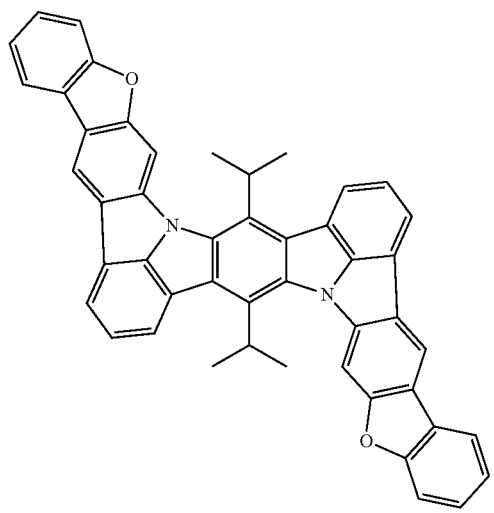
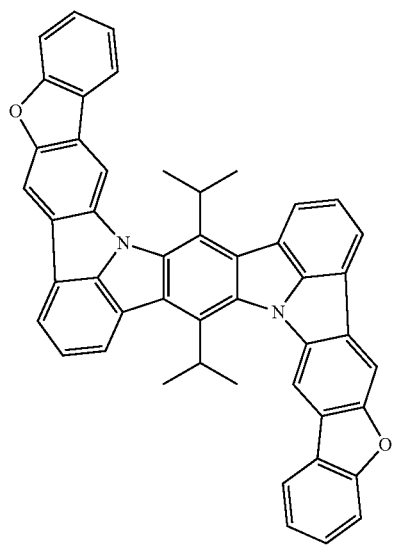
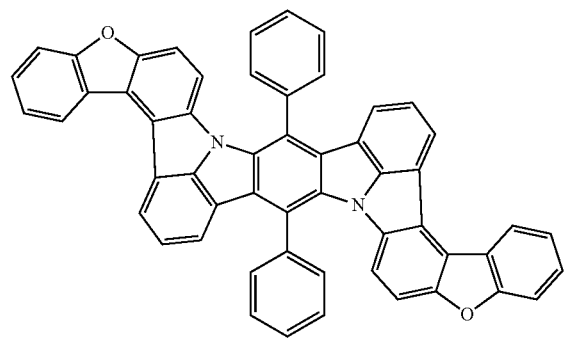

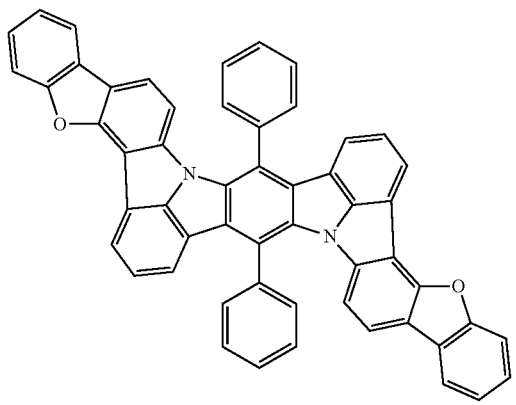
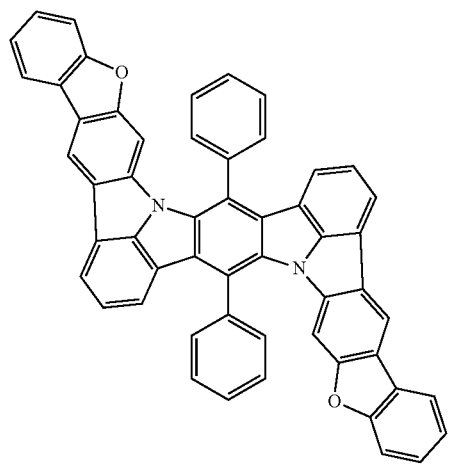
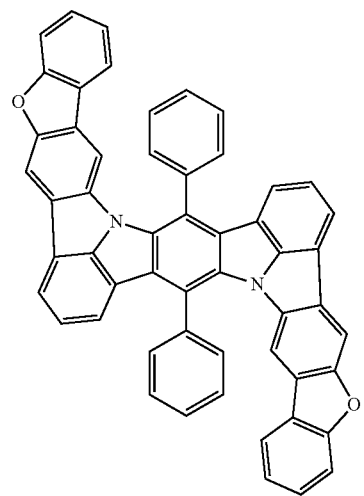

-continued
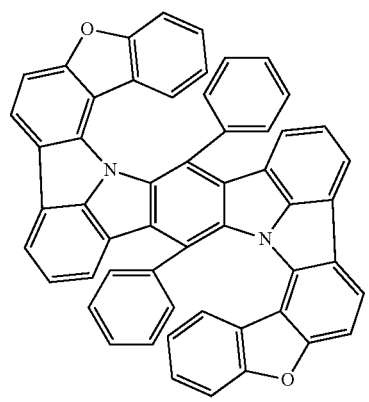
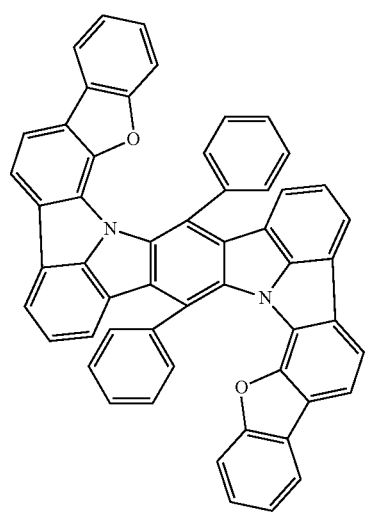
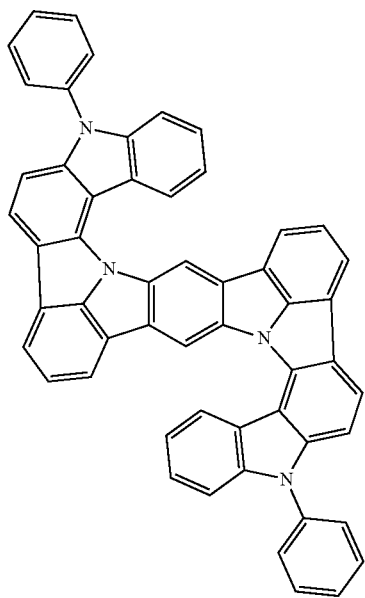

-continued
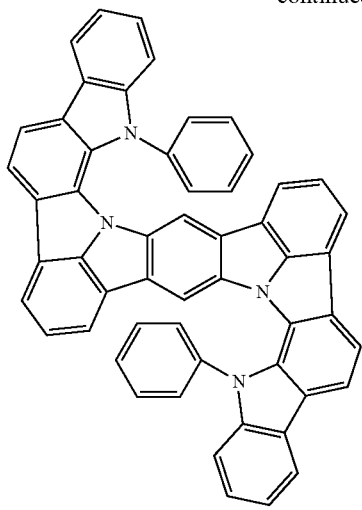
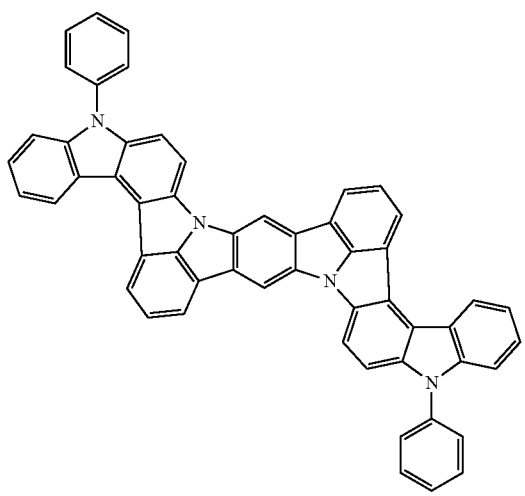
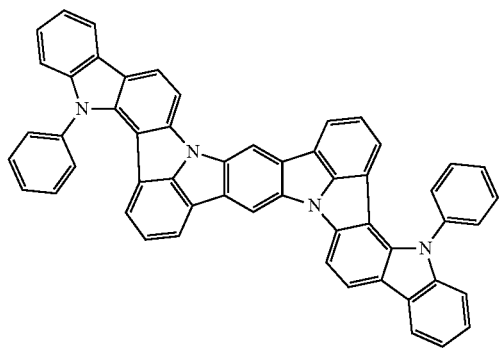

-continued
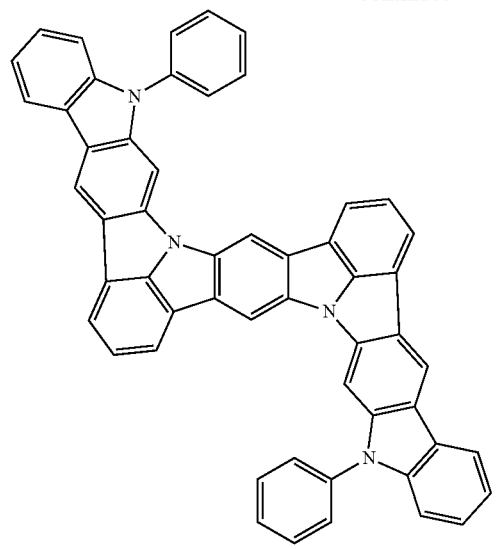
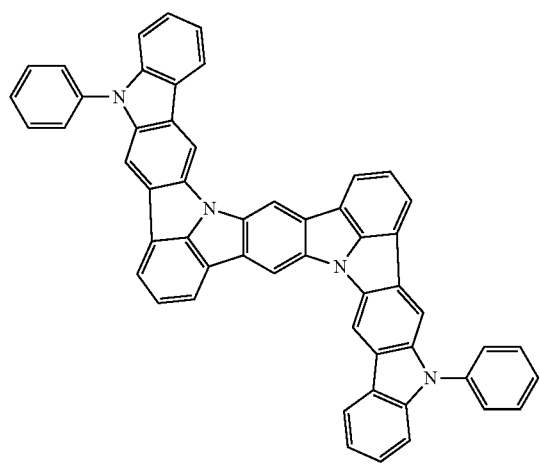
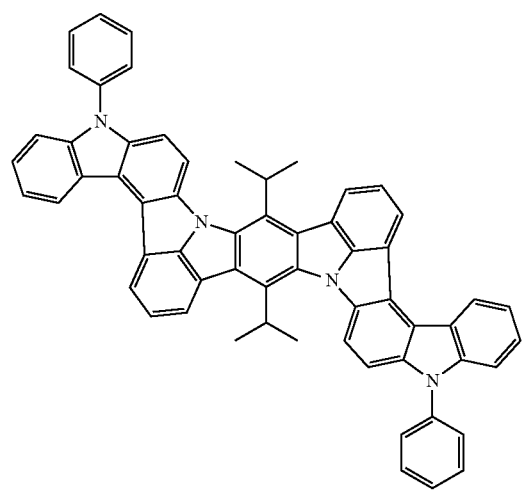

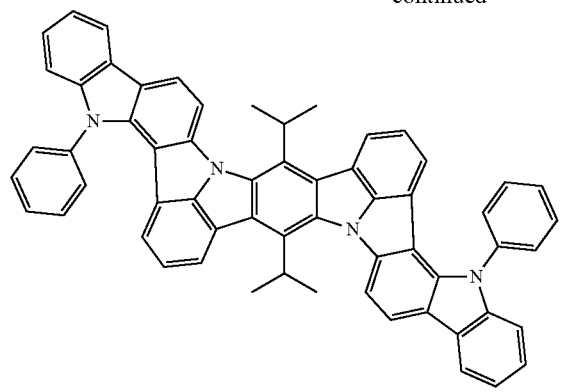
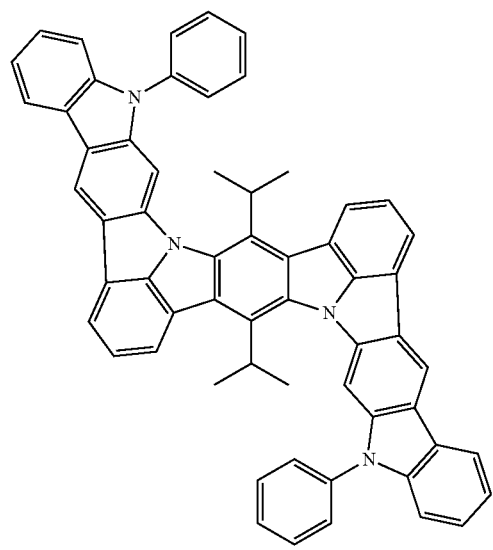
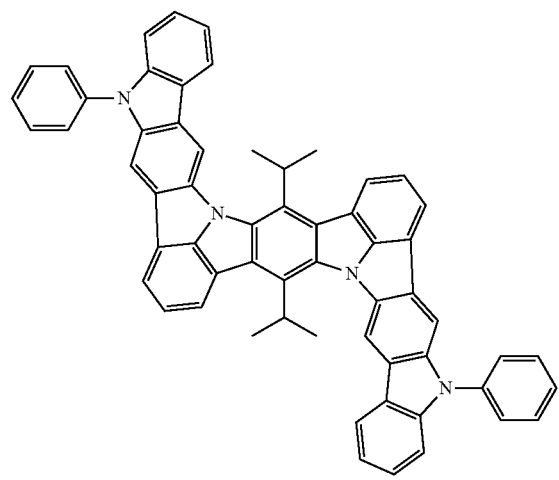

-continued
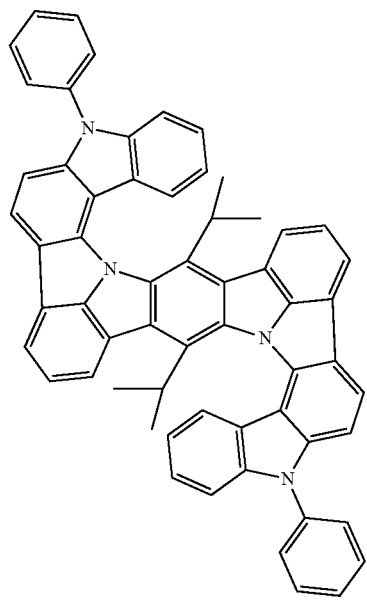
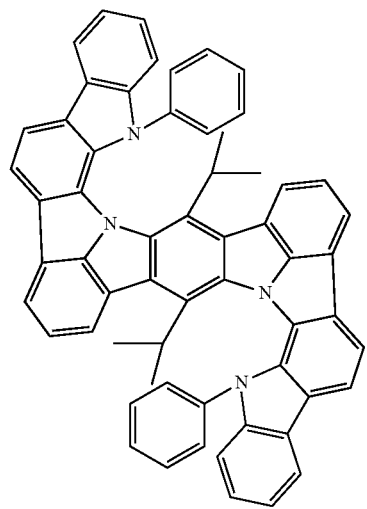
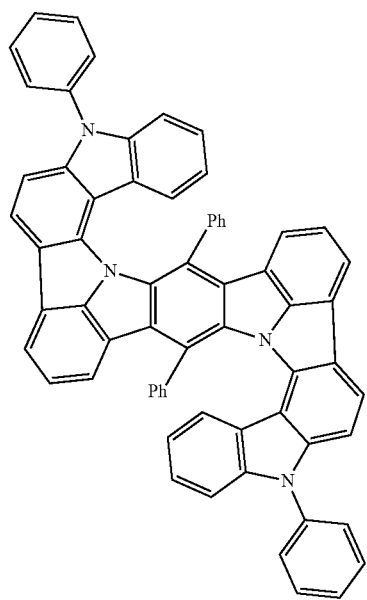

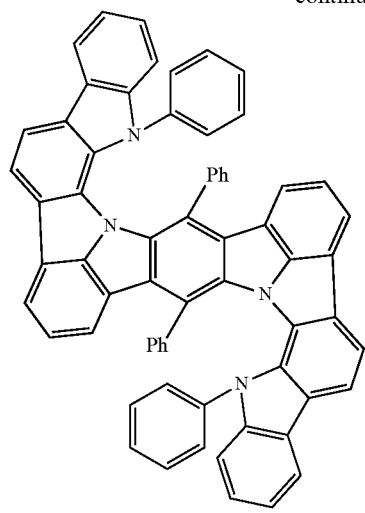
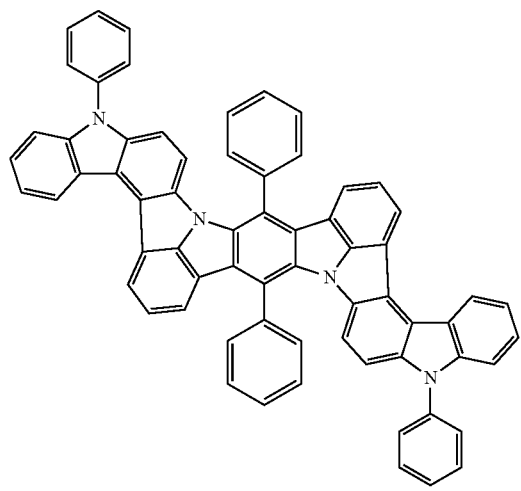
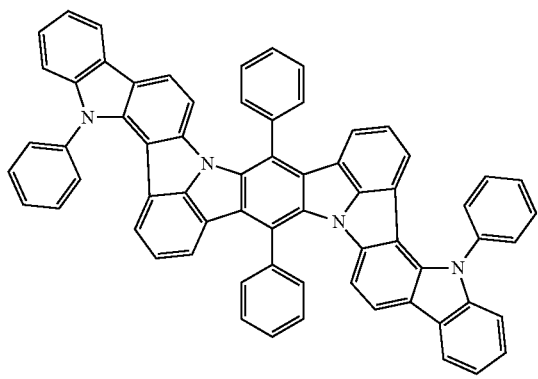

-continued
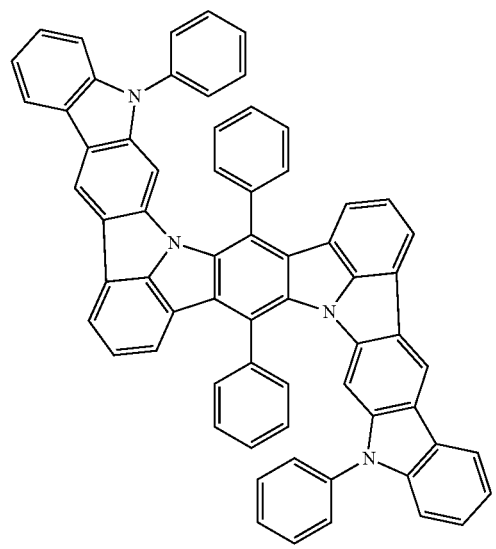
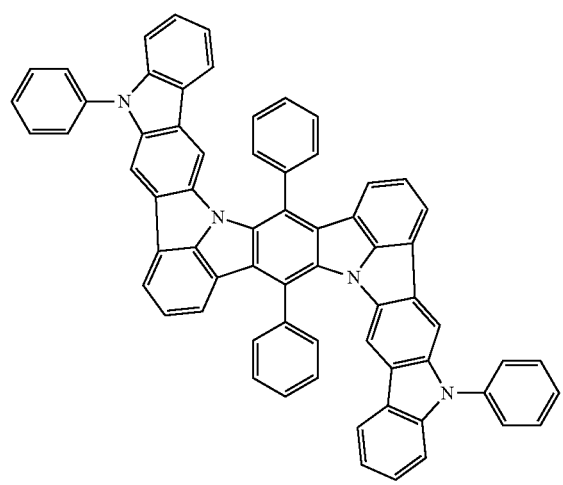
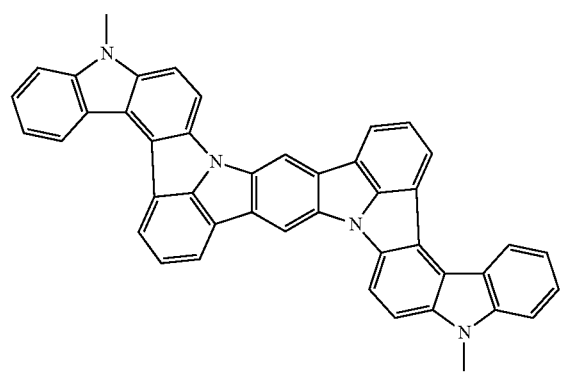

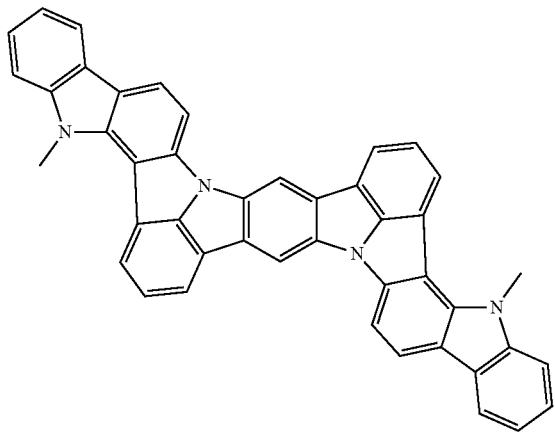
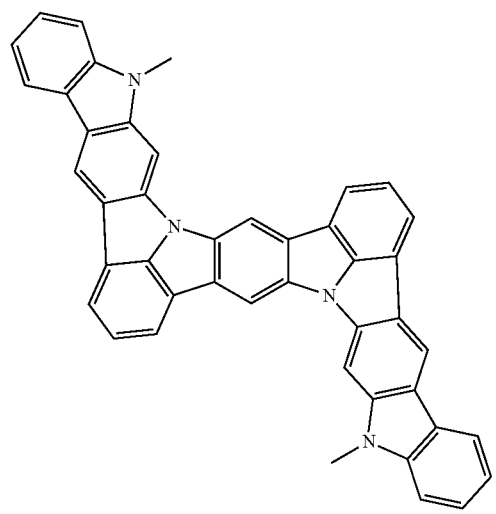
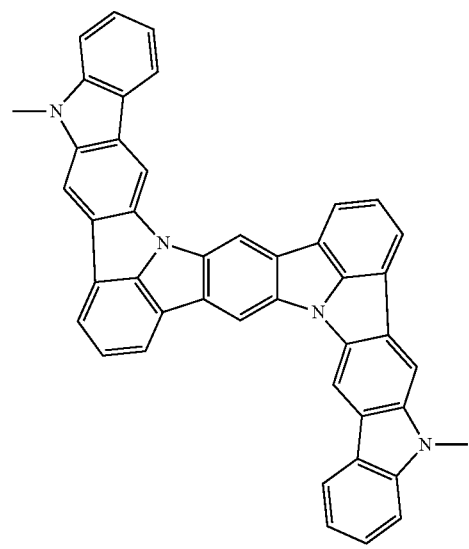

-continued
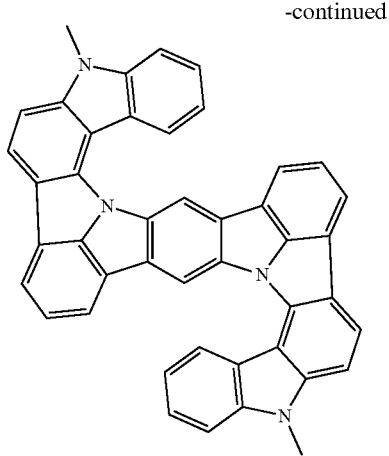
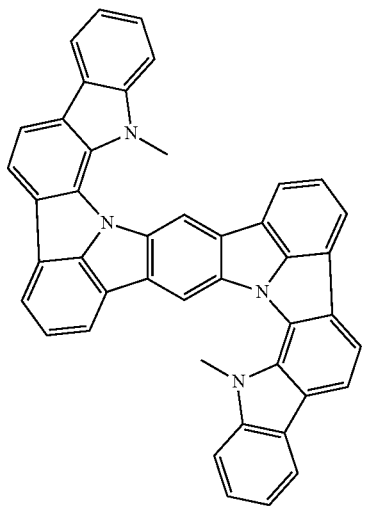
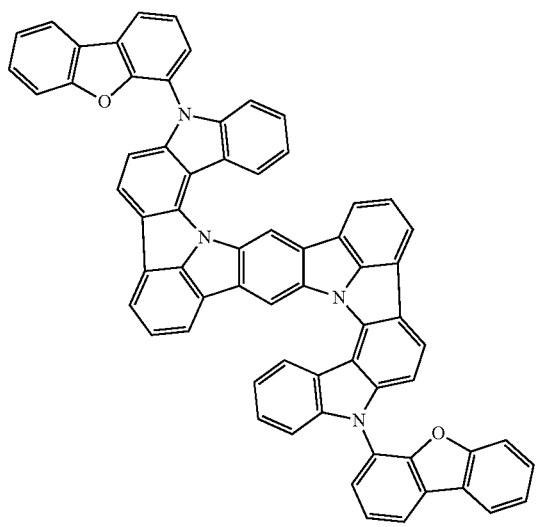

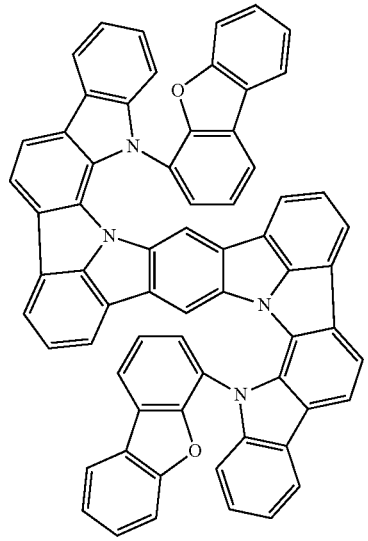
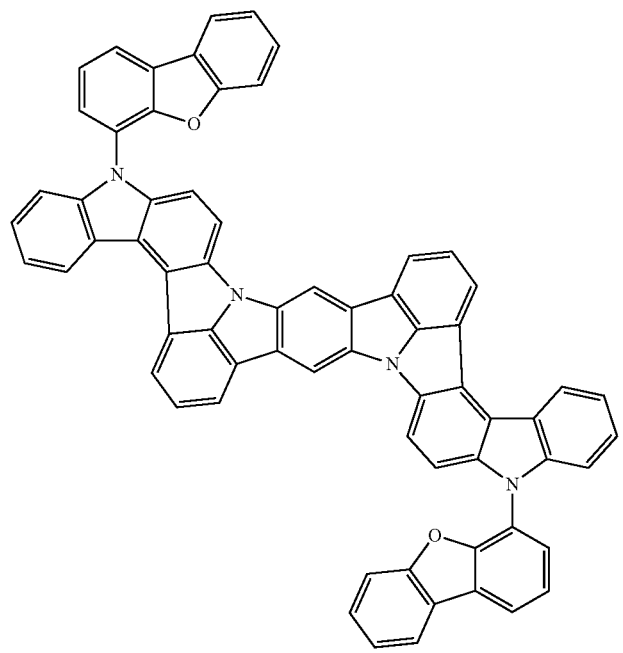
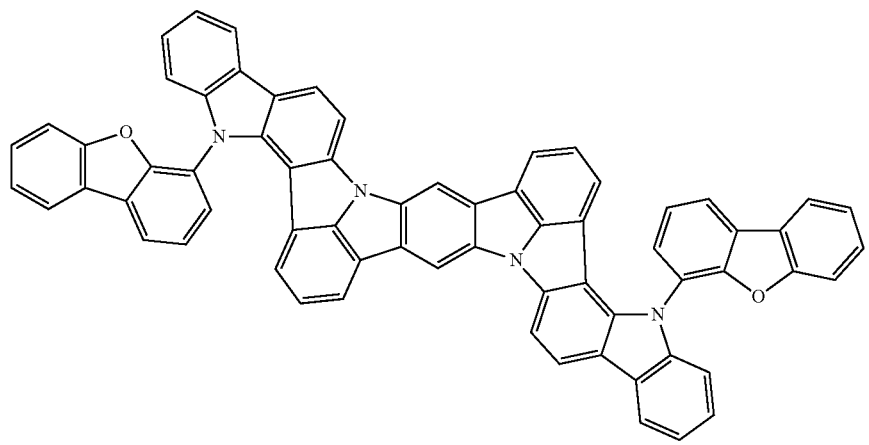

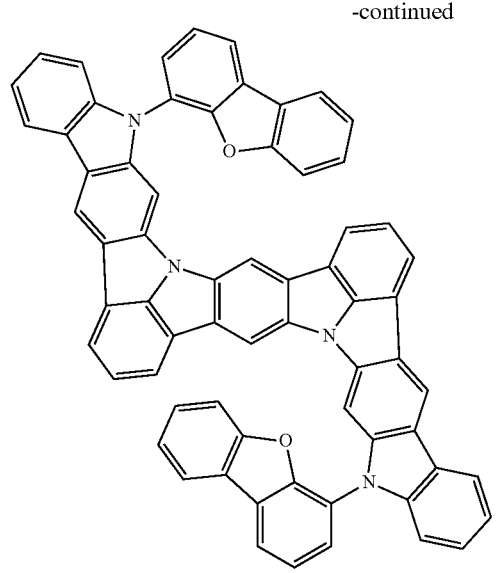
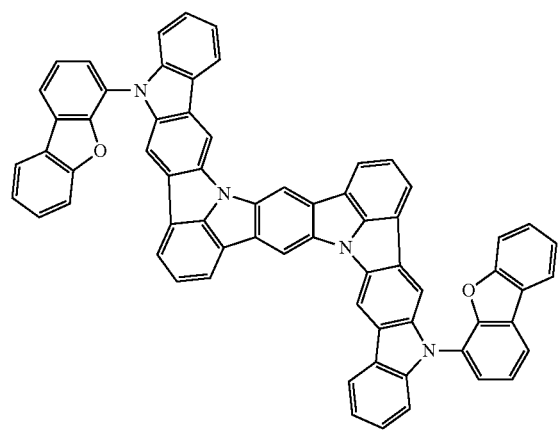
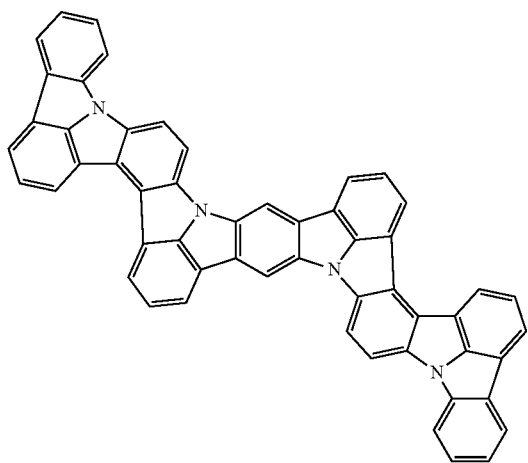

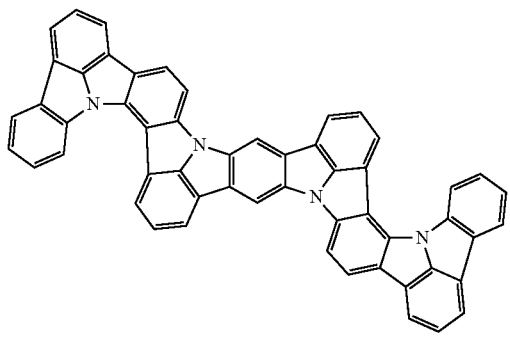
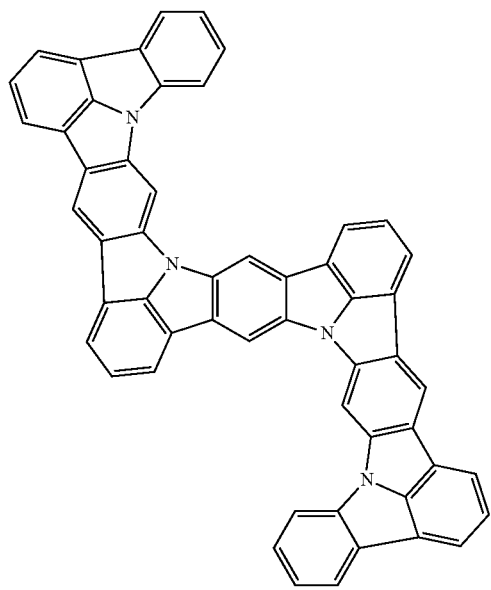
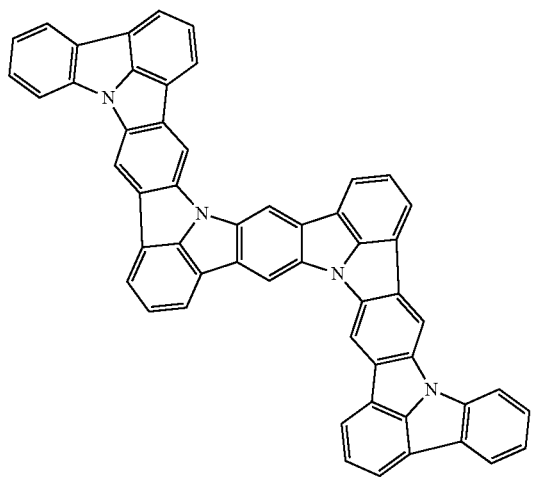

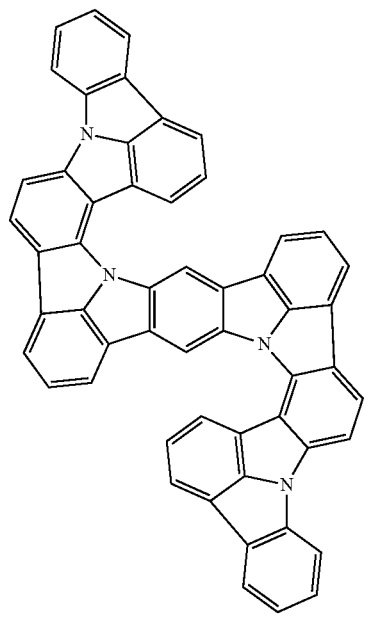
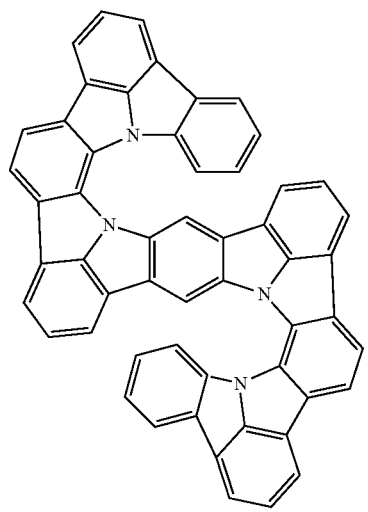
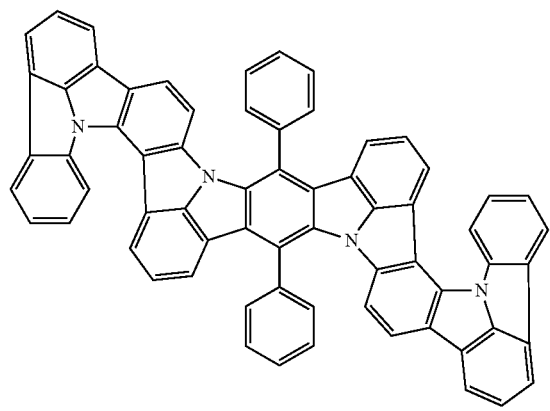

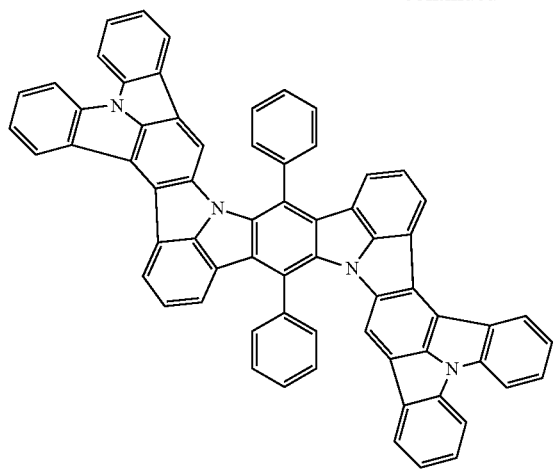
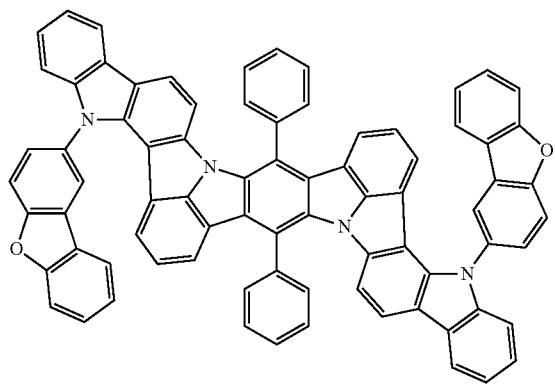
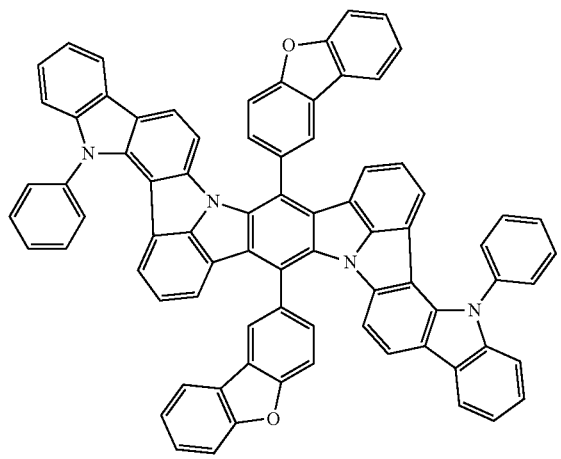

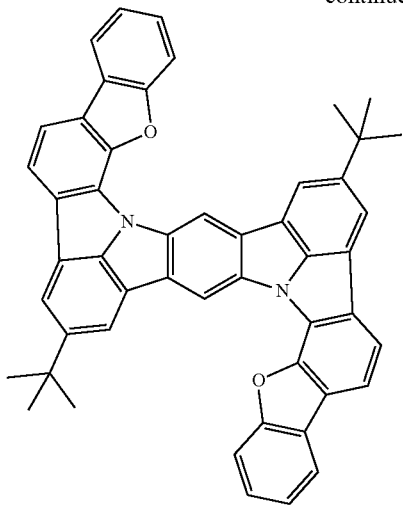
9. The compound according to claim 1, wherein the compound is any of the following compounds:
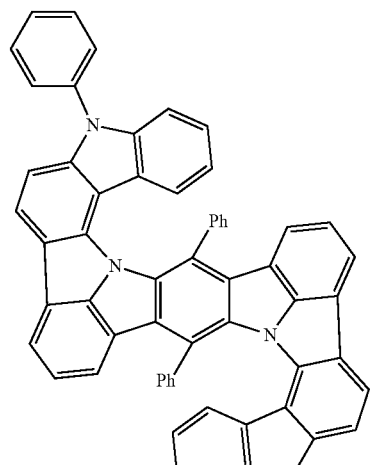
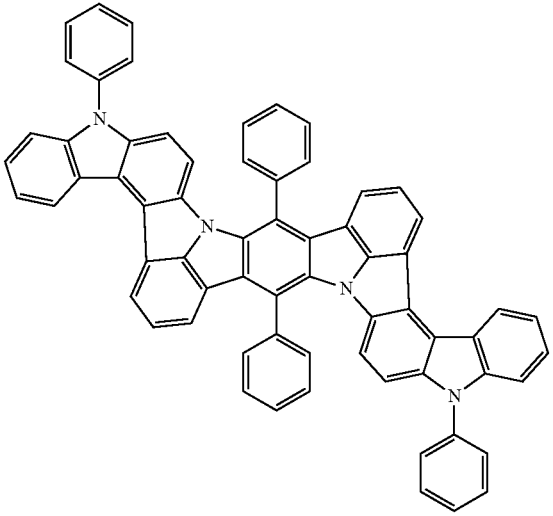
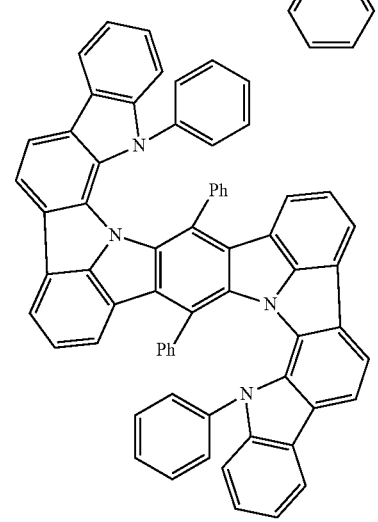
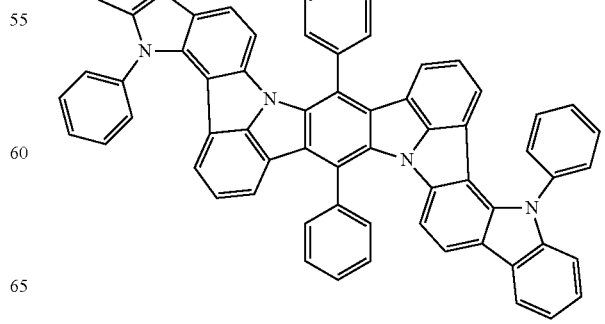

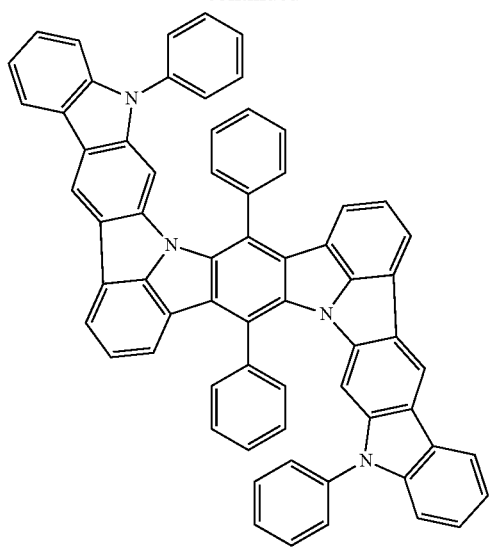

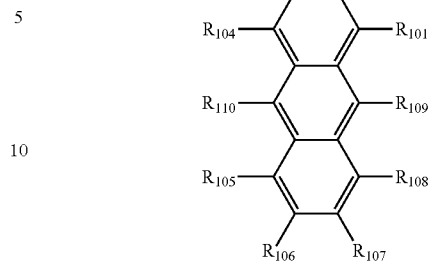

wherein, Ph represents a phenyl group.

10. A material for an organic electroluminescence device, comprising the compound according to claim 1.

11. An organic electroluminescence device, comprising:

a cathode, an anode, and one or more organic layers arranged between the cathode and the anode, wherein at least one layer of the one or more organic layers comprises the compound according to claim 1, and a compound represented by the following formula (10):

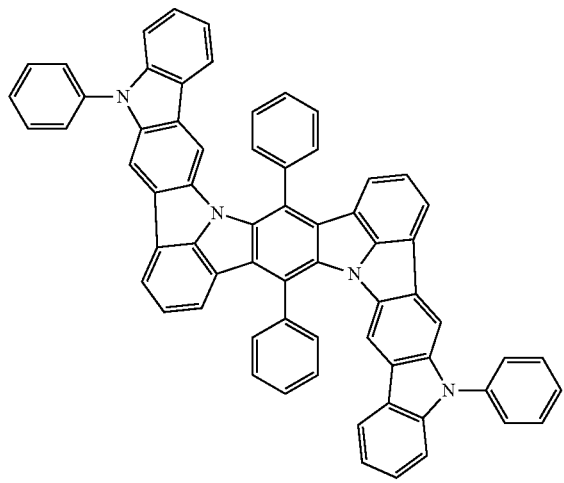

wherein, in the formulas (10), at least one of $R_{101}$ to $R_{110}$ is a group represented by the following formula (31); when two or more groups represented by the following formula (31) exist, the two or more groups represented by the following formula (31) may be the same with or different from each other;

$$-L_{101}-Ar_{101} \quad (31)$$

wherein, in the formula (31), $L_{101}$ is a single bond, a substituted or unsubstituted arylene group having 6 to 30 ring carbon atoms, or a substituted or unsubstituted divalent heterocyclic group having 5 to 30 ring atoms;

$Ar_{101}$ is a substituted or unsubstituted aryl group having 6 to 50 ring carbon atoms, or a substituted or unsubstituted monovalent heterocyclic group having 5 to 50 ring atoms;

one or more sets of two or more adjacent to each other among $R_{101}$ to $R_{110}$ that are not the group represented by the formula (31) form a substituted or unsubstituted and saturated or unsaturated ring, or do not form the ring; $R_{101}$ to $R_{110}$ that are neither the group represented by the formula (31) nor form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms;

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms; and when two or more of $R_{901}$ to $R_{907}$ exist, two or more of $R_{901}$ to $R_{907}$ may be the same with or different from each other.

12. The organic electroluminescence device according to claim 11, wherein the compound represented by the formula (10) is represented by the following formula (10-1) or (10-2):

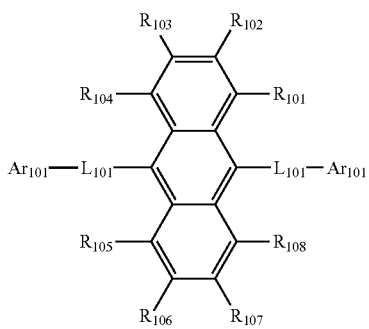

(10-1)

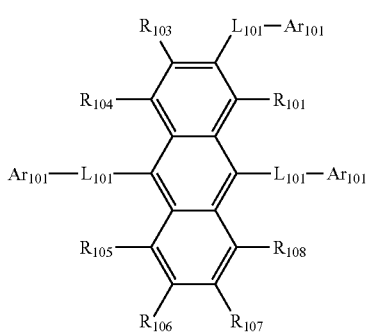

(10-2)

wherein, in the formula (10-1), $R_{101}$ to $R_{108}$, and $L_{101}$ and $Ar_{101}$ are as defined in the formula (10); and in the formula (10-2), $R_{101}$, $R_{103}$ to $R_{108}$, and $L_{101}$ and $Ar_{101}$ are as defined in the formula (10).

13. The organic electroluminescence device according to claim 11, wherein the compound represented by the formula (10) is represented by the following formula (10-3):

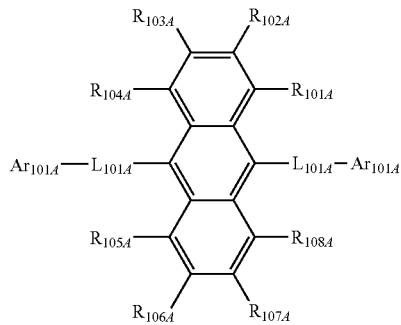

(10-3)

wherein, in the formula (10-3), $R_{101A}$ to $R_{108A}$ are independently a hydrogen atom, or a substituted or unsubstituted aryl group having 6 to 50 ring carbon atoms;

$L_{101A}$ is a single bond, or a substituted or unsubstituted arylene group having 6 to 30 ring carbon atoms, and two of $L_{101A}$ may be the same with or different from each other; and $Ar_{101A}$ is a substituted or unsubstituted aryl group having 6 to 50 ring carbon atoms, and two of $Ar_{101A}$ may be the same with or different from each other.

14. The organic electroluminescence device according to claim 11, wherein the compound represented by the formula (10) is represented by the following formula (10-4):

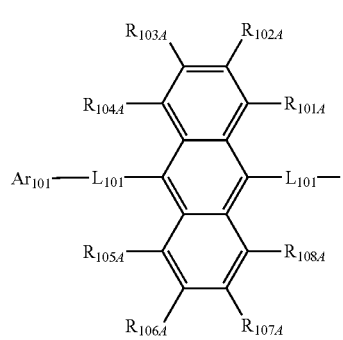

(10-4)

wherein, in the formula (10-4), $L_{101}$ and $Ar_{101}$ are as defined in the formula (10);

$R_{101A}$ to $R_{108A}$ are independently a hydrogen atom, or a substituted or unsubstituted aryl group having 6 to 50 ring carbon atoms;

$X_{11}$ is O, S or N($R_{61}$);

$R_{61}$ is a hydrogen atom, a substituted or unsubstituted alkyl group having 1 to 50 carbon atoms, or a substituted or unsubstituted aryl group having 6 to 50 ring carbon atoms;

one of $R_{62}$ to $R_{69}$ is bonded with $L_{101}$;

one or more sets of two or more adjacent to each other among $R_{62}$ to $R_{69}$ that are not bonded with $L_{101}$ form a substituted or unsubstituted and saturated or unsaturated ring, or do not form the ring; and $R_{62}$ to $R_{69}$ that are neither bonded with $L_{101}$ nor form the ring are independently a hydrogen atom, a substituted or unsubstituted alkyl group having 1 to 50 carbon atoms, or a substituted or unsubstituted aryl group having 6 to 50 ring carbon atoms.

15. The organic electroluminescence device according to claim 14, wherein the compound represented by the formula (10) is represented by the following formula (10-6):

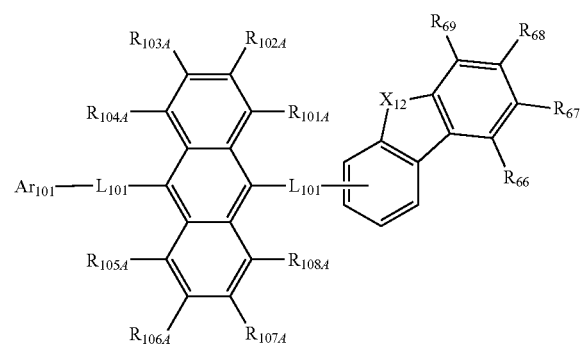

(10-6)

wherein, in the formula (10-6), $L_{101}$ and $Ar_{101}$ are as defined in the formula (10);

$R_{101A}$ to $R_{108A}$ are as defined in the formula (10-4);

$R_{66}$ to $R_{69}$ are as defined in the formula (10-4); and $X_{12}$ is O or S.

16. The organic electroluminescence device according to claim 14, wherein the compound represented by the formula (10) is represented by the following formula (10-7):

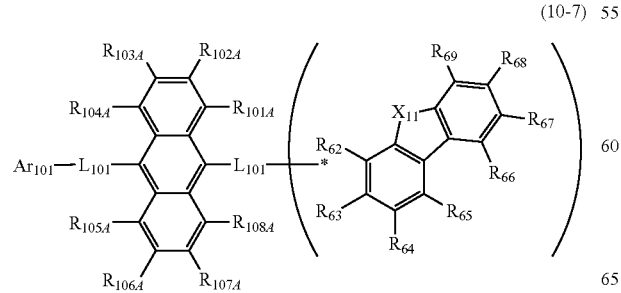

(10-7)

wherein, in the formula (10-7), $L_{101}$ and $Ar_{101}$ are as defined in the formula (10);

$R_{101A}$ to $R_{108A}$ are as defined in the formula (10-4);

$X_{11}$ is as defined in the formula (10-4);

$R_{62}$ to $R_{69}$ are as defined in the formula (10-4); in which any of one set of $R_{66}$ and $R_{67}$, $R_{67}$ and $R_{68}$, and $R_{68}$ and $R_{69}$ is bonded with each other to form a substituted or unsubstituted and saturated or unsaturated ring.

17. The organic electroluminescence device according to claim 11, wherein the compound represented by the formula (10) is represented by the following formula (10-8):

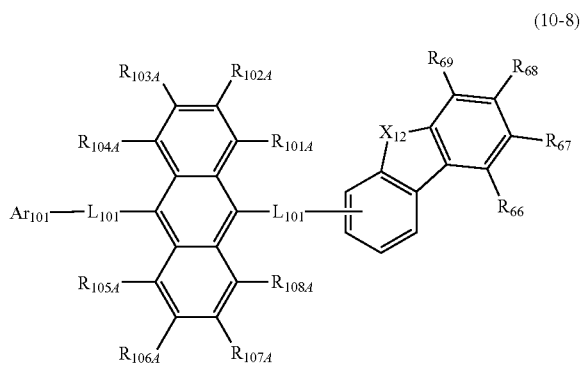

(10-8)

wherein, in the formula (10-8), $L_{101}$ and $Ar_{101}$ are as defined in the formula (10);

$R_{101A}$ and $R_{108A}$ are as defined in the formula (10-4);

$X_{12}$ is O or S;

$R_{66}$ to $R_{69}$ are as defined in the formula (10-4); in which any of one set of $R_{66}$ and $R_{67}$, $R_{67}$ and $R_{68}$, and $R_{68}$ and $R_{69}$ is bonded with each other to form a substituted or unsubstituted and saturated or unsaturated ring.

18. The organic electroluminescence device according to claim 16, wherein any of one set of $R_{66}$ and $R_{67}$, $R_{67}$ and $R_{68}$, and $R_{68}$ and $R_{69}$ is bonded with each other to form a ring represented by the following formula (10-8-1) or (10-8-2), and $R_{66}$ to $R_{69}$ that do not form the ring represented by the formula (10-8-1) or (10-8-2) do not form a substituted or unsubstituted and saturated or unsaturated ring:

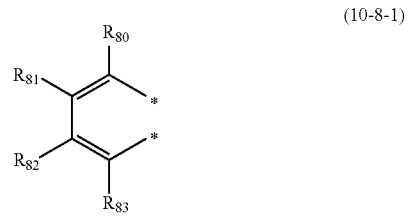

(10-8-1)

-continued

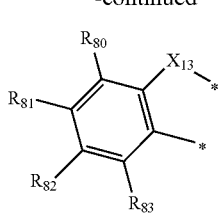
(10-8-2)

wherein, in the formulas (10-8-1) and (10-8-2),
two of * are bonded with any of one set of $R_{66}$ and $R_{67}$, $R_{67}$ and $R_{68}$, and $R_{68}$ and $R_{69}$, respectively;
$R_{80}$ to $R_{83}$ are independently a hydrogen atom, a substituted or unsubstituted alkyl group having 1 to 50 carbon atoms, or a substituted or unsubstituted aryl group having 6 to 50 ring carbon atoms; and
$X_{13}$ is O or S.

19. The organic electroluminescence device according to claim 14, wherein the compound represented by the formula (10) is represented by the following formula (10-9):

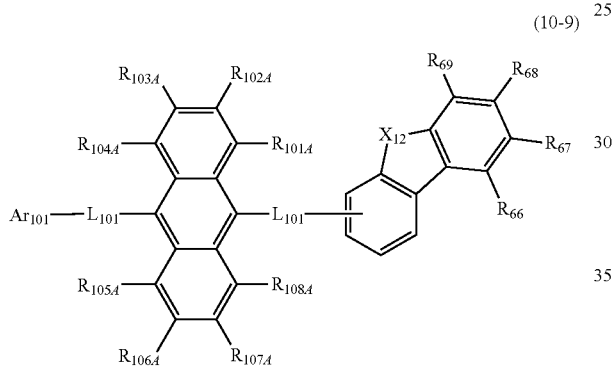
(10-9)

wherein, in the formula (10-9),
$L_{101}$ and $Ar_{101}$ are as defined in the formula (10);
$R_{101A}$ to $R_{108A}$ are as defined in the formula (10-4);
$R_{66}$ to $R_{69}$ are as defined in the formula (10-4); in which both of $R_{66}$ and $R_{67}$, $R_{67}$ and $R_{68}$, and $R_{68}$ and $R_{69}$ are neither bonded with each other nor form a substituted or unsubstituted and saturated or unsaturated ring; and
$X_{12}$ is O or S.

20. The organic electroluminescence device according to claim 11, wherein the compound represented by the formula (10) is represented by the following formula (10-4A):

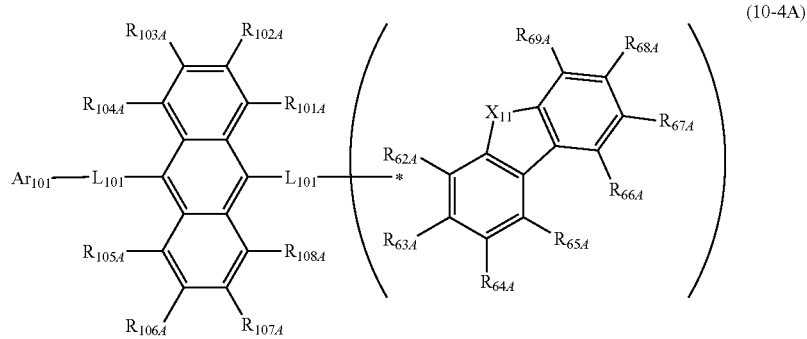
(10-4A)

wherein, in the formula (10-4A),
$L_{101}$ and $Ar_{101}$ are as defined in the formula (10);
$R_{101A}$ to $R_{108A}$ are independently a hydrogen atom, or a substituted or unsubstituted aryl group having 6 to 50 ring carbon atoms;
$X_{11}$ is O, S or $N(R_{61})$;
$R_{61}$ is a hydrogen atom, a substituted or unsubstituted alkyl group having 1 to 50 carbon atoms, or a substituted or unsubstituted aryl group having 6 to 50 ring carbon atoms;
any of one set of two adjacent to each other among $R_{62A}$ to $R_{69A}$ forms a ring represented by the following formula (10-4A-1):

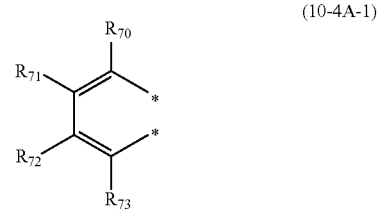
(10-4A-1)

wherein, in the formula (10-4A-1),
two of * are bonded with two adjacent to each other among $R_{62A}$ to $R_{69A}$, respectively;
one of $R_{70}$ to $R_{73}$ is bonded with $L_{101}$;
$R_{70}$ to $R_{73}$ that are not bonded with $L_{101}$ are independently a hydrogen atom, a substituted or unsubstituted alkyl group having 1 to 50 carbon atoms, or a substituted or unsubstituted aryl group having 6 to 50 ring carbon atoms;
one or more sets of two or more adjacent to each other among $R_{62A}$ to $R_{69A}$ that do not form the ring represented by the formula (10-4A-1) form a substituted or unsubstituted and saturated or unsaturated ring, or do not form the ring; and
$R_{62A}$ to $R_{69A}$ that do not form the ring represented by the formula (10-4A-1) or the substituted or unsubstituted and saturated or unsaturated ring are independently a hydrogen atom, a substituted or unsubstituted alkyl group having 1 to 50 carbon atoms, or a substituted or unsubstituted aryl group having 6 to 50 ring carbon atoms.

21. An electronic apparatus, comprising the organic electroluminescence device according to claim 11.

* * * * *